United States Patent
Gavai et al.

(10) Patent No.: US 9,273,014 B2
(45) Date of Patent: Mar. 1, 2016

(54) BIS(FLUOROALKYL)-1,4-BENZO-DIAZEPINONE COMPOUNDS AND PRODRUGS THEREOF

(71) Applicant: Bristol-Myers Squibb Company, Princeton, NJ (US)

(72) Inventors: Ashvinikumar V. Gavai, Princeton Junction, NJ (US); George V. DeLucca, Pennington, NJ (US); Daniel O'Malley, New Hope, NJ (US); Patrice Gill, Levittown, NJ (US); Claude A. Quesnelle, Skillman, NJ (US); Brian E. Fink, Yardley, PA (US); Yufen Zhao, Pennington, NJ (US); Francis Y. Lee, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/627,573

(22) Filed: Feb. 20, 2015

(65) Prior Publication Data

US 2015/0166489 A1  Jun. 18, 2015

Related U.S. Application Data

(63) Continuation of application No. 14/032,333, filed on Sep. 20, 2013, now Pat. No. 8,999,918.

(60) Provisional application No. 61/703,912, filed on Sep. 21, 2012.

(51) Int. Cl.
| | | |
|---|---|---|
| *A61K 38/00* | (2006.01) | |
| *A61K 47/00* | (2006.01) | |
| *C07D 243/24* | (2006.01) | |
| *A61K 31/5513* | (2006.01) | |

(Continued)

(52) U.S. Cl.
CPC ............ *C07D 243/24* (2013.01); *A61K 9/0019* (2013.01); *A61K 9/0095* (2013.01); *A61K 9/08* (2013.01); *A61K 31/138* (2013.01); *A61K 31/337* (2013.01); *A61K 31/506* (2013.01); *A61K 31/555* (2013.01); *A61K 31/5513* (2013.01); *A61K 31/573* (2013.01); *A61K 31/675* (2013.01); *A61K 38/05* (2013.01); *A61K 45/06* (2013.01); *C07D 243/18* (2013.01); *C07D 243/26* (2013.01); *C07D 401/04* (2013.01); *C07F 7/1852* (2013.01); *C07F 9/12* (2013.01); *C07F 9/38* (2013.01); *C07F 9/645* (2013.01); *C07K 5/06052* (2013.01); *A61K 9/4866* (2013.01); *A61K 47/48246* (2013.01)

(58) Field of Classification Search
CPC .................................................. A61K 31/5513
See application file for complete search history.

(56) References Cited

U.S. PATENT DOCUMENTS

| | | |
|---|---|---|
| 5,324,726 A | 6/1994 | Bock et al. |
| 5,852,010 A | 12/1998 | Graham et al. |
| 5,998,407 A | 12/1999 | Graham et al. |
| 6,331,408 B1 | 12/2001 | Zaczek et al. |
| 6,495,540 B2 | 12/2002 | Thompson |
| 6,503,901 B1 | 1/2003 | Thompson et al. |
| 6,503,902 B2 | 1/2003 | Olson et al. |
| 6,509,333 B2 | 1/2003 | Olson |
| 6,525,044 B2 | 2/2003 | Olson et al. |
| 6,544,978 B2 | 4/2003 | Wu et al. |

(Continued)

FOREIGN PATENT DOCUMENTS

| | | |
|---|---|---|
| WO | WO 97/36879 | 10/1997 |
| WO | WO 01/74796 | 10/2001 |
| WO | WO 01/90084 | 11/2001 |
| WO | WO 2007/067048 | 6/2007 |
| WO | WO 2009/023453 | 2/2009 |
| WO | WO 2012/129353 | 9/2012 |

OTHER PUBLICATIONS

Groth, C., et al., "Therapeutic approaches to modulating Notch signaling: Current challenges and future prospects," Seminars in Cell & Developmental Biology, (2012), doi:10.1016/j.semcdb2012.01.016; available online Mar. 7, 2012.

(Continued)

*Primary Examiner* — Marcela M Cordero Garcia
*Assistant Examiner* — Kaipeen Yang
(74) *Attorney, Agent, or Firm* — Gary D. Greenblatt

(57) ABSTRACT

Disclosed are compounds of Formula (I) and/or salts thereof:

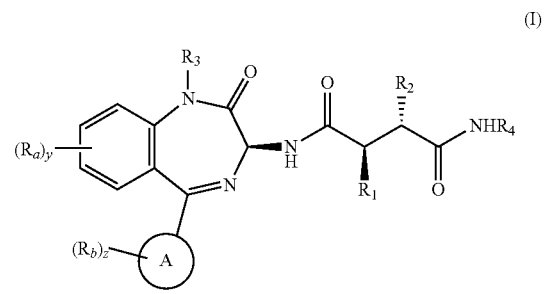

wherein $R_1$ is —$CH_2CH_2CF_3$; $R_2$ is —$CH_2CH_2CF_3$ or —$CH_2CH_2CH_2CF_3$; $R_3$ is H, —$CH_3$, or $R_x$; $R_4$ is H or $R_y$; Ring A is phenyl or pyridinyl; and $R_x$, $R_y$, $R_a$, $R_b$, y, and z are defined herein. Also disclosed are methods of using such compounds to inhibit the Notch receptor, and pharmaceutical compositions comprising such compounds. These compounds are useful in treating, preventing, or slowing the progression of diseases or disorders in a variety of therapeutic areas, such as cancer; or as prodrugs of such compounds.

11 Claims, 6 Drawing Sheets

(51) Int. Cl.

| | | |
|---|---|---|
| *A61K 31/573* | (2006.01) | |
| *A61K 31/675* | (2006.01) | |
| *A61K 38/05* | (2006.01) | |
| *A61K 45/06* | (2006.01) | |
| *C07D 401/04* | (2006.01) | |
| *C07F 9/645* | (2006.01) | |
| *C07K 5/062* | (2006.01) | |
| *C07D 243/18* | (2006.01) | |
| *C07D 243/26* | (2006.01) | |
| *C07F 9/12* | (2006.01) | |
| *A61K 9/00* | (2006.01) | |
| *A61K 9/08* | (2006.01) | |
| *A61K 31/138* | (2006.01) | |
| *A61K 31/337* | (2006.01) | |
| *A61K 31/506* | (2006.01) | |
| *A61K 31/555* | (2006.01) | |
| *C07F 7/18* | (2006.01) | |
| *C07F 9/38* | (2006.01) | |
| *A61K 9/48* | (2006.01) | |
| *A61K 47/48* | (2006.01) | |

(56) References Cited

U.S. PATENT DOCUMENTS

| | | | |
|---|---|---|---|
| 6,632,812 | B2 | 10/2003 | Han et al. |
| 6,653,303 | B1 | 11/2003 | Wu et al. |
| 6,713,476 | B2 | 3/2004 | Yang et al. |
| 6,737,038 | B1 | 5/2004 | Zaczek et al. |
| 6,756,511 | B2 | 6/2004 | Castro Pineiro et al. |
| 6,759,404 | B2 | 7/2004 | Olson et al. |
| 6,794,381 | B1 | 9/2004 | Olson et al. |
| 6,878,363 | B2 | 4/2005 | Zaczek et al. |
| 6,900,199 | B2 | 5/2005 | Han et al. |
| 6,958,329 | B2 | 10/2005 | Olson |
| 6,960,576 | B2 | 11/2005 | Olson et al. |
| 6,962,913 | B2 | 11/2005 | Olson et al. |
| 6,984,626 | B2 | 1/2006 | Nadin et al. |
| 7,001,901 | B2 | 2/2006 | Yang |
| 7,053,081 | B2 | 5/2006 | Olson et al. |
| 7,053,084 | B1 | 5/2006 | Olson |
| 7,101,870 | B2 | 9/2006 | Olson et al. |
| 7,105,509 | B2 | 9/2006 | Castro Pineiro et al. |
| 7,112,583 | B2 | 9/2006 | Olson et al. |
| 7,125,866 | B1 | 10/2006 | Glick et al. |
| 7,153,491 | B2 | 12/2006 | Zaczek et al. |
| 7,160,875 | B2 | 1/2007 | Flohr et al. |
| 7,276,495 | B2 | 10/2007 | Han et al. |
| 7,276,496 | B2 | 10/2007 | Olson et al. |
| 7,304,049 | B2 | 12/2007 | Olson |
| 7,304,055 | B2 | 12/2007 | Olson et al. |
| 7,304,056 | B2 | 12/2007 | Olson et al. |
| 7,342,008 | B2 | 3/2008 | Olson et al. |
| 7,354,914 | B2 | 4/2008 | Olson |
| 7,375,099 | B2 | 5/2008 | Galley et al. |
| 7,390,802 | B2 | 6/2008 | Han et al. |
| 7,390,896 | B2 | 6/2008 | Olson et al. |
| 7,423,033 | B2 | 9/2008 | Olson et al. |
| 7,456,172 | B2 | 11/2008 | Olson |
| 7,456,278 | B2 | 11/2008 | Olson |
| 7,498,324 | B2 | 3/2009 | Han et al. |
| 7,528,249 | B2 | 5/2009 | Olson et al. |
| 7,582,624 | B2 | 9/2009 | Carter et al. |
| 7,655,647 | B2 | 2/2010 | Han et al. |
| 7,718,795 | B2 | 5/2010 | Olson |
| 2007/0185094 | A1 | 8/2007 | Lattmann et al. |
| 2009/0181944 | A1 | 7/2009 | Boylan et al. |
| 2012/0245151 | A1 | 9/2012 | Gavai et al. |

OTHER PUBLICATIONS

Seiffert, D., et al., "Presenilin-1 and -2 Are Molecular Targets for gamma-Secretase Inhibitors," The Journal of Biological Chemistry, vol. 275, No. 44, pp. 34086-34091 (2000).

Beher, D., et al., "Pharmacological Knock-down of the Presenilin 1 Heterodimer by a Novel gamma-Secretase Inhibitor," The Journal of Biological Chemistry, vol. 276, No. 48, pp. 45394-45402 (2001).

Iben, L.G., et al., "Signal Peptide Peptidase and gamma-Secretase Share Equivalent Inhibitor Binding Pharmacology," The Journal of Biological Chemistry, vol. 282, No. 51, pp. 36829-36836 (2007).

Meredith, Jere, "Characterization of APP Activity and Notch Toxicity with gamma-Secretase Inhibitors," 8th International AD/PD Meeting, Salzberg, Austria, Mar. 17, 2007.

Prasad, C.V.C., et al., "Discovery of (S)-2-((S)-2(3,5-difluorophenyl)-2-hydroxyacetamido)-N-((S,Z)-3-methyl-4-oxo-4,5-dihydro-3H-benzo[*d*][1,2]diazepin-5-yl)propanamide (BMS-433796): A gamma-secretase inhibitor with A beta lowering activity in a transgenic mouse model of Alzheimer's disease," Bioorganic & Medicinal Chemistry Letters 17 pp. 4006-4011 (2007).

Jun, H.T., et al., "Top Notch Targets: Notch Signaling in Cancer," Drug Development Research, 69, pp. 319-328 (2008).

Meredith, J.E., et al., gamma-Secretase activity is not involved in presenilin-mediated regulation of beta-catenin, Biochemical and Biophysical Research Communications 299 pp. 744-750 (2002).

Shih, L., et al., Notch Signaling, gamma-Secretase Inhibitors, and Cancer Therapy, Cancer Res. 67, pp. 1879-1882 (2007).

Olson, Richard, "Optimizing gamma-secretase Inhibitors for safety and efficacy," 8th International AD/PD Meeting, Mar. 14-18, 2007, Salzberg, Austria.

PCT/US2013/060790 International Search Report mailed Nov. 7, 2013.

PCT/US2013/060790 Preliminary Report on Patentability issued Apr. 2, 2015.

U.S. Appl. No. 14/429,930, filed Mar. 20, 2015, Gavai et al.
U.S. Appl. No. 14/429,935, filed Mar. 20, 2015, Gavai et al.
U.S. Appl. No. 14/429,941, filed Mar. 20, 2015, Gavai et al.
U.S. Appl. No. 14/429,945, filed Mar. 20, 2015, Han et al.
U.S. Appl. No. 14/429,951, filed Mar. 20, 2015, Gavai et al.
U.S. Appl. No. 14/429,958, filed Mar. 20, 2015, Zhao et al.
U.S. Appl. No. 14/429,964, filed Mar. 20, 2015, Gill et al.
U.S. Appl. No. 14/429,923, filed Mar. 20, 2015, Shan et al.

BIS(FLUOROALKYL)-1,4-BENZO-DIAZEPINONE COMPOUNDS AND PRODRUGS THEREOF

CROSS-REFERENCE TO RELATED APPLICATIONS

This application is a Continuation of U.S. application Ser. No. 14/032,333 filed 20 Sep. 2013, which claims the priority benefit of U.S. Provisional Application No. 61/703,912, filed 20 Sep. 2012; the contents of which are herein incorporated by reference in their entirety.

The present invention generally relates to benzodiazepinone compounds useful as Notch inhibitors. The invention further pertains to pharmaceutical compositions comprising at least one compound according to the invention that is useful for the treatment of conditions related to the Notch pathway, such as cancer and other proliferative diseases.

Notch signaling has been implicated in a variety of cellular processes, such as cell fate specification, differentiation, proliferation, apoptosis, and angiogenesis. (Bray, *Nature Reviews Molecular Cell Biology*, 7:678-689 (2006); Fortini, *Developmental Cell* 16:633-647 (2009)). The Notch proteins are single-pass heterodimeric transmembrane molecules. The Notch family includes 4 receptors, NOTCH 1-4, which become activated upon binding to ligands from the DSL family (Delta-like 1, 3, 4 and Jagged 1 and 2).

The activation and maturation of NOTCH requires a series of processing steps, including a proteolytic cleavage step mediated by gamma secretase, a multiprotein complex containing Presenilin 1 or Presenilin 2, nicastrin, APH1, and PEN2. Once NOTCH is cleaved, NOTCH intracellular domain (NICD) is released from the membrane. The released NICD translocates to the nucleus, where it functions as a transcriptional activator in concert with CSL family members (RBPSUH, "suppressor of hairless", and LAG1). NOTCH target genes include HES family members, such as HES-1. HES-1 functions as transcriptional repressors of genes such as HERP1 (also known as HEY2), HERP2 (also known as HEY1), and HATH1 (also known as ATOH1).

The aberrant activation of the Notch pathway contributes to tumorigenesis. Activation of Notch signaling has been implicated in the pathogenesis of various solid tumors including ovarian, pancreatic, as well as breast cancer and hematologic tumors such as leukemias, lymphomas, and multiple myeloma. The role of Notch inhibition and its utility in the treatment of various solid and hematological tumors are described in Miele, L. et al., *Current Cancer Drug Targets*, 6:313-323 (2006); Bolos, V. et al., *Endocrine Reviews*, 28:339-363 (2007); Shih, I-M. et al., *Cancer Research*, 67:1879-1882 (2007); Yamaguchi, N. et al., *Cancer Research*, 68:1881-1888 (2008); Miele, L., *Expert Review Anti-cancer Therapy*, 8:1197-1201 (2008); Purow, B., *Current Pharmaceutical Biotechnology*, 10:154-160 (2009); Nefedova, Y. et al., *Drug Resistance Updates*, 11:210-218 (2008); Dufraine, J. et al., *Oncogene*, 27:5132-5137 (2008); and Jun, H. T. et al., *Drug Development Research*, 69:319-328 (2008).

There remains a need for compounds that are useful as Notch inhibitors and that have sufficient metabolic stability to provide efficacious levels of drug exposure. Further, there remains a need for compounds useful as Notch inhibitors that can be orally or intravenously administered to a patient.

U.S. Pat. No. 7,053,084 B1 discloses succinoylamino benzodiazepine compounds useful for treating neurological disorders such as Alzheimer's Disease. The reference discloses that these succinoylamino benzodiazepine compounds inhibit gamma secretase activity and the processing of amyloid precursor protein linked to the formation of neurological deposits of amyloid protein.

Applicants have found potent compounds that have activity as Notch inhibitors and have sufficient metabolic stability to provide efficacious levels of drug exposure upon intravenous or oral administration. These compounds are provided to be useful as pharmaceuticals with desirable stability, bioavailability, therapeutic index, and toxicity values that are important to their drugability.

SUMMARY OF THE INVENTION

The present invention fills the foregoing need by providing bis(fluoroalkyl) 1,4-benzodiazepinone compounds that are useful as selective inhibitors of Notch signaling pathway, including prodrugs thereof.

The present invention also provides pharmaceutical compositions comprising a pharmaceutically acceptable carrier; and at least one compound of Formula (I).

The present invention also provides a method of treating a disease or disorder associated with the activity of the Notch receptor, the method comprising administering to a mammalian patient at least one compound of Formula (I).

The present invention also provides processes and intermediates for making the compounds of Formula (I).

The present invention also provides the compounds of Formula (I) for use in therapy.

The present invention also provides the use of the compounds of Formula (I) for the manufacture of a medicament for the treatment of cancer.

The compounds of Formula (I) and compositions comprising the compounds may be used in treating, preventing or curing various Notch receptor-related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawings described below.

DETAILED DESCRIPTION

Figure 1:
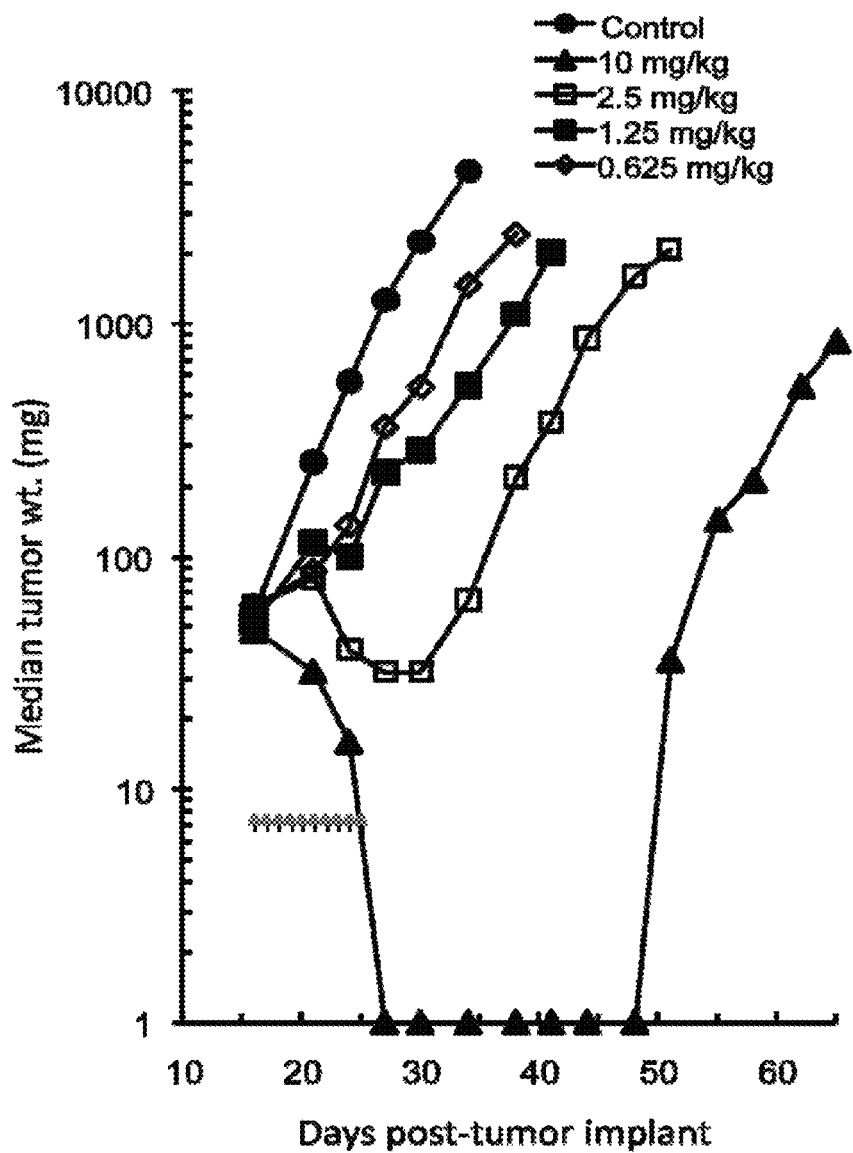
FIG. 1 shows the antitumor efficacy of Example 1 against TALL1 Human T-cell acute lymphoblastic leukemia. Dosed orally on days indicted by (↑); PO, QD×10. Each symbol represents the median tumor burden of a group of 8 mice. (●) Control; (◇) Example 1, 0.625 mg/kg/adm; (■) Example 1, 1.25 mg/kg/adm; (□) Example 1, 2.5 mg/kg/adm; (▲) Example 1, 10 mg/kg.

The first aspect of the present invention provides at least one compound of Formula (I):

(I)

[Structure of Formula (I)]

and/or at least one salt thereof; wherein:

$R_1$ is —$CH_2CH_2CF_3$;

$R_2$ is —$CH_2CH_2CF_3$ or —$CH_2CH_2CH_2CF_3$;

$R_3$ is H, —$CH_3$, or $R_x$;

$R_4$ is H or $R_y$;

$R_x$ is —$CH_2OC(O)CH(CH_3)NH_2$, —$CH_2OC(O)CH(NH_2)CH(CH_3)_2$, —$CH_2OC(O)CH((CH(CH_3)_2)NHC(O)CH(NH_2)CH(CH_3)_2$,

—$CH_2OC(O)CH_2$—[phenyl-OP(O)(OH)$_2$],

—$CH_2OC(O)CH_2C(CH_3)_2$—[substituted phenyl with $H_3C$, $CH_3$, $(HO)_2(O)PO$], or —$CH_2OC(O)$—[pyridinyl]—$CH_2OP(O)(OH)_2$;

$R_y$ is —$SCH_2CH(NH_2)C(O)OH$, —$SCH_2CH(NH_2)C(O)OCH_3$, or —$SCH_2CH(NH_2)C(O)OC(CH_3)_3$;

Ring A is phenyl or pyridinyl;

each $R_a$ is independently Cl, $C_{1-3}$ alkyl, —$CH_2OH$, —$CF_3$, cyclopropyl, —$OCH_3$, and/or —$O$(cyclopropyl);

each $R_b$ is independently F, Cl, —$CH_3$, —$CH_2OH$, —$CF_3$, cyclopropyl, and/or —$OCH_3$;

y is zero, 1, or 2; and z is zero, 1, or 2;

provided that if Ring A is phenyl and z is zero, then y is 1 or 2 and at least one $R_a$ is $C_{1-3}$ alkyl, —$CF_3$, cyclopropyl, or —$O$(cyclopropyl);

provided that if $R_3$ is $R_x$ then $R_4$ is H; and provided that if $R_4$ is $R_y$, then $R_3$ is H or —$CH_3$.

One embodiment provides at least one compound of Formula (I) wherein $R_3$ is H or —$CH_3$; $R_4$ is H; and $R_1$, $R_2$, Ring A, $R_a$, $R_b$, y, and z are defined in the first aspect. This embodiment includes the compounds of Formula (II) in which $R_3$ is H and $R_4$ is H:

(II)

[Structure of Formula (II)]

and the compounds of Formula (III) in which $R_3$ is —$CH_3$ and $R_4$ is H:

(III)

[Structure of Formula (III)]

The compounds of Formula (II) and Formula (III) are useful as selective inhibitors of the Notch signaling pathway.

One embodiment provides at least one compound of Formula (I) and/or at least one salt thereof, wherein either (i) $R_3$ is $R_x$ and $R_4$ is H; or (ii) $R_4$ is $R_y$ and $R_3$ is H or —$CH_3$; and $R_1$, $R_2$, Ring A, $R_a$, $R_b$, $R_x$, $R_y$, y, and z are defined in the first aspect. This embodiment includes the compounds of Formula (IV) in which $R_3$ is $R_x$ and $R_4$ is H:

(IV)

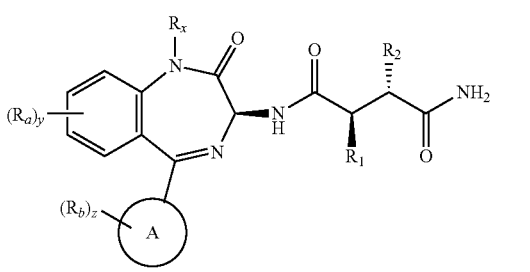

and the compounds of Formula (V) in which $R_4$ is $R_y$ and $R_3$ is H or —$CH_3$:

(V)

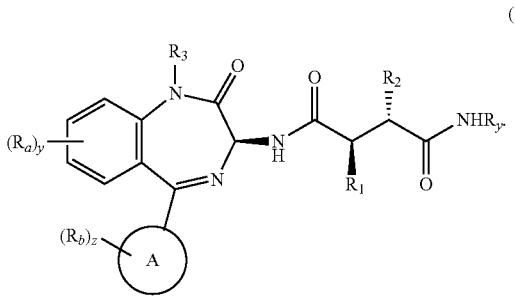

The compounds of this embodiment are useful as prodrugs of the compounds of Formula (II) and Formula (III).

One embodiment provides at least one compound of Formula (IV) and/or at least one salt thereof, wherein $R_3$ is $R_x$ and $R_4$ is H; and $R_1$, $R_2$, $R_x$, Ring A, $R_a$, $R_b$, y, and z are defined in the first aspect. Included in this embodiment are compounds in which Ring A is phenyl. The compounds of this embodiment are useful as prodrugs of the compounds of Formula (II) and Formula (III).

One embodiment provides at least one compound of Formula (V) and/or at least one salt thereof, wherein $R_4$ is $R_y$ and $R_3$ is H or —$CH_3$; and $R_1$, $R_2$, $R_y$, Ring A, $R_a$, $R_b$, y, and z are defined in the first aspect. Included in this embodiment are compounds in which $R_3$ is H and Ring A is phenyl. Also included in this embodiment are compounds in which $R_3$ is —$CH_3$ and Ring A is phenyl. The compounds of this embodiment are useful as prodrugs of the compounds of Formula (II) and Formula (III).

One embodiment provides at least one compound of Formula (I) and/or at least one salt thereof, wherein Ring A is phenyl; and $R_1$, $R_2$, $R_3$, $R_4$, $R_x$, $R_y$, $R_a$, $R_b$, y, and z are defined in the first aspect. Included in this embodiment are compounds in which $R_3$ is H. Also included in this embodiment are compounds in which $R_3$ is H and z is 1 or 2.

One embodiment provides at least one compound of Formula (I), wherein Ring A is phenyl; $R_3$ is H or $CH_3$; $R_4$ is H; and $R_1$, $R_2$, $R_a$, $R_b$, y, and z are defined in the first aspect. Included in this embodiment are compounds in which $R_3$ is H. Also included in this embodiment are compounds in which $R_3$ is H and z is 1 or 2.

One embodiment provides at least one compound of Formula (I) and/or at least one salt thereof, wherein $R_2$ is —$CH_2CH_2CF_3$ and $R_1$, $R_3$, $R_4$, Ring A, $R_x$, $R_y$, $R_a$, $R_b$, y, and z are defined in the first aspect. Included in this embodiment are compounds in which Ring A is phenyl. Also included in this embodiment are compounds in which z is 1 or 2.

One embodiment provides at least one compound of Formula (I) and/or at least one salt thereof, wherein $R_2$ is —$CH_2CH_2CH_2CF_3$ and $R_1$, $R_3$, $R_4$, Ring A, $R_a$, $R_b$, y, and z are defined in the first aspect. Included in this embodiment are compounds in which Ring A is phenyl. Also included in this embodiment are compounds in which z is 1 or 2.

One embodiment provides at least one compound of Formula (I) and/or at least one salt thereof, wherein Ring A is pyridinyl; and $R_1$, $R_2$, $R_3$, $R_4$, $R_a$, $R_b$, y, and z are defined in the first aspect. Included in this embodiment are compounds in which $R_3$ is H. Also included in this embodiment are compounds in which $R_3$ is H and z is 1 or 2.

One embodiment provides at least one compound of Formula (I) and/or at least one salt thereof, wherein $R_2$ is —$CH_2CH_2CF_3$; Ring A is phenyl; $R_a$ is $C_{1-3}$ alkyl or —$CH_2OH$; each $R_b$ is independently F and/or Cl; y is 1; z is 1 or 2; and $R_1$, $R_3$, and $R_4$ are defined in the first aspect.

One embodiment provides at least one compound of Formula (I) and/or at least one salt thereof, wherein y is 1, z is 1 or 2, and $R_1$, $R_2$, $R_3$, $R_4$, Ring A, $R_a$, and $R_b$ are defined in the first aspect. Included in the embodiment are compounds in which Ring A is phenyl. Also included in this embodiment are compounds in which Ring A is phenyl and z is 1.

One embodiment provides at least one compound of Formula (I) and/or at least salt thereof, having the structure:

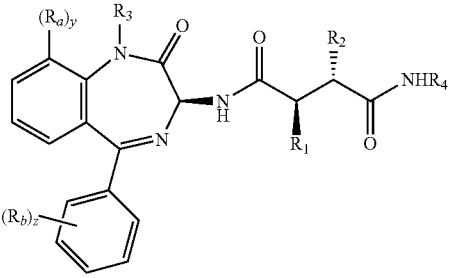

wherein:
$R_1$ is —$CH_2CH_2CF_3$;
$R_2$ is —$CH_2CH_2CF_3$ or —$CH_2CH_2CH_2CF_3$;
$R_3$ is H, —$CH_3$, or $R_x$;
$R_4$ is H or $R_y$;
$R_x$ is: —$CH_2OC(O)CH(CH_3)NH_2$, —$CH_2OC(O)CH(NH_2)CH(CH_3)_2$, —$CH_2OC(O)CH((CH(CH_3)_2)NHC(O)CH(NH_2)CH(CH_3)_2$,

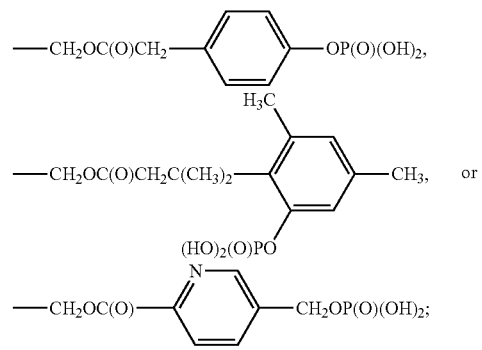

$R_y$ is: —$SCH_2CH(NH_2)C(O)OH$, —$SCH_2CH(NH_2)C(O)OCH_3$, or —$SCH_2CH(NH_2)C(O)OC(CH_3)_3$;
$R_a$ is Cl, —$CH_3$, —$CH(CH_3)_2$, —$CH_2OH$, —$CF_3$, cyclopropyl, —$OCH_3$, or —$O(cyclopropyl)$;

each $R_b$ is independently F, Cl, —CH$_2$OH, —CF$_3$, cyclopropyl, and/or —OCH$_3$;
y is zero or 1;
z is zero, 1, or 2;
provided that if z is zero, then y is 1 and $R_a$ is —CH$_3$, —CH$_2$OH, —CF$_3$, cyclopropyl, or —O(cyclopropyl).
Included in the embodiment are compounds in which y is 1; and z is zero, 1, or 2. Also included in this embodiment are compounds in which y is 1 and z is 1.

One embodiment provides at least one compound of Formula (I) and/or at least salt thereof, having the structure:

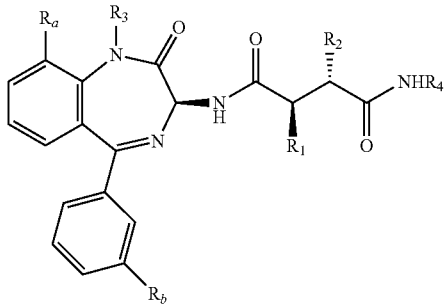

wherein $R_1$, $R_2$, $R_3$, $R_4$, $R_a$, and $R_b$ are defined in the first aspect. Included in this embodiment are compounds in which $R_a$ is Cl, —CH$_2$OH, or C$_{1-3}$ alkyl and $R_b$ is F, Cl, —CH$_3$, —CF$_3$, cyclopropyl, or —OCH$_3$. Also included in this embodiment are compounds in which $R_a$ is methyl and $R_b$ is F, Cl, or CF$_3$.

One embodiment provides at least one compound of Formula (I) and/or at least salt thereof, having the structure:

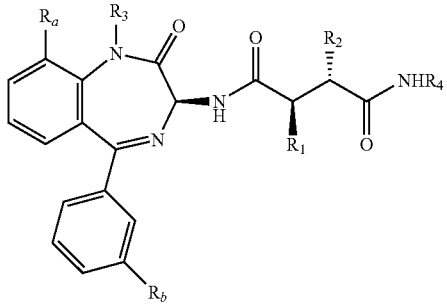

wherein $R_a$ is C$_{1-3}$ alkyl; $R_b$ is F or Cl; and $R_1$, $R_2$, $R_3$, and $R_4$ are defined in the first aspect. Included in this embodiment are compounds in which $R_2$ is —CH$_2$CH$_2$CF$_3$. Also included in this embodiment are compounds in which $R_2$ is —CH$_2$CH$_2$CF$_3$, $R_a$ is methyl, and $R_b$ is F or Cl.

One embodiment provides at least one compound of Formula (I) and/or at least salt thereof, having the structure:

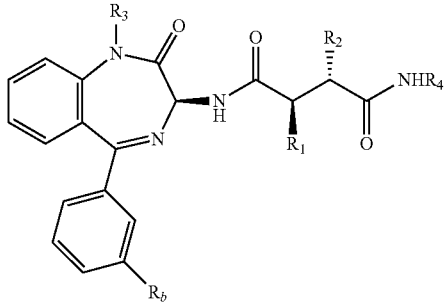

wherein y is zero and $R_1$, $R_2$, $R_3$, $R_4$, and $R_b$ are defined in the first aspect. Included in this embodiment are compounds in which $R_b$ is —CH$_3$, —CH$_2$OH, or —OCH$_3$. Also included in this embodiment are compounds in which $R_3$ is H or —CH$_3$ and $R_4$ is H.

One embodiment provides at least one compound of Formula (I) and/or at least one salt thereof, having the structure:

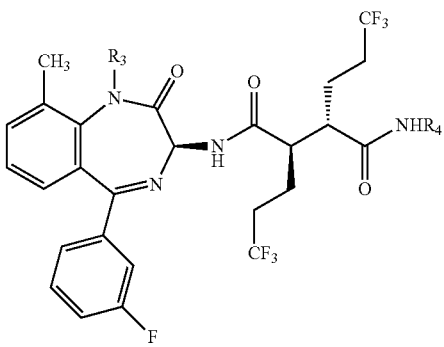

wherein $R_3$ and $R_4$ are defined in the first aspect. Included in this embodiment are compounds in which $R_3$ is H or —CH$_3$ and $R_4$ is H.

One embodiment provides at least one compound of Formula (I) and/or at least one salt thereof, having the structure:

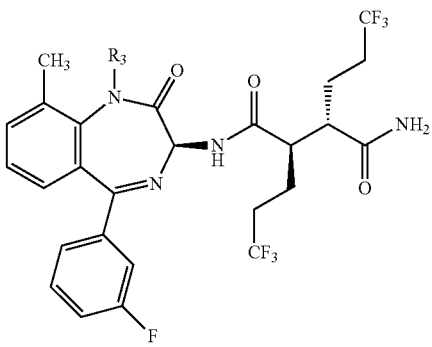

wherein $R_3$ is H, —CH$_3$, or $R_x$, wherein $R_x$ is defined in the first aspect. Also included in this embodiment are compounds in which $R_3$ is $R_x$.

One embodiment provides at least one compound of Formula (I) and/or at least one salt thereof, having the structure:

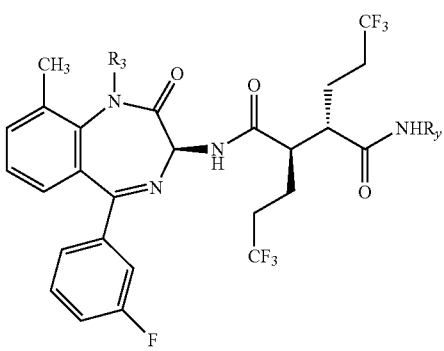

wherein $R_3$ is H or —CH$_3$, and $R_y$ is defined in the first aspect. Included in this embodiment are compounds in which $R_3$ is H. Also included in this embodiment are compounds in which $R_3$ is —CH$_3$.

One embodiment provides at least one compound of Formula (I) and/or at least one salt thereof, having the structure:

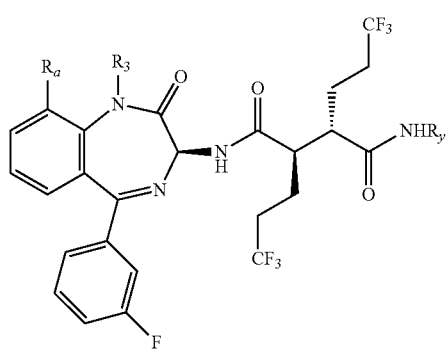

wherein $R_a$ is —CH₃ or —CH₂OH; $R_3$ is H or —CH₃, and $R_y$ is defined in the first aspect. Included in this embodiment are compounds in which $R_3$ is H. Also included in this embodiment are compounds in which $R_3$ is —CH₃.

One embodiment provides at least one compound of Formula (I) and/or salt thereof, having the structure:

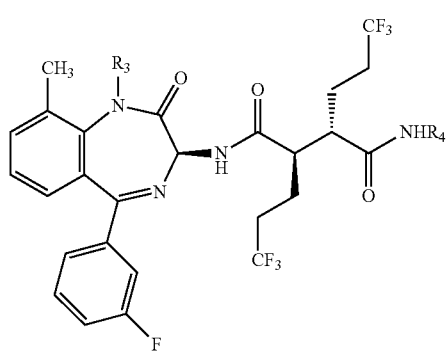

wherein $R_3$ is H or $R_x$; $R_4$ is H or $R_y$; provided that if $R_3$ is $R_x$ then $R_4$ is H; and provided that if $R_4$ is $R_y$ then $R_3$ is H; and wherein $R_x$ and $R_y$ are defined in the first aspect.

One embodiment provides at least one compound of Formula (I) having the structure:

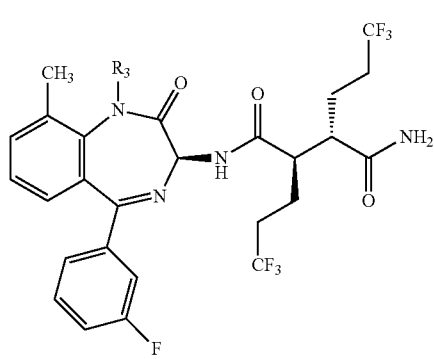

wherein $R_3$ is H or —CH₃.

One embodiment provides a compound of Formula (I) having the structure:

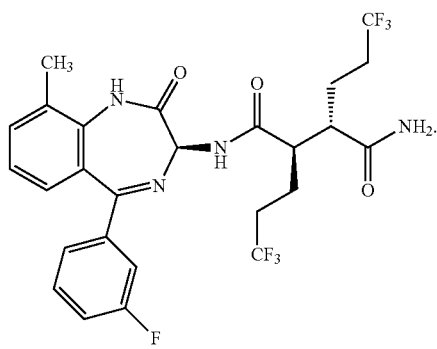 [SMILES: Cc1cccc2c1NC(=O)[C@@H](NC(=O)[C@H](CCC(F)(F)F)[C@H](CCC(F)(F)F)C(N)=O)N=C2c1cccc(F)c1]

One embodiment provides a compound of Formula (I) having the structure:

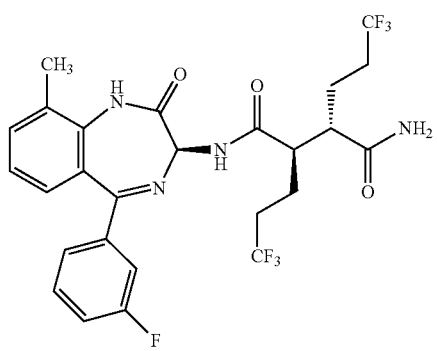 [SMILES: Cc1cccc2c1NC(=O)[C@@H](NC(=O)[C@H](CCC(F)(F)F)[C@H](CCC(F)(F)F)C(N)=O)N=C2c1cccc(F)c1]

or a compound of Formula (I) having a structure:

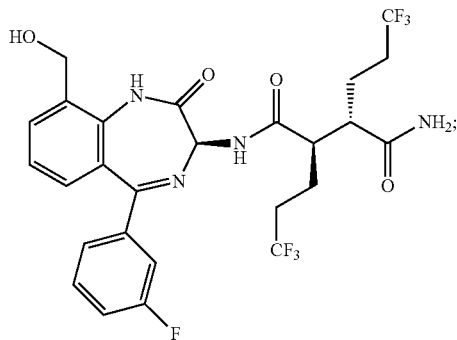 [SMILES: NC(=O)[C@@H](CCC(F)(F)F)[C@@H](CCC(F)(F)F)C(=O)N[C@H]1N=C(c2cccc(F)c2)c2cccc(CO)c2NC1=O]

or any mixture of the two compounds.

One embodiment provides at least one compound of Formula (I) and/or salt thereof, having the structure:

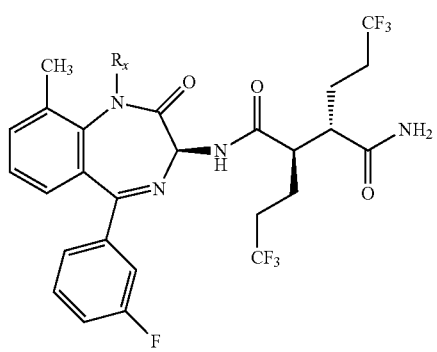

wherein $R_x$ is defined in the first aspect.

One embodiment provides at least one compound of Formula (I) and/or salt thereof, having the structure:

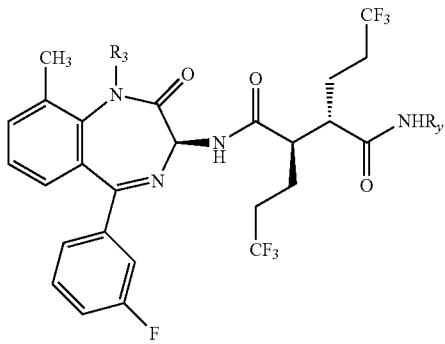

wherein $R_3$ is H or —$CH_3$; and $R_y$ is defined in the first aspect.

One embodiment provides a composition comprising: (i) at least one compound of Formula (I) having the structure:

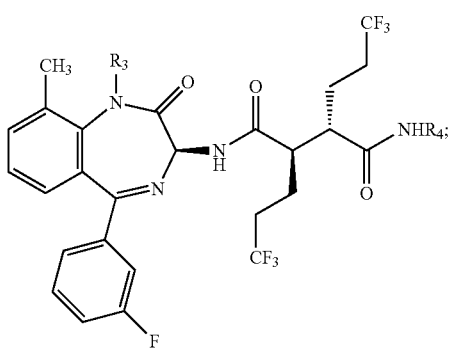

and/or salt thereof; (ii) a compound of Formula (I) having the structure:

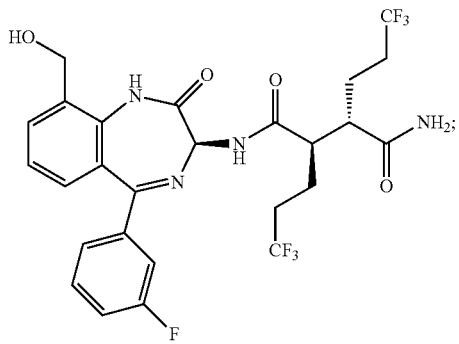 [SMILES: NC(=O)[C@@H](CCC(F)(F)F)[C@@H](CCC(F)(F)F)C(=O)N[C@H]1N=C(c2cccc(F)c2)c2cccc(CO)c2NC1=O]

or (iii) a mixture of (i) and (ii); wherein $R_3$ is H or $R_x$; $R_4$ is H or $R_y$; provided that if $R_3$ is $R_x$ then $R_4$ is H; and provided that if $R_4$ is $R_y$, then $R_3$ is H; and wherein $R_x$ and $R_y$ are defined in the first aspect.

One embodiment provides at least one compound of Formula (I) and/or salt thereof, having the structure:

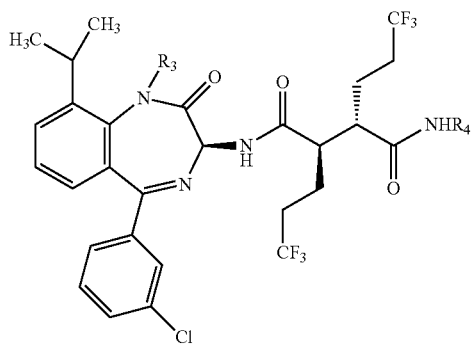

wherein $R_3$ is H or $R_x$; $R_4$ is H or $R_y$; provided that if $R_3$ is $R_x$ then $R_4$ is H; and provided that if $R_4$ is $R_y$ then $R_3$ is H; and wherein $R_x$ and $R_y$ are defined in the first aspect. Included in this embodiment are compounds in which $R_3$ is H or —$CH_3$; and $R_4$ is H. Also included in this embodiment are compounds in which $R_3$ is H and $R_4$ is H.

One embodiment provides at least one compound of Formula (I) and/or at least one salt thereof, wherein $R_1$, $R_2$, $R_3$, $R_4$, Ring A, $R_a$, $R_b$, y, and z are defined in the first aspect and provided that if Ring A is phenyl and z is zero, then y is 1 or 2 and at least one $R_a$ is methyl, isopropyl, —$CH_2OH$, cyclopropyl, and/or —O(cyclopropyl).

One embodiment provides at least one compound of Formula (I) and/or at least one salt thereof, wherein $R_3$ is H; and $R_1$, $R_2$, $R_4$, $R_a$, $R_b$, y, and z are defined in the first aspect. Included in this embodiment are compounds in which $R_3$ is deuterium (D) or tritium (T). Also included in this embodiment are compounds in which $R_2$ is —$CH_2CH_2CF_3$.

One embodiment provides at least compound of Formula (I) and/or at least one salt thereof, wherein $R_3$ is —$CH_3$; and $R_1$, $R_2$, $R_4$, $R_a$, $R_b$, y, and z are defined in the first aspect. $R_3$ includes methyl groups in which one or more hydrogen atoms are isotopically substituted with deuterium (D) and/or tritium (T). In one example of this embodiment, $R_3$ is —$CD_3$. Also included in this embodiment are compounds in which $R_2$ is —$CH_2CH_2CF_3$.

One embodiment provides at least one compound of Formula (I) and/or at least one salt thereof, wherein $R_1$, $R_2$, $R_3$, $R_4$, Ring A, $R_a$, $R_b$, y, and z are defined in the first aspect, with the proviso that the compound of Formula (I) or salt thereof is not:

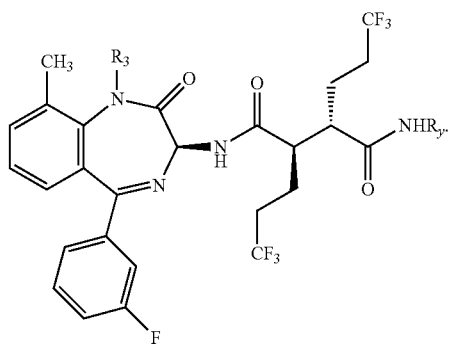

One embodiment provides at least one compound of Formula (I) wherein $R_3$ is H or —$CH_3$; $R_4$ is H; $R_1$, $R_2$, Ring A, $R_a$, $R_b$, y, and z are defined in the first aspect, with the proviso that the compound of Formula (I) is not:

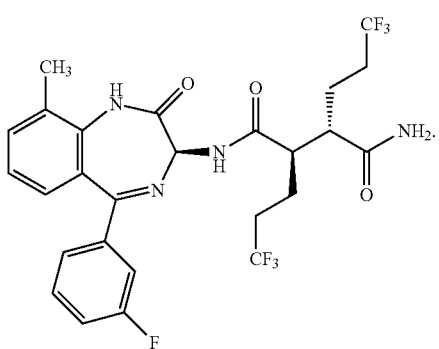 [SMILES: Cc1cccc2c1NC(=O)[C@@H](NC(=O)[C@H](CCC(F)(F)F)[C@H](CCC(F)(F)F)C(N)=O)N=C2c1cccc(F)c1]

One embodiment provides a compound of Formula (I) selected from: (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide (1); (2R,3S)—N-((3S)-5-(3-chlorophenyl)-9-ethyl-2-oxo-2,3-dihydro-1H-1,4-benzodiazepin-3-yl)-2,3-bis(3,3,3-trifluoropropyl)succinamide (2); (2R,3S)—N-((3S)-5-(3-chlorophenyl)-9-isopropyl-2-oxo-2,3-dihydro-1H-1,4-benzodiazepin-3-yl)-2,3-bis(3,3,3-trifluoropropyl)succinamide (3); (2R,3S)—N-(9-chloro-5-(3,4-dimethylphenyl)-2-oxo-2,3-dihydro-1H-1,4-benzodiazepin-3-yl)-3-(4,4,4-trifluorobutyl)-2-(3,3,3-trifluoropropyl)succinamide (4); (2R,3S)—N-(9-chloro-5-(3,5-dimethylphenyl)-2-oxo-2,3-dihydro-1H-1,4-benzodiazepin-3-yl)-3-(4,4,4-trifluorobutyl)-2-(3,3,3-trifluoropropyl)succinamide (5); (2R,3S)—N-((3S)-9-ethyl-5-(3-methylphenyl)-2-oxo-2,3-dihydro-1H-1,4-benzodiazepin-3-yl)-2,3-bis(3,3,3-trifluoropropyl)succinamide (6); (2R,3S)—N-((3S)-5-(3-chlorophenyl)-9-methyl-2-oxo-2,3-dihydro-1H-1,4-benzodiazepin-3-yl)-2,3-bis(3,3,3-trifluoropropyl)succinamide (7); (2R,3S)—N-((3S)-5-(3-chlorophenyl)-9-methyl-2-oxo-2,3-dihydro-1H-1,4-benzodiazepin-3-yl)-3-(4,4,4-trifluorobutyl)-2-(3,3,3-trifluoropropyl)succinamide (8); (2R,3S)—N-((3S)-5-(3-methylphenyl)-2-oxo-9-(trifluoromethyl)-2,3-dihydro-1H-1,4-benzodiazepin-3-yl)-2,3-bis(3,3,3-trifluoropropyl)succinamide (9); (2R,3S)—N-((3S)-9-chloro-5-(3,5-dimethylphenyl)-2-oxo-2,3-dihydro-1H-1,4-benzodiazepin-3-yl)-2,3-bis(3,3,3-trifluoropropyl)succinamide (10); (2R,3S)—N-((3S)-5-(3-methylphenyl)-2-oxo-9-(trifluoromethyl)-2,3-dihydro-1H-1,4-benzodiazepin-3-yl)-3-(4,4,4-trifluorobutyl)-2-(3,3,3-trifluoropropyl)succinamide (11); (2R,3S)—N-((3S)-9-isopropyl-5-(3-methylphenyl)-2-oxo-2,3-dihydro-1H-1,4-benzodiazepin-3-yl)-2,3-bis(3,3,3-trifluoropropyl)succinamide (12); (2R,3S)—N-((3S)-9-isopropyl-2-oxo-5-phenyl-2,3-dihydro-1H-1,4-benzodiazepin-3-yl)-2,3-bis(3,3,3-trifluoropropyl)succinamide (13); (2R,3S)—N-((3S)-9-(cyclopropyloxy)-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide (14); (2R,3S)—N-((3S)-9-(cyclopropyloxy)-5-(3-methylphenyl)-2-oxo-2,3-dihydro-1H-1,4-benzodiazepin-3-yl)-2,3-bis(3,3,3-trifluoropropyl)succinamide (15); (2R,3S)—N-((3S)-9-(cyclopropyloxy)-2-oxo-5-phenyl-2,3-dihydro-1H-1,4-benzodiazepin-3-yl)-3-(4,4,4-trifluorobutyl)-2-(3,3,3-trifluoropropyl)succinamide (16); (2R,3S)—N-((3S)-9-chloro-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide (17); (2R,3S)—N-((3S)-9-methyl-2-oxo-5-(3-(trifluoromethyl)phenyl)-2,3-dihydro-1H-1,4-benzodiazepin-3-yl)-3-(4,4,4-trifluorobutyl)-2-(3,3,3-trifluoropropyl)succinamide (18); (2R,3S)—N-((3S)-9-(cyclopropyloxy)-2-oxo-5-phenyl-2,3-dihydro-1H-1,4-benzodiazepin-3-yl)-2,3-bis(3,3,3-trifluoropropyl)succinamide (19); (2R,3S)—N-((3S)-9-methyl-2-oxo-5-(3-(trifluoromethyl)phenyl)-2,3-dihydro-1H-1,4-benzodiazepin-3-yl)-2,3-bis(3,3,3-trifluoropropyl)succinamide (20); (2R,3S)—N-((3S)-9-chloro-5-(2-methylphenyl)-2-oxo-2,3-dihydro-1H-1,4-benzodiazepin-3-yl)-2,3-bis(3,3,3-trifluoropropyl)succinamide (21); (2R,3S)—N-((3S)-5-(4-fluorophenyl)-9-methyl-2-oxo-2,3-dihydro-1H-1,4-benzodiazepin-3-yl)-2,3-bis(3,3,3-trifluoropropyl)succinamide (22); (2R,3S)—N-((3S)-9-methyl-2-oxo-5-phenyl-2,3-dihydro-1H-1,4-benzodiazepin-3-yl)-2,3-bis(3,3,3-trifluoropropyl)succinamide (23); (2R,3S)—N-((3S)-9-cyclopropyl-2-oxo-5-phenyl-2,3-dihydro-1H-1,4-benzodiazepin-3-yl)-2,3-bis(3,3,3-trifluoropropyl)succinamide (24); (2R,3S)—N-((3S)-9-chloro-5-(3-cyclopropylphenyl)-2-oxo-2,3-dihydro-1H-1,4-benzodiazepin-3-yl)-2,3-bis(3,3,3-trifluoropropyl)succinamide (25); (2R,3S)—N-((3S)-5-(3-chlorophenyl)-9-methoxy-2-oxo-2,3-dihydro-1H-1,4-benzodiazepin-3-yl)-2,3-bis(3,3,3-trifluoropropyl)succinamide (26); (2R,3S)—N-((3S)-5-(4-chlorophenyl)-9-methoxy-2-oxo-2,3-dihydro-1H-1,4-benzodiazepin-3-yl)-2,3-bis(3,3,3-trifluoropropyl)succinamide (27); (2R,3S)—N-((3S)-9-chloro-5-(3-methylphenyl)-2-oxo-2,3-dihydro-1H-1,4-benzodiazepin-3-yl)-2,3-bis(3,3,3-trifluoropropyl)succinamide (28); (2R,3S)—N-((3S)-5-(3-methylphenyl)-9-methoxy-2-oxo-2,3-dihydro-1H-1,4-benzodiazepin-3-yl)-2,3-bis(3,3,3-trifluoropropyl)succinamide (29); (2R,3S)—N-((3S)-5-(4-(hydroxymethyl)phenyl)-2-oxo-2,3-dihydro-1H-1,4-benzodiazepin-3-yl)-2,3-bis(3,3,3-trifluoropropyl)succinamide (30); (2R,3S)—N-((3S)-5-(2-methylphenyl)-2-oxo-2,3-dihydro-1H-1,4-benzodiazepin-3-yl)-2,3-bis(3,3,3-trifluoropropyl)succinamide (31); (2R,3S)—N-((3S)-5-(3-methylphenyl)-2-oxo-2,3-dihydro-1H-1,4-benzodiazepin-3-yl)-2,3-bis(3,3,3-trifluoropropyl)succinamide (32); (2R,3S)—N-((3S)-9-methoxy-2-oxo-5-(5-(trifluoromethyl)-2-pyridinyl)-2,3-dihydro-1H-1,4-benzodiazepin-3-yl)-2,3-bis(3,3,3-trifluoropropyl)succinamide (33); (2R,3S)—N-((3S)-5-(5-chloro-2-pyridinyl)-9-methoxy-2-oxo-2,3-dihydro-1H-1,4-benzodiazepin-3-yl)-2,3-bis(3,3,3-trifluoropropyl)succinamide (34); (2R,3S)—N-((3S)-5-(4-methoxyphenyl)-2-oxo-2,3-dihydro-1H-1,4-benzodiazepin-3-yl)-2,3-bis(3,3,3-trifluoropropyl)succinamide (35); (2R,3S)—N-((3S)-5-(4-methylphenyl)-2-oxo-2,3-dihydro-1H-1,4-benzodiazepin-3-yl)-2,3-bis(3,3,3-trifluoropropyl)succinamide (36); (2R,3S)—N-((3S)-5-(3-fluorophenyl)-9-(hydroxymethyl)-2-oxo-2,3-dihydro-1H-1,4-benzodiazepin-3-yl)-2,3-bis(3,3,3-trifluoropropyl)succinamide (37); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valinate (38); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-alaninate (39); S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteine (40); tert-butyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (41); methyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (42); ((3S)-3-(((2R,3S)-3-carbamoyl-6,6,6-trifluoro-2-(3,3,3-trifluoropropyl)hexanoyl)amino)-5-(3- fluorophenyl)-9-methyl-2-oxo-2,3-dihydro-1H-1,4-benzodiazepin-1-yl)methyl(4-(phosphonooxy)phenyl) acetate (43); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valyl-L-valinate (44); and salts thereof.

One embodiment provides a compound of Formula (I) selected from: (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide (1); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valinate (38); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-alaninate (39); S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteine (40); tert-butyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (41); methyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (42); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl(4-(phosphonooxy)phenyl) acetate (43); ((3S)-3-(((2R,3S)-3-carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valyl-L-valinate (44); and salts thereof.

One embodiment provides at least one compound of Formula (I) in which $R_3$ is H or —$CH_3$; and $R_4$ is H; wherein the compound of Formula (I) has a metabolic half life value of at least 45 minutes as measured in the human metabolic stability half-life assay described herein.

One embodiment provides at least one compound of Formula (I) in which $R_3$ is H or —$CH_3$; and $R_4$ is H; wherein the compound of Formula (I) has a metabolic half-life value of at least 60 minutes as measured in the human metabolic stability half-life assay described herein.

One embodiment provides at least one compound of Formula (I) in which $R_3$ is H or —$CH_3$; and $R_4$ is H; wherein the compound of Formula (I) has a metabolic half-life value of at least 70 minutes as measured in the human metabolic stability half-life assay described herein.

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe addition more embodiments. It is also to be understood that each individual element of the embodiments is meant to be combined with any and all other elements from any embodiment to describe an additional embodiment.

DEFINITIONS

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

The terms "halo" and "halogen", as used herein, refer to F, Cl, Br, or I.

The term "alkyl" as used herein, refers to both branched and straight chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-3}$ alkyl" denotes straight and branched chain alkyl groups with one to three carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s)" may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Any compound that can be converted in vivo to provide the bioactive agent (i.e., the compound of Formula (I)) is a prodrug within the scope and spirit of the invention. The compounds of Formula (I) in which either $R_3$ is $R_x$ or $R_4$ is $R_y$ are useful as prodrugs of the compounds of Formula (I) in which $R_3$ is H or —$CH_3$ and $R_4$ is H.

Various forms of prodrugs are well known in the art and are described in:

a) Wermuth, C. G. et al., *The Practice of Medicinal Chemistry*, Chapter 31, Academic Press (1996);

b) Bundgaard, H. ed., *Design of Prodrugs*, Elsevier (1985);

c) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to a NOTCH receptor, or effective to treat or prevent proliferative diseases such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or salts thereof can be administered by any means suitable for the condition to be treated, which can depend on the need for site-specific treatment or quantity of Formula (I) compound to be delivered.

Also embraced within this invention is a class of pharmaceutical compositions comprising the compound of Formula (I) and/or salt thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 1 to 2000 mg, preferably from about 1 to 500 mg, and more preferably from about 5 to 150 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., CAPTISOL®), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR® surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of Formula (I) are useful for the treatment of cancer, for example, cancers dependent upon Notch activation. Notch activation has been implicated in the pathogenesis of various solid tumors including ovarian, pancreatic, as well as breast cancer and hematologic tumors such as leukemias, lymphomas, and multiple myeloma.

In one embodiment, a method is provided for treating cancer comprising administering to a mammal in need thereof a compound of Formula (I) and/or a salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. For example, the method of this embodiment is used to treat breast cancer, colon cancer, or pancreatic cancer. Preferably, the mammal is a human. For example, a therapeutically effective amount for treating cancer may be administered in the method of the present embodiment. The method of this embodiment includes the administration of the compound having the structure:

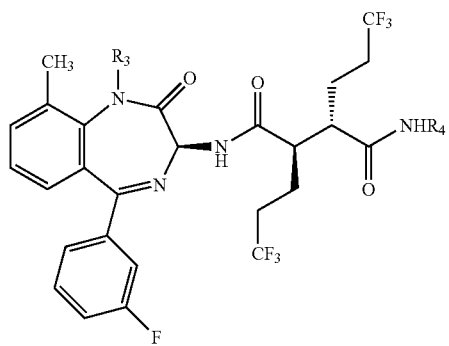

and/or at least one salt thereof. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is colorectal cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is triple negative breast cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer has a translocation of at least one of the Notch receptors. For example, human triple negative breast carcinoma HCC-1599 has a Notch 1 translocation.

In one embodiment, a method is provided for treating cancer comprising administering to a mammal in need thereof at least one compound of Formula (I) and/or at least one salt thereof, wherein said cancer is non-small cell lung cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is pancreatic cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is ovarian cancer. Preferably, the mammal is a human. For example, a therapeutically effective amount for treating cancer may be administered in the method of the present embodiment. Routes of administration in the present embodiment include parenteral administration and oral administration.

In one embodiment, a method is provided for treating cancer comprising administering to a mammal in need thereof at least one compound of Formula (I) and/or at least one salt thereof, wherein said cancer is melanoma. Preferably, the mammal is a human. For example, a therapeutically effective amount for treating cancer may be administered in the method of the present embodiment. Routes of administration in the present embodiment include parenteral administration and oral administration.

In one embodiment, the use of at least one compound of Formula (I) and/or at least one salt thereof, in the manufacture of a medicament for the treatment of cancer is provided. Preferably, in the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Suitable medicaments of the present embodiment include medicaments for parenteral administration, such as, for example, solutions and suspensions and medicaments for oral administration, such as, for example, tablets, capsules, solutions, and suspensions.

One embodiment provides at least one compound of Formula (I) and/or at least one salt thereof, for use in therapy in treating cancer. In the present embodiment, cancers subject to treatment include one or more of bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma.

In one embodiment, a method is provided for treating cancer in a mammal wherein the cancer is dependent upon Notch activation, comprising administering to the patient at least one compound of Formula (I) and/or at least one salt thereof. The method of this embodiment can be used to treat a variety of cancers, including, but not limited to, bladder cancer, breast cancer, colorectal cancer, gastric cancer, head and neck cancer, kidney cancer, liver cancer, lung cancer including non-small cell lung cancer (NSCLC), ovarian cancer, pancreatic cancer, gall bladder cancer, prostate cancer, thyroid cancer, osteosarcoma, rhabdomyosarcoma, malignant fibrous histiocytoma (MFH), fibrosarcoma, glioblastomas/astrocytomas, neuroblastoma, melanoma, T-cell acute lymphoblastic leukemia (T-ALL), and mesothelioma. Preferably, the method of this embodiment is used to treat breast cancer, colon cancer, or pancreatic cancer. Preferably, the mammal is a human. For example, a therapeutically effective amount for treating cancer may be administered in the method of the present embodiment. Suitable routes of administration include parenteral administration and oral administration.

In treating cancer, a combination of chemotherapeutic agents and/or other treatments (e.g., radiation therapy) is often advantageous. The second (or third) agent may have the same or different mechanism of action than the primary therapeutic agent. For example, drug combinations may be employed wherein the two or more drugs being administered act in different manners or in different phases of the cell cycle, and/or where the two or more drugs have nonoverlapping toxicities or side effects, and/or where the drugs being combined each has a demonstrated efficacy in treating the particular disease state manifested by the patient.

In one embodiment, a method is provided for treating cancer comprising administering to a mammal in need thereof at least one compound of Formula (I) and/or at least one salt thereof; and administering one or more additional anti-cancer agents.

The phrase "additional anti-cancer agent" refers to a drug selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MET inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

Accordingly, the compounds of the present invention may be administered in combination with other anti-cancer treatments useful in the treatment of cancer or other proliferative diseases. The invention herein further comprises use of at least one compound of Formula (I) and/or at least one salt thereof in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of at least one compound of Formula (I) and/or at least one salt thereof; and at least one additional agent in kit form, e.g., where they are packaged together or placed in separate packages to be sold together as a kit, or where they are packaged to be formulated together.

In one embodiment, a method is provided for treating cancer comprising administering to a mammal in need thereof at least one compound of Formula (I) and/or at least one salt thereof; administering dasatinib; and optionally, one or more additional anti-cancer agents.

In one embodiment, a method is provided for treating cancer comprising administering to a mammal in need thereof at least one compound of Formula (I) and/or at least one salt thereof; administering paclitaxel; and optionally, one or more additional anti-cancer agents.

In one embodiment, a method is provided for treating cancer comprising administering to a mammal in need thereof at least one compound of Formula (I) and/or at least one salt thereof; administering tamoxifen; and optionally, one or more additional anti-cancer agents.

In one embodiment, a method is provided for treating cancer comprising administering to a mammal in need thereof at least one compound of Formula (I) and/or at least one salt thereof; administering a glucocorticoid; and optionally, one or more additional anti-cancer agents. An example of a suitable glucocorticoid is dexamethasone.

In one embodiment, a method is provided for treating cancer comprising administering to a mammal in need thereof at least one compound of Formula (I) and/or at least one salt thereof; administering carboplatin; and optionally, one or more additional anti-cancer agents.

The compounds of the present invention can be formulated or co-administered with other therapeutic agents that are selected for their particular usefulness in addressing side effects associated with the aforementioned conditions. For example, compounds of the invention may be formulated with agents to prevent nausea, hypersensitivity and gastric irritation, such as antiemetics, and $H_1$ and $H_2$ antihistaminics.

In one embodiment, pharmaceutical compositions are provided comprising at least one compound of Formula (I) and/or at least one salt thereof; one or more additional agents selected from a kinase inhibitory agent (small molecule, polypeptide, and antibody), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds.

The specific dose level and frequency of dosage for any particular subject however, may be varied and generally depends on a variety of factors, including, but not limited to, for example, the bioavailability of the specific compound of Formula (I) in the administered form, metabolic stability and length of action of the specific compound of Formula (I), species, body weight, general health, sex, diet of subject, mode and time of administration, rate of excretion, drug combination, and severity of the particular condition. For example, a daily dose of about 0.001 to 100 mg/kg body weight, preferably between about 0.005 and about 50 mg/kg body weight and most preferably between about 0.01 to 10 mg/kg body weight, may be appropriate. The daily dose can be administered in one to four doses per day.

The administration can be continuous, i.e., every day, or intermittently. The terms "intermittent" or "intermittently" as used herein mean stopping and starting at either regular or irregular intervals. For example, intermittent administration includes administration one to six days per week; administration in cycles (e.g., daily administration for two to eight consecutive weeks followed by a rest period with no administration for up to one week); or administration on alternate days.

In one embodiment, the at least one compound of Formula (I) and/or at least one salt thereof is administered continuously to a patient in need thereof, one or more times daily. For example, a therapeutically effective amount of the compound of Formula (I) is administered to a patient in need thereof, one or more times daily for continuous days.

In one embodiment, at least one compound of Formula (I) and/or at least one salt thereof is administered intermittently to a patient in need thereof, one or more times daily. For example, a therapeutically effective amount of the compound of Formula (I) is administered to a patient in need thereof, one or more times daily according to an intermittent schedule.

In one embodiment, at least one compound of Formula (I) and/or at least one salt thereof is administered to a patient in need thereof, one or more times daily for continuous days followed by one or more days without administration. Preferably, a therapeutically effective amount of the compound of Formula (I) is administered. Examples of continuous dosing with a drug holiday are cycles of: 7 days on treatment followed by 7 days off treatment; 14 days on treatment followed by 7 days off treatment; and 7 days on treatment followed by 14 days off treatment. A cycle of on treatment/off treatment can be repeated multiple times as required to treat a patient.

In one embodiment, at least one compound of Formula (I) and/or at least one salt thereof is administered to a patient in need thereof, according to an intermittent dosing schedule. Intermittent dosing schedules are repeating schedules including days in which the patient is administered the compound of Formula (I) and days in which the patient is not administered the compound of Formula (I). Examples of intermittent dosing schedules are: dosing four days each week for three continuous weeks followed by a week without dosing, and repeating on a four week interval; dosing five days each week for two continuous weeks followed by a week without dosing, and repeating on a three week interval; and dosing four days each week for one week followed by two weeks without dosing, and repeating on a three week interval. Preferably, a therapeutically effective amount of the compound of Formula (I) is administered.

In one embodiment, at least one compound of Formula (I) and/or at least one salt thereof is administered on one day, followed by 6 days of rest, and repeated on a weekly schedule.

In one embodiment, at least one compound of Formula (I) and/or at least one salt thereof is administered on one day, followed by 6 days of rest, and repeated on a weekly schedule for 1 to 4 weeks, and then followed by one week or rest. For example, the compound of Formula (I) is administered on one day, followed by 6 days of rest for three weeks, and then followed by one week of rest. This four week cycle can be repeated one or more times.

In one embodiment, at least one compound of Formula (I) and/or at least one salt thereof is administered on two consecutive days, followed by 5 days of rest, and repeated on a weekly schedule.

In one embodiment, at least one compound of Formula (I) and/or at least one salt thereof is administered on three consecutive days followed by four days of rest, and repeated on a weekly schedule.

In one embodiment, at least one compound of Formula (I) and/or at least one salt thereof is administered on one day, followed by 10 to 13 days of rest.

In one embodiment, at least one compound of Formula (I) and/or at least one salt thereof is administered once each day (QD). This embodiment include once daily oral administration.

In one embodiment, at least one compound of Formula (I) and/or at least one salt thereof is administered twice each day (BID). This embodiment include twice daily oral administration.

In one embodiment, at least one compound of Formula (I) and/or at least one salt thereof is administered on alternate days: one day on followed by one day of rest. This two day cycle can be repeated one or more times.

METHODS OF PREPARATION

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes 1 to 7.

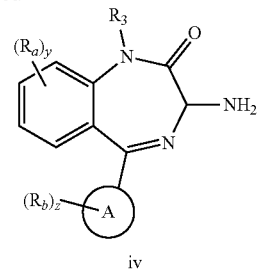

The preparation of benzodiazepinone (iv) may be accomplished in multitude of methods known to one skilled in the art. For example, as shown in Scheme 1, an appropriately substituted 2-aminobenzophenone (i) (for example, from Walsh, D. A., *Synthesis*, 677 (1980); and references cited therein, or other methods known to one skilled in the art) may be coupled to the protected glycine derivative (ii) (PG=protecting group, for example PG=CBz, see Katritzky, A. R. et al., *Org. Chem.*, 55:2206-2214 (1990)), treated with a reagent such as ammonia and subjected to cyclization to afford the benzodiazepinone (iii), according to the procedure outlined in the literature (for example Sherrill, R. G. et al., *J. Org. Chem.*, 60:730 (1995); or other routes known to one skilled in the art). The resulting racemic mixture may be separated (using procedures known to one skilled in the art) to afford the individual enantiomers, or used as a racemate. Also, if $R_3$ is H, (iii) may be, for example, treated with a reagent such as MeI and a base such as $K_2CO_3$ in a solvent such as DMF to prepare $R_3$ is methyl.

Step 2: The deprotection of (iii) may be accomplished in several ways known to one skilled in the art. For example, with PG=CBz, Compound (iii) may be treated with a reagent such as HBr in a solvent such as AcOH. Compound (iv) may be used as a racemate. Alternatively, compound (iv) may be subjected to enantiomeric resolution using standard methods (e.g., chiral preparative chromatography).

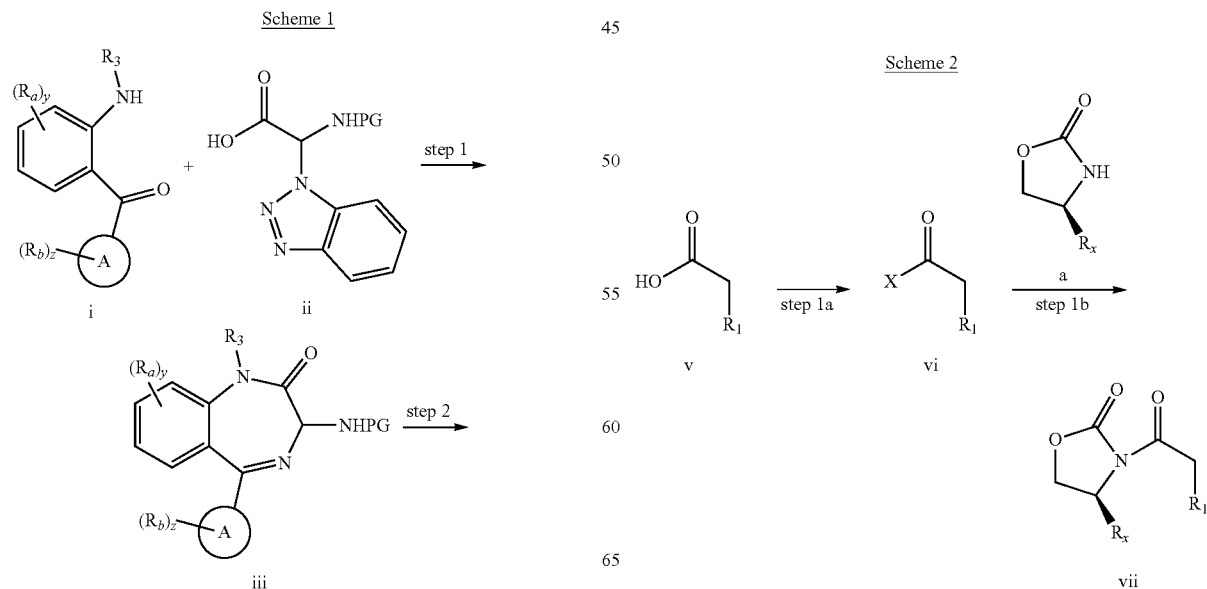

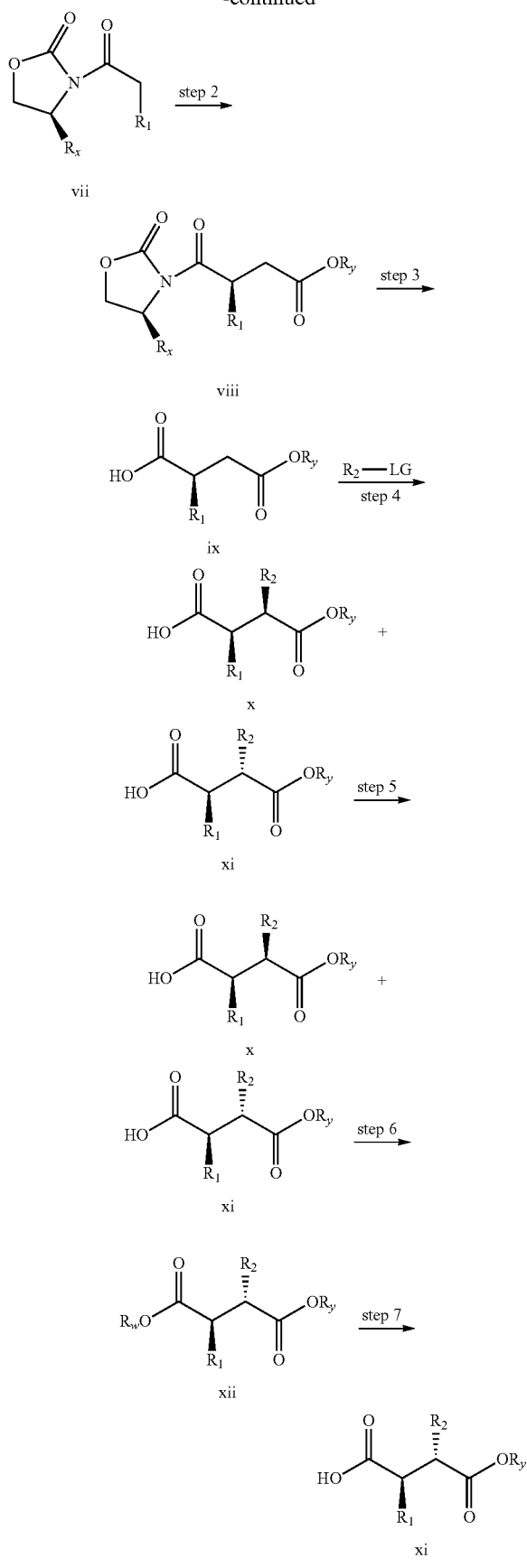

Compound (xii) in Scheme 2 may be prepared by a synthetic sequence outlined in Scheme 2.

Step 1: Acid (v) can be converted to compound (vii) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem Soc.*, 112:4011 (1990)).

Step 2: The second step of Scheme 2 is accomplished by treating compound (vii) with a base such as sodium bis(trimethylsilyl)-amide or lithium diisopropyl amide in a solvent such as THF at low temperature such as −78° C. under an inert atmosphere. The resulting enolate of (vii) is treated with a reagent such as tert-butyl bromoacetate to provide compound (viii, $R_y$=t-Butyl).

Step 3: Conversion of compound (viii) to (ix) may be accomplished by treating compound (viii) with hydrogen peroxide and lithium hydroxide at an appropriate temperature using a mixture of solvents such as THF/water.

Step 4: Compound (ix) may be converted to a mixture of compound (x) and compound (xi) by generating the enolate of (ix) with a base such as LDA in a solvent such as THF at low temperature such as −78° C. under an inert atmosphere and further treatment with a reagent ($R_2$-LG) bearing an appropriate leaving group (e.g., LG=triflate). The resulting mixture of diastereomers (x/xi) may then be utilized in subsequent synthetic steps.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound (x/xi) may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent step.

Step 7: The last step of Scheme 2 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized.

Alternatively, compound (xi) may be prepared according to the sequence of steps found in Scheme 3.

Scheme 3

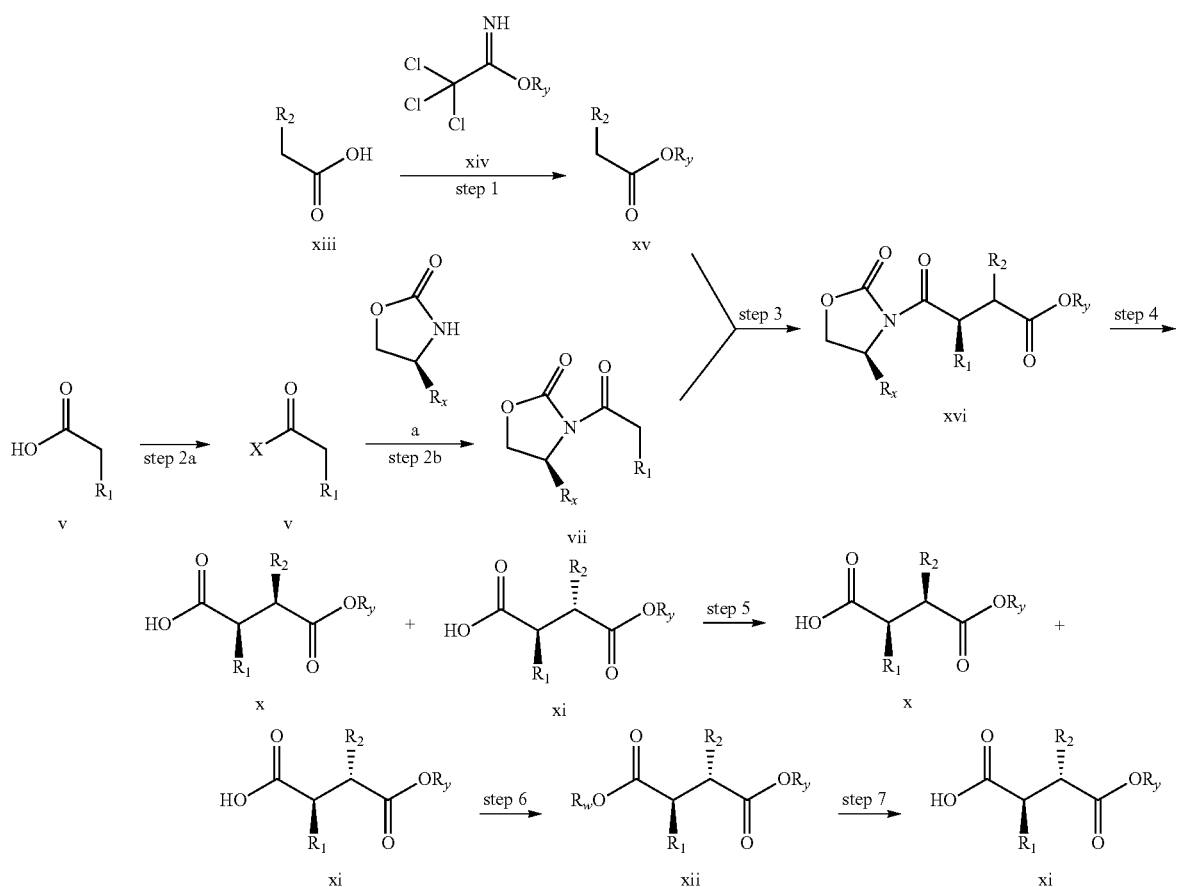

Step 1: The first step of Scheme 3 is accomplished by converting compound (xiii) to an ester (xv), employing one of the multiple ways known to one skilled in the art, such as treatment with a substituted acetimidate such as compound (xiv) in the presence of a reagent such as boron trifluoride etherate at an appropriate temperature in a solvent such as THF.

Step 2: Acid (v) can be converted to compound (vi) in multiple ways known to one skilled in the art. For example, treatment of acid (v) with a reagent such as oxalyl chloride in a solvent such as DCM gives the acid chloride (vi). Compound (vi) can be treated with an oxazolidinone (a) under standard conditions to give compound (vii) (Evans, D. A. et al., *J. Am. Chem Soc.*, 112:4011 (1990)).

Step 3: Compound (vii) can be converted to a mixture of diastereomers (xvi) in multiple ways (Baran, P. et al., *J. Am. Chem. Soc.*, 130(34):11546 (2008)). For example, compound (xv) is treated with a base such as LDA in a solvent such as toluene, at low temperature such as −78° C. under an inert atmosphere such as $N_2$. The resulting mixture is added to a solution of compound (vii) treated with lithium chloride and a base such as LDA in a solvent such as toluene under an inert atmosphere such as $N_2$. To the resulting mixture of the enolates of compounds (xv) and (vii) is added bis(2-ethylhexanoyloxy) copper at a low temperature such as −78° C. under an inert atmosphere such as $N_2$ and warmed to room temperature to provide compound (xvi).

Step 4: Conversion of compound (xvi) to a mixture of compound (x) and compound (xi) may be accomplished by treating it with hydrogen peroxide and lithium hydroxide at an appropriate temperature using a mixture of solvents such as THF/water. The resulting mixture of diastereomers may then be utilized in subsequent synthetic steps. If necessary, the resulting mixture of diastereomers may be separated at this point via silica gel chromatography or preparative HPLC.

Step 5: Alternately, the mixture (x/xi) may be subjected to epimerization conditions, for example by treatment with LDA and diethylaluminum chloride followed by quenching with methanol or acetic acid to enrich the desired diastereomer. The resulting diastereomerically enriched mixture of compound may then be utilized in subsequent synthetic steps or the mixture of diastereoisomers may be separated if desired, employing suitable conditions such as preparative HPLC, preparative chiral HPLC or silica gel chromatography, and the resulting pure desired diastereoisomer (xi) used in the subsequent steps.

Step 6: Alternatively, the mixture of diastereomeric acids (x) and (xi) may be protected by treatment with, for example, benzyl bromide in the presence of a base such as $K_2CO_3$ in a solvent such as DMF. The resulting mixture of diastereoisomers may be separated if desired, employing suitable conditions such as preparative HPLC, preparative chiral HPLC or silica gel chromatography, and the resulting pure desired diastereoisomer compound (xii) used in the subsequent steps.

Step 7: The last step of Scheme 3 is a deprotection step and may be accomplished in several ways known to one skilled in the art. For example, for $R_w$=benzyl in compound (xii), treatment under hydrogenation conditions using a catalyst such as palladium on carbon in a solvent such as MeOH under a hydrogen atmosphere may provide compound (xi) that may subsequently be utilized, for example, in step 1 of Scheme 4.

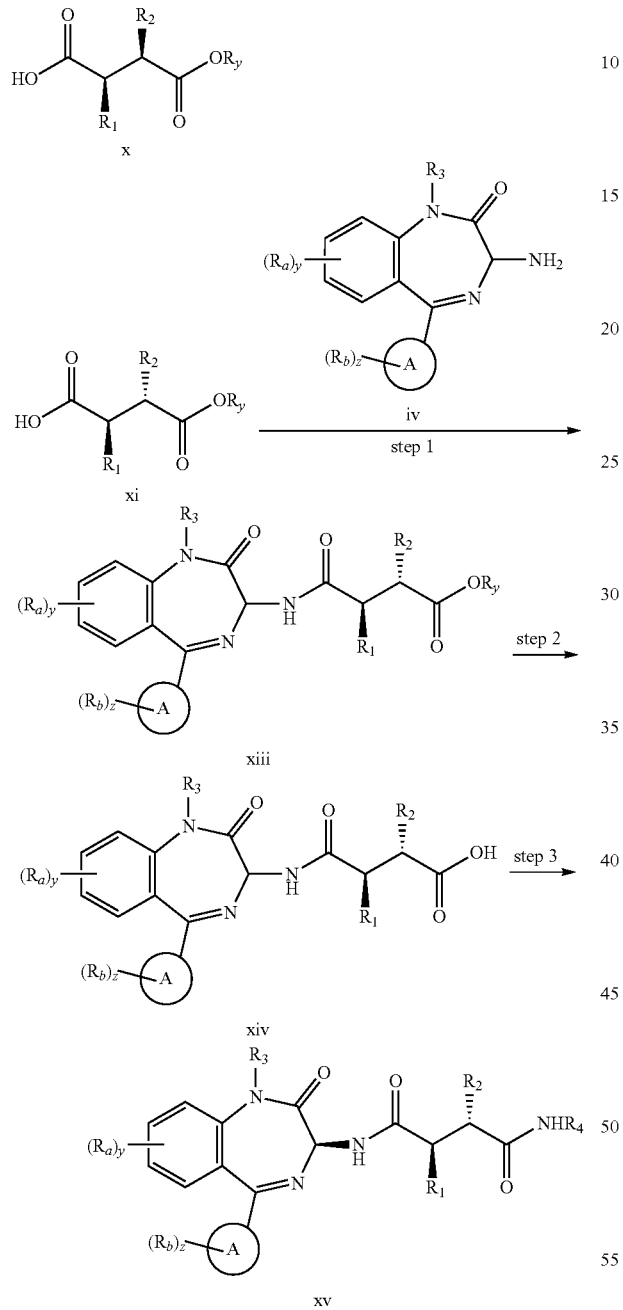

be purified using an appropriate separation technique, such as chiral preparative chromatography to provide the diastereomerically pure compounds.

Step 2: Treatment of compound (xiii) with an acid such as TFA at an appropriate temperature such as 0° C., in a solvent such as DCM provides compound (xiv) as either a diastereomerically pure compound or as a mixture of diastereoisomers. This mixture may be used as such in the subsequent step, or if desired, may be purified using an appropriate separation technique, such as chiral preparative chromatography to provide the diastereomerically pure compounds.

Step 3: Conversion of compound (xiv) to compound (xv, $R_4$=H) may be accomplished via coupling of compound (xiv) with an appropriate amine source such as ammonium chloride or ammonia, a carbodiimide such as EDC, HOBT and a base such as TEA in a solvent such as DMF. If necessary the diastereomeric mixture can be separated using an appropriate separation technique, such as chiral preparative chromatography.

Additional compounds of the current invention may be prepared from compound xv ($R_4$=H), according to Scheme 5.

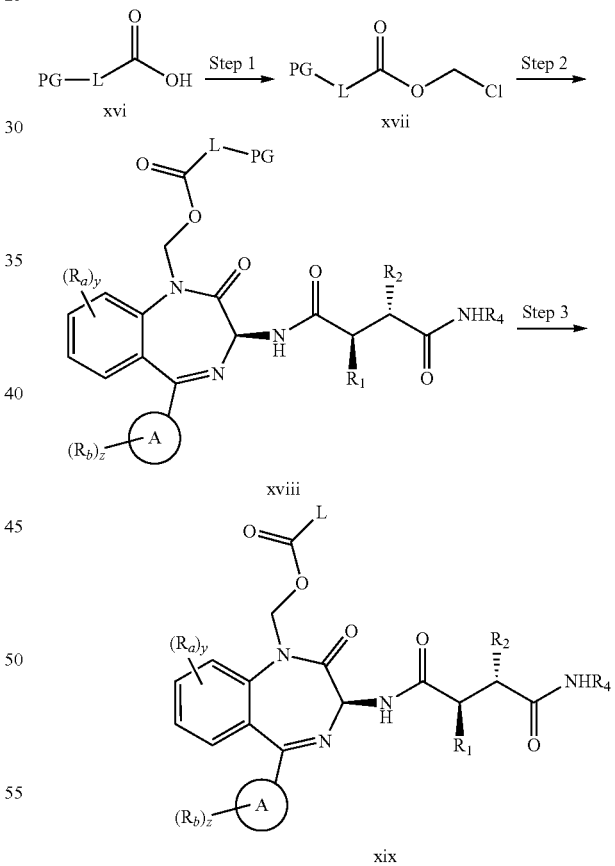

Step 1: Compounds of structure (iv) may be coupled to either pure diastereomer compound (xi) or a diastereomeric mixture of compounds (x/xi) in the presence of a coupling reagent such as TBTU and a base such as TEA, in a solvent such as DMF to provide compound (xiii) as either a diastereomerically pure compound or as a mixture of diastereoisomers, as appropriate, depending on the enantiomeric and/or diastereomeric purity of the coupling partners. This mixture may be used as such in the subsequent step, or if desired, may Step 1: An appropriately functionalized carboxylic acid (PG-L-CO$_2$H) or carboxylate salt (xvi) may be treated with an alkylating agent, such as chloromethyl chlorosulfate, in the presence of a base, such as Na$_2$CO$_3$, and a quaternary ammonium salt, such as tetrabutyl ammonium sulfate in a biphasic mixture of water and an appropriate organic solvent, such as DCM at low temperature, such as 0° C., to afford compound xvii.

Step 2: Treatment of compound xv with compound xvii in an appropriate solvent, such as DCM, in the presence of a base, such as K$_2$CO$_3$ affords compound xviii.

Step 3: The deprotection of compound xviii may be accomplished in several ways known to one skilled in the art. For example, where PG=tBu or Boc, compound xviii may be treated with a reagent such as trifluoroacetic acid in a solvent such as DCM to afford compound xix (—CH$_2$OC(O)L=R$_x$).

Alternatively, compounds xix may be prepared as described in Scheme 6.

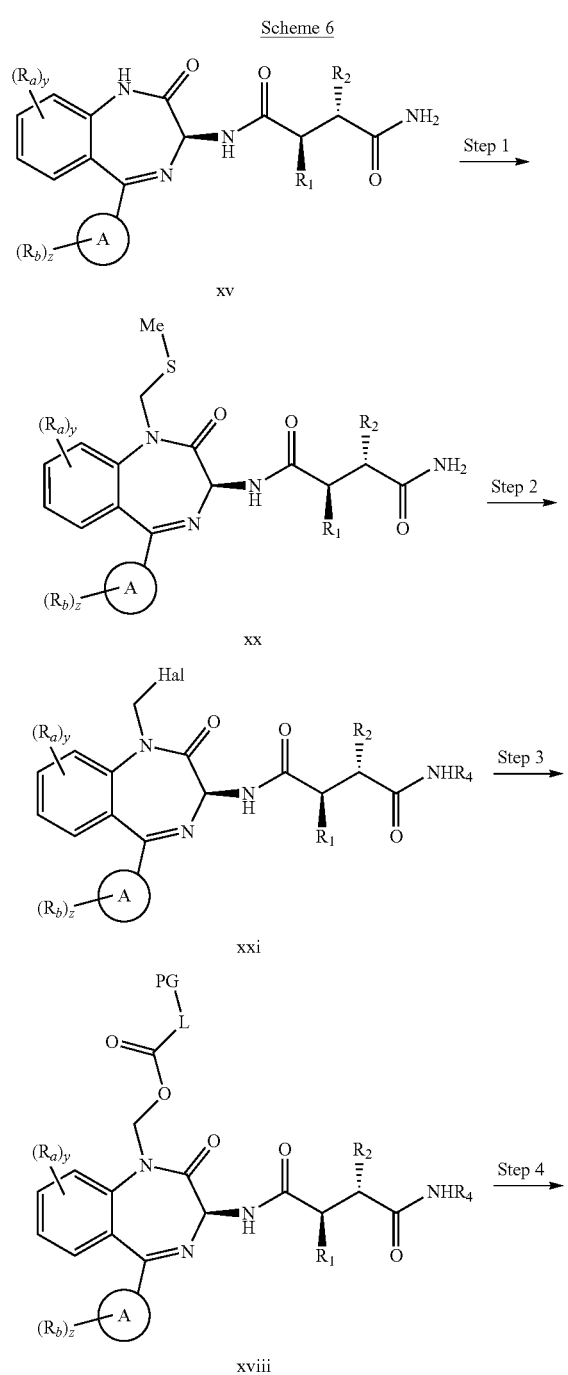

Scheme 6

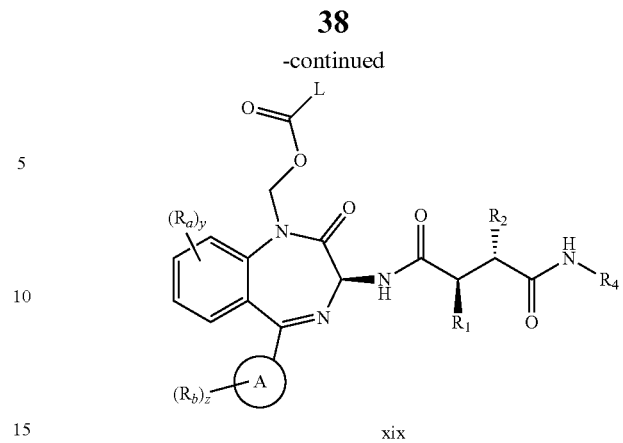

xix

Step 1: Various methods known in the art may be employed to prepare compounds xix. For example, as shown in Scheme 6, an appropriately substituted benzodiazepine (xv) may be treated with a haloalkyl thioether such as (chloromethyl)(methyl)sulfane in the presence of a base, such as cesium carbonate in an appropriate solvent such as N,N-dimethylformamide (DMF) to afford compounds of formula xx.

Step 2: Treatment of compound xx with a reagent such as sulfuryl chloride in the presence of an amine salt, such as triethylammonium chloride in an aprotic solvent such as dichloromethane (DCM) may be used to effect the transformation to compounds of formula xxi (Hal=chlorine).

Step 3: Compounds of formula xviii may then be prepared from compound xxi by treatment with an appropriately substituted carboxylic acid or carboxylate salt in the presence of a base (when starting from a carboxylic acid) such as potassium carbonate in an aprotic solvent such as acetonitrile or DMF.

Step 4: The deprotection of compound iv may be accomplished in several ways known to one skilled in the art. For example, where PG=tBu or Boc, compound xviii may be treated with a reagent such as trifluoroacetic acid in a solvent such as DCM to afford compound xix (—CH$_2$OC(O)L=R$_x$).

The preparation of sulfenamide-based prodrugs of the parent compound xv is shown in Scheme 7.

Scheme 7

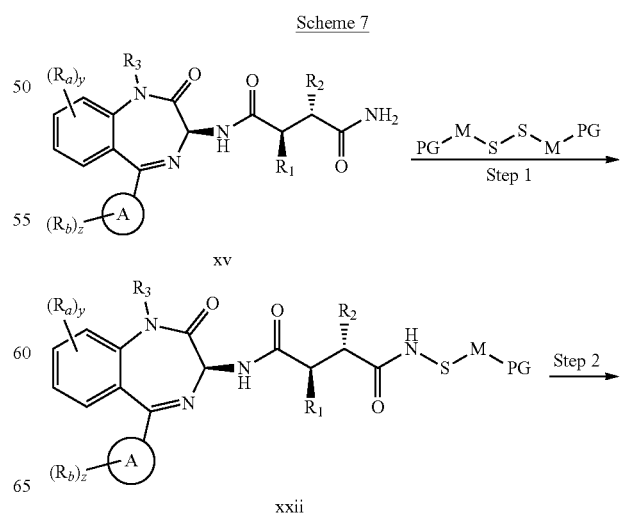

xxii

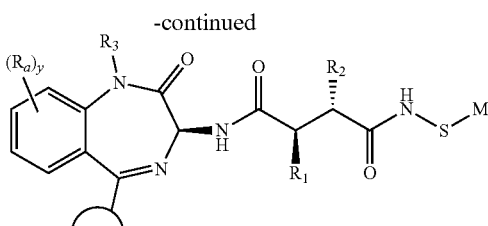

xxiii

Step 1: A mixture of a silver salt, such as silver nitrate, and a disulfide, such as tert-butyl 2,2'-disulfanediylbis(ethane-2,1-diyl)dicarbamate in an alcoholic solvent, such as MeOH may be treated with compound i in the presence of a base, such as triethylamine, to afford compound xxii.

Step 2: The deprotection of compound xxii may be accomplished in several ways known to one skilled in the art. For example, where PG=tBu or Boc, compound xxii may be treated with a reagent such as trifluoroacetic acid in a solvent such as DCM to afford compound xxiii (—S-M=R$_y$).

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

ABBREVIATIONS

ACN acetonitrile
AcOH acetic acid
AlMe$_3$ trimethyl aluminum
aq aqueous
Bn benzyl
Boc tert-butoxycarbonyl
Boc$_2$O di-tert-butyl dicarbonate
CBz benzyloxycarbonyl
DCC 1,3-dicyclohexylcarbodiimide
DCM dichloromethane
DIEA diisopropylethylamine
DMAP dimethylaminopyridine
DME 1,2-dimethoxyethane
DMF dimethylformamide
DMSO dimethyl sulfoxide
Pd(dppf)$_2$Cl$_2$ [1,1'-bis(diphenylphosphino)ferrocene]dichloropalladium(II)
EDC 1-(3-dimethylaminopropyl)-3-ethylcarbodiimide hydrochloride
Et$_2$AlCl diethyl aluminum chloride
Et$_3$N triethyl amine
Et$_2$O diethyl ether
EtOH ethanol
EtOAc ethyl acetate
equiv. equivalence(s)
g gram(s)
h or hr hour(s)
HOBt hydroxybenzotriazole
HPLC high pressure liquid chromatography
iPrOH isopropyl alcohol
KOtBu potassium tert-butoxide
LCMS Liquid Chromatography-Mass Spectroscopy
LDA lithium diisopropylamide
LiHMDS lithium bis(trimethylsilyl)amide
Me methyl
MeI methyl iodide
MeOH methanol
min minute(s)
mL milliliter(s)
mmol millimolar
MTBE methyl t-butyl ether
NaHMDS sodium bis(trimethylsilyl)amide
n-BuLi n-butyl lithium
NH$_4$OAc ammonium acetate
NMP N-methylpyrrolidinone
Pd(OAc)$_2$ palladium acetate
RT or Rt retention time
sat saturated
t-Bu tertiary butyl
t-BuLi t-butyl lithium
tBuOH tertiary butyl alcohol
tBuOMe tert-butyl methyl ether
TBTU O-(1H-benzotriazol-1-yl)-N,N,N',N'-tetramethyluronium tetrafluoroborate
TEA triethylamine
TFA trifluoroacetic acid
Tf$_2$O trifluoromethylsulfonic anhydride
THF tetrahydrofuran Intermediate S-1: (2R,3S)-3-(tert-Butoxycarbonyl)-6,6,6-trifluoro-2-(3,3,3-trifluoropropyl)hexanoic acid

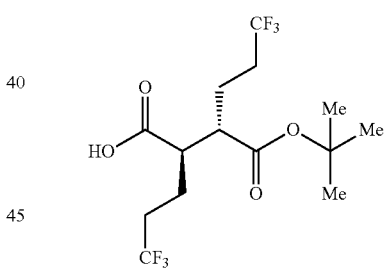

(S-1)

Intermediate S-1A: 3,3,3-Trifluoropropyl trifluoromethanesulfonate

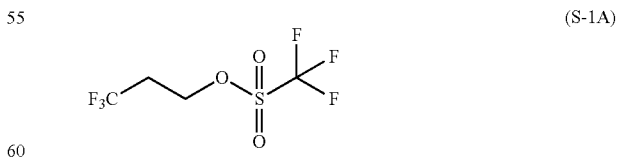

(S-1A)

To a cold (−25° C.) stirred solution of 2,6-lutidine (18.38 mL, 158 mmol) in DCM (120 mL) was added Tf$_2$O (24.88 mL, 147 mmol) over 3 min, and the mixture was stirred for 5 min. To the reaction mixture was added 3,3,3-trifluoropropan-1-ol (12 g, 105 mmol) over an interval of 3 min. After 2 hr, the reaction mixture was warmed to room temperature and stirred for 1 hr. The reaction mixture was concentrated to half its volume, then purified by loading directly on a silica gel column (330 g ISCO) and the product was eluted with DCM to afford Intermediate S-1A (13.74 g, 53%) as a colorless oil. ¹H NMR (400 MHz, CDCl₃) δ ppm 4.71 (2H, t, J=6.15 Hz), 2.49-2.86 (2H, m).

Intermediate S-1B: (4S)-4-Benzyl-3-(5,5,5-trifluoropentanoyl)-1,3-oxazolidin-2-one

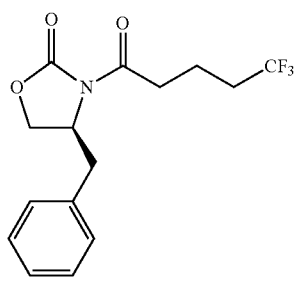

(S-1B)

To a stirring solution of 5,5,5-trifluoropentanoic acid (14.76 g, 95 mmol) and DMF (0.146 mL) in DCM (50 mL) was slowly added oxalyl chloride (8.27 mL, 95 mmol). After 2 h, the mixture was concentrated to dryness. A separate flask was changed with (S)-4-benzyloxazolidin-2-one (16.75 g, 95 mmol) in THF (100 mL) and then cooled to −78° C. To the solution was slowly added n-BuLi (2.5M, 37.8 mL, 95 mmol) over 10 min, stirred for 10 min, and then a solution of the above acid chloride in THF (50 mL) was slowly added over 5 min. The mixture was stirred for 30 min, and then warmed to room temperature. The reaction was quenched with sat aq NH₄Cl. Next, 10% aq LiCl was then added to the mixture, and the mixture was extracted with Et₂O. The organic layer was washed with sat aq NaHCO₃ then with brine, dried (MgSO₄), filtered and concentrated to dryness. The residue was purified by SiO₂ chromatography (ISCO, 330 g column, eluting with a gradient from 100% hexane to 100% EtOAc) to afford the product Intermediate S-1B; (25.25 g, 85%): ¹H NMR (400 MHz, CDCl₃) δ ppm 7.32-7.39 (2H, m), 7.30 (1H, d, J=7.05 Hz), 7.18-7.25 (2H, m), 4.64-4.74 (1H, m), 4.17-4.27 (2H, m), 3.31 (1H, dd, J=13.35, 3.27 Hz), 3.00-3.11 (2H, m), 2.79 (1H, dd, J=13.35, 9.57 Hz), 2.16-2.28 (2H, m), 1.93-2.04 (2H, m).

Intermediate S-1C: tert-Butyl(3R)-3-(((4S)-4-benzyl-2-oxo-1,3-oxazolidin-3-yl)carbonyl)-6,6,6-trifluorohexanoate

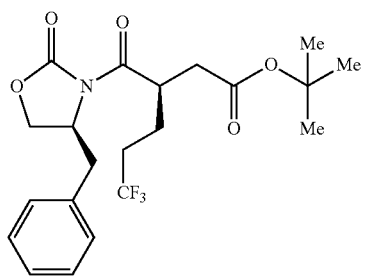

(S-1C)

To a cold (−78° C.), stirred solution of Intermediate S-1B (3.03 g, 9.61 mmol) in THF (20 mL) was added NaHMDS (1.0M in THF) (10.6 mL, 10.60 mmol) under a nitrogen atmosphere. After 2 hours, tert-butyl 2-bromoacetate (5.62 g, 28.8 mmol) was added neat via syringe at −78° C. and stirring was maintained at the same temperature. After 6 hours, the reaction mixture was warmed to room temperature. The reaction mixture was partitioned between saturated NH₄Cl and EtOAc. The organic phase was separated, and the aqueous phase was extracted with EtOAc (3×). The combined organics were washed with brine, dried (Na₂SO₄), filtered and concentrated under reduced pressure. The residue was purified by flash chromatography (Teledyne ISCO CombiFlash Rf, 5% to 100% solvent A/B=hexanes/EtOAc, REDISEP® SiO₂ 120 g). Concentration of the appropriate fractions provided Intermediate S-1C (2.79 g, 67.6%) as a colorless viscous oil: ¹H NMR (400 MHz, CDCl₃) δ ppm 7.34 (2H, d, J=7.30 Hz), 7.24-7.32 (3H, m), 4.62-4.75 (1H, m, J=10.17, 6.89, 3.43, 3.43 Hz), 4.15-4.25 (3H, m), 3.35 (1H, dd, J=13.60, 3.27 Hz), 2.84 (1H, dd, J=16.62, 9.57 Hz), 2.75 (1H, dd, J=13.35, 10.07 Hz), 2.47 (1H, dd, J=16.62, 4.78 Hz), 2.11-2.23 (2H, m), 1.90-2.02 (1H, m), 1.72-1.84 (1H, m), 1.44 (9H, s).

Intermediate S-1D: (2R)-2-(2-tert-Butoxy-2-oxoethyl)-5,5,5-trifluoropentanoic acid

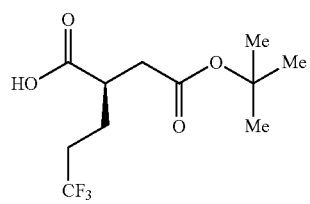

(S-1D)

To a cool (0° C.), stirred solution of Intermediate S-1C (2.17 g, 5.05 mmol) in THF (50 mL) and water (15 mL) was added a solution of LiOH (0.242 g, 10.11 mmol) and H₂O₂ (2.065 mL, 20.21 mmol) in H₂O (2 mL). After 10 min, the reaction mixture was removed from the ice bath, stirred for 1 h, and then cooled to 0° C. Saturated aqueous NaHCO₃ (25 mL) and saturated aqueous Na₂SO₃ (25 mL) were added to the reaction mixture, and the mixture was stirred for 10 min, and then partially concentrated. The resulting mixture was extracted with DCM (2×), cooled with ice and made acidic with conc. HCl to pH 3. The mixture was saturated with solid NaCl, extracted with EtOAc (3×), and then dried over MgSO₄, filtered and concentrated to a colorless oil to afford Intermediate S-1D, 1.2514 g, 92%): ¹H NMR (400 MHz, CDCl₃) δ ppm 2.83-2.95 (1H, m), 2.62-2.74 (1H, m), 2.45 (1H, dd, J=16.62, 5.79 Hz), 2.15-2.27 (2H, m), 1.88-2.00 (1H, m), 1.75-1.88 (1H, m), 1.45 (9H, s).

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-butoxycarbonyl)-6,6,6-trifluoro-2-(3,3,3-trifluoropropyl)hexanoic acid

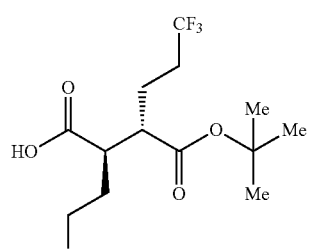

(S-1)

43

-continued

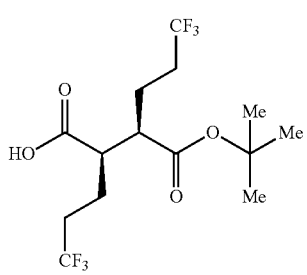

(S-1E)

To a cold (−78° C.) stirred solution of Intermediate S-1D (5 g, 18.50 mmol) in THF (60 mL) was slowly added LDA (22.2 mL, 44.4 mmol, 2.0M) over 7 min. After stirring for 2 hr, Intermediate S-1A (6.38 g, 25.9 mmol) was added to the reaction mixture over 3 min. After 60 min, the reaction mixture was warmed to −25° C. (ice/MeOH/dry ice) and stirred for an additional 60 min at which time sat aq NH$_4$Cl was added. The separated aqueous phase was acidified with 1N HCl to pH 3, and then extracted with Et$_2$O. The combined organic layers were washed with brine (2×), dried over MgSO$_4$, filtered and concentrated to provide a 1:4 (I1:I1E) mixture (as determined by $^1$H NMR) of Intermediate S-1 and Intermediate S-1E (6.00 g, 89%) as a pale yellow solid. $^1$H NMR (500 MHz, CDCl$_3$) δ ppm 2.81 (1H, ddd, J=10.17, 6.32, 3.85 Hz), 2.63-2.76 (1H, m), 2.02-2.33 (4H, m), 1.86-1.99 (2H, m), 1.68-1.85 (2H, m), 1.47 (9H, s).

To a cold (−78° C.), stirred solution of a mixture of Intermediate S-1 and Intermediate S-1E (5.97 g, 16.30 mmol) in THF (91 mL) was added LDA (19 mL, 38.0 mmol, 2.0M in THF/hexane/ethyl benzene) dropwise via syringe over 10 min (internal temperature never exceeded −65° C., J-KEM® probe in reaction solution). The mixture was stirred for 15 min, and then warmed to room temperature (24° C. water bath), stirred for 15 min, and then cooled to −78° C. for 15 min. To the reaction mixture was added Et$_2$AlCl (41 mL, 41.0 mmol, 1M in hexane) via syringe (internal temperature never exceeded −55° C.), and the mixture was stirred for 10 min, and then warmed to room temperature (24° C. bath) for 15 min and then back to −78° C. for 15 min. Meanwhile, a 1000 mL round bottom flask was charged with MeOH (145 mL) and precooled to −78° C. With vigorous stirring the reaction mixture was transferred via cannula over 5 min to the MeOH. The flask was removed from the bath, ice was added followed by the slow addition of 1N HCl (147 mL, 147 mmol). Gas evolution was observed as the HCl was added. The reaction mixture was allowed to warm to room temperature during which the gas evolution subsided. The reaction mixture was diluted with EtOAc (750 mL), saturated with NaCl, and the organic phase was separated, washed with a solution of potassium fluoride (8.52 g, 147 mmol) and 1N HCl (41 mL, 41.0 mmol) in water (291 mL), brine (100 mL), and then dried (Na$_2$SO$_4$), filtered and concentrated under vacuum. $^1$H NMR showed the product was a 9:1 mixture of Intermediate S-1 and Intermediate S-1E. The enriched mixture of Intermediate S-1 and Intermediate S-1E (6.12 g, >99% yield) was obtained as a dark amber solid: $^1$H NMR (400 MHz, CDCl$_3$) δ ppm 2.64-2.76 (2H, m), 2.04-2.35 (4H, m), 1.88-2.00 (2H, m), 1.71-1.83 (2H, m), 1.48 (9H, s).

44

Alternate Procedure to Make Intermediate S-1

Intermediate S-1F: (2R,3S)-1-Benzyl 4-tert-butyl 2,3-bis(3,3,3-trifluoropropyl)succinate

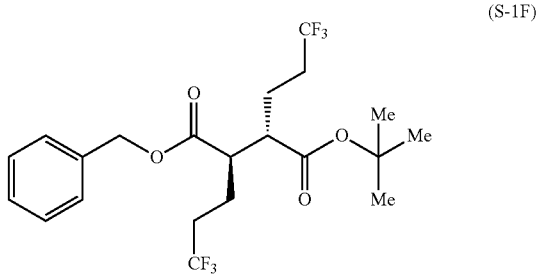 [SMILES: CC(C)(C)OC(=O)[C@@H](CCC(F)(F)F)[C@@H](CCC(F)(F)F)C(=O)OCc1ccccc1]

(S-1F)

To a stirred solution of a 9:1 enriched mixture of Intermediate S-1 and Intermediate S-1E (5.98 g, 16.33 mmol) in DMF (63 mL) were added potassium carbonate (4.06 g, 29.4 mmol) and benzyl bromide (2.9 mL, 24.38 mmol), the mixture was then stirred overnight at room temperature. The reaction mixture was diluted with EtOAc (1000 mL), washed with 10% LiCl (3×200 mL), brine (200 mL), dried (Na$_2$SO$_4$), filtered, concentrated, and then dried under vacuum. The residue was purified by SiO$_2$ chromatography using a toluene:hexane gradient. Diastereomerically purified Intermediate S-1F (4.81 g, 65%) was obtained as a colorless solid: $^1$H NMR (400 MHz, chloroform-d) δ 7.32-7.43 (m, 5H), 5.19 (d, J=12.10 Hz, 1H), 5.15 (d, J=12.10 Hz, 1H), 2.71 (dt, J=3.52, 9.20 Hz, 1H), 2.61 (dt, J=3.63, 9.63 Hz, 1H), 1.96-2.21 (m, 4H), 1.69-1.96 (m, 3H), 1.56-1.67 (m, 1H), 1.45 (s, 9H).

Intermediate S-1: (2R,3S)-3-(tert-Butoxycarbonyl)-6,6,6-trifluoro-2-(3,3,3-trifluoropropyl)hexanoic acid

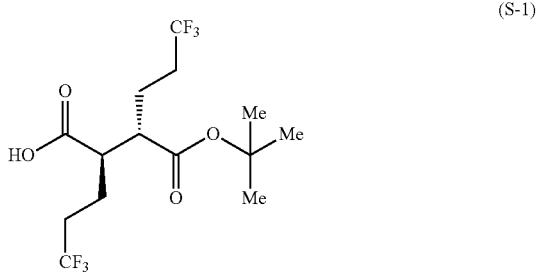 [SMILES: CC(C)(C)OC(=O)[C@@H](CCC(F)(F)F)[C@@H](CCC(F)(F)F)C(=O)O]

(S-1)

To a solution of Intermediate S-1F (4.81 g, 10.54 mmol) in MeOH (100 mL) was added 10% palladium on carbon (wet, Degussa type, 568.0 mg, 0.534 mmol) in a H$_2$-pressure flask. The vessel was purged with N$_2$ (4×), then purged with H$_2$ (2×), and finally, pressurized to 50 psi and shaken overnight. The reaction vessel was depressurized and purged with nitrogen. The mixture was filtered through CELITE®, washed with MeOH and then concentrated and dried under vacuum. Intermediate S-1 (3.81 g, 99% yield)) was obtained as a colorless solid: $^1$H NMR (400 MHz, chloroform-d) δ 2.62-2.79 (m, 2H), 2.02-2.40 (m, 4H), 1.87-2.00 (m, 2H), 1.67-1.84 (m, 2H), 1.48 (s, 9H).

Alternate Procedure to Make Intermediate S-1

Intermediate S-1: (2R,3S)-3-(tert-Butoxycarbonyl)-6,6,6-trifluoro-2-(3,3,3-trifluoropropyl)hexanoic acid

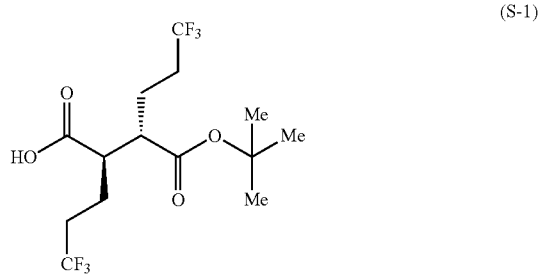 [SMILES: CC(C)(C)OC(=O)[C@@H](CCC(F)(F)F)[C@@H](CCC(F)(F)F)C(=O)O]

Intermediate S-1 as a mixture with Intermediate S-1E was prepared in a similar procedure as above from Intermediate S-1D to afford a 1:2.2 mixture of Intermediate S-1 and Intermediate S-1E (8.60 g, 23.48 mmol), which was enriched using LDA (2.0 M solution in THF, ethyl benzene and heptane, 28.2 mL, 56.4 mmol) and diethyl aluminum chloride (1.0 M solution in hexane, 59 mL, 59.0 mmol) in THF (91 mL). After workup as described above, the resulting residue was found to be a 13.2:1 (by $^1$H NMR) mixture of Intermediate S-1 and Intermediate S-1E, which was treated as follows: The crude material was dissolved in MTBE (43 mL). Hexanes (26 mL) were slowly charged to the reaction mixture while maintaining a temperature below 30° C. The reaction mixture was stirred for 10 min. Next, tert-butylamine (2.7 mL, 1.1 eq) was charged slowly over a period of 20 minutes while maintaining a temperature below 30° C. This addition was observed to be exothermic. The reaction mixture was stirred for 2 hrs below 30° C. and then filtered. The solid material was washed with 5:3 MTBE: hexane (80 mL), and the filtrate was concentrated and set aside. The filtered solid was dissolved in dichloromethane (300 mL), washed with 1N HCl (100 mL), and the organic layer was washed with brine (100 mL×2), and then concentrated under reduced pressure below 45° C. to afford Intermediate S-1 (5.46 g, 64%).

A Second Alternate Procedure for Preparing Intermediate S-1

Intermediate S-1G: tert-Butyl 5,5,5-trifluoropentanoate

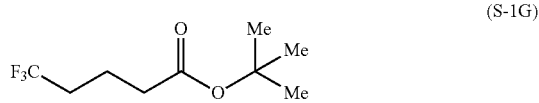 [SMILES: CC(C)(C)OC(=O)CCCC(F)(F)F]

To a stirred solution of 5,5,5-trifluoropentanoic acid (5 g, 32.0 mmol) in THF (30 mL) and hexane (30 mL) at 0° C., was added tert-butyl 2,2,2-trichloroacetimidate (11.46 mL, 64.1 mmol). The mixture was stirred for 15 min at 0° C. Boron trifluoride etherate (0.406 mL, 3.20 mmol) was added and the reaction mixture was allowed to warm to room temperature overnight. To the clear reaction mixture was added solid NaHCO$_3$ (5 g) and stirred for 30 min. The mixture was filtered through MgSO$_4$ and washed with hexanes (200 mL). The solution was allowed to rest for 45 min, and the resulting solid material was removed by filtering on the same MgSO$_4$ filter again, washed with hexanes (100 mL) and concentrated under reduced pressure without heat. The volume was reduced to about 30 mL, filtered through a clean fritted funnel, washed with hexane (5 mL), and then concentrated under reduced pressure without heat. The resulting neat oil was filtered through a 0.45 μm nylon membrane filter disk to provide Intermediate S-1G (6.6 g, 31.4 mmol 98% yield) as a colorless oil: $^1$H NMR (400 MHz, CDCl$_3$) δ ppm 1.38 (s, 9H) 1.74-1.83 (m, 2H) 2.00-2.13 (m, 2H) 2.24 (t, J=7.28 Hz, 2H).

Intermediate S-1H: (4S)-4-(Propan-2-yl)-3-(5,5,5-trifluoropentanoyl)-1,3-oxazolidin-2-one

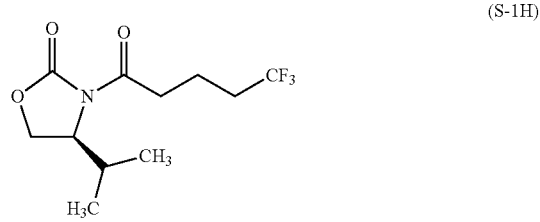 [SMILES: CC(C)[C@H]1COC(=O)N1C(=O)CCCC(F)(F)F]

To a stirred solution of 5,5,5-trifluoropentanoic acid (5.04 g, 32.3 mmol) in DCM (50 mL) and DMF (3 drops) was added oxalyl chloride (3.4 mL, 38.8 mmol) dropwise over 5 min. The solution was stirred until all bubbling subsided. The reaction mixture was concentrated under reduced pressure to give pale yellow oil. To a separate flask charged with a solution of (4S)-4-(propan-2-yl)-1,3-oxazolidin-2-one (4.18 g, 32.4 mmol) in THF (100 mL) at −78° C. was added n-BuLi (2.5M in hexane) (13.0 mL, 32.5 mmol) dropwise via syringe over 5 min. After stirring for 10 min, the above acid chloride, dissolved in THF (20 mL), was added via cannula over 15 min. The reaction mixture was warmed to 0° C., and was allowed to warm to room temperature as the bath warmed and stirred overnight. To the reaction mixture was added saturated NH$_4$Cl, and the mixture was extracted with EtOAc (2×). The combined organics were washed with brine, dried (Na$_2$SO$_4$), filtered and concentrated under reduced pressure. The crude material was purified by flash chromatography (Teledyne ISCO CombiFlash Rf, 5% to 60% solvent A/B=hexanes/EtOAc, REDISEP® SiO$_2$ 120 g). Concentration of the appropriate fractions provided Intermediate S-1H (7.39 g, 86%) as a colorless oil: $^1$H NMR (400 MHz, CDCl$_3$) δ ppm 4.44 (1H, dt, J=8.31, 3.53 Hz), 4.30 (1H, t, J=8.69 Hz), 4.23 (1H, dd, J=9.06, 3.02 Hz), 2.98-3.08 (2H, m), 2.32-2.44 (1H, m, J=13.91, 7.02, 7.02, 4.03 Hz), 2.13-2.25 (2H, m), 1.88-2.00 (2H, m), 0.93 (3H, d, J=7.05 Hz), 0.88 (3H, d, J=6.80 Hz).

Intermediate S-1I: (2S,3R)-tert-Butyl 6,6,6-trifluoro-3-((S)-4-isopropyl-2-oxooxazolidine-3-carbonyl)-2-(3,3,3-trifluoropropyl)hexanoate, and Intermediate S-1J: (2R,3R)-tert-Butyl 6,6,6-trifluoro-3-((S)-4-isopropyl-2-oxooxazolidine-3-carbonyl)-2-(3,3,3-trifluoropropyl)hexanoate

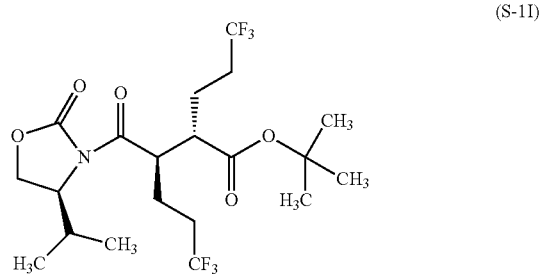

47

-continued

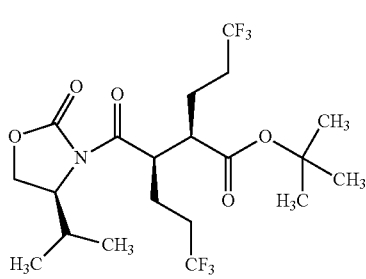

(S-1J)

To a cold (−78° C.), stirred solution of diisopropylamine (5.3 mL, 37.2 mmol) in THF (59 mL) under a nitrogen atmosphere was added n-BuLi (2.5M in hexane) (14.7 mL, 36.8 mmol). The mixture was then warmed to 0° C. to give a 0.5M solution of LDA. A separate vessel was charged with Intermediate S-1H (2.45 g, 9.17 mmol). The material was azeotroped twice with benzene (the RotoVap air inlet was fitted with a nitrogen inlet to completely exclude humidity), and then toluene (15.3 mL) was added. This solution was added to a flask containing dry lithium chloride (1.96 g, 46.2 mmol). To the resultant mixture, cooled to −78° C., was added the LDA solution (21.0 mL, 10.5 mmol) and the mixture was stirred at −78° C. for 10 min, then warmed to 0° C. for 10 min., and then cooled to −78° C. To a separate reaction vessel containing Intermediate S-1G (3.41 g, 16.07 mmol), also azeotroped twice with benzene, was added toluene (15.3 mL), cooled to −78° C. and LDA (37.0 mL, 18.5 mmol) was added. The resulting solution was stirred at −78° C. for 25 min. At this time the enolate derived from the ester was transferred via cannula into the solution of the oxazolidinone enolate and stirred at −78° C. for an additional 5 min, at which time the septum was removed and solid powdered bis(2-ethylhexanoyloxy)copper (9.02 g, 25.8 mmol) was rapidly added to the reaction vessel and the septum was replaced. The vessel was immediately removed from the cold bath and immersed into a warm water bath (40° C.) with rapid swirling and with a concomitant color change from the initial turquoise to brown. The reaction mixture was stirred for 20 min, was then poured into 5% aqueous NH$_4$OH (360 mL) and extracted with EtOAc (2×). The combined organics were washed with brine, dried (Na$_2$SO$_4$), filtered and concentrated under reduced pressure. The residue was purified by flash chromatography (Teledyne ISCO CombiFlash Rf, 0% to 60% solvent A/B=hexanes/EtOAc, REDISEP® SiO$_2$ 120 g). Concentration of the appropriate fractions provided a mixture of Intermediate S-1I and Intermediate S-1J (2.87 g, 66%) as a pale yellow viscous oil. $^1$H NMR showed the product was a 1.6:1 mixture of diastereomers S-1I:S-1J as determined by the integration of the multiplets at 2.74 and 2.84 ppm: $^1$H NMR (400 MHz, CDCl$_3$) δ ppm 4.43-4.54 (2H, m), 4.23-4.35 (5H, m), 4.01 (1H, ddd, J=9.54, 6.27, 3.51 Hz), 2.84 (1H, ddd, J=9.41, 7.28, 3.64 Hz), 2.74 (1H, ddd, J=10.29, 6.27, 4.02 Hz), 2.37-2.48 (2H, m, J=10.38, 6.98, 6.98, 3.51, 3.51 Hz), 2.20-2.37 (3H, m), 1.92-2.20 (8H, m), 1.64-1.91 (5H, m), 1.47 (18H, s), 0.88-0.98 (12H, m).

48

Intermediate S-1: (2R,3S)-3-(tert-Butoxycarbonyl)-6,6,6-trifluoro-2-(3,3,3-trifluoropropyl)hexanoic acid, and Intermediate S-1E: (2R,3R)-3-(tert-Butoxycarbonyl)-6,6,6-trifluoro-2-(3,3,3-trifluoropropyl)hexanoic acid

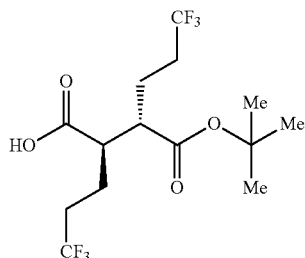

(S-1)

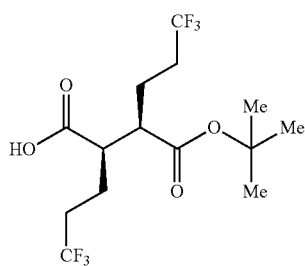

(S-1E)

To a cool (0° C.), stirred solution of Intermediate S-1I and Intermediate S-1J (4.54 g, 9.51 mmol) in THF (140 mL) and water (42 mL) were sequentially added hydrogen peroxide (30% in water) (10.3 g, 91 mmol) and LiOH (685.3 mg, 28.6 mmol). The mixture was stirred for 1 hr. At this time the reaction vessel was removed from the cold bath and then stirred for 1.5 hr. To the reaction mixture were added saturated NaHCO$_3$ (45 mL) and saturated Na$_2$S$_2$O$_3$ (15 mL), and then the mixture was partially concentrated under reduced pressure. The resulting crude solution was extracted with DCM (3×). The aqueous phase was acidified to pH-1-2 with 1N HCl, extracted with DCM (3×) and then EtOAc (1×). The combined organics were washed with brine, dried (Na$_2$SO$_4$), filtered and concentrated under reduced pressure to provide a mixture of Intermediates S-1 and S-1E (3.00 g, 86%) as a colorless oil: $^1$H NMR (400 MHz, CDCl$_3$) δ ppm 2.76-2.84 (1H, m, diastereomer 2), 2.64-2.76 (3H, m), 2.04-2.35 (8H, m), 1.88-2.00 (4H, m), 1.71-1.83 (4H, m), 1.48 (9H, s, diastereomer 1), 1.46 (9H, s, diastereomer 2); $^1$H NMR showed a 1.7:1 mixture of S-1E:S-1F by integration of the peaks for the t-butyl groups.

Intermediate S-1: (2R,3S)-3-(tert-Butoxycarbonyl)-6,6,6-trifluoro-2-(3,3,3-trifluoropropyl)hexanoic acid, and Intermediate S-1F: (2R,3R)-3-(tert-Butoxycarbonyl)-6,6,6-trifluoro-2-(3,3,3-trifluoropropyl)hexanoic acid

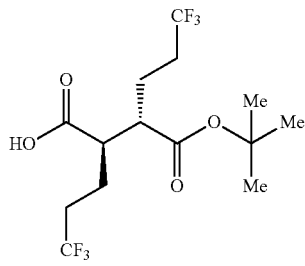

(S-1)

-continued

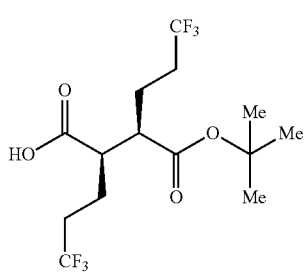

(S-1E)

To a cold (−78° C.) stirred solution of diisopropylamine (1.7 mL, 11.93 mmol) in THF (19 mL) under a nitrogen atmosphere was added n-BuLi (2.5M in hexanes) (4.8 mL, 12.00 mmol). The mixture was stirred for 5 min and then warmed to 0° C. In a separate vessel, to a cold (−78° C.) stirred solution of the mixture of Intermediates S-1 and S-1E (1.99 g, 5.43 mmol) in THF (18 mL) was added the LDA solution prepared above via cannula slowly over 25 min. The mixture was stirred for 15 min, then warmed to room temperature (placed in a 24° C. water bath) for 15 min, and then again cooled to −78° C. for 15 min. To the reaction mixture was added $Et_2AlCl$ (1M in hexane) (11.4 mL, 11.40 mmol) via syringe. The mixture was stirred for 10 min, warmed to room temperature for 15 min and then cooled back to −78° C. for 15 min. Methanol (25 mL) was rapidly added, swirled vigorously while warming to room temperature, and then concentrated to ~¼ the original volume. The mixture was dissolved in EtOAc and washed with 1N HCl (50 mL) and ice (75 g). The aqueous phase was separated and extracted with EtOAc (2×). The combined organics were washed with a mixture of KF (2.85 g in 75 mL water) and 1N HCl (13 mL) [resulting solution pH 3-4], then with brine, dried ($Na_2SO_4$), filtered and concentrated under reduced pressure to give a 9:1 (S-1:S-1E) enriched diastereomeric mixture (as determined by $^1$H NMR) of Intermediate S-1 and Intermediate S-1E (2.13 g, >99%) as a pale yellow viscous oil: $^1$H NMR (400 MHz, $CDCl_3$) δ ppm 2.64-2.76 (2H, m), 2.04-2.35 (4H, m), 1.88-2.00 (2H, m), 1.71-1.83 (2H, m), 1.48 (9H, s).

Intermediate S-2: (2R,3S)-3-(tert-Butoxycarbonyl)-6,6,6-trifluoro-2-(3-fluoropropyl)hexanoic acid

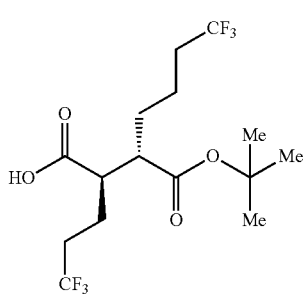

(S-2)

Intermediate S-2: (2R,3S)-3-(tert-Butoxycarbonyl)-7,7,7-trifluoro-2-(3,3,3-trifluoropropyl)heptanoic acid, and Intermediate S-2A: (2R,3R)-3-(tert-Butoxycarbonyl)-7,7,7-trifluoro-2-(3,3,3-trifluoropropyl)heptanoic acid

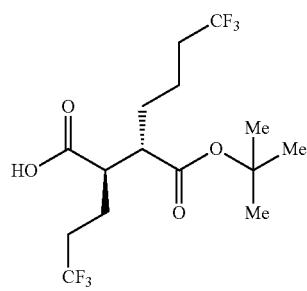

(S-2)

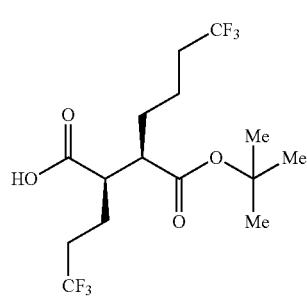

(S-2A)

To a cold (−78° C.), stirred solution of Intermediate S-1D (1.72 g, 6.36 mmol) in THF (30 mL) was slowly added LDA (7.32 mL, 14.6 mmol) over 7 min. After stirring for 1 h, 4,4,4-trifluorobutyltrifluoromethanesulfonate (2.11 g, 8.11 mmol) was added to the reaction mixture over 2 min. After 15 min, the reaction mixture was warmed to −25° C. (ice/MeOH/dry ice) for 1 h, and then cooled to −78° C. After 80 min, the reaction was quenched with a saturated aqueous $NH_4Cl$ solution (10 mL). The reaction mixture was further diluted with brine and the solution was adjusted to pH 3 with 1N HCl. The aqueous layer was extracted with ether. The combined organics were washed with brine, dried over anhydrous magnesium sulfate, and concentrated under reduced pressure to provide a mixture of Intermediates S-2 and S-2A (2.29 g, 95%) as a colorless oil. $^1$H NMR (400 MHz, chloroform-d) δ 2.83-2.75 (m, 1H), 2.64 (ddd, J=9.9, 6.7, 3.6 Hz, 1H), 2.32-2.03 (m, 5H), 1.98-1.70 (m, 3H), 1.69-1.52 (m, 3H), 1.50-1.42 (m, 9H). $^1$H NMR showed a 1:4.5 mixture (S-2:S-2A) of diastereomers by integration of the peaks for the t-Bu groups.

Intermediate S-2: (2R,3S)-3-(tert-Butoxycarbonyl)-7,7,7-trifluoro-2-(3,3,3-trifluoropropyl)heptanoic acid, and Intermediate S-2A: (2R,3R)-3-(tert-Butoxycarbonyl)-7,7,7-trifluoro-2-(3,3,3-trifluoropropyl)heptanoic acid

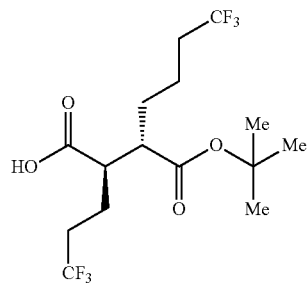

(S-2)

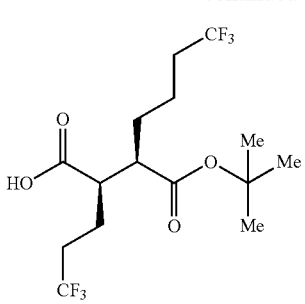

(S-2A)

A mixture of Intermediate S-2 and Intermediate S-2A (2.29 g, 6.02 mmol) was dissolved in THF (38 mL) to give a colorless solution which was cooled to −78° C. Then, LDA (7.23 mL, 14.5 mmol) (2.0M in heptane/THF/ethylbenzene) was slowly added to the reaction mixture over 3 min. After stirring for 15 min, the reaction mixture was placed in a room temperature water bath. After 15 min the reaction mixture was placed back in a −78° C. bath and then diethylaluminum chloride (14.5 mL, 14.5 mmol) (1M in hexane) was added slowly over 5 min. The reaction mixture was stirred at −78° C. After 15 min, the reaction mixture was placed in a room temperature water bath for 10 min, and then cooled back to −78° C. After 15 min, the reaction was quenched with MeOH (30.0 mL, 741 mmol), removed from the −78° C. bath and concentrated. To the reaction mixture was added ice and HCl (60.8 mL, 60.8 mmol) and the resulting mixture was extracted with EtOAc (2×200 mL). The organic layer was washed with potassium fluoride (3.50 g, 60.3 mmol) in 55 mL H$_2$O and 17.0 mL of 1N HCl. The organics were dried over anhydrous magnesium sulfate and concentrated under reduced pressure to provide an enriched mixture of Intermediate S-2 and Intermediate S-2A (2.25 g, 98% yield) as a light yellow oil. $^1$H NMR (400 MHz, chloroform-d) δ 2.83-2.75 (m, 1H), 2.64 (ddd, J=9.9, 6.7, 3.6 Hz, 1H), 2.32-2.03 (m, 5H), 1.98-1.70 (m, 3H), 1.69-1.52 (m, 3H), 1.50-1.42 (m, 9H). $^1$H NMR showed a 9:1 ratio in favor of the desired diastereomer Intermediate S-2.

Intermediate S-2B: (2R,3S)-1-Benzyl 4-tert-butyl 2,3-bis(4,4,4-trifluorobutyl)succinate

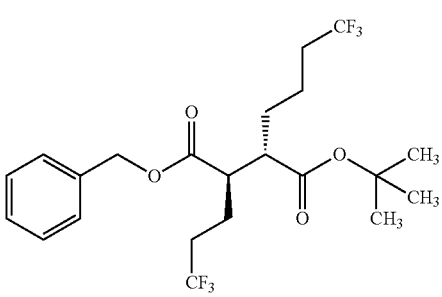

(S-2B)

To a stirred 9:1 mixture of Intermediate S-2 and Intermediate S-2A (2.24 g, 5.89 mmoL) and potassium carbonate (1.60 g, 11.58 mmol) in DMF (30 mL) was added benzyl bromide (1.20 mL, 10.1 mmoL)). The reaction mixture was stirred at room temperature for 19 h. The reaction mixture was diluted with ethyl acetate (400 mL) and washed with 10% LiCl solution (3×100 mL), brine (50 mL), and then dried over anhydrous magnesium sulfate, filtered and concentrated to dryness under vacuum. The residue was purified by flash chromatography (Teledyne ISCO CombiFlash 0% to 100% solvent A/B=hexane/EtOAc, REDISEP® SiO$_2$ 220 g, detecting at 254 nm, and monitoring at 220 nm). Concentration of the appropriate fractions provided Intermediate S-2B (1.59 g, 57.5%). HPLC: RT=3.863 min (CHROMOLITH® Speed-ROD column 4.6×50 mm, 10-90% aqueous methanol over 4 minutes containing 0.1% TFA, 4 mL/min, monitoring at 220 nm), $^1$H NMR (400 MHz, chloroform-d) δ 7.40-7.34 (m, 5H), 5.17 (d, J=1.8 Hz, 2H), 2.73-2.64 (m, 1H), 2.55 (td, J=10.0, 3.9 Hz, 1H), 2.16-1.82 (m, 5H), 1.79-1.57 (m, 3H), 1.53-1.49 (m, 1H), 1.45 (s, 9H), 1.37-1.24 (m, 1H).

Intermediate S-2: (2R,3S)-3-(tert-Butoxycarbonyl)-6,6,6-trifluoro-2-(4,4,4-trifluorobutyl)hexanoic acid

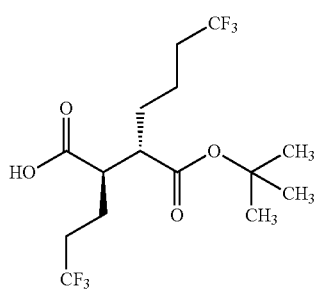

(S-2)

To a stirred solution of Intermediate S-2B (1.59 g, 3.37 mmoL) in MeOH (10 mL) and EtOAc (10 mL) under nitrogen was added 10% Pd/C (510 mg). The atmosphere was replaced with hydrogen and the reaction mixture was stirred at room temperature for 2.5 h. The palladium catalyst was filtered off through a 4 μM polycarbonate film and rinsed with MeOH. The filtrate was concentrated under reduced pressure to give intermediate S-2 (1.28 g, 99%). $^1$H NMR (400 MHz, chloroform-d) δ 2.76-2.67 (m, 1H), 2.65-2.56 (m, 1H), 2.33-2.21 (m, 1H), 2.17-2.08 (m, 3H), 1.93 (dtd, J=14.5, 9.9, 5.2 Hz, 1H), 1.84-1.74 (m, 2H), 1.70-1.52 (m, 3H), 1.48 (s, 9H).

Intermediate A-1: (2-Amino-3-methylphenyl)(3-fluorophenyl)methanone

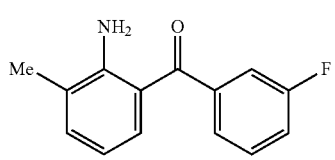

(A-1)

Intermediate A-1A: 2-Amino-N-methoxy-N,3-dimethylbenzamide

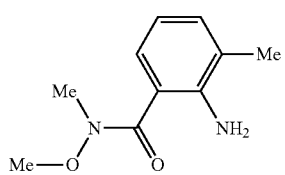

(A-1A)

In a 1 L round-bottomed flask was added 2-amino-3-methylbenzoic acid (11.2 g, 74.1 mmol) and N,O-dimethylhydroxylamine hydrochloride (14.45 g, 148 mmol) in DCM (500 mL) to give a pale brown suspension. The reaction mixture was treated with Et$_3$N (35 mL), HOBT (11.35 g, 74.1 mmol) and EDC (14.20 g, 74.1 mmol) and then stirred at room temperature for 24 hours. The mixture was then washed with 10% LiCl, and then acidified with 1N HCl. The organic layer was washed successively with 10% LiCl and aq NaHCO$_3$. The organic layer was decolorized with charcoal, filtered, and the filtrate was dried over MgSO$_4$. The mixture was filtered and concentrated to give 13.22 g (92% yield) of Intermediate A-1A. MS(ES): m/z=195.1 [M+H$^+$]; HPLC: RT=1.118 min. (H$_2$O/MeOH with TFA, CHROMOLITH® ODS S5 4.6×50 mm, gradient=4 min, wavelength=220 nm); $^1$H NMR (500 MHz, chloroform-d) δ 7.22 (dd, J=7.8, 0.8 Hz, 1H), 7.12-7.06 (m, 1H), 6.63 (t, J=7.5 Hz, 1H), 4.63 (br. s., 2H), 3.61 (s, 3H), 3.34 (s, 3H), 2.17 (s, 3H).

Intermediate A-1:
(2-Amino-3-methylphenyl)(3-fluorophenyl)methanone

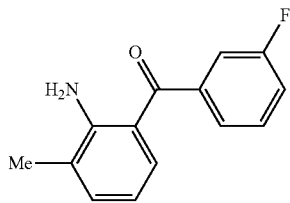

(A-1)

In a 500 mL round-bottomed flask, a solution of 1-fluoro-3-iodobenzene (13.61 mL, 116 mmol) in THF (120 mL) was cooled in a −78° C. bath. A solution of n-BuLi, (2.5M in hexane, 46.3 mL, 116 mmol) was added dropwise over 10 minutes. The solution was stirred at −78° C. for 30 minutes and then treated with a solution of Intermediate A-1A (6.43 g, 33.1 mmol) in THF (30 mL). After 1.5 hours, the reaction mixture was added to a mixture of ice and 1N HCl (149 mL, 149 mmol) and the reaction flask was rinsed with THF (5 ml) and combined with the aqueous mixture. The resulting mixture was diluted with 10% aq LiCl and the pH was adjusted to 4 with 1N NaOH. The mixture was then extracted with Et$_2$O, washed with brine, dried over MgSO$_4$, filtered and concentrated. The resulting residue was purified by silica gel chromatography (220 g ISCO) eluting with a gradient from 10% EtOAc/hexane to 30% EtOAc/hexane to afford Intermediate A-1 (7.11 g, 94% yield) as an oil. MS(ES): m/z=230.1 [M+H$^+$]; HPLC: RT=2.820 min Purity=99%. (H$_2$O/MeOH with TFA, CHROMOLITH® ODS S5 4.6×50 mm, gradient=4 min, wavelength=220 nm).

The compounds listed below in Table 1 (Intermediates A-2 to A-9) were prepared according to the general synthetic procedure described for Intermediate A-1, using the appropriate aniline and organometallic reagent.

TABLE 1

| Intermediate | Structure | Name | HPLC RT (min.) | LC/MS [M + H]$^+$ |
|---|---|---|---|---|
| A-2 | 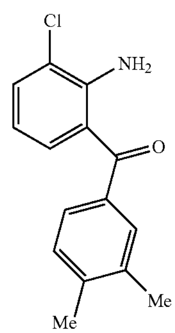 [SMILES: Cc1ccc(C(=O)c2cccc(Cl)c2N)cc1C] | (2-amino-3-chlorophenyl)(3,4-dimethylphenyl)methanone | 1.15[1] | 260 |
| A-3 | 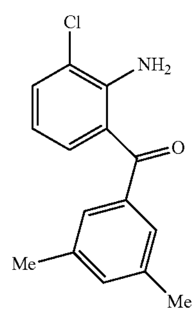 [SMILES: Cc1cc(C)cc(C(=O)c2cccc(Cl)c2N)c1] | (2-amino-3-chlorophenyl)(3,5-dimethylphenyl)methanone | 1.16[1] | 260 |
| A-4 | 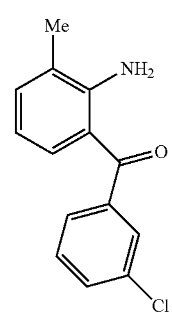 [SMILES: Cc1cccc(C(=O)c2cccc(Cl)c2)c1N] | (2-amino-3-methylphenyl)(3-chlorophenyl)methanone | 2.61[2] | 246.2 |

TABLE 1-continued

| Intermediate | Structure | Name | HPLC RT (min.) | LC/MS [M + H]+ |
| --- | --- | --- | --- | --- |
| A-5 | 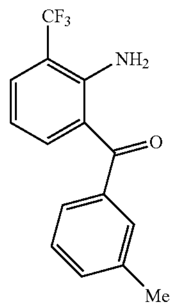 [SMILES: Cc1cccc(C(=O)c2cccc(C(F)(F)F)c2N)c1] | (2-amino-3-(trifluoromethyl)phenyl)(m-tolyl)methanone | 2.71[2] | 280.3 |
| A-6 | 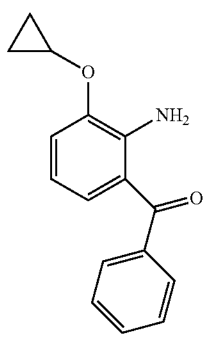 [SMILES: Nc1c(OC2CC2)cccc1C(=O)c1ccccc1] | (2-amino-3-cyclopropoxyphenyl)(phenyl)methanone | 3.32[3] | 254 |
| A-7 | 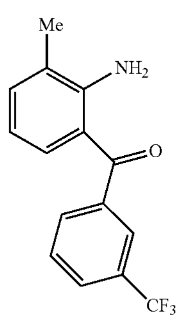 [SMILES: Cc1cccc(C(=O)c2cccc(C(F)(F)F)c2)c1N] | (2-amino-3-methylphenyl)(3-(trifluoromethyl)phenyl)methanone | 1.09[4] | 279.9 |
| A-8 | 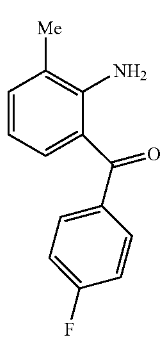 [SMILES: Cc1cccc(C(=O)c2ccc(F)cc2)c1N] | (2-amino-3-methylphenyl)(4-fluorophenyl)methanone | 2.08[5] | 230.09 |

TABLE 1-continued

| Intermediate | Structure | Name | HPLC RT (min.) | LC/MS [M + H]+ |
|---|---|---|---|---|
| A-9 | ![structure] | (2-amino-3-methylphenyl)(phenyl)methanone | 0.98[1] | 212 |

[1]$H_2O/CH_3CN$ with TFA, BEH C18 1.75 μm, 2.1 × 50 mm, gradient = 2 min, wavelength = 220 nm.
[2]$H_2O$/MeOH with 0.1% TFA, Luna C18 3 μm, 4.6 × 30 mm, gradient = 3.5 min, wavelength = 220.
[3]MeOH/$H_2O$/0.1% TFA, Waters Sunfire C18 3.5 μ, 2.1 × 30 mm, 1 mL/min, 4 min gradient, wavelength = 254 nm.
[4]$H_2O/CH_3CN$ with 0.05% TFA, BEH C18 1.7 μm, 2.1 × 50 mm, gradient (2%-98%) = 1 min, wavelength = 220.
[5]$H_2O$/MeOH with 0.1% TFA, PHENOMENEX ® 2.5 μm, 2.0 × 30 mm, gradient = 2 min, wavelength = 220.

Intermediate A-10: (2-Amino-3-isopropylphenyl)(3-chlorophenyl)methanone

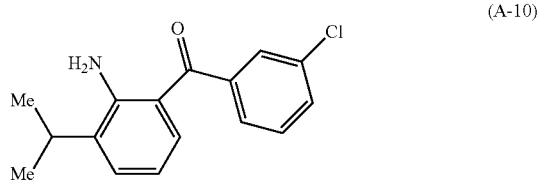 [SMILES: CC(C)c1cccc(C(=O)c2cccc(Cl)c2)c1N]

(A-10)

2-Isopropylaniline (3 mL, 21.19 mmol) was added dropwise to a solution of trichloroborane (1M in dichloromethane) (23.31 mL, 23.31 mmol) and dichloroethane (50 mL) at 0° C. and the mixture was stirred for 10 min. Next, 3-chlorobenzonitrile (5.83 g, 42.4 mmol), followed by aluminum trichloride (3.11 g, 23.31 mmol) were added and the mixture was stirred at 0° C. for 25 minutes. The ice bath was removed and the mixture was heated to 75° C. overnight. The mixture was then cooled to room temperature. Next, 6N HCl (60 mL, 10 eq) was added and the mixture was heated to 75° C. After 4 hrs, 12N HCl (10 mL) was added and heating was continued overnight at 75° C. The mixture was cooled to room temperature, transferred to an Erlenmeyer flask, diluted with ethyl acetate, cooled to 0° C., and cautiously raised to pH 10 with 50% aqueous NaOH. The resulting mixture was extracted with ethyl acetate (4×). The ethyl acetate extracts were combined, washed with brine, dried over anhydrous sodium sulfate, filtered and concentrated to give a clear amber oil. The oil was suspended in a minimum of heptane and purified on an ISCO companion chromatography system (220 g silica cartridge, eluting with 0-20% ethyl acetate/heptane, 150 mL/min) to provide Intermediate A-10 (2.85 g, 10.41 mmol, 49.1% yield). HPLC RT=3.876 min 10/90 to 90/10 (MeOH/$H_2O$/0.1% TFA, Waters Sunfire C18 3.5 μm, 2.1×30 mm, 1 mL/min, 4 min gradient, wavelength=254 nm); MS(ES): m/z=274 [M+H]+; $^1$H NMR (400 MHz, chloroform-d) δ 7.63 (t, J=1.7 Hz, 1H), 7.55-7.48 (m, 2H), 7.44-7.29 (m, 3H), 6.65 (t, J=7.7 Hz, 1H), 6.43 (br. s., 2H), 3.11-2.87 (m, 1H), 1.34 (d, J=6.8 Hz, 6H).

The compounds listed below in Table 2 (Intermediates A-11 to A-14) were prepared according to the general synthetic procedure described for Intermediate A-10, using the appropriate aniline and aryl nitrile, obtained by methods known to one skilled in the art.

TABLE 2

| Intermediate | Structure | Name | HPLC RT (min)[1] | LC/MS [M + H]+ |
|---|---|---|---|---|
| A-11 | ![structure Et/NH2/C=O/Cl phenyl] | (2-amino-3-ethylphenyl)(3-chlorophenyl)methanone | 3.65 | 260 |

TABLE 2-continued

| Intermediate | Structure | Name | HPLC RT (min)[1] | LC/MS [M + H]+ |
|---|---|---|---|---|
| A-12 | 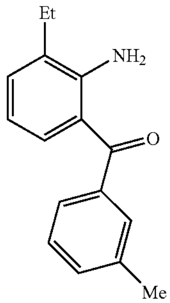 [SMILES: CCc1cccc(C(=O)c2cccc(C)c2)c1N] | (2-amino-3-ethylphenyl)(m-tolyl)methanone | 3.59 | 240 |
| A-13 | 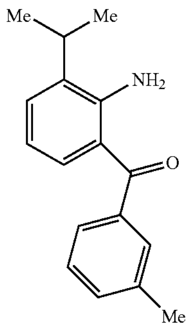 [SMILES: Cc1cccc(C(=O)c2cccc(C(C)C)c2N)c1] | (2-amino-3-isopropylphenyl)(m-tolyl)methanone | 3.68 | 254 |
| A-14 | 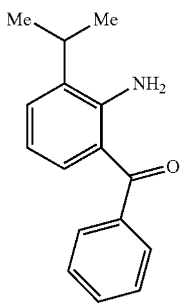 [SMILES: CC(C)c1cccc(C(=O)c2ccccc2)c1N] | (2-amino-3-isopropylphenyl)(phenyl)methanone | 3.45 | 240 |

[1]MeOH/H₂O/0.1% TFA, Waters Sunfire C18 3.5 μ, 2.1 × 30 mm, 1 mL/min, 4 min gradient, wavelength = 254 nm.

Intermediate A-15:
(2-Amino-3-cyclopropoxyphenyl)(m-tolyl)methanone

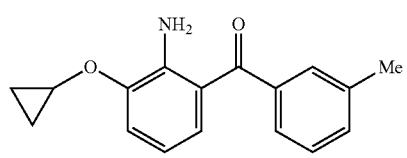

(A-15)

Intermediate A-15A: 3-Hydroxy-2-nitrobenzoic acid

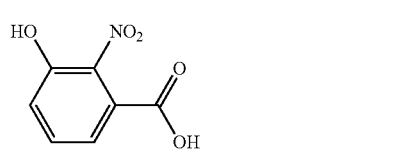

(A-15A)

To a 250 mL flask were added 3-chloro-2-nitrobenzoic acid (10 g, 49.6 mmol) and a potassium hydroxide solution (40 g, 727 mmol) in water (70 mL). The thick slurry was heated to reflux for 12 hours. The solution was cooled in ice and cautiously brought to pH 3 with concentrated HCl. The aqueous mixture was extracted with EtOAc (3×). The organic layers were combined, washed with brine, dried with sodium sulfate and concentrated in vacuo. The crude product mixture was dissolved in dichloromethane and the resulting yellow precipitate was filtered to afford Intermediate A-15A (6 g, 32.8 mmol, 66.0% yield). HPLC: RT=0.85 min (H₂O/MeOH with TFA, Sunfire C18 3.5 μm, 2.1×30 mm, gradient=4 min, wavelength=220 nm); MS(ES): m/z=206 [M+Na]+; ¹H NMR (400 MHz, chloroform-d) δ 7.56-7.35 (m, 1H), 7.23 (dd, J=7.9, 1.5 Hz, 1H).

Intermediate A-15B: Methyl 3-hydroxy-2-nitrobenzoate

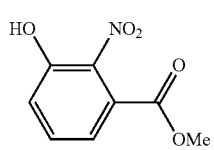

(A-15B)

To a 100 mL flask containing MeOH (60 mL) at 0° C. was slowly added thionyl chloride (9.96 mL, 137 mmol). The solution was stirred at 0° C. for 30 minutes, and then Intermediate A-15A (10 g, 54.6 mmol) was added. The reaction solution was heated to reflux for 6 hrs. The reaction mixture was concentrated to dryness to give a bright yellow residue. The crude product mixture was purified via silica gel chromatography (0% to 100% of EtOAC/heptane over 15 minutes, 80 g column) giving the desired product (10.2 g, 95% yield). HPLC: RT=1.75 min (H$_2$O/MeOH with TFA, Sunfire C18 3.5 μm, 2.1×30 mm, gradient=4 min, wavelength=220 nm); MS(ES): m/z=220 [M+Na]$^+$; $^1$H NMR (400 MHz, chloroform-d) δ 7.60 (dd, J=8.5, 7.4 Hz, 1H), 7.33-7.22 (m, 5H), 7.10 (dd, J=7.5, 1.3 Hz, 1H), 3.96 (s, 3H).

Intermediate A-15C: Methyl 2-nitro-3-(vinyloxy)benzoate

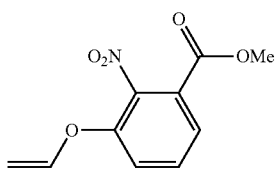

(A-15C)

A mixture of copper (II) acetate (11.98 g, 65.9 mmol) and dichloromethane (80 mL) were stirred at room temperature for 10 minutes, before the addition of 2,4,6-trivinyl-1,3,5,2,4,6-trioxatriborinane compound:pyridine (1:1) (10.63 g, 44.2 mmol, 0.67 eq), Intermediate A-15B (13 g, 65.9 mmol), pyridine (26.7 mL, 330 mmol), and molecular sieves (1 g). The resulting deep blue mixture was stirred at room temperature for 5 days, with the reaction mixture opened to the air. The reaction mixture was filtered through a pad of CELITE® and washed with dichloromethane. The filtrate was washed with 3M aqueous ammonium acetate (2×), water, brine, and then dried and concentrated in vacuo. The crude product mixture was purified via silica gel chromatography (0% to 20% of EtOAC/DCM over 15 minutes, 120 g column) to give Intermediate A-15C (7.42 g, 33.2 mmol, 50.4% yield). HPLC: RT=2.487 min (H$_2$O/MeOH with TFA, Sunfire C18 3.5 μm, 2.1×30 mm, gradient=4 min, wavelength=220 nm); MS(ES): m/z=246 [M+Na]$^+$; $^1$H NMR (400 MHz, chloroform-d) δ 7.77 (dd, J=7.8, 1.2 Hz, 1H), 7.55 (t, J=8.1 Hz, 1H), 7.38 (dd, J=8.4, 1.3 Hz, 1H), 6.61 (dd, J=13.6, 5.9 Hz, 1H), 4.95 (dd, J=13.6, 2.4 Hz, 1H), 4.69 (dd, J=5.9, 2.4 Hz, 1H), 3.93 (s, 3H), 1.56 (s, 1H), 0.03 (s, 1H).

Intermediate A-15D: Methyl 3-cyclopropoxy-2-nitrobenzoate

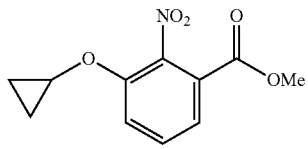

(A-15D)

A solution of 2,2,2-trichloroacetic acid (16.30 g, 100 mmol) in dichloromethane (100 mL) was slowly added via an addition funnel to a solution of diethylzinc (1M hexanes, 100 mL, 100 mmol) at −10° C. under a nitrogen atmosphere. The reaction mixture was stirred for 10 min, and then diiodomethane (8 mL, 100 mmol) was added dropwise via syringe, and the reaction mixture was stirred for 10 min. A solution of Intermediate A-15C (7.42 g, 33.2 mmol) in dichloromethane (20 mL) was added slowly via an addition funnel. The solution was allowed to warm to room temperature overnight. The reaction mixture was then cooled to 0° C. and quenched with 1M HCl. The reaction mixture was transferred to a separatory funnel, and the aqueous layer was extracted with dichloromethane (3×). The combined extracts were washed with saturated sodium bicarbonate, water and brine, dried over anhydrous sodium sulfate, filtered and concentrated. The crude product mixture was purified by silica gel chromatography (0% of EtOAC/heptane over 15 minutes, 220 g column) to provide Intermediate A-15D (4.7 g, 19.81 mmol, 60.0% yield). HPLC: RT=2.66 min (H$_2$O/MeOH with TFA, Sunfire C18 3.5 μm, 2.1×30 mm, gradient=4 min, wavelength=220 nm); MS(ES): m/z=260 [M+Na]$^+$; $^1$H NMR (400 MHz, chloroform-d) δ 7.68-7.57 (m, 2H), 7.57-7.41 (m, 1H), 4.03-3.82 (m, 4H), 0.94-0.78 (m, 4H).

Intermediate A-15E: 3-Cyclopropoxy-2-nitrobenzoic acid

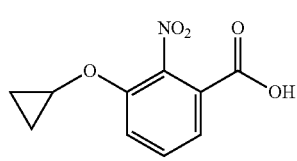

(A-15E)

A solution of Intermediate A-15D (4.7 g, 19.81 mmol) in THF (30 mL) and MeOH (30 mL) was treated with a solution of lithium hydroxide (2.88 g, 120 mmol) in water (15 mL, 833 mmol). The mixture was stirred at room temperature for 2 hours. The organic solvents were removed under reduced pressure. The resulting aqueous slurry was diluted with water, acidified with 1M HCl and extracted with ethyl acetate (3×). The extracts were combined and washed with brine, dried over anhydrous sodium sulfate, filtered and concentrated to provide Intermediate A-15E (4.35 g, 19.8 mmol, 98% yield). HPLC: RT=2.186 min (H$_2$O/MeOH with TFA, Sunfire C18 3.5 μm, 2.1×30 mm, gradient=4 min, wavelength=220 nm); MS(ES): m/z=246 [M+Na]$^+$; $^1$H NMR (400 MHz, chloroform-d) δ 7.76 (dd, J=7.7, 1.8 Hz, 1H), 7.68-7.46 (m, 2H), 4.02 (tt, J=6.0, 2.9 Hz, 1H), 1.00-0.52 (m, 4H).

Intermediate A-15F: 2-Amino-3-cyclopropoxybenzoic acid

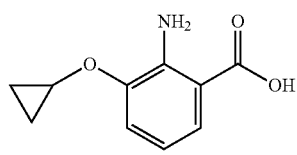

(A-15F)

A mixture of Intermediate A-15E (420 mg, 1.882 mmol), zinc (1230 mg, 18.82 mmol), and ammonium chloride (1007 mg, 18.82 mmol) in ethanol (10 mL) and water (5 mL) was stirred at room temperature for 5 minutes. The reaction mixture was concentrated in vacuo and then the reaction mixture was diluted with water. The mixture was made slightly acidic and then extracted with DCM (2×). The combined organics were dried over Na$_2$SO$_4$, and concentrated to give Intermediate A-15F as a tan oil. HPLC: RT=1.96 min (H$_2$O/MeOH with TFA, Sunfire C18 3.5 μm, 2.1×30 mm, gradient=4 min, wavelength=220 nm); MS(ES): m/z=194.12 [M+H]$^+$; $^1$H NMR (400 MHz, methanol-d$_4$) δ 7.67-7.43 (m, 1H), 7.23 (dd, J=7.9, 1.1 Hz, 1H), 6.62 (s, 1H), 3.82 (s, 1H), 0.82-0.63 (m, 4H).

Intermediate A-15G: 8-Cyclopropoxy-2-methyl-4H-benzo[d][1,3]oxazin-4-one

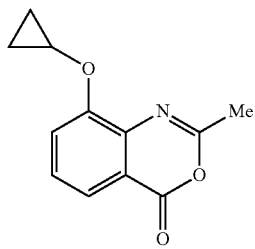
(A-15G)

A solution of Intermediate A-15F (1 g, 5.18 mmol) and acetic anhydride (4.88 mL 51.8 mmol) was heated to 140° C. for 1 hour. The reaction mixture was cooled and concentrated in vacuo, and the residue was diluted with toluene and concentrated to afford Intermediate A-15G. HPLC: RT=1.22 min (H$_2$O/MeOH with TFA, Sunfire C18 3.5 μm, 2.1×30 mm, gradient=4 min, wavelength=220 nm); MS(ES): m/z=218.12 [M+H]$^+$; $^1$H NMR (400 MHz, chloroform-d) δ 7.82 (dd, J=7.9, 1.3 Hz, 1H), 7.71 (dd, J=8.1, 1.3 Hz, 1H), 7.55-7.37 (m, 1H), 4.02-3.75 (m, 1H), 2.52 (s, 3H), 1.08-0.74 (m, 4H).

Intermediate A-15H: N-(2-Cyclopropoxy-6-(3-methylbenzoyl)phenyl)acetamide

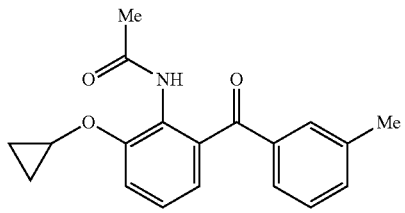
(A-15H)

A solution of Intermediate A-15G (1 g, 4.60 mmol) in ether (5 mL) and toluene (10 mL) was cooled to −10° C. (methanol/ice). A solution of m-tolylmagnesium bromide (5.06 mL, 5.06 mmol) was added dropwise over a period of 10 minutes. After the addition was complete, the flask was removed from the ice bath and stirred at room temperature for 1.5 h. The solution was then cooled to −10° C. and 40 mL of 1N HCl was added. The mixture was diluted with ethyl acetate (50 mL). The organic phase was washed with 0.5 M NaOH, then with water, and then concentrated in vacuo. The residue was used as is in the next reaction. HPLC: RT=2.808 min (H$_2$O/MeOH with TFA, Sunfire C18 3.5 μm, 2.1×30 mm, gradient=4 min, wavelength=220 nm); MS(ES): m/z=310.05 [M+H]$^+$.

Intermediate A-15: (2-Amino-3-cyclopropoxyphenyl)(m-tolyl)methanone

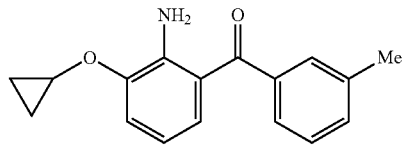
(A-15)

A solution of Intermediate A-15H (495 mg, 1.6 mmol) in ethanol (10 mL) and 6N HCl (5 mL) was heated at 90° C. for 4.5 hours. The reaction mixture was concentrated, and then diluted with 10 mL water, and extracted with ethyl acetate (3×50 mL). The pooled organic phases were washed with 1N sodium hydroxide, dried over Na$_2$SO$_4$ and concentrated in vacuo. The crude product mixture was purified via silica gel chromatography (0% to 100% of EtOAC/heptane over 10 minutes, 12 g column) to isolate Intermediate A-15 (250 mg, 0.935 mmol, 58.4% yield) as a yellow oil. HPLC: RT=3.58 min (H$_2$O/MeOH with TFA, Sunfire C18 3.5 μm, 2.1×30 mm, gradient=4 min, wavelength=220 nm); MS(ES): m/z=268.02 [M+H]$^+$.

The compounds listed below in Table 3 (Intermediates A-16 to A-17) were prepared according to the general synthetic procedure described for Intermediate A-15, using the appropriate aniline and organometallic reagent, obtained by methods known to one skilled in the art.

TABLE 3

| Intermediate | Structure | Name | HPLC RT (min)$^1$ | LC/MS [M + H]$^+$ |
| --- | --- | --- | --- | --- |
| A-16 | ![structure] | (2-amino-3-methoxyphenyl)(3-chlorophenyl)methanone | 2.15 | 262 |

TABLE 3-continued

| Intermediate | Structure | Name | HPLC RT (min)[1] | LC/MS [M + H]+ |
|---|---|---|---|---|
| A-17 | 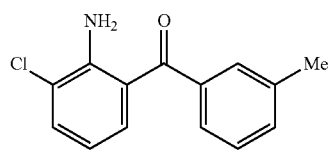 | (2-amino-3-methoxyphenyl)(4-chlorophenyl)methanone | 2.14 | 262 |

[1]$H_2O/CH_3CN$ with $NH_4OAc$, PUROSPHER® STAR RP-18 3.5 μm, 4 × 55 mm, gradient = 2 min, wavelength = 220 nm.

Intermediate A-18:
(2-Amino-3-chlorophenyl)(m-tolyl)methanone

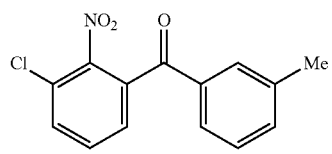

(A-18)

Intermediate A-18A:
(3-Chloro-2-nitrophenyl)(m-tolyl)methanone (A-18A)

A solution of 3-chloro-2-nitrobenzoic acid (2.5 g, 12.40 mmol) in tetrahydrofuran (50 mL) was treated with oxalyl chloride (1.194 mL, 13.64 mmol) followed by DMF (0.096 mL, 1.240 mmol). The reaction mixture was stirred at room temperature for 2 hrs. After cooling to 0° C., a 1M solution of m-tolylmagnesium bromide (24.81 mL, 24.81 mmol) was added. After 1 hr another portion of m-tolylmagnesium bromide (24.81 mL, 24.81 mmol) was added. After 1 hour, the reaction mixture was partitioned between ethyl acetate (200 mL) and 1N HCl (150 mL). The aqueous layer was extracted with ethyl acetate (2×100 mL). The combined organic phases were dried over $Na_2SO_4$, filtered and concentrated. The crude material was purified by flash chromatography (Teledyne ISCO CombiFlash Rf, 0% to 100% solvent A/B=ethyl acetate/heptane, REDISEP® $SiO_2$ 120 g) to provided Intermediate A-18A (0.700 g, 21%). $^1$H NMR (400 MHz, DMSO-$d_6$) δ 8.04 (dd, J=8.1, 1.1 Hz, 1H), 7.82 (t, J=7.9 Hz, 1H), 7.71 (dd, J=7.7, 1.1 Hz, 1H), 7.66-7.54 (m, 3H), 7.52-7.46 (m, 1H), 2.40 (s, 3H).

Intermediate A-18

A mixture of Intermediate A-18A (0.710 g, 2.58 mmol) in THF (7.5 mL), ethanol (14.75 mL) and water (3.7 mL) was treated with saturated aqueous ammonium chloride (4 mL) and iron powder (0.647 g, 11.59 mmol). The mixture was then heated to 100° C. with stirring. After 2 hours, the reaction mixture was filtered through CELITE® and the filtrate was partitioned between ethyl acetate (100 mL) and sat aq $NaHCO_3$ (75 mL). The aqueous layer was extracted with ethyl acetate (1×50 mL). The combined organic phases were dried with $Na_2SO_4$, filtered and concentrated. The crude material was purified by flash chromatography (Teledyne ISCO CombiFlash Rf, 0% to 100% solvent A/B=ethyl acetate/heptane, REDISEP® $SiO_2$ 24 g) to provided Intermediate A-18 (0.417 g, 66%). $^1$H NMR (400 MHz, DMSO-$d_6$) δ 7.56 (dd, J=7.8, 1.4 Hz, 1H), 7.47-7.35 (m, 4H), 7.31 (dd, J=8.0, 1.4 Hz, 1H), 7.01 (s, 2H), 6.61 (t, J=7.9 Hz, 1H), 2.39 (s, 3H).

Intermediate A-19:
(2-Amino-3-methoxyphenyl)(m-tolyl)methanone

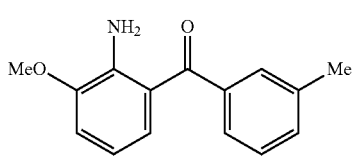

(A-19)

Intermediate A-19 was prepared from 3-methoxy-2-nitrobenzoic acid according to the general synthetic procedure described for Intermediate A-18. HPLC RT=2.21 min ($H_2O$/$CH_3CN$ with TFA, Sunfire C18 3.5 μm, 2.1×30 mm, gradient=2 min, wavelength=220 nm). [M+H+]=246.

Intermediate A-20: (2-Amino-3-chlorophenyl)(o-tolyl)methanone

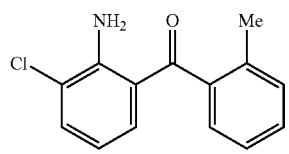

(A-20)

Intermediate A-20A: 7-Chloro-3-hydroxy-3-(o-tolyl)indolin-2-one

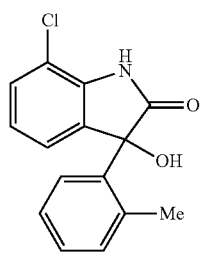

(A-20A)

In a 100 mL round-bottomed flask, a solution of 7-chloroindoline-2,3-dione (1 g, 5.51 mmol) in THF (10 mL) was cooled in an ice/water bath. A solution of o-tolylmagnesium bromide (2M, 5.51 mL, 11.01 mmol) was added, and the reaction mixture was removed from the cooling bath and warmed to room temperature. After 1 hour, the reaction mixture was quenched with saturated aqueous $NH_4Cl$ and extracted with EtOAc. The organic layer was dried over $MgSO_4$, filtered and concentrated to give Intermediate A-20A. MS(ES): m/z=272 [M–H$^-$]; HPLC: RT=2.478 min ($H_2O$/MeOH with TFA, CHROMOLITH® ODS S5 4.6×50 mm, gradient=4 min, wavelength=220 nm).

Intermediate A-20

In a 250 mL round-bottomed flask, a solution of potassium ferrocyanide (5.28 g, 14.33 mmol), $NaHCO_3$ (1.25 g, 14.88 mmol) and NaOH (0.22 g, 5.51 mmol) in water (45 mL) was heated to 100° C. After 30 min, a solution of Intermediate A-20A (1.5 g, 5.51 mmol) in THF (2 mL) was added dropwise over a 5 min period and the reaction mixture was heated at 100° C. for 17 hours, and then cooled to room temperature. The mixture was diluted with saturated aqueous $NaHCO_3$ and extracted with EtOAc. The organic layer was treated with activated charcoal, dried over $MgSO_4$, filtered and concentrated to give Intermediate A-20 (1.208 g, 89%). MS(ES): m/z=246 [M+H$^+$]; HPLC: RT=3.208 min ($H_2O$/MeOH with TFA, CHROMOLITH® ODS S5 4.6×50 mm, gradient=4 min, wavelength=220 nm). $^1$H NMR (500 MHz, DMSO-$d_6$) δ 7.55 (dd, J=7.6, 1.5 Hz, 1H), 7.48-7.37 (m, 3H), 7.33 (d, J=7.5 Hz, 1H), 7.29 (t, J=7.5 Hz, 1H), 7.22 (dd, J=7.6, 1.2 Hz, 1H), 7.05 (dd, J=8.2, 1.5 Hz, 1H), 6.54 (t, J=7.9 Hz, 1H), 2.16 (s, 3H).

The compounds listed below in Table 4 (Intermediate A-21 to A-22) were prepared according to the general synthetic procedure described for Intermediate A-20 using the appropriate isatin and organometallic reagent.

TABLE 4

| Intermediate | Structure | Name | HPLC RT (min) | LC/MS [M + H]$^+$ |
|---|---|---|---|---|
| A-21 | (structure) | (2-amino-3-chlorophenyl)(3-cyclopropylphenyl)methanone | 3.69[1] | 272 |
| A-22 | (structure) | (2-amino-3-bromophenyl)(phenyl)methanone | 1.89[2] | 330 |

[1] MeOH/$H_2O$/0.1% TFA, Waters Sunfire C18 3.5 μm, 2.1 × 30 mm, 1 mL/min, 4 min gradient, wavelength = 254 nm.
[2] $H_2O$/$CH_3CN$ with TFA, Sunfire C18 3.5 μm, 2.1 × 30 mm, gradient = 4 min, wavelength = 220 nm.

Intermediate A-23: (2-Aminophenyl)(m-tolyl)methanone

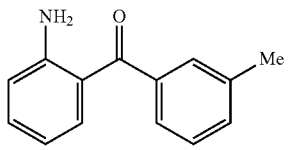
(A-23)

To a 250 mL round-bottomed flask charged with magnesium (0.947 g, 39.0 mmol) and diethyl ether (50.0 ml) was added 2 drops of dibromoethane. The reaction mixture was heated to 60° C. for 5 min and then removed from the heat. Next, 1-bromo-3-methylbenzene (5 g, 29.2 mmol) in diethyl ether (50 ml) was added slowly in portions until reflux was achieved. The remaining bromide was added dropwise to maintain reflux. After the addition, the reaction mixture was refluxed for 3 hrs. Next, 2-aminobenzonitrile (1.151 g, 9.74 mmol) in diethyl ether (50.0 ml) was added slowly over 10 min. The resulting mixture was refluxed overnight. The volume of the reaction mixture was reduced to ⅓ and 100 g of crushed ice and 50 ml of 6N HCl was added while stirring. After 3 hrs at room temperature, the pH was adjusted to pH 8 with 5N NaOH and the reaction was diluted with sat NaHCO$_3$ (50 mL). The two phases were separated and the aqueous layer was extracted with ethyl acetate (2×200 mL). The combined organic layers were dried with MgSO$_4$, filtered and concentrated. The crude material was purified by flash chromatography (Teledyne ISCO CombiFlash Rf, 0% to 70% solvent A/B=ethyl acetate/heptane, REDISEP® SiO$_2$ 80 g) to provide Intermediate A-23 (1.84 g, 89%). $^1$H NMR (400 MHz, DMSO-d$_6$) δ 7.44-7.23 (m, 6H), 7.08 (br. s., 2H), 6.86 (d, J=8.1 Hz, 1H), 6.50 (t, J=7.5 Hz, 1H), 2.38 (s, 3H).

The compounds listed below in Table 5 (Intermediates A-24 to A-27) were prepared according to the general synthetic procedure described for Intermediate A-23, using the appropriate aryl halide and aryl nitrile.

TABLE 5

| Intermediate | Structure | Name | HPLC RT[1] min. | LC/MS [M + H]+ |
|---|---|---|---|---|
| A-24 | 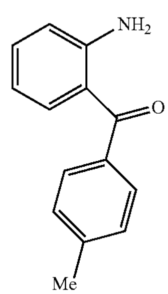 [SMILES: Cc1ccc(C(=O)c2ccccc2N)cc1] | (2-aminophenyl)(p-tolyl)methanone | 1.90 | 212 |
| A-25 | 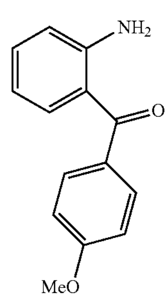 [SMILES: COc1ccc(C(=O)c2ccccc2N)cc1] | (2-aminophenyl)(4-methoxyphenyl)methanone | 1.73 | 228 |
| A-26 | 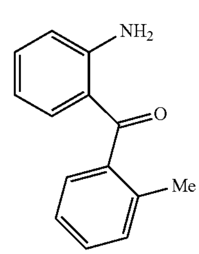 [SMILES: Cc1ccccc1C(=O)c1ccccc1N] | (2-aminophenyl)(o-tolyl)methanone | 1.90 | 212 |

TABLE 5-continued

| Intermediate | Structure | Name | HPLC RT[1] min. | LC/MS [M + H]+ |
|---|---|---|---|---|
| A-27 | 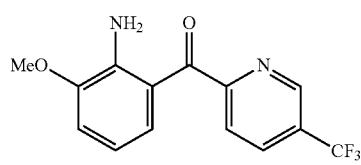 | (2-aminophenyl)(4-(((tert-butyldimethylsilyl)oxy)methyl)phnyl)methanone | 2.55 | 342 |

[1]H$_2$O/CH$_3$CN with TFA, Sunfire C18 3.5 μm, 2.1 x 30 mm, gradient = 2 min, wavelength = 220 nm.

Intermediate A-28: (2-Amino-3-methoxyphenyl)(5-(trifluoromethyl)pyridin-2-yl)methanone (A-28)

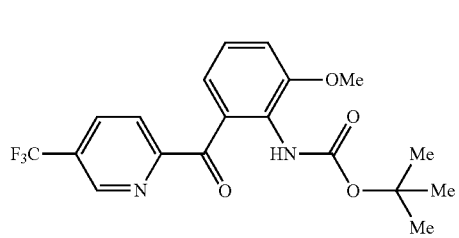

Intermediate A-28A: tert-Butyl(2-methoxy-6-(5-(trifluoromethyl)picolinoyl)phenyl)carbamate (A-28A)

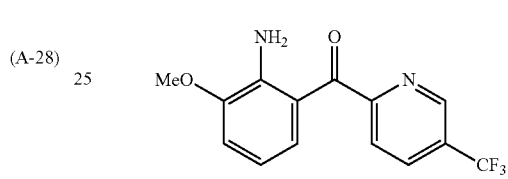

To a cold (−23° C.), stirred solution of tert-butyl 2-methoxyphenylcarbamate (443.3 mg, 1.986 mmol) in ether (5 mL) under N$_2$ was added t-BuLi (2.6 mL, 4.42 mmol). The reaction mixture was stirred for 2 h, and then cooled to −78° C. To the reaction mixture was added a solution of methyl 5-(trifluoromethyl)picolinate (501.3 mg, 2.44 mmol) in ether (10 mL) dropwise via cannula over 5 min. After 2 h, the reaction mixture was warmed to room temperature, stirred for an additional hour, and then the reaction was quenched by the addition of water with vigorous stirring. The reaction mixture was diluted with EtOAc, the organic phase was separated, washed with sat NaCl then dried (Na$_2$SO$_4$), filtered and concentrated to yield a yellow solid. The residue was purified by flash chromatography (Teledyne ISCO CombiFlash Rf, 0% to 100% solvent A/B=hexane/EtOAc, REDISEP® SiO$_2$ 40 g) to obtained Intermediate A-28A (546.8 mg, 69.5% yield)) as a yellow solid: $^1$H NMR (400 MHz, chloroform-d) δ ppm 8.83-8.88 (1H, m), 8.24 (1H, d, J=8.4 Hz), 8.07 (1H, dd, J=8.4, 1.8 Hz), 7.25 (1H, d, J=1.5 Hz), 7.18-7.24 (1H, m), 7.09 (1H, dd, J=8.0, 1.7 Hz), 6.95 (1H, s), 3.93 (3H, s), 1.25 (9H, s).

Intermediate A-28

(A-28)

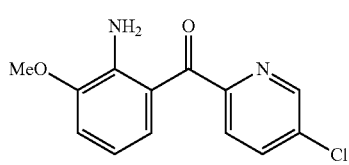

To a stirred solution of Intermediate A-28A (545 mg, 1.375 mmol) in DCM (15 mL) was added TFA (0.106 mL, 1.375 mmol). After 2 h, the reaction mixture was diluted with toluene (30 mL) and then concentrated. The residue was purified by flash chromatography (Teledyne ISCO CombiFlash Rf, 0% to 20% solvent A/B=DCM/MeOH, REDISEP® SiO$_2$ 40 g, loaded as DCM solution) to provide the product Intermediate A-28 (376.8 mg, 93% yield)): $^1$H NMR (400 MHz, chloroform-d) δ ppm 8.94-8.99 (1H, m), 8.11 (1H, dt, J=8.1, 1.1 Hz), 7.86 (1H, d, J=8.1 Hz), 7.17 (1H, dd, J=8.4, 1.1 Hz), 6.89 (1H, dd, J=7.9, 1.1 Hz), 6.55 (1H, m, J=16.1 Hz), 3.92 (3H, s).

Intermediate A-29: (2-Amino-3-methoxyphenyl)(5-chloropyridin-2-yl)methanone (A-29)

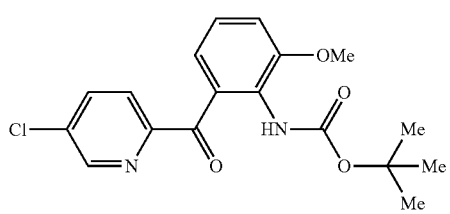

Intermediate A-28A: tert-Butyl(2-(5-chloropicolinoyl)-6-methoxyphenyl)carbamate (A-29A)

To a cold (−23° C.), stirred solution of tert-butyl 2-methoxyphenylcarbamate (548 mg, 2.454 mmol) in ether (6 mL) under $N_2$ was added t-BuLi (3.2 mL, 5.44 mmol). After stirring for 2.5 h, the reaction mixture was cooled to −78° C. To the reaction mixture was added a solution of ethyl 5-chloropicolinate (564.5 mg, 3.04 mmol) in ether (12 mL) dropwise via cannula over 5 min. The reaction mixture was stirred for 60 min, and then warmed to room temperature. After 1.5 h, to the reaction mixture was added $H_2O$ with vigorous stirring. The reaction mixture was diluted with EtOAc, and the organic phase was separated, washed with sat NaCl then dried ($Na_2SO_4$), filtered and concentrated to yield the product Intermediate A-29A (511.5 mg, 57.4% yield)) as a yellow solid: $^1H$ NMR (400 MHz, chloroform-d) δ ppm 8.55 (1H, dd, J=2.3, 0.6 Hz), 8.08 (1H, dd, J=8.4, 0.7 Hz), 7.80 (1H, dd, J=8.4, 2.4 Hz), 7.16-7.25 (2H, m), 7.06 (1H, dd, J=7.5, 2.2 Hz), 6.90 (1H, s), 3.92 (3H, s), 1.28 (9H, s).

Intermediate A-29

To a stirred solution of Intermediate A-29A (511.5 mg, 1.410 mmol) in DCM (14 mL) was added TFA (14 mL, 182 mmol). After 60 min, the reaction mixture was concentrated in vacuo, redissolved in DCM, washed with sat. $NaHCO_3$, dried ($MgSO_4$), filtered and concentrated to provide Intermediate A-29 (402.1 mg, 100% yield)) as an amber solid: HPLC RT=2.763 min. (Waters Sunfire C18 2.5 μm 2.1×30 mm, MeOH/$H_2O$/TFA, 4 min gradient, wavelength=254 nm), $^1H$ NMR (400 MHz, chloroform-d) δ ppm 8.66 (1H, dd, J=2.4, 0.7 Hz), 7.85 (1H, dd, J=8.4, 2.4 Hz), 7.75 (1H, dd, J=8.4, 0.7 Hz), 7.25 (1H, dd, J=8.4, 1.1 Hz), 6.89 (1H, dd, J=7.7, 1.1 Hz), 6.55 (1H, dd, J=8.3, 7.8 Hz), 4.74 (2H, br. s.), 3.91 (3H, s). MS(ES): m/z=263 [M+H$^+$].

Intermediate B-1: (S)-3-Amino-5-(3-fluorophenyl)-9-methyl-1H-benzo[e][1,4]diazepin-2(3H)-one

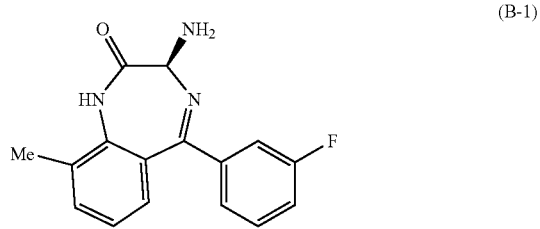 [SMILES: Cc1cccc2c1NC(=O)[C@@H](N)N=C2c1cccc(F)c1]

(B-1)

Intermediate B-1A: (S)-Benzyl(5-(3-fluorophenyl)-9-methyl-2-oxo-2,3-dihydro-1H-benzo[e][1,4]diazepin-3-yl)carbamate

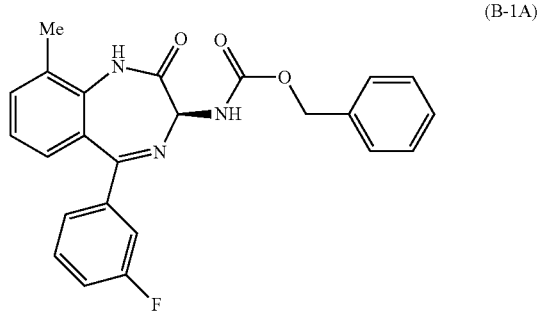 [SMILES: Cc1cccc2c1NC(=O)[C@@H](NC(=O)OCc1ccccc1)N=C2c1cccc(F)c1]

(B-1A)

In a 1 L round-bottomed flask, a solution of 2-(1H-benzo[d][1,2,3]triazol-1-yl)-2-((phenoxycarbonyl)amino)acetic acid (*J. Org. Chem.*, 55:2206-2214 (1990)) (19.37 g, 62.0 mmol) in THF (135 mL) was cooled in an ice/water bath and treated with oxalyl chloride (5.43 mL, 62.0 mmol) and 4 drops of DMF. The reaction mixture was stirred for 4 hours. Next, a solution of Intermediate A-1 (7.11 g, 31.0 mmol) in THF (35 mL) was added and the resulting solution was removed from the ice/water bath and stirred at room temperature for 1.5 hours. The mixture was then treated with a solution of ammonia, (7M in MeOH) (19.94 mL, 140 mmol). After 15 mins, another portion of ammonia, (7M in MeOH) (19.94 mL, 140 mmol) was added and the resulting mixture was sealed under $N_2$ and stirred overnight at room temperature. The reaction mixture was then concentrated to ~½ volume and then diluted with AcOH (63 mL) and stir at room temperature for 4 hours. The reaction mixture was then concentrated, and the residue was diluted with 500 mL water to give a precipitate. Hexane and $Et_2O$ were added and the mixture was stirred at room temperature for 1 hour to form an orange solid. $Et_2O$ was removed under a stream of nitrogen and the aqueous layer was decanted. The residue was triturated with 40 mL of iPrOH and stirred at room temperature to give a white precipitate. The solid was filtered and washed with iPrOH, then dried on a filter under a stream of nitrogen to give racemic Intermediate B-1A (5.4 g, 41.7% yield).

Racemic Intermediate B-1A (5.9 g, 14.3 mmol) was resolved using the Chiral SFC conditions described below. The desired stereoisomer was collected as the second peak in the elution order: Instrument: Berger SFC MGIII, Column: CHIRALPAK® IC 25×3 cm, 5 cm; column temp: 45° C.; Mobile Phase: $CO_2$/MeOH (45/55); Flow rate: 160 mL/min; Detection at 220 nm.

After evaporation of the solvent, Intermediate B-1A (2.73 g, 46% yield) was obtained as a white solid. HPLC: RT=3.075 min. ($H_2O$/MeOH with TFA, CHROMOLITH® ODS S5 4.6×50 mm, gradient=4 min, wavelength=220 nm). Chiral HPLC RT: 8.661 min (AD, 60% (EtOH/MeOH)/heptane) >99% ee. MS(ES): m/z=418.3 [M+H$^+$]; $^1H$ NMR (500 MHz, DMSO-$d_6$) δ 10.21 (s, 1H), 8.38 (d, J=8.3 Hz, 1H), 7.57-7.47 (m, 2H), 7.41-7.29 (m, 8H), 7.25-7.17 (m, 2H), 5.10-5.04 (m, 3H), 2.42 (s, 3H).

Intermediate B-1: (S)-3-Amino-5-(3-fluorophenyl)-9-methyl-1H-benzo[e][1,4]diazepin-2(3H)-one In a 100 mL round-bottomed flask, a solution of Intermediate B-1A (2.73 g, 6.54 mmol) in acetic acid (12 mL) was treated with HBr, 33% in HOAc (10.76 mL, 65.4 mmol) and the mixture was stirred at room temperature for 1 hour. The solution was diluted with $Et_2O$ to give a yellow precipitate. The yellow solid was filtered and rinsed with $Et_2O$ under nitrogen. The solid was transferred to 100 mL round bottom flask and water was added (white precipitate formed). The slurry was slowly made basic with saturated $NaHCO_3$. The resulting tacky precipitate was extracted with EtOAc. The organic layer was washed with water, dried over $MgSO_4$, and then filtered and concentrated to dryness to give Intermediate B-1 (1.68 g, 91% yield) as a white foam solid. MS(ES): m/z=284.2 [M+H$^+$]; HPLC: RT=1.72 min ($H_2O$/MeOH with TFA, CHROMOLITH® ODS S5 4.6×50 mm, gradient=4 min, wavelength=220 nm). $^1H$ NMR (400 MHz, DMSO-$d_6$) δ 10.01 (br. s., 1H), 7.56-7.44 (m, 2H), 7.41-7.26 (m, 3H), 7.22-7.11 (m, 2H), 4.24 (s, 1H), 2.55 (br. s., 2H), 2.41 (s, 3H).

The compounds listed below in Table 6 (Intermediates B-2 to B-3) were prepared according to the general synthetic procedure described for Intermediate B-1, using the starting materials Intermediate A-10 and Intermediate A-4, respectively.

TABLE 6

| Intermediate | Structure | Name | HPLC RT (min.) | LC/MS [M + H]+ |
|---|---|---|---|---|
| B-2[a] | Me, Me structure with NH2, Cl | (S)-3-amino-5-(3-chlorophenyl)-9-isopropyl-1H-benzo[e][1,4]diazepin-2(3H)-one | 2.61[1] | 328 |
| B-3[b] | Me structure with NH2, Cl | (S)-3-amino-5-(3-chlorophenyl)-9-methyl-1H-benzo[e][1,4]diazepin-2(3H)-one | 0.73[2] | 330.1 |

[1]MeOH/H$_2$O/0.1% TFA, Waters Sunfire C18 3.5 µm, 2.1 × 30 mm, 1 mL/min, 4 min gradient, wavelength = 254 nm.
[2]H$_2$O/CH$_3$CN with 0.05% TFA, BEH C18 1.7 µm, 2.1 × 50 mm, gradient (2%-98%) = 1 min, wavelength = 220 nm.
Chiral Separation Conditions:
[a]Instrument: Berger SFC MGIII; Column: Lux Cell-4, 250 × 30 mm ID, 5 µm, column temp: 45° C.; Mobile Phase: CO$_2$/MeOH (70/30); Flow Rate: 200 mL/min; Detection 220 nm.
[b]Instrument: Berger SFC MGIII; Column: CHIRALPAK ® IC 25 × 3 cm, 5 µm; column temp: 45° C.; Mobile Phase: CO$_2$/MeOH (55/45); Flow rate: 180 mL/min; Detection at 220 nm.

Intermediate B-4: (S)-3-Amino-9-methyl-5-phenyl-1H-benzo[e][1,4]diazepin-2(3H)-one

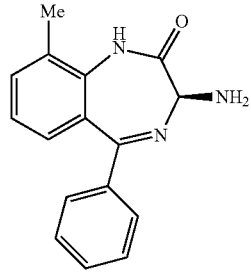

(B-4)

Intermediate B-4A: (S)-Benzyl(9-methyl-2-oxo-5-phenyl-2,3-dihydro-1H-benzo[e][1,4]diazepin-3-yl)carbamate

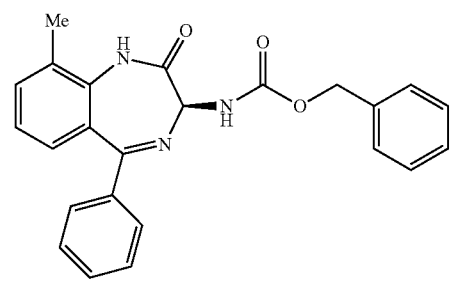

(B-4A)

A mixture of 2-(1H-benzo[d][1,2,3]triazol-1-yl)-2-(((benzyloxy)carbonyl)amino)acetic acid (5.50 g, 16.87 mmol) was suspended in THF (40.9 mL) and cooled to 0° C. Oxalyl chloride (1.477 ml, 16.87 mmol) was added, followed by the addition of 50 µL of DMF. Gas evolution was observed. After 2 h, a solution of Intermediate A-9 (1.62 g, 7.67 mmol) and N-methylmorpholine (2.53 ml, 23.00 mmol) in THF (20 mL) was added, and the reaction mixture was allowed to warm gradually. After 3.5 h, ammonia (7 M in MeOH) (21.29 ml, 149 mmol) was added and the reaction mixture was allowed to stir at room temperature overnight. To this mixture was added 5 mL of 7M ammonia and the reaction mixture was stirred for 5 hours. The mixture was then diluted with EtOAc, washed with H$_2$O, 1 M NaOH, and brine. The organic layer was concentrated and then suspended in acetic acid (15.34 ml) and ammonium acetate (2.96 g, 38.3 mmol) was added. After 4.5 hours, H$_2$O was added to precipitate the product. The precipitate was collected by filtration, washed with water, and air dried to afford Intermediate B-4A (2.48 g, 81%). HPLC: RT=1.01 min (H$_2$O/CH$_3$CN with TFA, BEH C18 1.75 µm, 2.1×50 mm, gradient=2 min, wavelength=220 nm); MS(ES): m/z=400.3 [M+H]+.

Racemic Intermediate B-4A (10.8 g, 27.0 mmol) was resolved using the Chiral SFC conditions described below. The desired stereoisomer was collected as the first peak in the elution order: Instrument: Berger SFC MGIII, Column: OJ-H 25×3 cm, 5 cm; column temp: 45° C.; Mobile Phase: CO$_2$/MeOH (70/30); Flow rate: 200 mL/min; Detection at 220 nm. After evaporation of the solvent, Intermediate B-4A (2.67 g, 6.68 mmol) was obtained as a white solid. HPLC: RT=2.761 min (H$_2$O/MeOH with TFA, CHROMOLITH® SpeedROD 4.6×50 mm, gradient=4 min, wavelength=220 nm). MS(ES): m/z=400.3 [M+H]$^+$.

Intermediate B-4

A solution of Intermediate B-4A (2.6 g, 6.51 mmol) in 33% HBr in HOAc (10.71 ml, 65.1 mmol) was stirred at room temperature for 2 h. Diethyl ether was added, and the resulting yellow solid was collected by filtration and rinsed with ether. The hygroscopic solid was dissolved in MeOH, concentrated and dried under vacuum to afford Intermediate B-4 (2.59 g, 93%). HPLC: RT=1.433 min (H$_2$O/MeOH with TFA, CHROMOLITH® SpeedROD 4.6×50 mm, gradient=4 min, wavelength=220 nm). MS(ES): m/z=266.0 [M+H]$^+$.

Intermediate B-5: 3-Amino-5-(4-(((tert-butyldimethylsilyl)oxy)methyl)phenyl)-1H-benzo[e][1,4]diazepin-2(3H)-one

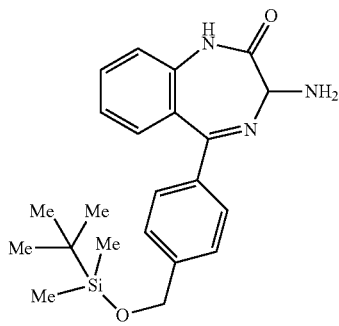

(B-5)

Intermediate B-5A: Benzyl(5-(4-(((tert-butyldimethylsilyl)oxy)methyl)phenyl)-2-oxo-2,3-dihydro-1H-benzo[e][1,4]diazepin-3-yl)carbamate

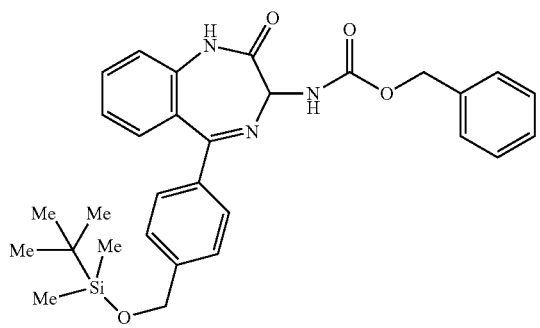

(B-5A)

In a 100 mL round-bottomed flask, a suspension of 2-(1H-benzo[d][1,2,3]triazol-1-yl)-2-(benzyloxycarbonylamino)acetic acid (0.952 g, 2.92 mmol) and Intermediate A-27 (0.83 g, 2.430 mmol) in DCM (20 mL) was treated with a solution of DCC (0.602 g, 2.92 mmol) in DCM (5 mL). The reaction mixture was stirred at room temperature under nitrogen overnight. To the reaction mixture was added saturated Na$_2$CO$_3$ (25 mL) and the mixture was stirred at room temperature for 1 h. The suspension was filtered, the layers were separated and the organic phase was concentrated to dryness. The crude reaction mixture was diluted with MeOH (10 mL) and 2N ammonia in methanol (14.58 mL, 29.2 mmol) was added. The reaction mixture was then stirred at room temperature overnight. AcOH (13.91 mL, 243 mmol) was then added directly to the reaction mixture and the mixture was stirred at room temperature under nitrogen for 72 hrs. The pH of the reaction was adjusted to pH 12 with saturated NaHCO$_3$. The reaction mixture was partitioned between DCM (100 mL) and brine (50 mL). The aqueous layer was back extracted with DCM (2×50 mL). The combined organic phases were dried with Na$_2$SO$_4$, filtered and concentrated under reduced pressure. The crude material was purified by flash chromatography (Teledyne ISCO CombiFlash Rf, 0% to 75% solvent A/B=ethyl acetate/heptane, REDISEP® SiO$_2$ 80 g). Concentration of appropriate fractions provided a sample that was purified again by flash chromatography (Teledyne ISCO CombiFlash Rf, 0% to 60% solvent A/B=ethyl acetate/heptane, REDISEP® SiO$_2$ 40 g). Concentration of the appropriate fractions provided Intermediate B-5A (0.368 g, 29%). LC/MS RT=2.472 min 10/90 to 90/10 (MeOH/H$_2$O/0.1% TFA, Waters Sunfire C18 3.5 μm, 2.1×30 mm, 1 mL/min, 2 min gradient, wavelength=220 nm); MS(ES): m/z=530 [M+1]; $^1$H NMR (400 MHz, DMSO-d$_6$) δ 10.84 (s, 1H), 8.39 (d, J=8.6 Hz, 1H), 7.64 (t, J=7.7 Hz, 1H), 7.50-7.43 (m, 1H), 7.43-7.28 (m, 10H), 7.29-7.21 (m, 1H), 5.09 (s, 1H), 5.05 (d, J=8.4 Hz, 1H), 4.98 (s, 1H), 4.78 (s, 2H), 0.95-0.88 (m, 9H), 0.13-0.03 (m, 6H).

Intermediate B-5

A solution of Intermediate B-5A (330 mg, 0.623 mmol) in ethyl acetate (20 mL) was treated with 20% Pd/C (50% water) (200 mg, 0.623 mmol) to give a suspension. The reaction mixture was purged 3 times with vacuum and nitrogen then purged three times with vacuum and hydrogen. The mixture was stirred under a hydrogen atmosphere for 4 hrs. The reaction mixture was filter on CELITE® and the filtrate was concentrated under reduced pressure to afford Intermediate B-5 (0.190 g, 77%). HPLC: RT=2.0.3 min (H$_2$O/CH$_3$CN with TFA, Sunfire C18 3.5 μm, 2.1×30 mm, gradient=2 min, wavelength=220 nm). LC/MS: M+H=396; $^1$H NMR (400 MHz, DMSO-d$_6$) δ 10.66 (br. s., 1H), 7.59 (ddd, J=8.3, 7.1, 1.5 Hz, 1H), 7.49-7.43 (m, 2H), 7.41-7.34 (m, 2H), 7.30-7.24 (m, 3H), 7.24-7.17 (m, 1H), 4.77 (s, 1H), 4.71 (s, 1H), 4.24 (s, 2H), 0.94-0.91 (m, 9H), 0.10 (s, 6H).

The compounds listed below in Table 7 (Intermediates B-6 to B-26) were prepared according to the general synthetic procedure described for Intermediate B-1 and Intermediates B-4 through B-5, using the indicated starting material.

TABLE 7
| Intermediate | Structure | Name | HPLC RT (min) | LC/MS [M + H]+ | Starting Material |
|---|---|---|---|---|---|
| B-6 | 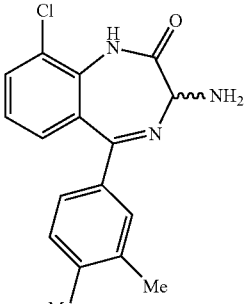 | 3-amino-9-chloro-5-(3,4-dimethylphenyl)-1H-benzo[e][1,4]diazepin-2(3H)-one | 0.73[1] | 314 | A-2 |
| B-7 | 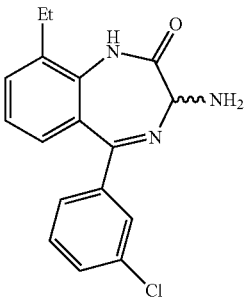 [SMILES: CCc1cccc2c1NC(=O)C(N)N=C2c1cccc(Cl)c1] | 3-amino-5-(3-chlorophenyl)-9-ethyl-1H-benzo[e][1,4]diazepin-2(3H)-one | 2.24[2] | 314.11 | A-11 |
| B-8 | 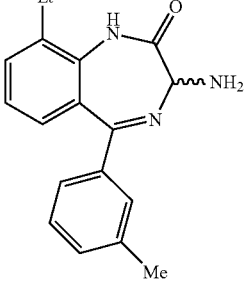 | 3-amino-9-ethyl-5-(m-tolyl)-1H-benzo[e][1,4]diazepin-2(3H)-one | 2.33[2] | 294.13 | A-12 |
| B-9 | 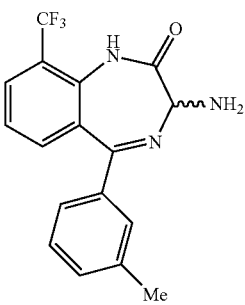 [SMILES: Cc1cccc(C2=NC(N)C(=O)Nc3c(Cl)cccc32)c1] | 3-amino-5-(m-tolyl)-9-(trifluoromethyl)-1H-benzo[e][1,4]diazepin-2(3H)-one | 1.84[3] | 334.3 | A-5 |
| B-10 | 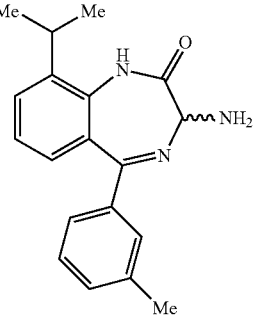 | 3-amino-9-isopropyl-5-(m-tolyl)-1H-benzo[e][1,4]diazepin-2(3H)-one | 2.51[2] | 308 | A-13 |

TABLE 7-continued

| Intermediate | Name | HPLC RT (min) | LC/MS [M + H]+ | Starting Material |
|---|---|---|---|---|
| B-11 | 3-amino-9-isopropyl-5-phenyl-1H-benzo[e][1,4]diazepin-2(3H)-one | 2.29[2] | 294 | A-14 |
| B-12 | 3-amino-9-cyclopropoxy-5-(m-tolyl)-1H-benzo[e][1,4]diazepin-2(3H)-one | 2.36[2] | 333.08 | A-15 |
| B-13 | 3-amino-9-cyclopropoxy-5-phenyl-1H-benzo[e][1,4]diazepin-2(3H)-one | 2.18[2] | 308.14 | A-6 |
| B-14 | 3-amino-9-chloro-5-(m-tolyl)-1H-benzo[e][1,4]diazepin-2(3H)-one | 1.47[4] | 300 | A-18 |

TABLE 7-continued

| Intermediate | Structure | Name | HPLC RT (min) | LC/MS [M + H]+ | Starting Material |
|---|---|---|---|---|---|
| B-15 | 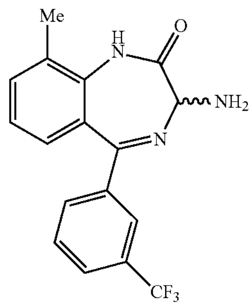 [SMILES: Cc1cccc2c1NC(=O)C(N)N=C2c1cccc(C(F)(F)F)c1] | 3-amino-9-methyl-5-(3-(trifluoromethyl)phenyl)-1H-benzo[e][1,4]diazepin-2(3H)-one | 0.73[6] | 334.0 | A-7 |
| B-16 | 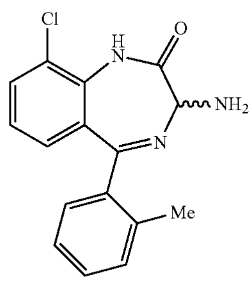 [SMILES: Cc1ccccc1C1=NC(N)C(=O)Nc2c(Cl)cccc21] | 3-amino-9-chloro-5-(o-tolyl)-1H-benzo[e][1,4]diazepin-2(3H)-one | 1.78[7] | 300 | A-20 |
| B-17 | 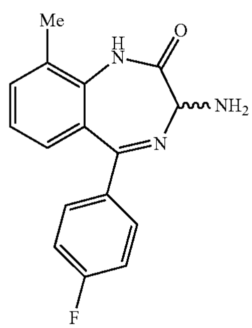 [SMILES: Cc1cccc2c1NC(=O)C(N)N=C2c1ccc(F)cc1] | 3-amino-5-(4-fluorophenyl)-9-methyl-1H-benzo[e][1,4]diazepin-2(3H)-one | 0.65[6] | 284.0 | A-8 |
| B-18 | 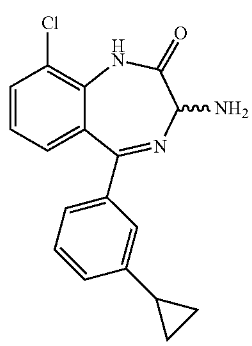 [SMILES: NC1N=C(c2cccc(C3CC3)c2)c2cccc(Cl)c2NC1=O] | 3-amino-9-chloro-5-(3-cyclopropylphenyl)-1H-benzo[e][1,4]diazepin-2(3H)-one | 2.29[2] | 326.12 | A-21 |
| B-19 | 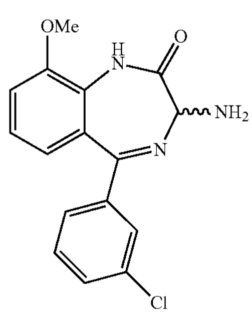 [SMILES: COc1cccc2c1NC(=O)C(N)N=C2c1cccc(Cl)c1] | 3-amino-5-(3-chlorophenyl)-9-methoxy-1H-benzo[e][1,4]diazepin-2(3H)-one | 2.18[4] | 316 | A-16 |

TABLE 7-continued
| Intermediate | Structure | Name | HPLC RT (min) | LC/MS [M + H]+ | Starting Material |
|---|---|---|---|---|---|
| B-20 | 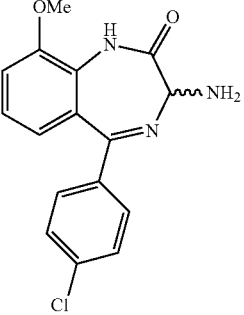 [SMILES: COc1cccc2c1NC(=O)C(N)N=C2c1ccc(Cl)cc1] | 3-amino-5-(4-chlorophenyl)-9-methoxy-1H-benzo[e][1,4]diazepin-2(3H)-one | 2.23[4] | 316 | A-17 |
| B-21 | 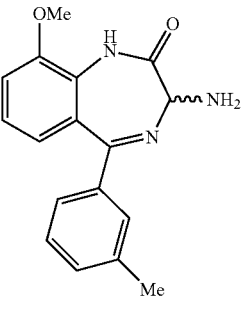 [SMILES: COc1cccc2c1NC(=O)C(N)N=C2c1cccc(C)c1] | 3-amino-9-methoxy-5-(m-tolyl)-1H-benzo[e][1,4]diazepin-2(3H)-one | 1.45[4] | 296 | A-19 |
| B-22 | 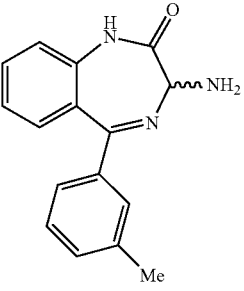 [SMILES: Cc1cccc(C2=NC(N)C(=O)Nc3ccccc32)c1] | 3-amino-5-(m-tolyl)-1H-benzo[e][1,4]diazepin-2(3H)-one | 1.39[4] | 266 | A-23 |
| B-23 | 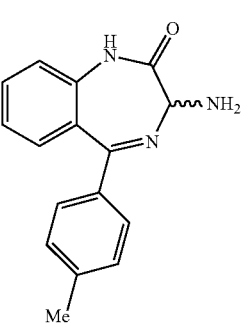 [SMILES: Cc1ccc(C2=NC(N)C(=O)Nc3ccccc32)cc1] | 3-amino-5-(p-tolyl)-1H-benzo[e][1,4]diazepin-2(3H)-one | 1.38[4] | 266 | A-24 |

TABLE 7-continued

| Intermediate | Structure | Name | HPLC RT (min) | LC/MS [M + H]+ | Starting Material |
|---|---|---|---|---|---|
| B-24 | 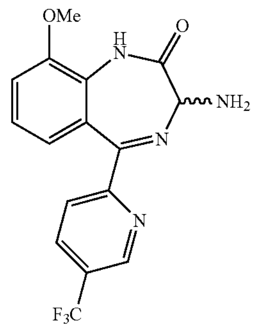 [SMILES: COc1cccc2c1NC(=O)C(N)N=C2c1ccc(C(F)(F)F)cn1] | 3-amino-9-methoxy-5-(5-(trifluoromethyl)pyridin-2-yl)-1H-benzo[e][1,4]diazepin-2(3H)-one | 1.79[5] | 351 | A-28 |
| B-25 | 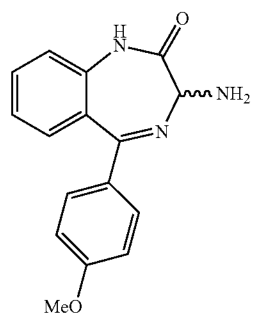 [SMILES: COc1ccc(C2=NC(N)C(=O)Nc3ccccc32)cc1] | 3-amino-5-(4-methoxyphenyl)-1H-benzo[e][1,4]diazepin-2(3H)-one | 1.28[4] | 282 | A-25 |
| B-26 | 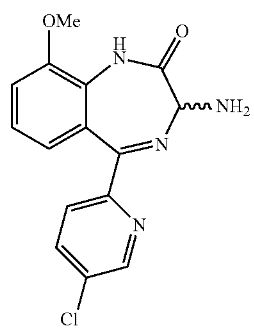 [SMILES: COc1cccc2c1NC(=O)C(N)N=C2c1ccc(Cl)cn1] | 3-amino-5-(5-chloropyridin-2-yl)-9-methoxy-1H-benzo[e][1,4]diazepin-2(3H)-one | 1.58[5] | 317 | A-29 |
| B-27 | 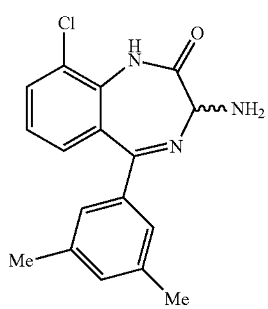 [SMILES: Cc1cc(C)cc(C2=NC(N)C(=O)Nc3c(Cl)cccc32)c1] | 3-amino-9-chloro-5-(3,5-dimethylphenyl)-1H-benzo[e][1,4]diazepin-2(3H)-one | 0.72[1] | 314 | A-3 |

[1]$H_2O/CH_3CN$ with TFA, BEH C18 1.75 μm, 2.1 × 50 mm, gradient = 2 min, wavelength = 220 nm.
[2]$MeOH/H_2O/0.1\%$ TFA, Waters Sunfire C18 3.5 μm, 2.1 × 30 mm, 1 mL/min, 4 min gradient, wavelength = 254 nm.
[3]$H_2O/MeOH$ with 0.1% TFA, Luna C18 3 μm, 4.6 × 30 mm, gradient = 3.5 min, wavelength = 220 nm.
[4]$H_2O/CH_3CN$ with TFA, Sunfire C18 3.5 μm, 2.1 × 30 mm, gradient = 2 min, wavelength = 220 nm.
[5]Waters Sunfire C18 2.1 × 30 mm 3.5 μm; $H_2O/MeOH/TFA$, gradient = 4 min, wavelength = 254 nm.
[6]$H_2O/CH_3CN$ with 0.05% TFA, BEH C18 1.7 μm, 2.1 × 50 mm, gradient (2%-98%) = 1 min, wavelength = 220.
[7]$H_2O/MeOH$ with TFA, CHROMOLITH® ODS S5, 4.6 × 50 mm, gradient = 4 min, wavelength = 220 nm.

Intermediate B-28: 3-Amino-9-cyclopropyl-5-phenyl-1H-benzo[e][1,4]diazepin-2(3H)-one

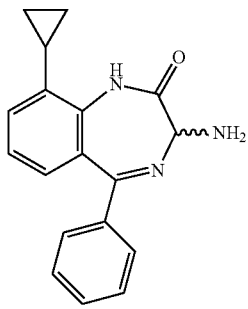

(B-28)

Intermediate B-28A: Benzyl(9-bromo-2-oxo-5-phenyl-2,3-dihydro-1H-benzo[e][1,4]diazepin-3-yl)carbamate

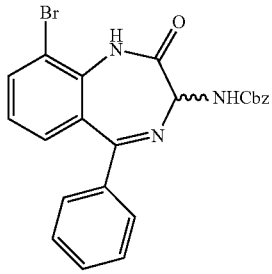

(B-28A)

Intermediate B-28A was prepared from Intermediate A-22 by the general procedures given for Intermediate B-1. HPLC: RT=2.048 min (H₂O/MeOH with TFA, Ascentis Express C18 2.7 μm, 2.1×50 mm, gradient=4 min, wavelength=220 nm); MS(ES): m/z=464 [M+H⁺].

Intermediate B-28B: Benzyl(9-cyclopropyl-2-oxo-5-phenyl-2,3-dihydro-1H-benzo[e][1,4]diazepin-3-yl)carbamate

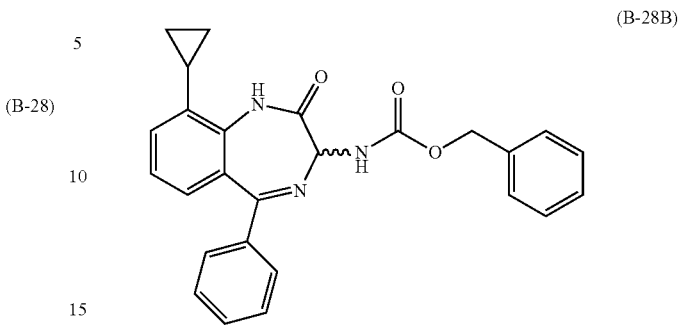

(B-28B)

To a stirred mixture of Intermediate B-28A (2.00 g, 4.31 mmol), Pd(dppf)₂Cl₂ (946 mg, 1.29 mmol), potassium phosphate dibasic (2.25 g, 12.9 mmol) and cyclopropylboronic acid methyliminodiacetic acid ester (1.70 g, 8.61 mmol) in dioxane (12 mL) under nitrogen was added water (3 mL). The reaction mixture was heated at 85° C. for 20 h and then cooled to room temperature. The mixture was diluted with EtOAc (40 mL) and filtered through a 1 inch pad of silica gel that was topped by a ½ inch pad of CELITE®. This was further eluted with EtOAc. The filtrate was concentrated under reduced pressure and purified by flash chromatography (Teledyne ISCO CombiFlash 0% to 17% solvent A/B=DCM/acetone, REDISEP® SiO₂ 120 g, detecting at 254 nM, and monitoring at 220 nM). Concentration of the appropriate fractions provided Intermediate B-28B (1.20 g, 65%). HPLC: RT=3.246 min (CHROMOLITH® SpeedROD column 4.6×50 mm, 10-90% aqueous methanol over 4 minutes containing 0.1% TFA, 4 mL/min, monitoring at 220 nm). MS(ES): m/z=426.1 [M+H⁺]; ¹H NMR (400 MHz, DMSO-d₆) δ 10.29 (s, 1H), 8.38 (d, J=8.6 Hz, 1H), 7.57-7.32 (m, 10H), 7.30 (d, J=7.5 Hz, 1H), 7.20 (t, J=7.6 Hz, 1H), 7.11 (d, J=7.3 Hz, 1H), 5.08 (s, 2H), 5.04 (d, J=8.4 Hz, 1H), 2.26-2.13 (m, 1H), 1.09-0.95 (m, 2H), 0.87-0.78 (m, 1H), 0.61-0.52 (m, 1H).

Intermediate B-28

Intermediate B-28 was prepared from Intermediate B-28A by treatment with 33% HBr/acetic acid according to the general procedure detailed for Intermediate B-1. HPLC: RT=2.085 min (CHROMOLITH® SpeedROD column 4 6×50 mm, 10-90% aqueous methanol over 4 minutes containing 0.1% TFA, 4 mL/min, monitoring at 220 nm). LC/MS: M+H=292.1. ¹H NMR (400 MHz, DMSO-d₆) δ 10.78 (s, 1H), 9.01 (br. s., 3H), 7.65-7.48 (m, 5H), 7.38 (dd, J=7.6, 1.2 Hz, 1H), 7.26 (t, J=7.8 Hz, 1H), 7.19-7.14 (m, 1H), 2.27-2.16 (m, 1H), 1.14-0.98 (m, 2H), 0.91-0.80 (m, 1H), 0.67-0.56 (m, 1H).

The following Intermediates (B-29 to B-30) were prepared by the general methods described for Intermediate B-5 from the indicated starting material.

TABLE 8

| Intermediate | Structure | Name | HPLC RT (min)[1] | LC/MS [M + H]⁺ | Starting Material |
|---|---|---|---|---|---|
| B-29 | 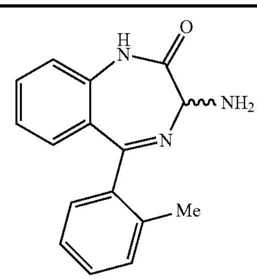 | 3-amino-5-(o-tolyl)-1H-benzo[e][1,4]diazepin-2(3H)-one | 1.33 | 266 | A-26 |

TABLE 8-continued

| Intermediate | Structure | Name | HPLC RT (min)[1] | LC/MS [M + H]+ | Starting Material |
|---|---|---|---|---|---|
| B-30 | 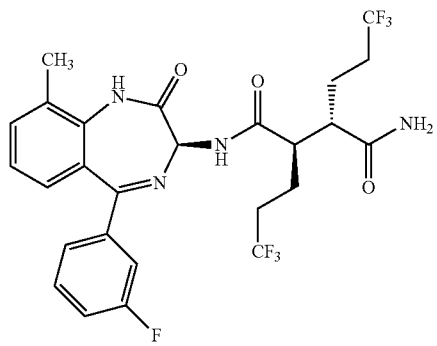 [SMILES: Cc1cccc2c1NC(=O)[C@@H](NC(=O)[C@H](CCC(F)(F)F)[C@H](CCC(F)(F)F)C(N)=O)N=C2c1cccc(F)c1] | 3-amino-5-(4-methoxyphenyl)-1H-benzo[e][1,4]diazepin-2(3H)-one | 1.28 | 282 | A-25 |

[1]$H_2O/CH_3CN$ with TFA, Sunfire C18 3.5 μm, 2.1 × 30 mm, gradient = 2 min, wavelength = 220 nm.

Example 1

(2R,3S)—N-((3S)-5-(3-Fluorophenyl)-9-methyl-2-oxo-2,3-dihydro-1H-1,4-benzodiazepin-3-yl)-2,3-bis(3,3,3-trifluoropropyl)succinamide

Intermediate 1A: (2S,3R)-tert-Butyl 6,6,6-trifluoro-3-(((S)-5-(3-fluorophenyl)-9-methyl-2-oxo-2,3-dihydro-1H-benzo[e][1,4]diazepin-3-yl)carbamoyl)-2-(3,3,3-trifluoropropyl)hexanoate (1A)

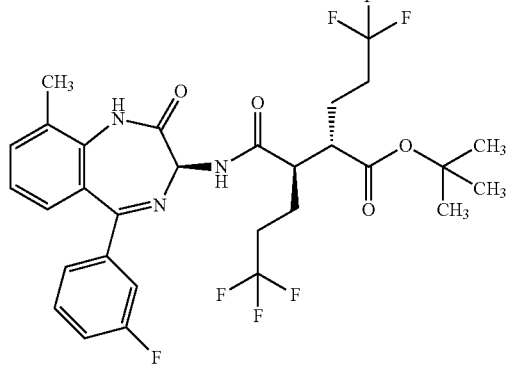

In a 100 mL round-bottomed flask, a solution of Intermediate B-1 (1683 mg, 5.94 mmol), Et₃N (1.656 mL, 11.88 mmol), and Intermediate S-1 in DMF (20 mL) was treated with o-benzotriazol-1-yl-N,N,N',N'-tetramethyluronium tetrafluoroborate (3815 mg, 11.88 mmol) and stirred at room temperature for 1 hour. The reaction mixture was diluted with water and saturated aqueous $NaHCO_3$. An off white precipitate formed and was filtered and washed with water. The resulting solid was dried on the filter under a stream of nitrogen to give Intermediate 1A (3.7 g, 99% yield). MS(ES): m/z=632.4[M+H+]; HPLC: RT=3.635 min Purity=98%. ($H_2O$/MeOH with TFA, CHROMOLITH® ODS S5 4.6×50 mm, gradient=4 min, wavelength=220 nm). $^1H$ NMR (400 MHz, methanol-$d_4$) δ 7.53 (t, J=4.5 Hz, 1H), 7.46-7.30 (m, 3H), 7.28-7.23 (m, 1H), 7.23-7.18 (m, 2H), 5.37 (s, 1H), 2.88 (td, J=10.4, 3.4 Hz, 1H), 2.60 (td, J=10.2, 4.1 Hz, 1H), 2.54-2.40 (m, 1H), 2.47 (s, 3H), 2.33-2.12 (m, 3H), 1.98-1.69 (m, 4H), 1.51 (s, 9H).

Intermediate 1B: (2S,3R)-6,6,6-Trifluoro-3-(((S)-5-(3-fluorophenyl)-9-methyl-2-oxo-2,3-dihydro-1H-benzo[e][1,4]diazepin-3-yl)carbamoyl)-2-(3,3,3-trifluoropropyl)hexanoic acid (1B)

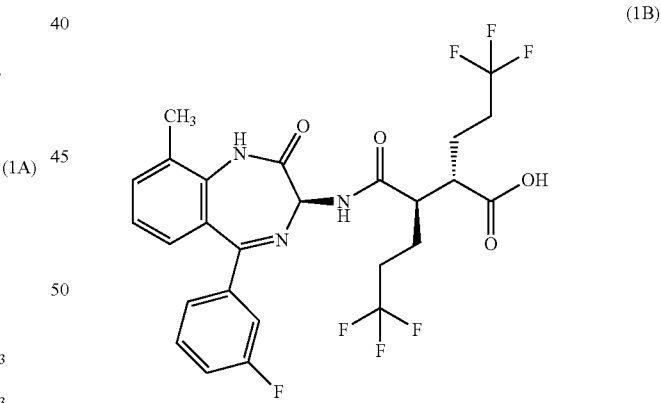

In a 250 mL round-bottomed flask, a solution of Intermediate 1A (3.7 g, 5.86 mmol) in DCM (25 mL) was treated with TFA (25 mL) and the resulting pale orange solution was stirred at room temperature for 1.5 hours. The reaction mixture was then concentrated to give Intermediate 1B. HPLC: RT=3.12 min ($H_2O$/MeOH with TFA, CHROMOLITH® ODS S5 4.6×50 mm, gradient=4 min, wavelength=220 nm). MS(ES): m/z=576.3 (M+H)+. $^1H$ NMR (400 MHz, methanol-$d_4$) δ 7.54 (t, J=4.5 Hz, 1H), 7.49-7.29 (m, 3H), 7.28-7.15 (m, 3H), 5.38 (br. s., 1H), 2.89 (td, J=10.3, 3.7 Hz, 1H), 2.67 (td, J=9.9, 4.2 Hz, 1H), 2.56-2.38 (m, 1H), 2.48 (s, 3H), 2.34-2.13 (m, 3H), 2.00-1.71 (m, 4H).

Example 1

In a 250 mL round-bottomed flask, a solution of Intermediate 1B (4.04 g, 5.86 mmol) in THF (50 mL) was treated with ammonia (2M in iPrOH) (26.4 mL, 52.7 mmol), followed by HOBT (1.795 g, 11.72 mmol) and EDC (2.246 g, 11.72 mmol). The resulting white suspension was stirred at room temperature overnight. The reaction mixture was diluted with water and saturated aqueous NaHCO$_3$. The resulting solid was filtered, rinsed with water and then dried on the filter under a stream of nitrogen. The crude product was suspended in 20 mL of iPrOH and stirred at room temperature for 20 min and then filtered and washed with iPrOH and dried under vacuum to give 2.83 g of solid. The solid was dissolved in refluxing EtOH (100 mL) and slowly treated with 200 mg activated charcoal added in small portions. The hot mixture was filtered through CELITE® and rinsed with hot EtOH. The filtrate was reduced to half volume, allowed to cool and the white precipitate formed was filtered and rinsed with EtOH to give 2.57 g of white solid. A second recrystallization from EtOH (70 mL) afforded Example 1 (2.39 g, 70% yield) as a white solid. HPLC: RT=10.859 min (H$_2$O/CH$_3$CN with TFA, Sunfire C18 3.5 μm, 3.0×150 mm, gradient=15 min, wavelength=220 and 254 nm); MS(ES): m/z=575.3 [M+H$^+$]; $^1$H NMR (400 MHz, methanol-d$_4$) δ 7.57-7.50 (m, 1H), 7.47-7.30 (m, 3H), 7.29-7.15 (m, 3H), 5.38 (s, 1H), 2.85-2.75 (m, 1H), 2.59 (td, J=10.5, 4.0 Hz, 1H), 2.53-2.41 (m, 4H), 2.31-2.10 (m, 3H), 1.96-1.70 (m, 4H).

Example 2

(2R,3S)—N-((3S)-5-(3-Chlorophenyl)-9-ethyl-2-oxo-2,3-dihydro-1H-1,4-benzodiazepin-3-yl)-2,3-bis(3,3,3-trifluoropropyl)succinamide

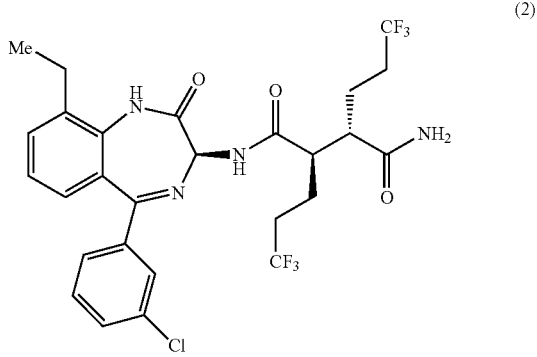

(2)

Intermediate 2A: (2S,3R)-tert-Butyl 3-((5-(3-chlorophenyl)-9-ethyl-2-oxo-2,3-dihydro-1H-benzo[e][1,4]diazepin-3-yl)carbamoyl)-6,6,6-trifluoro-2-(3,3,3-trifluoropropyl)hexanoate

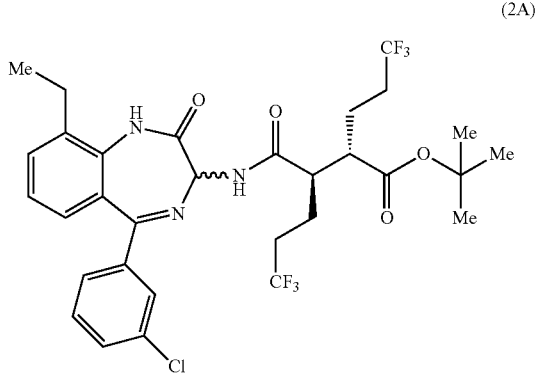

(2A)

To a solution of Intermediate B-7 dihydrobromide (130 mg, 0.273 mmol), Intermediate S-1 (100 mg, 0.273 mmol) and TBTU (105 mg, 0.328 mmol) in DMF (2 mL) was added TEA (0.190 mL, 1.367 mmol) dropwise. The mixture was stirred at room temperature for 16 hr. The reaction mixture was slowly poured into a stirred solution of water with some sat. NaHCO$_3$. The product mixture was extracted with DCM, washed with 10% LiCl solution, dried and concentrated in vacuo. The crude product mixture was purified via silica gel chromatography (ISCO, 0% to 50% of EtOAC/heptane over 10 minutes, using a 12 g column) to give Intermediate 2A (116 mg, 0.175 mmol, 64.1% yield). HPLC RT=1.20 min H$_2$O/CH$_3$CN with TFA, BEH C18 1.75 μm, 2.1×50 mm, gradient=2 min, wavelength=220 nm. MS(ES): m/z=662.3 [M+H$^+$].

Intermediate 2B: (2S,3R)-3-((5-(3-Chlorophenyl)-9-ethyl-2-oxo-2,3-dihydro-1H-benzo[e][1,4]diazepin-3-yl)carbamoyl)-6,6,6-trifluoro-2-(3,3,3-trifluoropropyl)hexanoic acid

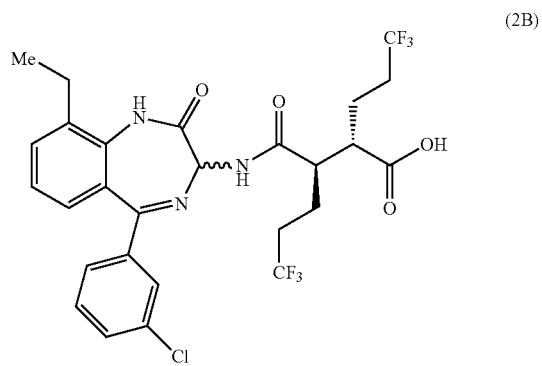

(2B)

A solution of Intermediate 2A (115 mg, 0.174 mmol) in DCM (3 mL) was treated with TFA (0.668 mL, 1.737 mmol). The reaction mixture was stirred at room temperature for 2 hours and then concentrated to dryness. The crude mixture was diluted with toluene and again concentrated to dryness to afford Intermediate 2B (87 mg, 0.144 mmol, 83% yield). HPLC RT=3.695 (H$_2$O/CH$_3$CN with TFA, Waters Sunfire C18 2.1×30 mm 3.5 um, 4 min gradient, detection at 220 nm). MS(ES): m/z=606.1 [M+H$^+$].

Example 2

A solution of Intermediate 2B (101 mg, 0.167 mmol), HOBT (77 mg, 0.500 mmol), and EDC (96 mg, 0.500 mmol) in THF (2381 μl) was treated with 2N ammonia in IPA (583 μl, 1.167 mmol). The reaction mixture was stirred at room temperature for 2 hours. The reaction mixture was then diluted with water (5 mL) and extracted with DCM. The combined organic layers were washed with brine, dried and then concentrated in vacuo. The crude product mixture was purified by silica gel chromatography (ISCO, 0% to 100% of EtOAC/heptane over 15 minutes, using a 12 g column) After separation of the diastereomers (Berger SFC MGII, Chiral IC, 25×3 cm ID, 5 μm, 92/8 CO$_2$/MeOH, 85 mL/min, detection at 220 nm), Example 2 (38 mg, 38%) was obtained. HPLC: RT=9.656 min (H$_2$O/CH$_3$CN with TFA, Sunfire C18 3.5 μm, 4.6×150 mm, gradient=15 min, wavelength=220 and 254 nm); MS(ES): m/z=605.1 [M+H$^+$]; $^1$H NMR (400 MHz, methanol-d$_4$) δ 7.70-7.63 (m, 1H), 7.61-7.56 (m, 1H), 7.55-7.45 (m, 2H), 7.44-7.37 (m, 1H), 7.33-7.19 (m, 2H), 5.38 (s, 1H), 3.38-3.26 (m, 2H), 3.08-2.88 (m, 1H), 2.87-2.70 (m, 2H), 2.69-2.40 (m, 2H), 2.36-2.02 (m, 3H), 2.01-1.69 (m, 3H), 1.34 (t, J=7.5 Hz, 3H).

The following Examples were prepared according to the general methods described for Example 1 and Example 2.

Example 3

(2R,3S)—N-((3S)-5-(3-Chlorophenyl)-9-isopropyl-2-oxo-2,3-dihydro-1H-1,4-benzodiazepin-3-yl)-2,3-bis(3,3,3-trifluoropropyl)succinamide

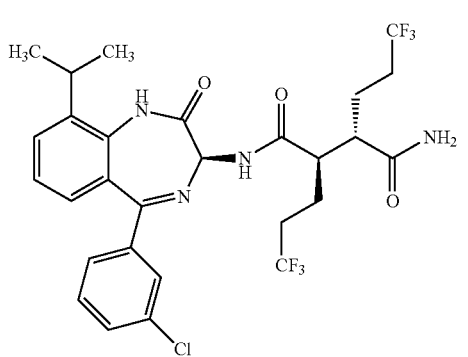

(3)

Example 3 was prepared from chiral Intermediate B-2 and Intermediate S-1 according to the general procedures described above. Example 3 was obtained. HPLC: RT=10.134 min (H$_2$O/CH$_3$CN with TFA, Sunfire C18 3.5 μm, 4.6×150 mm, gradient=15 min, wavelength=220 and 254 nm); MS(ES): m/z=619 [M+H$^+$]; $^1$H NMR (400 MHz, methanol-d$_4$) δ 7.67 (m, 2H), 7.48 (m, 2H), 7.42 (m, 1H), 7.33 (m, 1H), 7.23 (m, 1H), 5.38 (s, 1H), 3.56-3.38 (m, 1H), 2.92-2.74 (m, 1H), 2.68-2.42 (m, 2H), 2.38-2.09 (m, 3H), 2.00-1.69 (m, 4H), 1.41 (d, J=6.6 Hz, 3H), 1.29 (d, J=6.8 Hz, 3H).

Example 4

(2R,3S)—N-(9-Chloro-5-(3,4-dimethylphenyl)-2-oxo-2,3-dihydro-1H-1,4-benzodiazepin-3-yl)-3-(4,4,4-trifluorobutyl)-2-(3,3,3-trifluoropropyl)succinamide

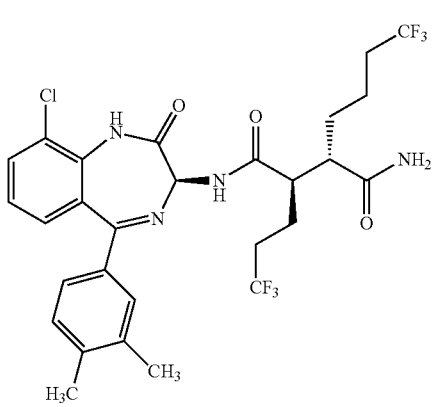

(4)

Example 4 was prepared from Intermediate B-6 and Intermediate S-2 according to the general procedures described above. After separation of the diastereomers by chiral SFC (Instrument: Berger SFC MGII, Column: Chiral IC 25×3 cm, 5 μm; Mobile Phase: 88/12 CO$_2$/MeOH Flow rate: 85 mL/min; Detection at 220 nm), Example 4 was obtained. HPLC: RT=9.771 min (H$_2$O/CH$_3$CN with TFA, Sunfire C18 3.5 μm, 4.6×150 mm, gradient=15 min, wavelength=220 and 254 nm); MS(ES): m/z=619 [M+H$^+$]; $^1$H NMR (400 MHz, methanol-d$_4$) δ 7.76 (dd, J=7.8, 1.7 Hz, 1H), 7.39 (s, 1H), 7.34-7.15 (m, 4H), 5.35 (s, 1H), 2.75 (td, J=10.6, 4.3 Hz, 1H), 2.58-2.48 (m, 1H), 2.32 (s, 3H), 2.28 (s, 3H), 2.25-2.05 (m, 3H), 1.86-1.66 (m, 4H), 1.65-1.45 (m, 3H).

Example 5

(2R,3S)—N-(9-Chloro-5-(3,5-dimethylphenyl)-2-oxo-2,3-dihydro-1H-1,4-benzodiazepin-3-yl)-3-(4,4,4-trifluorobutyl)-2-(3,3,3-trifluoropropyl)succinamide

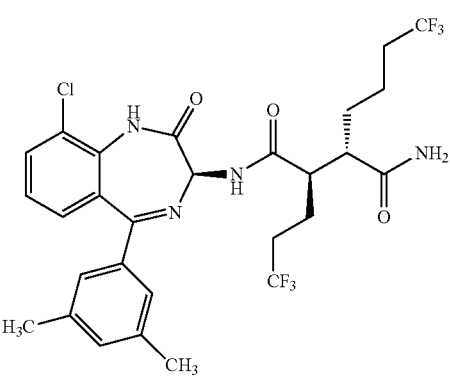

(5)

Example 5 was prepared from Intermediate B-27 and Intermediate S-2 according to the general procedures described above. After separation of the diastereomers by chiral SFC (Instrument: Berger SFC MGII, Column: RR Whelk O1 25×3 cm, 5 μm; Mobile Phase: 85/15 CO$_2$/MeOH Flow rate: 85 mL/min; Detection at 220 nm), Example 5 was obtained. HPLC: RT=9.824 min (H$_2$O/CH$_3$CN with TFA, Sunfire C18 3.5 μm, 4.6×150 mm, gradient=15 min, wavelength=220 and 254 nm); MS(ES): m/z=619 [M+H$^+$]; $^1$H NMR (400 MHz, methanol-d$_4$) δ 7.76 (dd, J=7.7, 1.8 Hz, 1H), 7.32-7.23 (m, 2H), 7.16 (s, 3H), 5.36 (s, 1H), 2.81-2.71 (m, 1H), 2.53 (d, J=10.3 Hz, 1H), 2.31 (s, 6H), 2.24-2.04 (m, 3H), 1.84-1.69 (m, 3H), 1.62-1.47 (m, 3H), 1.29 (s, 1H).

Example 6

(2R,3S)—N-((3S)-9-Ethyl-5-(3-methylphenyl)-2-oxo-2,3-dihydro-1H-1,4-benzodiazepin-3-yl)-2,3-bis(3,3,3-trifluoropropyl)succinamide

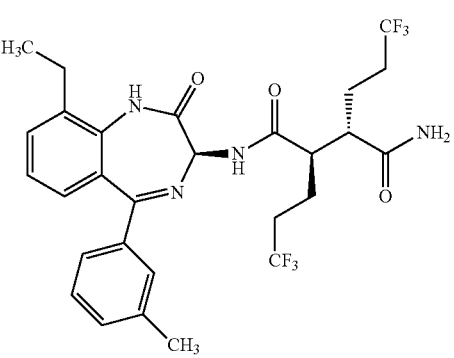

(6)

Example 6 was prepared from Intermediate B-8 and Intermediate S-1 according to the general procedures described above. Separation of the diastereomers (Berger SFC MGII, CHIRALPAK® IC, 25×3 cm ID, 5 μm, 92/8 $CO_2$/MeOH, 85 mL/min, detection at 220 nm) afforded Example 6. HPLC: RT=9.556 min ($H_2O$/$CH_3CN$ with TFA, Sunfire C18 3.5 μm, 4.6×150 mm, gradient=15 min, wavelength=220 and 254 nm); MS(ES): m/z 585.2=[M+H$^+$]; $^1$H NMR (400 MHz, methanol-$d_4$) δ 7.60-7.52 (m, 1H), 7.49-7.43 (m, 1H), 7.38-7.16 (m, 5H), 5.37 (s, 1H), 3.04-2.89 (m, 1H), 2.87-2.71 (m, 2H), 2.68-2.39 (m, 2H), 2.37 (s, 3H), 2.33-2.09 (m, 3H), 1.99-1.65 (m, 4H), 1.34 (t, J=7.5 Hz, 3H).

Example 7

(2R,3S)—N-((3S)-5-(3-Chlorophenyl)-9-methyl-2-oxo-2,3-dihydro-1H-1,4-benzodiazepin-3-yl)-2,3-bis(3,3,3-trifluoropropyl)succinamide (7)

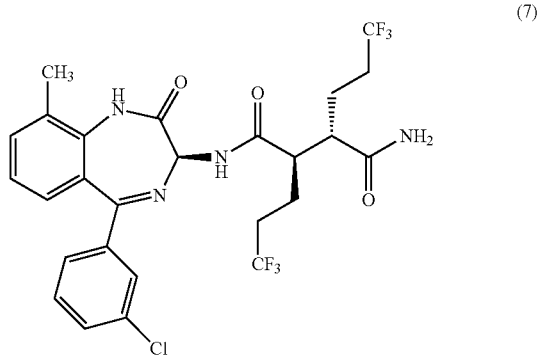 [SMILES: Cc1cccc2c1NC(=O)[C@@H](NC(=O)[C@H](CCC(F)(F)F)[C@H](CCC(F)(F)F)C(N)=O)N=C2c1cccc(Cl)c1]

Example 7 was prepared from Intermediate B-3 and Intermediate S-1 according to the general procedures described above. Separation of the diastereomers by preparative SFC chromatography (Instrument: Berger SFC MGII, Column: Chiral OD-H 25×3 cm, 5 mm; Mobile Phase: 90/10 $CO_2$/MeOH Flow rate: 85 mL/min; Detection at 220 nm.) afforded Example 7. HPLC: RT=9.328 min ($H_2O$/$CH_3CN$ with TFA, Sunfire C18 3.5 μm, 3.0×150 mm, gradient=15 min, wavelength=220 and 254 nm); MS(ES): m/z=591.2 [M+H$^+$]; $^1$H NMR (400 MHz, methanol-$d_4$) δ 7.65 (t, J=1.9 Hz, 1H), 7.59-7.50 (m, 2H), 7.50-7.44 (m, 1H), 7.44-7.37 (m, 1H), 7.27-7.20 (m, 2H), 5.39 (s, 1H), 2.86-2.76 (m, 1H), 2.66-2.56 (m, 1H), 2.56-2.46 (m, 4H), 2.33-2.14 (m, 3H), 1.95-1.74 (m, 4H).

Example 8

(2R,3S)—N-((3S)-5-(3-Chlorophenyl)-9-methyl-2-oxo-2,3-dihydro-1H-1,4-benzodiazepin-3-yl)-3-(4,4,4-trifluorobutyl)-2-(3,3,3-trifluoropropyl)succinamide (8)

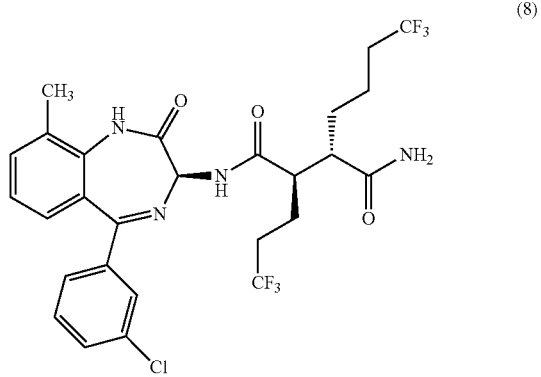 [SMILES: Cc1cccc2c1NC(=O)[C@@H](NC(=O)[C@H](CCC(F)(F)F)[C@H](CCCC(F)(F)F)C(N)=O)N=C2c1cccc(Cl)c1]

Example 8 was prepared from Intermediate B-3 and Intermediate S-2 according to the general procedures described above. Separation of the diastereomers by preparative SFC chromatography (Instrument: Berger SFC MGII, Column: Regis Welk-O R,R 25×3 cm, 5 mm; Mobile Phase: 85/15 $CO_2$/MeOH Flow rate: 85 mL/min; Detection at 220 nm.) afforded Example 8. HPLC: RT=9.531 min ($H_2O$/$CH_3CN$ with TFA, Sunfire C18 3.5 μm, 3.0×150 mm, gradient=15 min, wavelength=220 and 254 nm); MS(ES): m/z=605.2 [M+H$^+$]; $^1$H NMR (400 MHz, methanol-$d_4$) δ 7.69 (d, J=1.8 Hz, 1H), 7.58-7.50 (m, 2H), 7.47-7.40 (m, 2H), 7.27-7.19 (m, 2H), 5.37 (s, 1H), 2.78 (td, J=10.3, 4.0 Hz, 1H), 2.60-2.46 (m, 5H), 2.30-2.11 (m, 3H), 1.89-1.71 (m, 3H), 1.67-1.50 (m, 3H).

Example 9

(2R,3S)—N-((3S)-5-(3-Methylphenyl)-2-oxo-9-(trifluoromethyl)-2,3-dihydro-1H-1,4-benzodiazepin-3-yl)-2,3-bis(3,3,3-trifluoropropyl)succinamide (9)

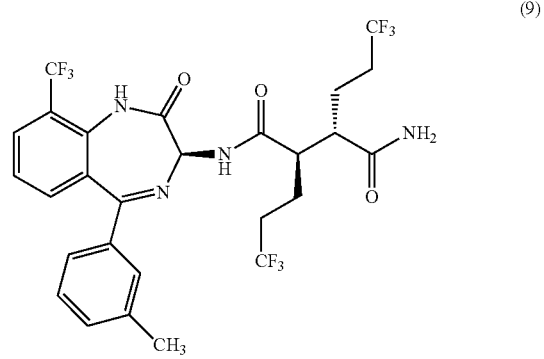 [SMILES: Cc1cccc(C2=N[C@H](NC(=O)[C@H](CCC(F)(F)F)[C@H](CCC(F)(F)F)C(N)=O)C(=O)Nc3c2cccc3C(F)(F)F)c1]

Example 9 was prepared from Intermediate B-9 and Intermediate S-1 according to the general procedures described above. Separation of the diastereomers by preparative SFC chromatography (Instrument: Berger SFC MGII, Column: Chiral OD-H 25×3 cm, 5 μm; Mobile Phase: 92/8 $CO_2$/MeOH Flow rate: 85 mL/min; Detection at 220 nm.) afforded Example 9. HPLC: RT=9.488 min ($H_2O$/$CH_3CN$ with TFA, Sunfire C18 3.5 μm, 3.0×150 mm, gradient=15 min, wavelength=220 and 254 nm); MS(ES): m/z=625.3[M+H$^+$]; $^1$H NMR (400 MHz, methanol-$d_4$) δ 8.03 (d, J=6.8 Hz, 1H), 7.68-7.62 (m, 1H), 7.53-7.45 (m, 2H), 7.40-7.30 (m, 3H), 5.47 (s, 1H), 2.82 (td, J=10.5, 4.0 Hz, 1H), 2.60 (td, J=10.5, 3.7 Hz, 1H), 2.53-2.41 (m, 1H), 2.38 (s, 3H), 2.32-2.14 (m, 3H), 1.99-1.71 (m, 4H).

Example 10

(2R,3S)—N-((3S)-9-Chloro-5-(3,5-dimethylphenyl)-2-oxo-2,3-dihydro-1H-1,4-benzodiazepin-3-yl)-2,3-bis(3,3,3-trifluoropropyl)succinamide (10)

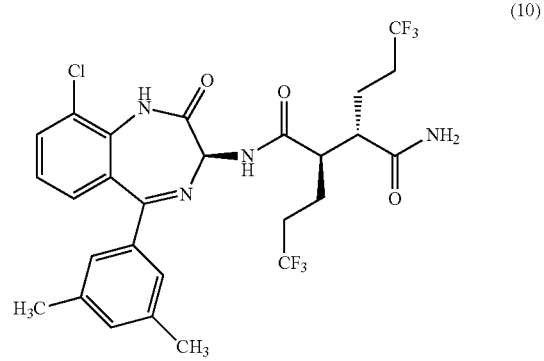 [SMILES: Cc1cc(C)cc(C2=N[C@H](NC(=O)[C@H](CCC(F)(F)F)[C@H](CCC(F)(F)F)C(N)=O)C(=O)Nc3c(Cl)cccc32)c1]

Example 10 was prepared from Intermediate B-27 and Intermediate S-1 according to the general procedures described above. Separation of the diastereomers by chiral SFC (Instrument: Berger SFC MGIII, Column: CHIRALCEL® OD-H 25×3 cm, 5 μm; Mobile Phase: 92/18 CO$_2$/MeOH Flow rate: 150 mL/min; Detection at 220 nm) afforded Example 10. HPLC: RT=10.878 min (H$_2$O/CH$_3$CN with TFA, Sunfire C18 3.5 μm, 4.6×150 mm, gradient=15 min, wavelength=220 and 254 nm); MS(ES): m/z=605 [M+H$^+$]; $^1$H NMR (400 MHz, methanol-d$_4$) δ 7.76 (dd, J=7.7, 1.5 Hz, 1H), 7.33-7.23 (m, 2H), 7.15 (s, 3H), 5.39 (s, 1H), 2.84-2.75 (m, 1H), 2.59 (td, J=10.3, 4.2 Hz, 1H), 2.51-2.39 (m, 1H), 2.30 (s, 6H), 2.26-2.12 (m, 3H), 1.95-1.70 (m, 4H).

Example 11

(2R,3S)—N-((3S)-5-(3-Methylphenyl)-2-oxo-9-(trifluoromethyl)-2,3-dihydro-1H-1,4-benzodiazepin-3-yl)-3-(4,4,4-trifluorobutyl)-2-(3,3,3-trifluoropropyl)succinamide (11)

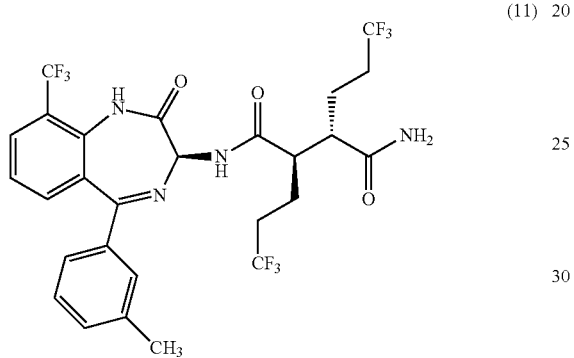

Example 11 was prepared from Intermediate B-9 and Intermediate S-2 according to the general procedures described above. Separation of the diastereomers by preparative SFC chromatography (Instrument: Berger SFC MGII, Column: Chiral OD-H 25×3 cm, 5 μm; Mobile Phase: 92/8 CO$_2$/MeOH Flow rate: 85 mL/min; Detection at 220 nm) afforded Example 11. HPLC: RT=9.699 min (H$_2$O/CH$_3$CN with TFA, Sunfire C18 3.5 μm, 3.0×150 mm, gradient=15 min, wavelength=220 and 254 nm); MS(ES): m/z=639.3 [M+H$^+$]; $^1$H NMR (400 MHz, methanol-d$_4$) δ 8.03 (d, J=6.8 Hz, 1H), 7.67-7.61 (m, 1H), 7.52-7.44 (m, 2H), 7.41-7.31 (m, 3H), 5.45 (s, 1H), 2.83-2.74 (m, 1H), 2.61-2.42 (m, 2H), 2.39 (s, 3H), 2.35-2.05 (m, 3H), 1.90-1.69 (m, 3H), 1.68-1.48 (m, 3H).

Example 12

(2R,3S)—N-((3S)-9-Isopropyl-5-(3-methylphenyl)-2-oxo-2,3-dihydro-1H-1,4-benzodiazepin-3-yl)-2,3-bis(3,3,3-trifluoropropyl)succinamide (12)

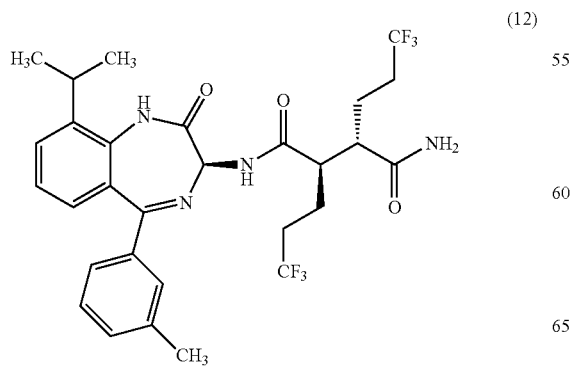

Example 12 was prepared from Intermediate B-10 and Intermediate S-1 according to the general procedures described above. Separation of the diastereomers (Instrument: Berger SFC MGIII, Column: Lux Cell-4, 250×30 mm, 5 μm; Column Temp: 45° C., Mobile Phase: 88/12 CO$_2$/MeOH; Detection at 220 nm) afforded Example 12. HPLC: RT=15.924 min (MeOH/H$_2$O with TFA, Sunfire C18 3.5 μm, 4.6×150 mm, gradient=15 min, wavelength=220 and 254); MS(ES): m/z=599 [M+H$^+$]; $^1$H NMR (400 MHz, methanol-d$_4$) δ 7.63 (dd, J=7.7, 1.3 Hz, 1H), 7.45 (s, 1H), 7.37-7.24 (m, 4H), 7.19 (d, J=1.5 Hz, 1H), 5.36 (s, 1H), 3.52-3.37 (m, 1H), 2.86-2.74 (m, 1H), 2.64-2.42 (m, 2H), 2.36 (s, 3H), 2.32-2.11 (m, 3H), 1.96-1.69 (m, 4H), 1.39 (d, J=6.8 Hz, 3H), 1.28 (d, J=6.8 Hz, 3H).

Example 13

(2R,3S)—N-((3S)-9-Isopropyl-2-oxo-5-phenyl-2,3-dihydro-1H-1,4-benzodiazepin-3-yl)-2,3-bis(3,3,3-trifluoropropyl)succinamide (13)

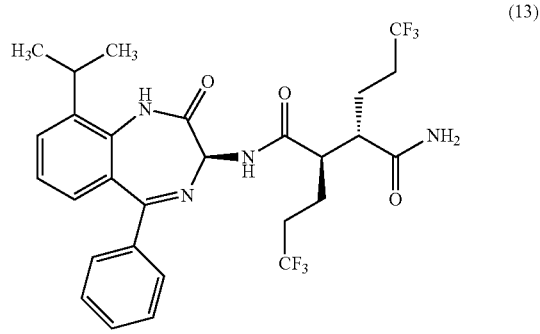 [SMILES: CC(C)c1cccc2c1NC(=O)[C@@H](NC(=O)[C@H](CCC(F)(F)F)[C@H](CCC(F)(F)F)C(N)=O)N=C2c1ccccc1]

Example 13 was prepared from Intermediate B-11 and Intermediate S-1 according to the general procedures described above. Separation of the diastereomers (Instrument: Berger SFC MGII, Column: CHIRALPAK® IC 250×30 mm, 5 μm; Mobile Phase: 90/10 CO$_2$/MeOH Flow rate: 85 mL/min; Detection at 220 nm) afforded Example 13. HPLC: RT=15.481 min (H$_2$O/CH$_3$CN with TFA, Sunfire C18 3.5 mm, 4.6×150 mm, gradient=15 min, wavelength=220 and 254 nm); MS(ES): m/z=586 [M+H$^+$]; $^1$H NMR (400 MHz, methanol-d$_4$) δ 7.70-7.56 (m, 3H), 7.56-7.47 (m, 1H), 7.47-7.36 (m, 2H), 7.36-7.25 (m, 1H), 7.25-7.12 (m, 1H), 5.39 (s, 1H), 3.53-3.38 (m, 1H), 2.83 (m, 1H), 2.70-2.41 (m, 2H), 2.37-2.05 (m, 3H), 2.00-1.69 (m, 4H), 1.40 (d, J=6.6 Hz, 3H), 1.35-1.21 (m, 3H).

Example 14

(2R,3S)—N-((3S)-9-(Cyclopropyloxy)-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide (14)

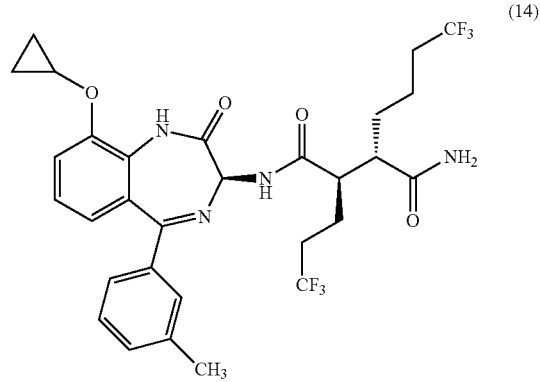 [SMILES: Cc1cccc(C2=N[C@H](NC(=O)[C@H](CCC(F)(F)F)[C@H](CCCC(F)(F)F)C(N)=O)C(=O)Nc3c(OC4CC4)cccc32)c1]

Example 14 was prepared from Intermediate B-12 and Intermediate S-2 according to the general procedures described above. Separation of the diastereomers (Berger SFC MGII, Chiral AS-H 25×3 cm ID, 5 μm, 80/20 CO$_2$/MeOH, 85 mL/min, detection at 220 nm) afforded Example 14. HPLC: RT=10.064 min (H$_2$O/CH$_3$CN with TFA, Sunfire C18 3.5 μm, 4.6×150 mm, gradient=15 min, wavelength=220 and 254 nm); MS(ES): m/z=627.20 [M+H$^+$]; $^1$H NMR (400 MHz, methanol-d$_4$) δ 7.65-7.56 (m, 1H), 7.46-7.39 (m, 1H), 7.37-7.16 (m, 4H), 7.00-6.84 (m, 1H), 5.37 (s, 1H), 4.06-3.91 (m, 1H), 2.87-2.68 (m, 1H), 2.64-2.44 (m, 2H), 2.37 (s, 3H), 2.32-2.00 (m, 3H), 1.98-1.50 (m, 4H), 1.50-1.22 (m, 2H), 1.05-0.84 (m, 4H).

Example 15

(2R,3S)—N-((3S)-9-(Cyclopropyloxy)-5-(3-methylphenyl)-2-oxo-2,3-dihydro-1H-1,4-benzodiazepin-3-yl)-2,3-bis(3,3,3-trifluoropropyl)succinamide

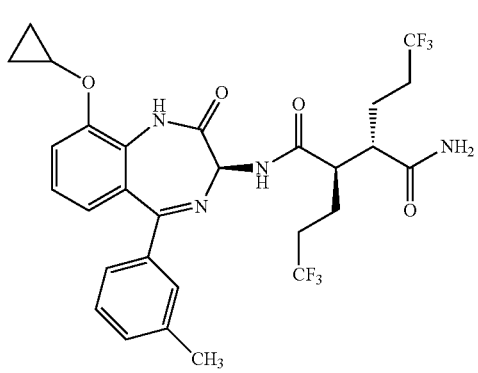

(15)

Example 15 was prepared from Intermediate B-12 and Intermediate S-1 according to the general procedures described above. Separation of the diastereomers (Berger SFC MGII, Chiral AS-H 25×3 cm ID, 5 μm, 80/20 CO$_2$/MeOH, 85 mL/min, detection at 220 nm) afforded Example 15. HPLC: RT=9.844 min (H$_2$O/CH$_3$CN with TFA, Sunfire C18 3.5 μm, 4.6×150 mm, gradient=15 min, wavelength=220 and 254 nm); MS(ES): m/z=613.25 [M+H$^+$]; $^1$H NMR (400 MHz, methanol-d$_4$) δ 7.63-7.58 (m, 1H), 7.47-7.39 (m, 1H), 7.38-7.20 (m, 4H), 6.98-6.91 (m, 1H), 5.40 (s, 1H), 4.04-3.94 (m, 1H), 2.88-2.75 (m, 1H), 2.66-2.55 (m, 1H), 2.55-2.39 (m, 1H), 2.39-2.33 (m, 2H), 2.32-2.09 (m, 3H), 2.01-1.65 (m, 3H), 1.52-1.23 (m, 3H), 1.03-0.84 (m, 4H).

Example 16

(2R,3S)—N-((3S)-9-(Cyclopropyloxy)-2-oxo-5-phenyl-2,3-dihydro-1H-1,4-benzodiazepin-3-yl)-3-(4,4,4-trifluorobutyl)-2-(3,3,3-trifluoropropyl)succinamide

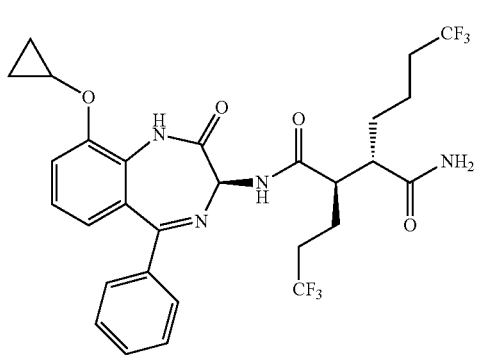

(16)

Example 16 was prepared from Intermediate B-13 and Intermediate S-2 according to the general procedures described above. Separation of the diastereomers (Berger SFC MGII, Chiral AS-H 25×3 cm ID, 5 μm, 80/20 CO$_2$/MeOH, 85 mL/min, detection at 220 nm) afforded Example 16. HPLC: RT=9.74 min (H$_2$O/CH$_3$CN with TFA, Sunfire C18 3.5 μm, 4.6×150 mm, gradient=15 min, wavelength=220 and 254 nm); MS(ES): m/z=613.2 [M+H$^+$]; $^1$H NMR (400 MHz, methanol-d$_4$) δ 7.64-7.55 (m, 3H), 7.55-7.49 (m, 1H), 7.44 (d, J=7.5 Hz, 2H), 7.26 (s, 1H), 6.98-6.91 (m, 1H), 5.38 (s, 1H), 4.04-3.96 (m, 1H), 2.81-2.71 (m, 1H), 2.62-2.41 (m, 2H), 2.18 (s, 4H), 1.90-1.68 (m, 3H), 1.68-1.33 (m, 3H), 0.93-0.86 (m, 4H).

Example 17

(2R,3S)—N-((3S)-9-Chloro-5-(3-methylphenyl)-2-oxo-2,3-dihydro-1H-1,4-benzodiazepin-3-yl)-3-(4,4,4-trifluorobutyl)-2-(3,3,3-trifluoropropyl)succinamide

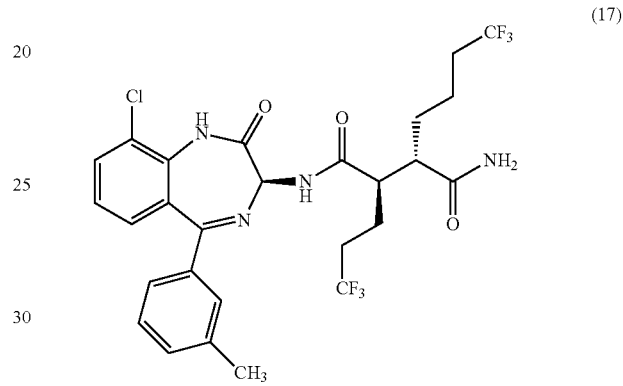

(17)

Example 17 was prepared from Intermediate B-14 and Intermediate S-2 according to the general procedures described above. This solid was purified by preparative SFC chromatography (Berger SFC MGII, AD-H 250×30 mm ID, 5 cm, 75/25 CO$_2$/IPA, 150 mL/min) to afford Example 17. HPLC: RT=11.04 min (H$_2$O/CH$_3$CN with TFA, Sunfire C18 3.5 μm, 4.6×150 mm, gradient=15 min, wavelength=220 and 254 nm); MS(ES): m/z=605.3 [M+H$^+$]; $^1$H NMR (400 MHz, DMSO-d$_6$) δ 10.45 (s, 1H), 9.45 (d, J=6.8 Hz, 1H), 7.84 (dd, J=5.9, 3.3 Hz, 1H), 7.62 (br. s., 1H), 7.41 (s, 1H), 7.38-7.34 (m, 2H), 7.33-7.26 (m, 3H), 7.03 (s, 1H), 5.21 (d, J=6.8 Hz, 1H), 2.79-2.70 (m, 1H), 2.69-2.59 (m, 1H), 2.46-2.38 (m, 1H), 2.34 (s, 3H), 2.31-2.19 (m, 2H), 2.18-2.07 (m, 1H), 1.65-1.53 (m, 3H), 1.49-1.41 (m, 1H), 1.39-1.29 (m, 2H).

Example 18

(2R,3S)—N-((3S)-9-Methyl-2-oxo-5-(3-(trifluoromethyl)phenyl)-2,3-dihydro-1H-1,4-benzo diazepin-3-yl)-3-(4,4,4-trifluorobutyl)-2-(3,3,3-trifluoropropyl)succinamide

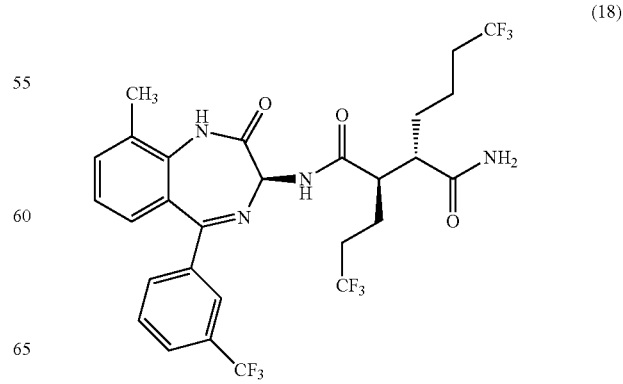

(18)

Example 18 was prepared from Intermediate B-15 and Intermediate S-2 according to the general procedures described above. Separation of the diastereomers by preparative SFC chromatography (Instrument: Berger SFC MGII, Column: Regis Welk-O R,R 25×3 cm, 5 mm; Mobile Phase: 90/10 CO$_2$/MeOH Flow rate: 85 mL/min; Detection at 220 nm.) afforded Example 18. HPLC: RT=9.678 min (H$_2$O/CH$_3$CN with TFA, Sunfire C18 3.5 μm, 3.0×150 mm, gradient=15 min, wavelength=220 and 254 nm); MS(ES): m/z=639.4 [M+H$^+$]; $^1$H NMR (400 MHz, methanol-d$_4$) δ 8.01 (s, 1H), 7.83 (d, J=7.7 Hz, 1H), 7.77 (d, J=7.7 Hz, 1H), 7.68-7.60 (m, 1H), 7.57 (d, J=7.0 Hz, 1H), 7.28-7.17 (m, 2H), 5.40 (s, 1H), 2.79 (td, J=10.5, 4.0 Hz, 1H), 2.62-2.45 (m, 5H), 2.35-2.18 (m, 2H), 2.16-2.03 (m, 1H), 1.91-1.70 (m, 3H), 1.69-1.48 (m, 3H).

Example 19

(2R,3S)—N-((3S)-9-(Cyclopropyloxy)-2-oxo-5-phenyl-2,3-dihydro-1H-1,4-benzodiazepin-3-yl)-2,3-bis(3,3,3-trifluoropropyl)succinamide

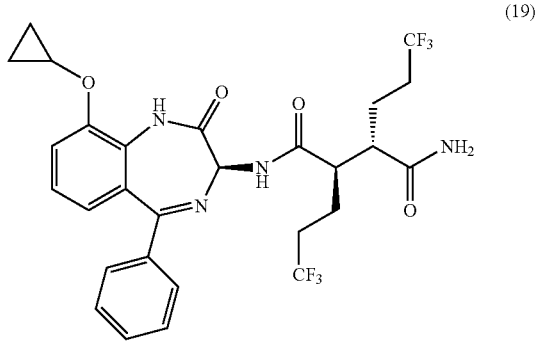 [SMILES: NC(=O)[C@@H](CCC(F)(F)F)[C@@H](CCC(F)(F)F)C(=O)N[C@H]1N=C(c2ccccc2)c2cccc(OC3CC3)c2NC1=O]

(19)

Example 19 was prepared from Intermediate B-13 and Intermediate S-1 according to the general procedures described above. Separation of the diastereomers (Berger SFC MGII, Chiral AS-H 25×3 cm ID, 5 μm, 80/20 CO$_2$/MeOH, 85 mL/min, detection at 220 nm) afforded Example 19. HPLC: RT=14.967 min (H$_2$O/CH$_3$CN with TFA, Sunfire C18 3.5 μm, 4.6×150 mm, gradient=15 min, wavelength=220 and 254 nm); MS(ES): m/z=599.1 [M+H$^+$]; $^1$H NMR (400 MHz, methanol-d$_4$) δ 7.61 (dd, J=8.1, 1.3 Hz, 1H), 7.59-7.54 (m, 2H), 7.54-7.47 (m, 1H), 7.47-7.37 (m, 2H), 7.25 (t, J=8.0 Hz, 1H), 6.95 (dd, J=7.9, 1.1 Hz, 1H), 5.41 (s, 1H), 4.00 (t, J=4.4 Hz, 1H), 2.82 (d, J=4.0 Hz, 1H), 2.61 (d, J=3.7 Hz, 1H), 2.55-2.38 (m, 1H), 2.36-2.11 (m, 3H), 2.07-1.70 (m, 4H), 0.91 (d, J=4.4 Hz, 4H).

Example 20

(2R,3S)—N-((3S)-9-Methyl-2-oxo-5-(3-(trifluoromethyl)phenyl)-2,3-dihydro-1H-1,4-benzodiazepin-3-yl)-2,3-bis(3,3,3-trifluoropropyl)succinamide

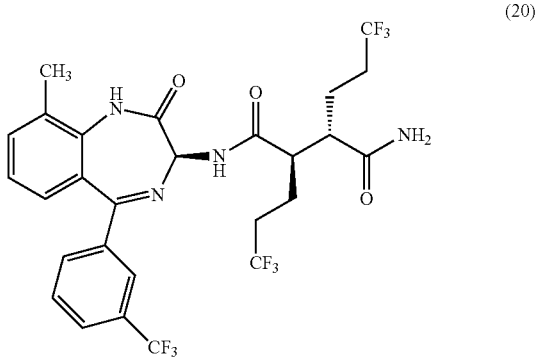 [SMILES: Cc1cccc(C2=N[C@H](NC(=O)[C@H](CCC(F)(F)F)[C@H](CCC(F)(F)F)C(N)=O)C(=O)Nc3c(Cl)cccc32)c1]

(20)

Example 20 was prepared from Intermediate B-15 and Intermediate S-1 according to the general procedures described above. Separation of the diastereomers by preparative SFC chromatography (Instrument: Berger SFC MGII, Column: PHENOMENEX® Lux Cellulose 2 25×3 cm, 5 μm; Mobile Phase: 92/8 CO$_2$/MeOH Flow rate: 85 mL/min; Detection at 220 nm.) afforded Example 20. HPLC: RT=9.483 min (H$_2$O/CH$_3$CN with TFA, Sunfire C18 3.5 μm, 3.0×150 mm, gradient=15 min, wavelength=220 and 254 nm); MS(ES): m/z=625.1 [M+H$^+$]; $^1$H NMR (400 MHz, methanol-d$_4$) δ 7.97 (s, 1H), 7.81 (dd, J=13.1, 7.8 Hz, 2H), 7.67-7.60 (m, 1H), 7.57 (dd, J=6.8, 1.3 Hz, 1H), 5.43 (s, 1H), 2.83 (td, J=10.5, 4.0 Hz, 1H), 2.61 (td, J=10.3, 3.5 Hz, 1H), 2.57-2.46 (m, 4H), 2.32-2.12 (m, 3H), 1.98-1.74 (m, 4H).

Example 21

(2R,3S)—N-((3S)-9-Chloro-5-(2-methylphenyl)-2-oxo-2,3-dihydro-1H-1,4-benzodiazepin-3-yl)-2,3-bis(3,3,3-trifluoropropyl)succinamide

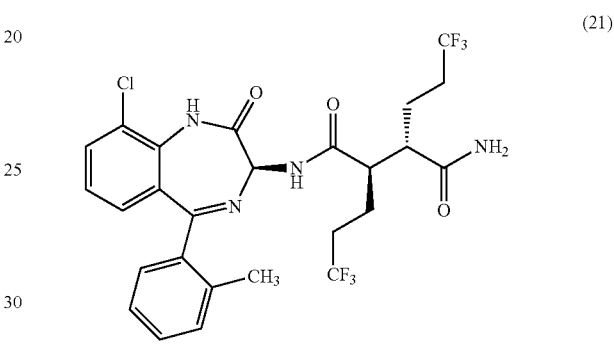

(21)

Example 21 was prepared from Intermediate B-16 and Intermediate S-1 according to the general procedures described above. The desired stereoisomer was collected as the second peak in the elution order using SFC chromatography (Instrument: Berger SFC MGII, Column: Chiral OD-H 25×3 cm, 5 mm; Mobile Phase: 85/15 CO$_2$/MeOH Flow rate: 85 mL/min; Detection at 220 nm), to afford Example 21. HPLC: RT=11.11 min (H$_2$O/CH$_3$CN with TFA, Sunfire C18 3.5 μm, 4.6×150 mm, gradient=15 min, wavelength=220 and 254 nm); MS(ES): m/z=591[M+H$^+$]; $^1$H NMR (500 MHz, methanol-d$_4$) δ 7.73 (dd, J=8.0, 1.4 Hz, 1H), 7.40-7.32 (m, 1H), 7.29-7.21 (m, 3H), 7.18 (t, J=7.9 Hz, 1H), 7.08 (dd, J=7.9, 1.5 Hz, 1H), 5.45 (s, 1H), 2.79 (td, J=10.5, 4.0 Hz, 1H), 2.59 (td, J=10.4, 3.9 Hz, 1H), 2.51-2.38 (m, 1H), 2.30-2.08 (m, 3H), 2.04 (s, 3H), 1.94-1.67 (m, 4H).

Example 22

(2R,3S)—N-((3S)-5-(4-Fluorophenyl)-9-methyl-2-oxo-2,3-dihydro-1H-1,4-benzodiazepin-3-yl)-2,3-bis(3,3,3-trifluoropropyl)succinamide

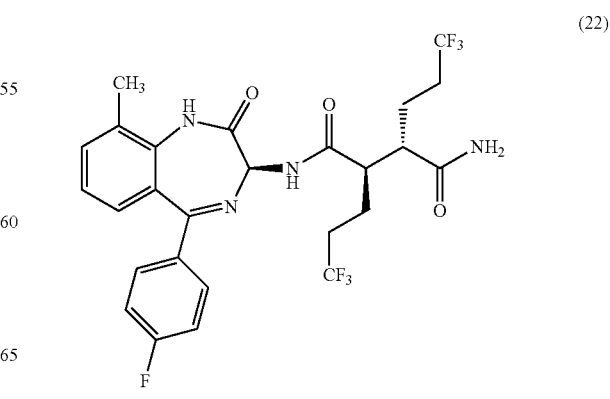

(22)

Example 22 was prepared from Intermediate B-17 and Intermediate S-1 according to the general procedures described above. Separation of the diastereomers by preparative SFC chromatography (Instrument: Berger SFC MGII, Column: Chiral IC 25×3 cm, 5 µm; Mobile Phase: 92/8 CO₂/MeOH Flow rate: 85 mL/min; Detection at 220 nm.) afforded Example 22. HPLC: RT=9.016 min (H₂O/CH₃CN with TFA, Sunfire C18 3.5 µm, 3.0×150 mm, gradient=15 min, wavelength=220 and 254 nm); MS(ES): m/z=575.1 [M+H⁺]; ¹H NMR (400 MHz, methanol-d₄) δ 7.69-7.60 (m, 2H), 7.53 (dd, J=5.8, 2.5 Hz, 1H), 7.24-7.18 (m, 2H), 7.17-7.09 (m, 2H), 5.36 (s, 1H), 2.80 (td, J=10.4, 4.1 Hz, 1H), 2.58 (td, J=10.5, 3.6 Hz, 1H), 2.53-2.43 (m, 4H), 2.31-2.11 (m, 3H), 1.95-1.73 (m, 4H).

Example 23

(2R,3S)—N-((3S)-9-Methyl-2-oxo-5-phenyl-2,3-dihydro-1H-1,4-benzodiazepin-3-yl)-2,3-bis(3,3,3-trifluoropropyl)succinamide

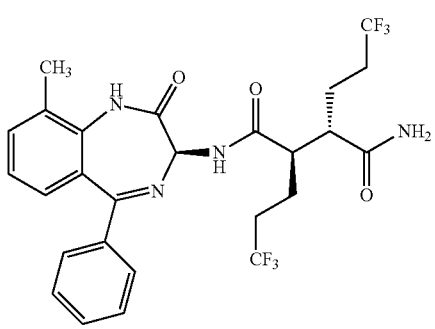

(23)

Example 23 was prepared from Intermediate B-4 and Intermediate S-1 according to the general procedures described above. HPLC: RT=7.843 min (H₂O/CH₃CN with TFA, Sunfire C18 3.5 µm, 4.6×150 mm, gradient=15 min, wavelength=220 and 254 nm); MS(ES): m/z=557.4 [M+H⁺]; ¹H NMR (400 MHz, methanol-d₄) δ 7.63-7.57 (m, 1H), 7.56-7.47 (m, 1H), 7.46-7.37 (m, 1H), 7.25-7.18 (m, 1H), 5.39 (s, 1H), 2.82 (td, J=10.5, 4.0 Hz, 1H), 2.61 (td, J=10.5, 3.5 Hz, 1H), 2.56-2.40 (m, 4H), 2.36-2.07 (m, 3H), 1.99-1.70 (m, 4H).

Example 24

(2R,3S)—N-((3S)-9-Cyclopropyl-2-oxo-5-phenyl-2,3-dihydro-1H-1,4-benzodiazepin-3-yl)-2,3-bis(3,3,3-trifluoropropyl)succinamide

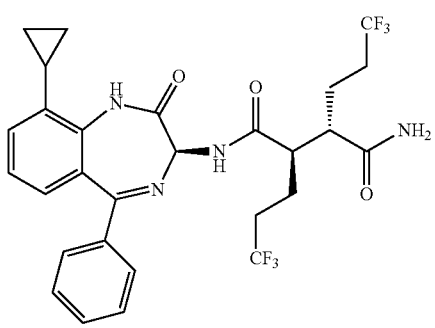

(24)

Example 24 was prepared from Intermediate B-28 and Intermediate S-1 according to the general procedures described above. This solid was purified by preparative SFC chromatography (Berger SFC MGII, Chiral IC 250×30 mm ID, 5 µm, 85/15 CO₂/MeOH, 85 mL/min) to afford Example 24. HPLC: RT=11.56 min (H₂O/CH₃CN with TFA, Sunfire C18 3.5 µm, 4.6×150 mm, gradient=15 min, wavelength=220 and 254 nm); MS(ES): m/z=583.2 [M+H⁺]; ¹H NMR (400 MHz, DMSO-d₆) δ 10.28 (s, 1H), 9.45 (d, J=7.3 Hz, 1H), 7.65 (br. s., 1H), 7.56-7.49 (m, 3H), 7.47-7.40 (m, 2H), 7.28 (dd, J=7.7, 1.3 Hz, 1H), 7.20 (t, J=7.7 Hz, 1H), 7.15-7.08 (m, 2H), 5.24 (d, J=7.3 Hz, 1H), 2.81 (td, J=9.8, 5.1 Hz, 1H), 2.54 (br. s., 1H), 2.31-2.07 (m, 4H), 1.78-1.53 (m, 5H), 1.11-0.96 (m, 2H), 0.84-0.76 (m, 1H), 0.71-0.62 (m, 1H).

Example 25

(2R,3S)—N-((3S)-9-Chloro-5-(3-cyclopropylphenyl)-2-oxo-2,3-dihydro-1H-1,4-benzodiazepin-3-yl)-2,3-bis(3,3,3-trifluoropropyl)succinamide

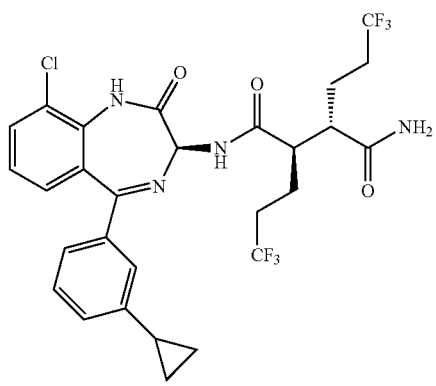

(25)

Example 25 was prepared from Intermediate B-18 and Intermediate S-1 according to the general procedures described above. Separation of the diastereomers (Instrument: Berger SFC MGII, Chiral IC 25×3 cm ID, 5 µm, 90/10 CO₂/MeOH, 85 mL/min, detection at 220 nm) afforded Example 25. HPLC: RT=8.81 min (H₂O/CH₃CN with TFA, Sunfire C18 3.5 µm, 4.6×150 mm, gradient=15 min, wavelength=220 and 254 nm); MS(ES): m/z=617.0 [M+H⁺]; ¹H NMR (400 MHz, methanol-d₄) δ 7.88-7.70 (m, 1H), 7.45-7.11 (m, 6H), 5.46-5.31 (m, 1H), 2.82 (td, J=10.4, 4.1 Hz, 1H), 2.69-2.40 (m, 2H), 2.36-2.06 (m, 3H), 2.00-1.58 (m, 5H), 1.06-0.94 (m, 2H), 0.80-0.62 (m, 2H).

Example 26

(2R,3S)—N-((3S)-5-(3-Chlorophenyl)-9-methoxy-2-oxo-2,3-dihydro-1H-1,4-benzodiazepin-3-yl)-2,3-bis(3,3,3-trifluoropropyl)succinamide

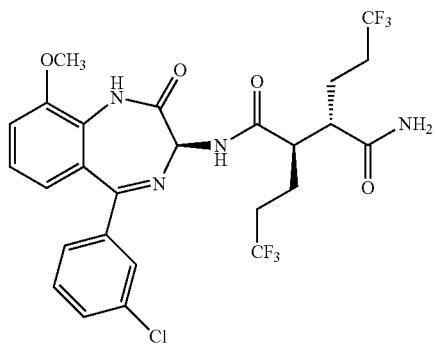

(26)

Example 26 was prepared from Intermediate B-19 and Intermediate S-1 according to the general procedures described above. The solid was purified by preparative SFC chromatography (Instrument: Berger SFC MGII, AS-H 250× 30 mm ID, 5 μm, 82/18 CO$_2$/MeOH, 85 mL/min) to afford Example 26. HPLC: RT=9.32 min (H$_2$O/CH$_3$CN with TFA, Sunfire C18 3.5 μm, 4.6×150 mm, gradient=15 min, wavelength=220 and 254 nm); MS(ES): m/z=607 [M+H$^+$]; $^1$H NMR (400 MHz, methanol-d$_4$) δ 10.13 (s, 1H), 9.51 (d, J=7.3 Hz, 1H), 7.68-7.59 (m, 3H), 7.52-7.45 (m, 1H), 7.42-7.32 (m, 2H), 7.30-7.24 (m, 1H), 7.13 (s, 1H), 6.92 (dd, J=7.9, 1.1 Hz, 1H), 5.25 (d, J=7.3 Hz, 1H), 3.94 (s, 3H), 2.85-2.75 (m, 1H), 2.63-2.54 (m, 1H), 2.31-2.09 (m, 4H), 1.75-1.52 (m, 4H).

Example 27

(2R,3S)—N-((3S)-5-(4-Chlorophenyl)-9-methoxy-2-oxo-2,3-dihydro-1H-1,4-benzodiazepin-3-yl)-2,3-bis(3,3,3-trifluoropropyl)succinamide (27)

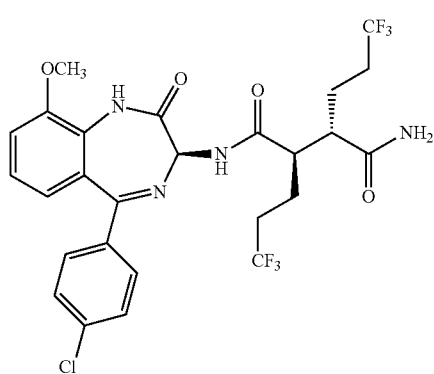

Example 27 was prepared from Intermediate B-20 and Intermediate S-1 according to the general procedures described above. The solid was purified by preparative SFC chromatography (Instrument: Berger SFC MGII, AS-H 250× 30 mm ID, 5 μm, 82/18 CO$_2$/MeOH, 85 mL/min) to afford Example 27. HPLC: RT=9.44 min (H$_2$O/CH$_3$CN with TFA, Sunfire C18 3.5 μm, 4.6×150 mm, gradient=15 min, wavelength=220 and 254 nm); MS(ES): m/z=607 [M+H$^+$]; $^1$H NMR (400 MHz, DMSO-d$_6$) δ 10.12 (s, 1H), 9.51 (d, J=7.3 Hz, 1H), 7.66 (br. s., 1H), 7.58-7.50 (m, 4H), 7.36-7.31 (m, 1H), 7.30-7.22 (m, 1H), 7.14 (s, 1H), 6.90 (dd, J=7.8, 1.2 Hz, 1H), 5.24 (d, J=7.3 Hz, 1H), 3.93 (s, 3H), 2.82-2.74 (m, 1H), 2.64-2.55 (m, 1H), 2.30-2.08 (m, 4H), 1.76-1.51 (m, 4H).

Example 28

(2R,3S)—N-((3S)-9-Chloro-5-(3-methylphenyl)-2-oxo-2,3-dihydro-1H-1,4-benzodiazepin-3-yl)-2,3-bis(3,3,3-trifluoropropyl)succinamide (28)

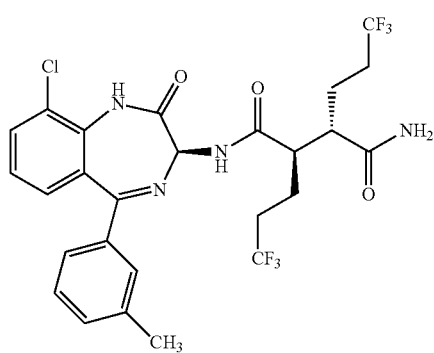

Example 28 was prepared from Intermediate B-14 and Intermediate S-1 according to the general procedures described above. The solid was purified by preparative SFC chromatography (Instrument: Berger SFC MGII, IC-H 250× 30 mm ID, 5 μm, 92/8 CO$_2$/MeOH, 85 mL/min) to afford Example 28. HPLC: RT=9.36 min (H$_2$O/CH$_3$CN with TFA, Sunfire C18 3.5 μm, 4.6×150 mm, gradient=15 min, wavelength=220 and 254 nm); MS(ES): m/z=591 [M+H$^+$]; $^1$H NMR (400 MHz, DMSO-d$_6$) δ 10.48 (br. s., 1H), 9.40 (br. s., 1H), 7.87-7.60 (m, 2H), 7.47-7.04 (m, 5H), 5.15 (br. s., 1H), 4.15 (dd, J=5.7, 3.3 Hz, 1H), 2.81 (td, J=9.9, 4.8 Hz, 1H), 2.40-2.02 (m, 5H), 1.83-1.53 (m, 4H), 1.45-1.18 (m, 3H), 0.98-0.79 (m, 2H).

Example 29

(2R,3S)—N-((3S)-5-(3-Methylphenyl)-9-methoxy-2-oxo-2,3-dihydro-1H-1,4-benzodiazepin-3-yl)-2,3-bis(3,3,3-trifluoropropyl)succinamide (29)

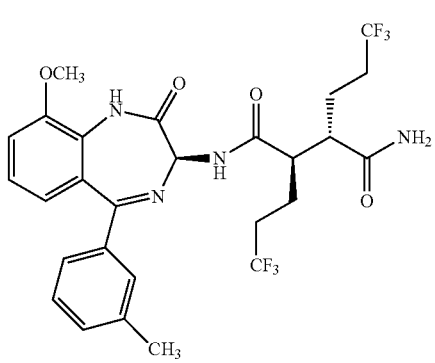

Example 29 was prepared from Intermediate B-21 and Intermediate S-1 according to the general procedures described above. The crude material was purified via preparative HPLC with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B:95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative HPLC with the following conditions: Column: Waters XBridge C18, 19×250 mm, 5-μm particles; GuardColumn: Waters XBridge C18, 19×10 mm, 5-μm particles; Mobile Phase A: 5:95 acetonitrile:water with 10-mM ammonium acetate; Mobile Phase B:95:5 acetonitrile:water with 10-mM ammonium acetate; Gradient: 20-55% B over 40 minutes, then a 15-minute hold at 55% B; Flow: 20 mL/min. Fractions containing the desired product were combined and dried via centrifugal evaporation. The material was further purified via preparative HPLC with the following conditions: Column: Waters XBridge C18, 19×100 mm, 5-μm particles; GuardColumn: Waters XBridge C18, 19×10 mm, 5-μm particles; Mobile Phase A: 5:95 acetonitrile:water with 10-mM ammonium acetate; Mobile Phase B:95:5 acetonitrile:water with 10-mM ammonium acetate; Gradient: 5-100% B over 10 minutes, then a 5-minute hold at 100% B; Flow: 20 mL/min. Fractions containing the desired product were combined and dried via centrifugal evaporation to afford Example 29. HPLC: RT=2.38 min (H$_2$O/CH$_3$CN with TFA, SUPELCO® Ascentis Express C18, 4.6×50 mm, 2.7 um, gradient=4 min, wavelength=220); MS(ES): m/z=586 [M+H$^+$]; $^1$H NMR (500 MHz, DMSO-d$_6$) δ 10.12 (br. s., 1H), 9.53 (d, J=7.4 Hz, 1H), 7.69 (d, J=1.5 Hz, 1H), 7.43-7.10 (m, 7H), 6.87 (dd, J=7.9, 1.0 Hz, 1H), 5.24 (d, J=7.4 Hz, 1H), 3.93 (s, 3H), 2.80 (td, J=10.0, 4.7 Hz, 1H), 2.63-2.54 (m, 1H), 2.33 (s, 3H), 2.30-2.09 (m, 3H), 1.78-1.53 (m, 4H).

Example 30

(2R,3S)—N-((3S)-5-(4-(Hydroxymethyl)phenyl)-2-oxo-2,3-dihydro-1H-1,4-benzodiazepin-3-yl)-2,3-bis(3,3,3-trifluoropropyl)succinamide

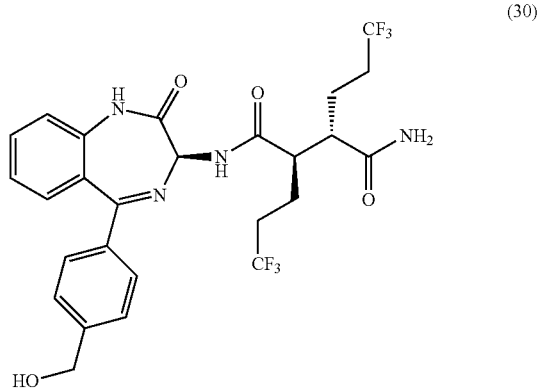 [SMILES: NC(=O)[C@@H](CCC(F)(F)F)[C@@H](CCC(F)(F)F)C(=O)N[C@H]1N=C(c2ccc(CO)cc2)c2ccccc2NC1=O]

(30)

Example 30 was prepared from Intermediate B-5 and Intermediate S-1 according to the general procedures described above. The solid was purified by preparative SFC chromatography (Instrument: Berger SFC MGII, Lux Cellulose-2 250×30 mm ID, 5 μm, 85/15 CO$_2$/MeOH, 85 mL/min) to afford Example 30. HPLC: RT=6.91 min (H$_2$O/CH$_3$CN with TFA, Sunfire C18 3.5 μm, 4.6×150 mm, gradient=15 min, wavelength=220 and 254 nm); MS(ES): m/z=573 [M+H$^+$]; $^1$H NMR (400 MHz, DMSO-d$_6$) δ 10.84 (s, 1H), 9.49 (d, J=7.3 Hz, 1H), 7.70-7.60 (m, 2H), 7.51-7.43 (m, 2H), 7.42-7.36 (m, 2H), 7.36-7.29 (m, 2H), 7.29-7.22 (m, 1H), 7.14 (br. s., 1H), 5.30 (t, J=5.7 Hz, 1H), 5.25 (d, J=7.5 Hz, 1H), 4.57 (d, J=5.7 Hz, 2H), 2.88-2.73 (m, 1H), 2.64-2.54 (m, 2H), 2.31-2.00 (m, 3H), 1.85-1.43 (m, 4H).

Example 31

(2R,3S)—N-((3S)-5-(2-Methylphenyl)-2-oxo-2,3-dihydro-1H-1,4-benzodiazepin-3-yl)-2,3-bis(3,3,3-trifluoropropyl)succinamide

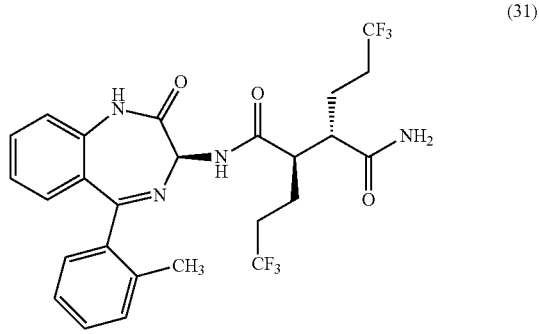 [SMILES: Cc1ccccc1C1=N[C@H](NC(=O)[C@H](CCC(F)(F)F)[C@H](CCC(F)(F)F)C(N)=O)C(=O)Nc2ccccc21]

(31)

Example 31 was prepared from Intermediate B-29 and Intermediate S-1 according to the general procedures described above. The solid was purified by preparative SFC chromatography (Instrument: Berger SFC MGII, Lux Cellulose-2 250×30 mm ID, 5 μm, 90/10 CO$_2$/MeOH, 85 mL/min) to afford Example 31. HPLC: RT=8.68 min (H$_2$O/CH$_3$CN with TFA, Sunfire C18 3.5 μm, 4.6×150 mm, gradient=15 min, wavelength=220 and 254 nm); MS(ES): m/z=557 [M+H$^+$]; $^1$H NMR (400 MHz, DMSO-d$_6$) δ 10.94 (br. s., 1H), 9.47 (d, J=7.5 Hz, 1H), 7.69-7.55 (m, 2H), 7.41-7.21 (m, 4H), 7.20-7.11 (m, 3H), 7.05 (dd, J=7.9, 1.3 Hz, 1H), 5.29 (d, J=7.5 Hz, 1H), 2.78 (td, J=10.0, 4.7 Hz, 1H), 2.31-2.07 (m, 3H), 2.02-1.94 (m, 3H), 1.76-1.51 (m, 4H).

Example 32

(2R,3S)—N-((3S)-5-(3-Methylphenyl)-2-oxo-2,3-dihydro-1H-1,4-benzodiazepin-3-yl)-2,3-bis(3,3,3-trifluoropropyl)succinamide

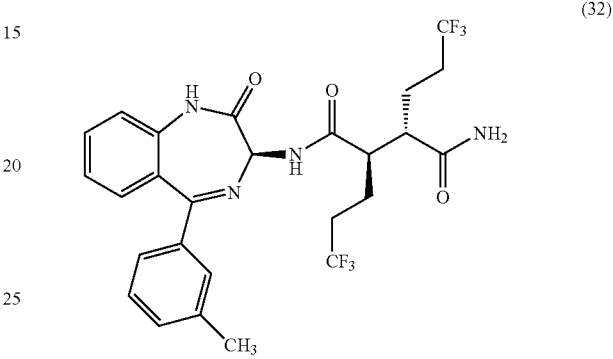

(32)

Example 32 was prepared from Intermediate B-22 and Intermediate S-1 according to the general procedures described above. This solid was purified by preparative SFC chromatography (Instrument: Berger SFC MGII, PHENOMENEX® Lux Cellulose-2 250×30 mm ID, 5 μm, 90/10 CO$_2$/MeOH, 85 mL/min) to afford Example 32. HPLC: RT=9.35 min (H$_2$O/CH$_3$CN with TFA, Sunfire C18 3.5 μm, 4.6×150 mm, gradient=15 min, wavelength=220 and 254 nm); MS(ES): m/z=557 [M+H$^+$]; $^1$H NMR (400 MHz, DMSO-d$_6$) δ 10.84 (s, 1H), 9.50 (d, J=7.5 Hz, 1H), 7.69-7.61 (m, 2H), 7.40-7.18 (m, 7H), 7.14 (br. s., 1H), 5.26 (d, J=7.3 Hz, 1H), 2.87-2.75 (m, 1H), 2.55 (d, J=2.0 Hz, 2H), 2.33 (s, 3H), 2.30-2.06 (m, 3H), 1.80-1.50 (m, 4H).

Example 33

(2R,3S)—N-((3S)-9-Methoxy-2-oxo-5-(5-(trifluoromethyl)-2-pyridinyl)-2,3-dihydro-1H-1,4-benzodiazepin-3-yl)-2,3-bis(3,3,3-trifluoropropyl)succinamide

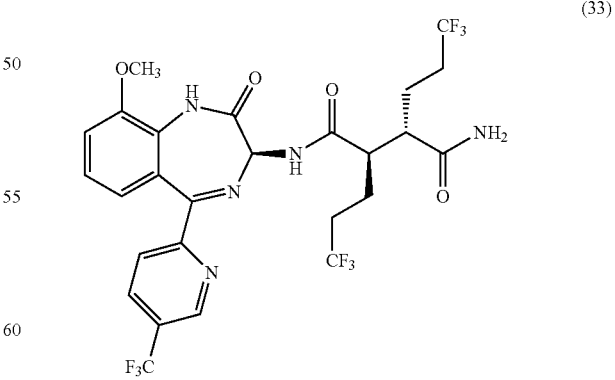

(33)

Example 33 was prepared from Intermediate B-24 and Intermediate S-1 according to the general procedures described above. After separation of the diastereomers (Instrument: Berger SFC MGII, AS-H 250×46 mm ID, 5 μm, 80/20 CO$_2$/MeOH, 85 mL/min), Example 33 was obtained.

HPLC: RT=9.364 min (H₂O/CH₃CN with TFA, Sunfire C18 3.5 μm, 4.6×150 mm, gradient=15 min, wavelength=220 and 254 nm); MS(ES): m/z=642 [M+H⁺]; ¹H NMR (400 MHz, DMSO-d₆) δ ppm 10.19 (1H, s), 9.58 (1H, d, J=7.5 Hz), 8.98 (1H, d, J=0.9 Hz), 8.40 (1H, dd, J=8.4, 2.0 Hz), 8.15 (1H, d, J=8.4 Hz), 7.65 (1H, br. s.), 7.30 (1H, dd, J=8.4, 1.1 Hz), 7.20 (1H, t, J=8.0 Hz), 7.14 (1H, br. s.), 6.93 (1H, dd, J=7.9, 1.1 Hz), 5.35 (1H, d, J=7.3 Hz), 3.92 (3H, s), 2.74-2.85 (1H, m), 2.55-2.65 (1H, m), 2.05-2.31 (4H, m), 1.47-1.77 (4H, m).

Example 34

(2R,3S)—N-((3S)-5-(5-Chloro-2-pyridinyl)-9-methoxy-2-oxo-2,3-dihydro-1H-1,4-benzodiazepin-3-yl)-2,3-bis(3,3,3-trifluoropropyl)succinamide

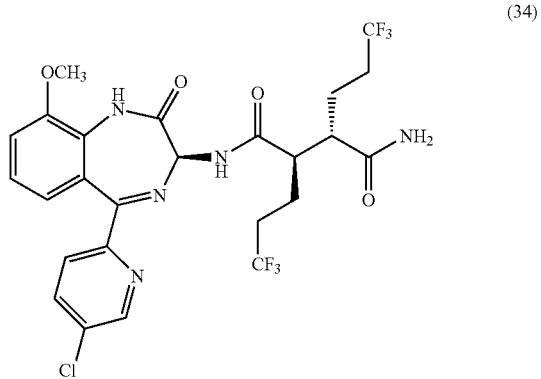 [SMILES: COc1cccc2c1NC(=O)[C@@H](NC(=O)[C@H](CCC(F)(F)F)[C@H](CCC(F)(F)F)C(N)=O)N=C2c1ccc(Cl)cn1]

(34)

Example 34 was prepared from Intermediate B-26 and Intermediate S-1 according to the general procedures described above. This solid was purified by preparative SFC chromatography (Instrument: Berger SFC MGII, AS-H 250× 46 mm ID, 5 μm, 75/25 CO₂/MeOH, 85 mL/min) to afford Example 34. HPLC: RT=8.43 min (H₂O/CH₃CN with TFA, Sunfire C18 3.5 μm, 4.6×150 mm, gradient=15 min, wavelength=220 and 254 nm); MS(ES): m/z=587 [M+H⁺]; ¹H NMR (400 MHz, DMSO-d₆) δ 10.14 (s, 1H), 9.55 (d, J=7.5 Hz, 1H), 8.68-8.58 (m, 1H), 8.11 (dd, J=8.5, 2.5 Hz, 1H), 7.99 (d, J=8.6 Hz, 1H), 7.66 (br. s., 1H), 7.33-7.26 (m, 1H), 7.21 (t, J=8.0 Hz, 1H), 7.14 (br. s., 1H), 6.93 (dd, J=7.9, 1.1 Hz, 1H), 5.30 (d, J=7.3 Hz, 1H), 3.92 (s, 3H), 2.84-2.72 (m, 1H), 2.65-2.56 (m, 1H), 2.31-2.04 (m, 3H), 1.76-1.47 (m, 4H).

Example 35

(2R,3S)—N-((3S)-5-(4-Methoxyphenyl)-2-oxo-2,3-dihydro-1H-1,4-benzodiazepin-3-yl)-2,3-bis(3,3,3-trifluoropropyl)succinamide

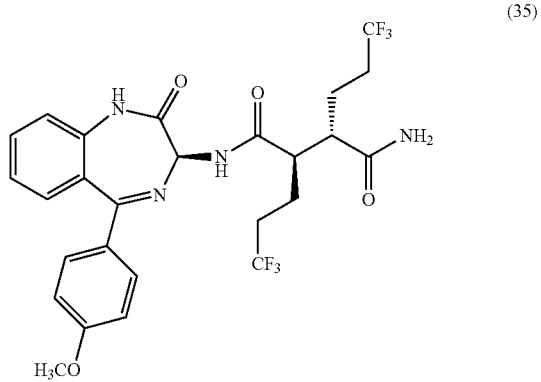 [SMILES: COc1ccc(C2=N[C@H](NC(=O)[C@H](CCC(F)(F)F)[C@H](CCC(F)(F)F)C(N)=O)C(=O)Nc3ccccc32)cc1]

(35)

Example 35 was prepared from Intermediate B-25 and Intermediate S-1 according to the general procedures described above. The diastereomers were separated by Chiral HPLC (CHIRALPAK® AD 5 cm×50 cm 10 μM isocratic 30% i-propanol: heptane 100 ml/min) to afford Example 35. HPLC: RT=8.68 min (H₂O/CH₃CN with TFA, Sunfire C18 3.5 μm, 4.6×150 mm, gradient=15 min, wavelength=220 and 254 nm); MS(ES): m/z=573 [M+H⁺]; ¹H NMR (400 MHz, DMSO-d₆) δ 10.81 (d, J=6.6 Hz, 1H), 9.48 (d, J=5.5 Hz, 1H), 7.64 (t, J=6.4 Hz, 1H), 7.46 (dd, J=8.7, 4.1 Hz, 2H), 7.39-7.22 (m, 3H), 7.00 (dd, J=8.8, 3.3 Hz, 2H), 5.22 (dd, J=9.4, 7.6 Hz, 1H), 3.82 (s, 3H), 2.97-2.84 (m, 1H), 2.37-2.08 (m, 4H), 1.85-1.55 (m, 4H), 1.43-1.32 (m, 3H).

Example 36

(2R,3S)—N-((3S)-5-(4-Methylphenyl)-2-oxo-2,3-dihydro-1H-1,4-benzo diazepin-3-yl)-2,3-bis(3,3,3-trifluoropropyl)succinamide

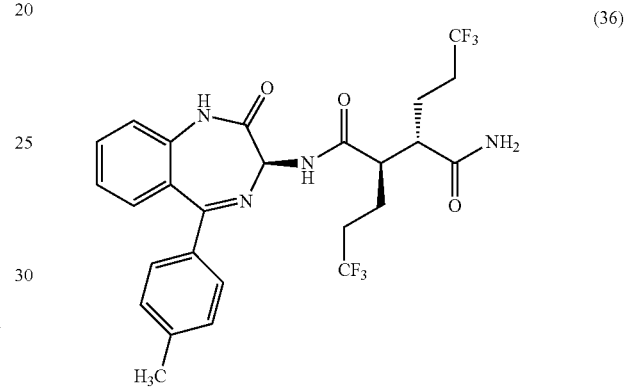

(36)

Example 36 was prepared from Intermediate B-23 and Intermediate S-1 according to the general procedures described above. The diastereomers were separated by Prep Chiral HPLC (CHIRALPAK® AD 5 cm×50 cm 10 μM isocratic 20% i-propanol:heptane 100 ml/min) to afford Example 36. HPLC: RT=9.32 min (H₂O/CH₃CN with TFA, Sunfire C18 3.5 μm, 4.6×150 mm, gradient=15 min, wavelength=220 and 254 nm); MS(ES): m/z=557 [M+H⁺]; ¹H NMR (400 MHz, DMSO-d₆) δ 10.80 (s, 1H), 9.46 (d, J=7.5 Hz, 1H), 7.70-7.57 (m, 2H), 7.39 (d, J=8.1 Hz, 2H), 7.35-7.19 (m, 5H), 7.12 (s, 1H), 5.23 (d, J=7.3 Hz, 1H), 2.84-2.74 (m, 1H), 2.36 (s, 3H), 2.27-2.07 (m, 3H), 1.77-1.52 (m, 5H).

Example 37

(2R,3S)—N-((3S)-5-(3-Fluorophenyl)-9-(hydroxymethyl)-2-oxo-2,3-dihydro-1H-1,4-benzodiazepin-3-yl)-2,3-bis(3,3,3-trifluoropropyl)succinamide

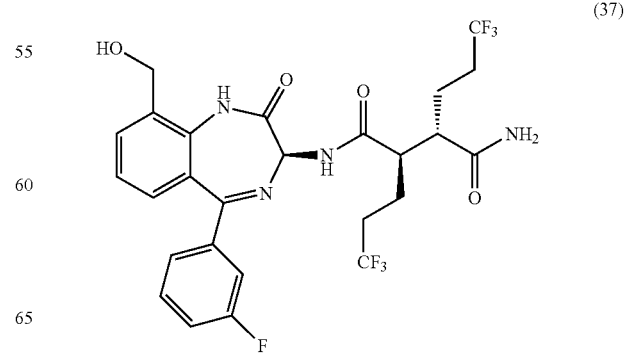

(37)

Intermediate 37A: N-Methoxy-N,3-dimethyl-2-nitrobenzamide

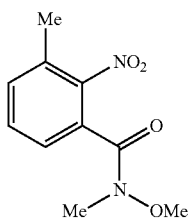

(37A)

To a suspension of 3-methyl-2-nitrobenzoic acid (5 g, 27.6 mmol) in DCM (50 mL) was added oxalyl chloride (4.83 mL, 55.2 mmol) followed by 2 drops of DMF. The mixture was stirred at room temperature for 1.5 h and then concentrated and azeotroped with DCM/toluene resulting in a white solid which was dried under high vacuum overnight. To a mixture of N,O-dimethylhydroxylamine, HCl (5.38 g, 55.2 mmol) and TEA (11.54 mL, 83 mmol) in DCM (80 mL) at 0° C. was slowly added a solution of the above acid chloride in DCM (20 mL). The reaction was then stirred for 30 min, and then quenched with water and extracted with DCM. The organic layer was separated, washed with 1N HCl, sat. NaHCO$_3$ and brine and then dried and concentrated to give Intermediate 37A (6.05 g, 98%). HPLC: RT=1.27 min (CHROMOLITH® SpeedROD column 4 6×50 mm, 10-90% aqueous methanol over 4 minutes containing 0.1% TFA, 4 mL/min, monitoring at 220 nm), $^1$H NMR (400 MHz, chloroform-d) δ 7.52-7.45 (m, 1H), 7.42-7.35 (m, 2H), 3.48 (br. s., 3H), 3.33 (s, 3H), 2.51 (s, 3H).

Intermediate 37B: 3-(Bromomethyl)-N-methoxy-N-methyl-2-nitrobenzamide

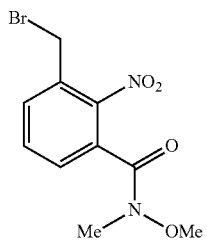

(37B)

A mixture of Intermediate 37A (5.5 g, 24.53 mmol), NBS (5.24 g, 29.4 mmol) and benzoyl peroxide (0.594 g, 2.453 mmol) in CCl$_4$ (80 mL) was purged with nitrogen and then heated to 80° C. for 4.5 h. The reaction mixture was cooled to room temperature and then quenched with water. The mixture was extracted with DCM and the combined extracts were washed with saturated NaHCO$_3$ and brine and then dried (Na$_2$SO$_4$), filtered and concentrated to dryness. The crude material was purified by flash chromatography (SiO$_2$, 80 g column, EtOAc/hexane=0-100%) to afford Intermediate 37B.

Intermediate 37C: 3-(Hydroxymethyl)-N-methoxy-N-methyl-2-nitrobenzamide

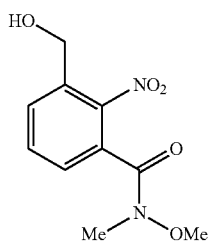

(37C)

A mixture of Intermediate 37B (3.7 g, 4.88 mmol) and calcium carbonate (2.93 g, 29.3 mmol) in dioxane (25 mL)/water (25 mL) was stirred at reflux for 5 h. The mixture was then cooled to room temperature, the solid was removed by filtration and the filtrate was extracted with EtOAc. The combined organic layers were washed with brine, dried (MgSO$_4$), filtered and concentrated to dryness. The crude residue was purified by flash chromatography (SiO$_2$, 80 g column, EtOAc/hexane=20-100%) to afford Intermediate 37C (1.079 g, 78%). HPLC: RT=0.75 min (CHROMOLITH® SpeedROD column 4 6×50 mm, 10-90% aqueous methanol over 4 minutes containing 0.1% TFA, 4 mL/min, monitoring at 220 nm), MS(ES): m/z=241.0 [M+H$^+$].

Intermediate 37D: 3-(((tert-Butyldimethylsilyl)oxy)methyl)-N-methoxy-N-methyl-2-nitrobenzamide

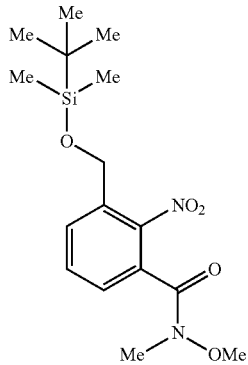

(37D)

To a solution of Intermediate 37C (1.079 g, 4.49 mmol) and TBDMS-Cl (1.016 g, 6.74 mmol) in DMF (4 mL) was added imidazole (0.612 g, 8.98 mmol). The mixture was stirred at room temperature for 1 h. Water was added, and the mixture was extracted with EtOAc. The combined extracts were washed with 10% LiCl and brine, dried over MgSO$_4$, filtered and concentrated to dryness. The crude material was purified by flash chromatography (SiO$_2$, 40 g column, EtOAc/hexane=0-30%) to afford Intermediate 37D (1.25 g, 79%). HPLC: RT=3.05 min (CHROMOLITH® SpeedROD column 4 6×50 mm, 10-90% aqueous methanol over 4 minutes containing 0.1% TFA, 4 mL/min, monitoring at 220 nm), MS(ES): m/z=355.0 [M+H$^+$]. $^1$H NMR (400 MHz, chloroform-d) δ 7.90 (d, J=7.7 Hz, 1H), 7.70-7.62 (m, 1H), 7.47 (d, J=7.7 Hz, 1H), 4.98 (s, 2H), 3.46 (br. s., 3H), 3.36 (br. s., 3H), 0.98 (s, 9H), 0.15 (s, 6H).

Intermediate 37E: 2-Amino-3-(((tert-butyldimethylsilyl)oxy)methyl)-N-methoxy-N-methylbenzamide

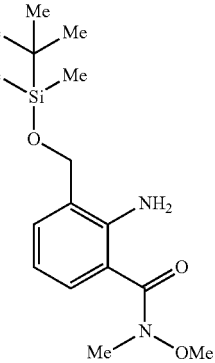

(37E)

A mixture of Intermediate 37D (1.25 g, 3.53 mmol) and 10% Pd/C (200 mg, 0.188 mmol) in EtOAc (50 mL) was purged with hydrogen. The mixture was then stirred under a hydrogen atmosphere for 1.5 h. The suspension was filtered, and the filtrate was concentrated to dryness. The crude material was purified by flash chromatography (SiO$_2$, 24 g column, EtOAc/hexane=0-40%) to afford Intermediate 37E (939 mg, 82%). HPLC: RT=2.986 min (CHROMOLITH® SpeedROD column 4 6×50 mm, 10-90% aqueous methanol over 4 minutes containing 0.1% TFA, 4 mL/min, monitoring at 220 nm), MS(ES): m/z=325.2 [M+H⁺]; ¹H NMR (400 MHz, chloroform-d) δ 7.32 (dd, J=7.7, 1.5 Hz, 1H), 7.11 (dd, J=7.5, 1.5 Hz, 1H), 6.68-6.62 (m, 1H), 5.21 (br. s., 2H), 4.71 (s, 2H), 3.61 (s, 3H), 3.36 (s, 3H), 0.92 (s, 9H), 0.09 (s, 6H).

Intermediate 37F: (2-Amino-3-(((tert-butyldimethyl-silyl)oxy)methyl)phenyl)(3-fluorophenyl)methanone (37F)

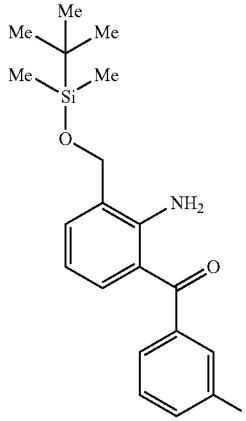

To a solution of 1-fluoro-3-iodobenzene (0.782 mL, 6.66 mmol) in THF (6 mL) at −78° C. was added nBuLi (2.5M in hexane, 2.66 mL, 6.66 mmol) dropwise. After the addition was completed, the mixture was stirred at −78° C. for 40 min. Then a solution of Intermediate 37E (540 mg, 1.664 mmol) in THF (2.5 mL) was added dropwise. The mixture was then stirred at −78° C. for 2 h. The resulting mixture was poured into ice with HCl (7.49 mL, 7.49 mmol) and extracted with EtOAc. The combined extracts were washed with brine, dried and concentrated. The crude material was purified by flash chromatography (SiO₂, 12 g column, EtOAc/hexane=0-15%) to afford Intermediate 37F (271 mg, 45%) HPLC: RT=3.70 min (CHROMOLITH® SpeedROD column 4 6×50 mm, 10-90% aqueous methanol over 4 minutes containing 0.1% TFA, 4 mL/min, monitoring at 220 nm), MS(ES): m/z=360.4 [M+H⁺]; ¹H NMR (400 MHz, chloroform-d) δ 7.49-7.33 (m, 4H), 7.27-7.20 (m, 2H), 6.84 (br. s., 2H), 6.57 (t, J=7.6 Hz, 1H), 4.77 (s, 2H), 0.95 (s, 9H), 0.13 (s, 6H).

Intermediate 37G: (Benzyl(9-(((tert-butyldimethylsilyl)oxy)methyl)-5-(3-fluorophenyl)-2-oxo-2,3-dihydro-1H-benzo[e][1,4]diazepin-3-yl)carbamate (37G)

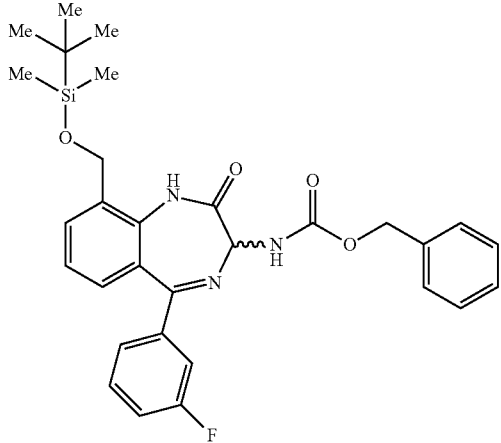

To a solution of 2-(1H-benzo[d][1,2,3]triazol-1-yl)-2-(((benzyloxy)carbonyl)amino)acetic acid (608 mg, 1.864 mmol) in THF (7 mL) cooled at 0° C. was added oxalyl chloride (0.157 mL, 1.789 mmol), followed by DMF (0.02 mL). The resulting mixture was stirred at 0° C. for 1.5 h. Then a solution of Intermediate 37F (268 mg, 0.745 mmol) and 4-methylmorpholine (0.246 mL, 2.236 mmol) in THF (3 mL) were slowly added. After the addition, the reaction mixture was warmed to room temperature and stirred for 1 h. Next, 7N ammonia in MeOH (4 mL, 28.0 mmol) was added and the mixture was stirred at room temperature overnight. The resulting mixture was concentrated and the residue was treated with EtOAc and water. The organic layer was separated, and the aqueous layer was extracted with EtOAc. The combined organic extracts were washed with 1N NaOH, sat NaHCO₃ and brine and then dried over MgSO₄, filtered and concentrated. The residue was then dissolved in acetic acid (1.5 mL, 26.2 mmol), and treated with ammonium acetate (287 mg, 3.73 mmol). The mixture was stirred at 40° C. for 2 h. The reaction mixture was then treated with water and extracted with EtOAc. The combined extracts were washed with water, saturated NaHCO₃, and brine and then dried and concentrated. The crude material was purified by flash chromatography (SiO₂, 12 g column, EtOAc/hexane=0-40%) to afford Intermediate 37G (256 mg, 63%). HPLC: RT=3.61 min (CHROMOLITH® SpeedROD column 4 6×50 mm, 10-90% aqueous methanol over 4 minutes containing 0.1% TFA, 4 mL/min, monitoring at 220 nm), MS(ES): m/z=548.5 [M+H⁺].

Intermediate 37H: 3-Amino-5-(3-fluorophenyl)-9-(hydroxymethyl)-1H-benzo[e][1,4]diazepin-2(3H)-one (37H)

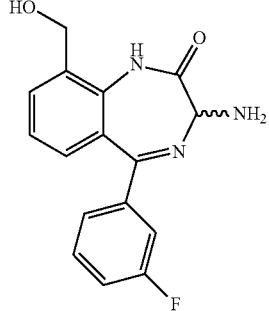

A mixture of Intermediate 37G (255 mg, 0.466 mmol) in 33% HBr in HOAc (1149 µl, 6.98 mmol) was stirred at room temperature for 1 h. Ether was added and the resulting solid precipitate was collected by filtration and rinsed with ether. The solid was dissolved in MeOH (10 mL) and K₂CO₃ (1.3 g) was added. The mixture was stirred for 40 min. and then filtered and concentrated to dryness to afford Intermediate 37H (133 mg). HPLC: RT=1.102 min (CHROMOLITH® SpeedROD column 4 6×50 mm, 10-90% aqueous methanol over 4 minutes containing 0.1% TFA, 4 mL/min, monitoring at 220 nm), MS(ES): m/z=300.2 [M+H⁺].

Intermediate 37I: (2S,3R)-tert-Butyl 6,6,6-trifluoro-3-((5-(3-fluorophenyl)-9-(hydroxymethyl)-2-oxo-2,3-dihydro-1H-benzo[e][1,4]diazepin-3-yl)carbamoyl)-2-(3,3,3-trifluoropropyl)hexanoate

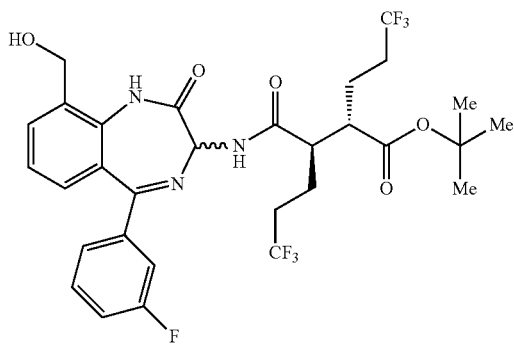

(37I)

To a solution of Intermediate 37H (130 mg, 0.434 mmol), Intermediate S-1 (159 mg, 0.434 mmol) and TBTU (167 mg, 0.521 mmol) in DMF (1.5 mL) was added TEA (0.133 mL, 0.956 mmol). The mixture was stirred at room temperature for 45 min. Water was added and the solid was collected by filtration, rinsed with water, and dried. The resulting solid was purified by flash chromatography (SiO$_2$, 12 g column, EtOAc/hexane=0-80%) to afford Intermediate 37I (66 mg 23%). HPLC: RT=3.27 min (CHROMOLITH® SpeedROD column 4 6×50 mm, 10-90% aqueous methanol over 4 minutes containing 0.1% TFA, 4 mL/min, monitoring at 220 nm), MS(ES): m/z=648.3 [M+H$^+$].

Intermediate 37J: (2S,3R)-6,6,6-Trifluoro-3-((5-(3-fluorophenyl)-9-(hydroxymethyl)-2-oxo-2,3-dihydro-1H-benzo[e][1,4]diazepin-3-yl)carbamoyl)-2-(3,3,3-trifluoropropyl) hexanoic acid

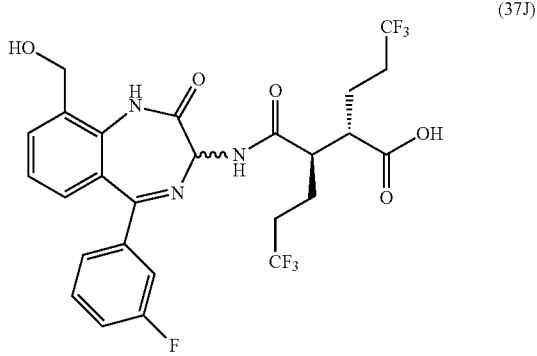 [SMILES: O=C1Nc2c(CO)cccc2C(c2cccc(F)c2)=NC1NC(=O)[C@H](CCC(F)(F)F)[C@H](CCC(F)(F)F)C(=O)O]

(37J)

To a solution of Intermediate 37I (65 mg, 0.100 mmol) in DCM (2 mL) was added TFA (2 mL). The mixture was stirred at room temperature for 3 h and then concentrated to dryness. The crude material was purified by preparative reversed-phase HPLC (aq. MeOH, containing 0.1% TFA). The desired fractions were combined and concentrated to dryness to afford Intermediate 37J (30 mg, 51%). HPLC: RT=2.680 min (CHROMOLITH® SpeedROD column 4 6×50 mm, 10-90% aqueous methanol over 4 minutes containing 0.1% TFA, 4 mL/min, monitoring at 220 nm), MS(ES): m/z=592.3 [M+H$^+$].

Example 37

To a mixture of Intermediate 37J (30 mg, 0.051 mmol), EDC (34.0 mg, 0.178 mmol) and HOBT (27.2 mg, 0.178 mmol) in THF (2 mL) was added 2M ammonia in IPA (0.507 mL, 1.014 mmol). The mixture was stirred at room temperature overnight and then concentrated. Water was added to the residue and the mixture was extracted with EtOAc. The combined organic extracts were washed with saturated NaHCO$_3$ and brine, and then dried (MgSO$_4$) and concentrated to afford 30 mg of the crude product as a mixture of two diastereomers. The diastereomers were separated by chiral SFC (Berger SFC MGII, Chiral ID 25×3 cm ID, 5 μm, 85/15 CO$_2$/MeOH, 85 mL/min, detection at 220 nm) to afford Example 37 (10 mg, 35%). HPLC: RT=7.44 min (H$_2$O/CH$_3$CN with TFA, Xbridge Phenyl 3.5 um, 4.6×150 mm, gradient=15 min, wavelength=220 and 254 nm); MS(ES): m/z=591.2 [M+H$^+$]; $^1$H NMR (400 MHz, methanol-d$_4$) δ 7.68-7.62 (m, 1H), 7.46-7.39 (m, 1H), 7.38-7.20 (m, 5H), 5.43 (s, 1H), 4.94-4.88 (m, 1H), 4.80-4.73 (m, 1H), 2.80 (td, J=10.3, 4.0 Hz, 1H), 2.59 (td, J=10.5, 3.7 Hz, 1H), 2.54-2.39 (m, 1H), 2.31-2.10 (m, 3H), 1.96-1.70 (m, 4H).

Example 38

((3S)-3-(((2R,3S)-3-Carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valinate

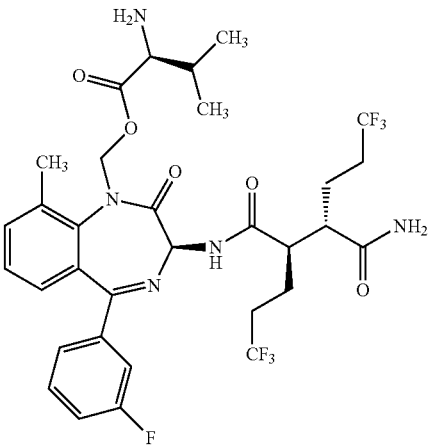

(38)

Intermediate 38A: (S)-Chloromethyl 2-((tert-butoxycarbonyl)amino)-3-methylbutanoate

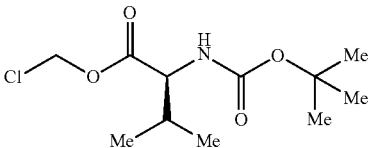

(38A)

To a vigorously stirred mixture of (S)-2-((tert-butoxycarbonyl)amino)-3-methylbutanoic acid (4 g, 18.41 mmol), tetrabutylammonium hydrogen sulfate (1.25 g, 3.68 mmol), and Na$_2$CO$_3$ (9.76 g, 92 mmol) in DCM 80 (mL) and water (80 mL), cooled in an ice/water bath, was slowly added chloromethyl chlorosulfate (3.8 mL, 36.8 mmol) over 4 min. After stirring in the ice/water bath for 30 min, the cold bath was removed and the reaction mixture was allowed to stir at room temperature. After stirring 16 h at room temperature, the reaction mixture was diluted with water and extracted with DCM. The aqueous layer was back extracted with DCM and the combined organic layers were dried over MgSO$_4$, filtered and concentrated to afford Intermediate 38A (5.45 g).

Intermediate 38B: (S)—((S)-3-(((2R,3S)-3-Carbamoyl-6,6,6-trifluoro-2-(3,3,3-trifluoropropyl)hexanamido)-5-(3-fluorophenyl)-9-methyl-2-oxo-2,3-dihydro-1H-benzo[e][1,4]diazepin-1-yl)methyl 2-((tert-butoxycarbonyl)amino)-3-methylbutanoate

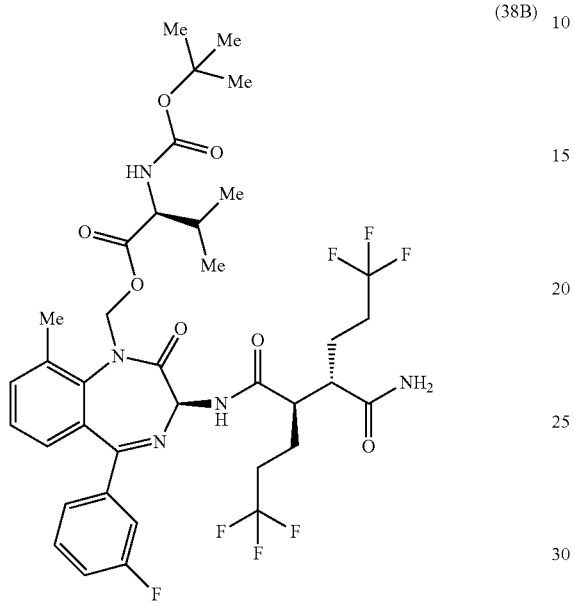

(38B)

To a stirred mixture of Example 1 (400 mg, 0.696 mmol) and K$_2$CO$_3$ (289 mg, 2.089 mmol) in DMF (4 mL) was slowly added Intermediate 38A (555 mg, 2.089 mmol) in DMF (3 mL). After stirring at room temperature for 22 h, the reaction mixture was diluted with EtOAc and washed 3 times with 10% aqueous LiCl solution. The organic layer was dried over MgSO$_4$, filtered and concentrated. The crude material was purified by flash chromatography (Teledyne ISCO Combi-Flash 20% to 70% solvent A/B=hexane/acetone, REDISEP® SiO$_2$ 120 g, detecting at 254 nm, and monitoring at 220 nm) to afford Intermediate 38B (213.3 mg, 38.1%). HPLC: RT=3.428 min (CHROMOLITH® SpeedROD column 4 6×50 mm, 10-90% aqueous methanol over 4 minutes containing 0.1% TFA, 4 mL/min, monitoring at 220 nm), MS(ES): m/z=804.5 [M+H$^+$].

Example 38

To a stirred mixture of Intermediate 38B (213.3 mg, 0.265 mmol) in DCM (6 mL) was added 4N HCl in dioxane (0.663 mL, 2.65 mmol) at room temperature. After stirring 1.5 h, the reaction mixture was concentrated and the crude material was purified by Preparative HPLC (YMC C18, 30×100, 10-90% aqueous methanol over 12 minutes containing 0.1% TFA, 30 mL/min, detecting and monitoring at 220 nM). The fractions containing product were combined and then concentrated via lyophilization to afford Example 38 (154 mg, 70.3%) as a TFA salt. HPLC: RT=10.854 min (H$_2$O/CH$_3$CN with TFA, Sunfire C18 3.5 μm, 4.6×150 mm, gradient=15 min, wavelength=220 and 254 nm); MS(ES): m/z=704.6[M+H$^+$]; $^1$H NMR (500 MHz, DMSO-d$_6$) δ 9.46 (d, J=6.7 Hz, 1H), 8.14 (br. s., 3H), 7.72-7.62 (m, 2H), 7.57-7.50 (m, 1H), 7.47-7.37 (m, 4H), 7.27 (d, J=7.8 Hz, 1H), 7.13 (s, 1H), 6.15 (d, J=10.3 Hz, 1H), 5.50 (d, J=10.3 Hz, 1H), 5.38 (d, J=6.7 Hz, 1H), 2.83 (td, J=10.2, 4.3 Hz, 1H), 2.45 (s, 4H), 2.29-2.18 (m, 1H), 2.17-2.06 (m, 2H), 1.81-1.72 (m, 1H), 1.72-1.48 (m, 4H), 0.66 (d, J=6.9 Hz, 3H), 0.62 (d, J=6.9 Hz, 3H).

Example 39

((3S)-3-(((2R,3S)-3-Carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-alaninate

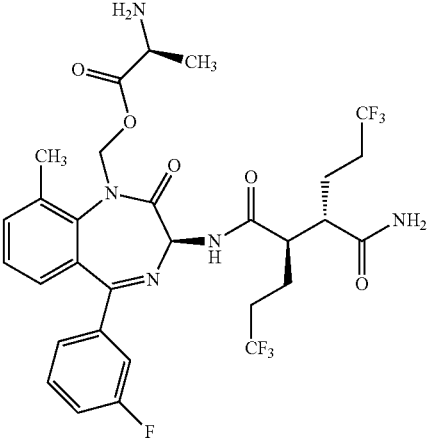

(39)

Intermediate 39A: (S)-Chloromethyl 2-((tert-butoxycarbonyl)amino)propanoate

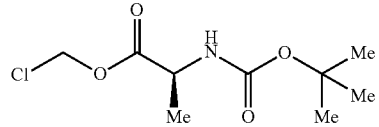

(39A)

To a vigorously stirred mixture of (S)-2-((tert-butoxycarbonyl)amino) propanoic acid (1 g, 5.29 mmol), tetrabutylammonium hydrogen sulfate (0.359 g, 1.057 mmol), and Na$_2$CO$_3$ (2.80 g, 26.4 mmol) in DCM 20 (mL) and water (20 mL), cooled in an ice/water bath, was slowly added chloromethyl chlorosulfate (1.09 mL, 10.57 mmol) over a 4 min period. After stirring in an ice/water bath for 30 min, the cold bath was removed and the reaction mixture was allowed to stir at room temperature. After stirring 16 h at room temperature the reaction mixture was diluted with water and extracted with DCM. The aqueous layer was back extracted with DCM and the combined organic layers were dried over MgSO$_4$, filtered and concentrated. The crude material (1.64 g) was used as is without further purification.

Example 39

Example 39 was prepared from Example 1 and Intermediate 39A according to the general procedure shown for Example 38. HPLC: RT=7.443 min (H$_2$O/CH$_3$CN with TFA, Sunfire C18 3.5 μm, 4.6×150 mm, gradient=15 min, wavelength=220 and 254 nm); MS(ES): m/z=676 [M+H$^+$]; $^1$H NMR (500 MHz, DMSO-d$_6$) δ 9.45 (d, J=6.7 Hz, 1H), 8.17 (br. s., 3H), 7.72-7.63 (m, 2H), 7.58-7.49 (m, 1H), 7.48-7.36 (m, 4H), 7.25 (d, J=6.9 Hz, 1H), 7.14 (br. s., 1H), 6.15 (d, J=10.3 Hz, 1H), 5.50 (d, J=10.3 Hz, 1H), 5.38 (d, J=6.7 Hz, 1H), 2.83 (td, J=10.1, 4.2 Hz, 1H), 2.45 (s, 3H), 2.29-2.06 (m, 3H), 1.77-1.48 (m, 4H), 0.94 (d, J=7.2 Hz, 3H).

Example 40

S-(((2S,3R)-6,6,6-Trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteine (40)

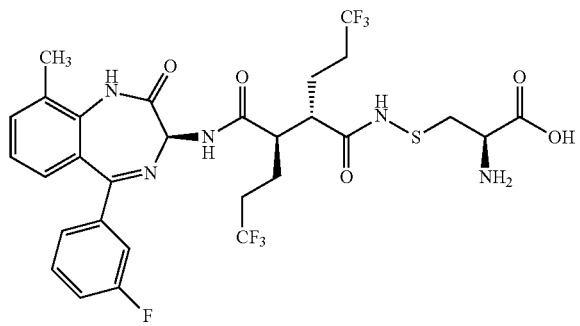

Intermediate 40A: (2R,2'R)-Di-tert-butyl 3,3'-disulfanediylbis(2-((tert-butoxycarbonyl)amino)propanoate)

(40A)

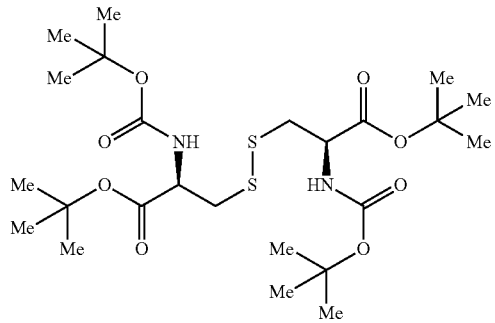

A suspension of (2R,2'R)-di-tert-butyl 3,3'-disulfanediyl-bis(2-aminopropanoate)dihydrochloride (1.9 g, 4.47 mmol) in DMF (50 mL) at room temperature was treated with TEA (1.556 mL, 11.17 mmol), followed by di-tert-butyl dicarbonate (2.437 g, 11.17 mmol). The mixture was stirred at room temperature overnight. The reaction mixture was poured in EtOAc (100 mL) and washed with 0.1N HCl (2×100 mL), followed by sat. aq. NaHCO₃ (100 mL) and brine (100 mL). The organic layer was dried (Na₂SO₄) filtered and concentrated to dryness. The crude product was dissolved in a small amount of DCM and purified by flash chromatography (SiO₂, 0% ethyl acetate/hexanes to 20% ethyl acetate/hexanes, 120 g column, 30 min gradient) to afford Intermediate 40A (1.65 g, 66.8%). ¹H NMR (400 MHz, chloroform-d) δ 5.34 (d, J=5.9 Hz, 2H), 4.46 (d, J=5.9 Hz, 2H), 3.27-3.07 (m, 4H), 1.49 (s, 18H), 1.46 (s, 18H).

Intermediate 40B: (R)-tert-Butyl 2-((tert-butoxycarbonyl)amino)-3-(((2S,3R)-6,6,6-trifluoro-3-(((S)-5-(3-fluorophenyl)-9-methyl-2-oxo-2,3-dihydro-1H-benzo[e][1,4]diazepin-3-yl)carbamoyl)-2-(3,3,3-trifluoropropyl)hexanamido)thio)propanoate (40B)

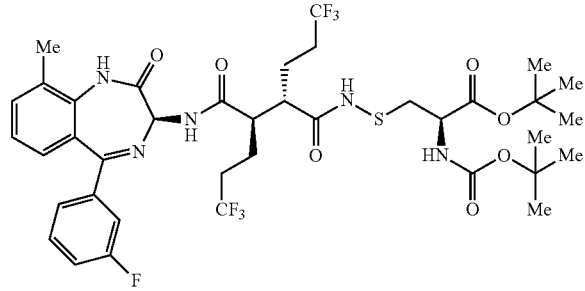

A slight suspension of silver nitrate (118 mg, 0.696 mmol) in methanol (18 mL) was treated with Intermediate 40A (385 mg, 0.696 mmol). The reaction mixture was stirred for 30 min and then Example 1 (100 mg, 0.174 mmol) and TEA (97 μl, 0.696 mmol) were added. The reaction was stirred at room temperature overnight and then concentrated to dryness. The crude product was dissolved in a small amount of DCM and purified by flash chromatography (SiO₂, 0% ethyl acetate/hexanes to 100% ethyl acetate/hexanes, 24 g column, 30 min gradient) to afford Intermediate 40B (78 mg, 52.7%). HPLC TR=3.443 min (CHROMOLITH® SpeedROD, 5.0 um, 4.6 mm×50 mm, 10-90% aqueous methanol containing 0.1% TFA, 4 min gradient, monitored at 220 nm). [M+H+]=850.5.

Example 40

A solution of Intermediate 40B (78 mg, 0.092 mmol) in DCM (5 mL) at 0° C. was treated with TFA (0.5 mL, 6.49 mmol) and slowly warmed to room temperature. The reaction mixture was stirred at room temperature overnight and then concentrated to dryness. The crude reaction product was dissolved in a small amount of MeOH and purified by reversed phase HPLC (YMC ODS C18 5 um 30×100 mm, 10-90% aqueous methanol containing 0.1% TFA, 15 mL/min, 30 min gradient, monitored at 220 nm). The product (retention time=24.980 minutes) was isolated and lyophilized to dryness. The resulting solid was suspended in water and treated with 0.1N HCl (1 mL) at 0° C. The solution was again lyophilized to dryness to afford Example 40 as an HCl salt (29 mg, 41.5%). HPLC RT: =9.328 min (Sunfire C18 3.5 um, 3×150 mm, 10% 95/5 water/ACN with 0.05% TFA to 100% 5/95 water/ACN with 0.05% TFA, 15 minute gradient, flow rate=0.5 mL/min, monitored at 220 and 254 nm). MS(ES): m/z=694.4 [M+H⁺]. ¹H NMR (400 MHz, DMSO-d₆) δ 10.23 (s, 1H), 9.65 (s, 1H), 9.52 (d, J=7.5 Hz, 1H), 8.44 (br. s., 2H), 7.55 (dd, J=6.6, 1.5 Hz, 1H), 7.51-7.44 (m, 1H), 7.42-7.33 (m, 2H), 7.28-7.23 (m, 1H), 7.22-7.17 (m, 2H), 5.25 (d, J=7.3 Hz, 1H), 4.02-3.94 (m, 1H), 3.27 (dd, J=15.1, 4.1 Hz, 1H), 3.02 (dd, J=15.1, 8.9 Hz, 1H), 2.92 (td, J=10.6, 3.3 Hz, 1H), 2.74-2.65 (m, 1H), 2.28-2.11 (m, 4H), 1.85-1.74 (m, 1H), 1.73-1.64 (m, 1H), 1.64-1.54 (m, 1H), 1.48-1.36 (m, 1H).

Example 41 tert-Butyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate (41)

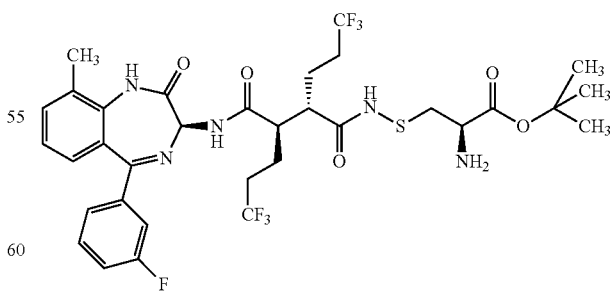

A solution of Intermediate 40B (417 mg, 0.491 mmol) in DCM (20 mL) was treated with TFA (2 mL, 26.0 mmol) and stirred at room temperature for 24 h. The resulting solution was concentrated to dryness. The crude reaction product was dissolved in a small amount of MeOH and purified by reversed phase HPLC (YMC ODS C18 5 um 20×100 mm, 10-90% aqueous methanol containing 0.1% TFA, 15 mL/min, 30 min gradient, monitored at 220 nm). The product (retention time=27.037 minutes) was isolated and lyophilized to dryness. The resulting material was free based with sat. aq. NaHCO$_3$ to afford Example 41 (12 mg, 3.03%). HPLC: RT=8.726 min (Xbridge Phenyl 3.5 um, 3×150 mm, 10% 95/5 water/ACN with 0.05% TFA to 100% 5/95 water/ACN with 0.05% TFA, 15 minute gradient, flow rate=[flow rate], monitored at 220 and 254 nm). MS(ES): m/z=750.4.4 [M+H$^+$]. $^1$H NMR (400 MHz, DMSO-d$_6$) δ 10.25 (s, 1H), 9.62 (s, 1H), 9.54 (d, J=7.3 Hz, 1H), 8.46 (br. s., 3H), 7.56 (dd, J=6.6, 1.8 Hz, 1H), 7.53-7.45 (m, 2H), 7.43-7.33 (m, 2H), 7.29-7.24 (m, 1H), 7.23-7.17 (m, 2H), 5.26 (d, J=7.3 Hz, 1H), 3.98 (br. s., 1H), 3.24 (dd, J=15.0, 4.2 Hz, 1H), 3.03 (dd, J=15.0, 9.0 Hz, 1H), 2.94 (td, J=10.3, 3.4 Hz, 1H), 2.76-2.66 (m, 1H), 2.48-2.44 (m, 1H), 2.29-2.12 (m, 3H), 1.87-1.77 (m, 1H), 1.75-1.67 (m, 1H), 1.65-1.54 (m, 1H), 1.49 (d, J=2.2 Hz, 1H), 1.46 (s, 9H).

Example 42

Methyl S-(((2S,3R)-6,6,6-trifluoro-3-(((3S)-5-(3-fluorophenyl)-9-methyl-2-oxo-2,3-dihydro-1H-1,4-benzodiazepin-3-yl)carbamoyl)-2-(3,3,3-trifluoropropyl)hexanoyl)amino)-L-cysteinate

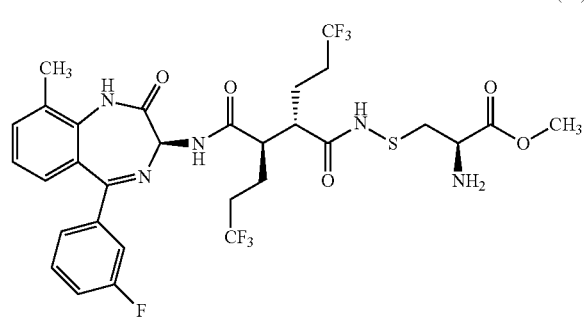

(42)

Intermediate 42A: (R)-Methyl 2-((tert-butoxycarbonyl)amino)-3-(((2S,3R)-6,6,6-trifluoro-3-(((S)-5-(3-fluorophenyl)-9-methyl-2-oxo-2,3-dihydro-1H-benzo[e][1,4]diazepin-3-yl)carbamoyl)-2-(3,3,3-trifluoropropyl)hexanamido)thio)propanoate

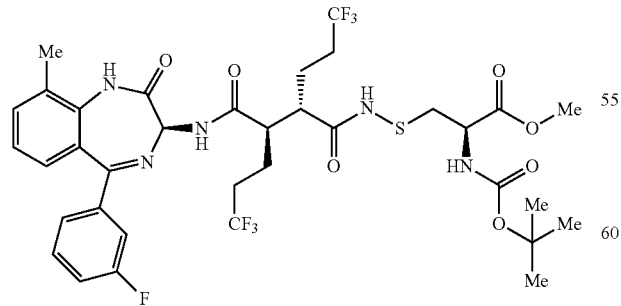

(42A)

A solution of silver nitrate (118 mg, 0.696 mmol) in methanol (9 mL) was treated with (2R,2'R)-dimethyl 3,3'-disulfanediylbis(2-((tert-butoxycarbonyl)amino) propanoate) (326 mg, 0.696 mmol). The reaction mixture was stirred for 30 minutes and then Example 1 (100 mg, 0.174 mmol) and TEA (0.097 mL, 0.696 mmol) were added. The mixture was stirred at room temperature overnight and then concentrated to dryness. The crude product was dissolved in a small amount of CH$_2$Cl$_2$ and purified by flash chromatography (SiO$_2$, 0% ethyl acetate/hexanes to 80% ethyl acetate/hexanes, 4 g column) to afford Intermediate 42A. (80 mg, 57%). HPLC RT=3.20 min (CHROMOLITH® SpeedROD, 5.0 um, 4.6 mm×50 mm, 10-90% aqueous methanol containing 0.1% TFA, 4 min gradient, monitored at 220 nm). MS(ES): m/z=808.3 [M+H$^+$].

Example 42

To a solution of Intermediate 42A (80 mg, 0.099 mmol) in DCM (2 mL) at 0° C. was added TFA (0.5 mL). The mixture was stirred for 2.5 h while warming to room temperature. The reaction mixture was then concentrated and the residue was purified by flash silica gel chromatography (4 g column, 0-8% MeOH/DCM with 0.1% NH$_4$OH) to give a white solid, which was further treated with ether to give the purified product (29.5 mg, 41%). HPLC RT=2.570 min (CHROMOLITH® SpeedROD, 5.0 um, 4.6 mm×50 mm, 10-90% aqueous methanol containing 0.1% TFA, 4 min gradient, monitored at 220 nm). MS(ES): m/z=708.2 [M+H$^+$]. $^1$H NMR (400 MHz, methanol-d$_4$) δ 7.58-7.52 (m, 1H), 7.48-7.32 (m, 3H), 7.30-7.19 (m, 3H), 5.39 (s, 1H), 3.75 (s, 3H), 3.63 (dd, J=8.7, 4.1 Hz, 1H), 3.30-3.24 (m, 1H), 2.90 (td, J=10.4, 3.6 Hz, 1H), 2.78 (dd, J=14.3, 8.6 Hz, 1H), 2.69 (td, J=10.0, 3.6 Hz, 1H), 2.57-2.38 (m, 4H), 2.36-2.06 (m, 3H), 2.05-1.90 (m, 1H), 1.89-1.74 (m, 2H), 1.63 (tt, J=12.5, 4.3 Hz, 1H).

Example 43

((3S)-3-(((2R,3S)-3-Carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl(4-(phosphonooxy)phenyl)acetate

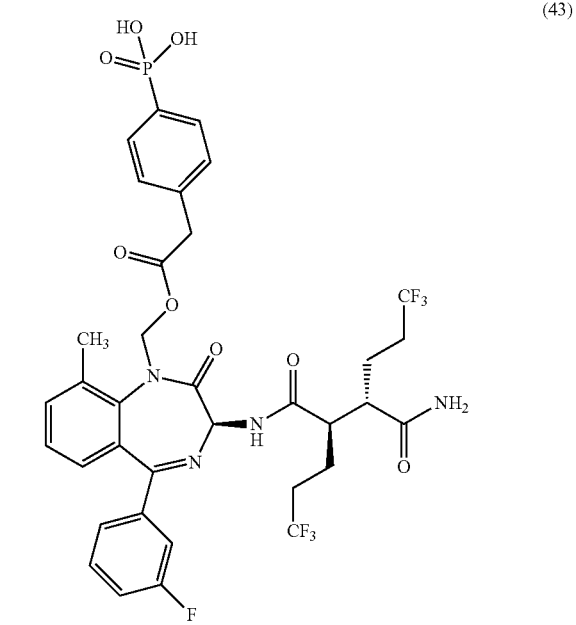 [SMILES: Cc1cccc2c1N(COC(=O)Cc1ccc(P(=O)(O)O)cc1)C(=O)[C@@H](NC(=O)[C@H](CCC(F)(F)F)[C@H](CCC(F)(F)F)C(N)=O)N=C2c1cccc(F)c1]

(43)

Intermediate 43A: (2R,3S)-3-(Trifluoropropyl)-N1-((S,Z)-1-(methylthiomethyl)-2-oxo-5-(3-fluorophenyl)-9-methyl-2,3-dihydro-1H-benzo[e][1,4]diazepin-3-yl)methyl-2-(3,3,3-trifluoropropyl) succinamide

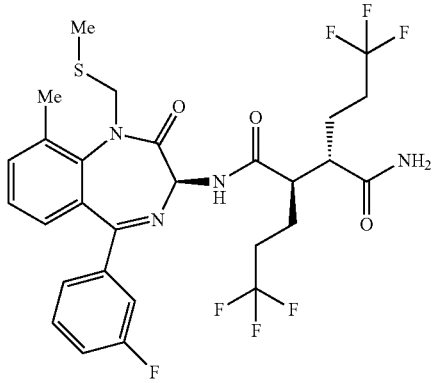

(43A)

To a mixture of Example 1 (278 mg, 0.484 mmol) in DMF (2.75 mL) was added Cs$_2$CO$_3$ (315 mg, 0.968 mmol) and (chloromethyl)(methyl)sulfane (0.081 mL, 0.919 mmol) under nitrogen. This mixture was stirred at room temperature for 110 min, and then diluted with water. The aqueous layer was extracted with EtOAc. The combined EtOAc extracts were washed with brine. The organic layer was dried over anhydrous magnesium sulfate, filtered and concentrated under reduced pressure to give the crude product. The crude material was purified by flash chromatography (Teledyne ISCO CombiFlash 0% to 100% solvent A/B=hexane/EtOAc, REDISEP® SiO$_2$ 40 g, detecting at 254 nM, and monitoring at 220 nM). Concentration of the appropriate fractions provided Intermediate 43A (198 mg, 64.5%). HPLC: RT=3.205 min (CHROMOLITH® SpeedROD column 4 6×50 mm, 10-90% aqueous methanol over 4 minutes containing 0.1% TFA, 4 mL/min, monitoring at 220 nm), MS(ES): m/z=635.4 [M+H$^+$]; $^1$H NMR (400 MHz, DMSO-d$_6$) δ 9.49 (d, J=7.3 Hz, 1H), 7.63 (d, J=8.4 Hz, 2H), 7.57-7.51 (m, 1H), 7.49-7.36 (m, 4H), 7.23 (d, J=7.5 Hz, 1H), 7.13 (s, 1H), 5.57 (d, J=14.1 Hz, 1H), 5.33 (d, J=7.0 Hz, 1H), 4.38 (d, J=14.3 Hz, 1H), 2.80 (td, J=9.8, 4.1 Hz, 1H), 2.61-2.54 (m, 1H), 2.46-2.44 (m, 1H), 2.42 (s, 3H), 2.30-2.06 (m, 4H), 1.68 (s, 3H), 1.64-1.48 (m, 3H).

Intermediate 43B: Methyl 2-(4-(di-tert-butoxyphosphoryloxy)phenyl)acetate

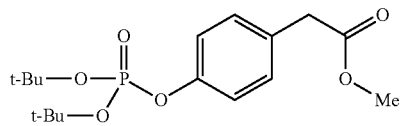

(43B)

A stirred solution of methyl 2-(4-hydroxyphenyl)acetate (1.80 g, 10.83 mmol) was combined with 1H-tetrazole in MeCN (65 mL, 10.83 mmol) and then di-tert-butyl diethylphosphoramidite (5.91 g, 23.70 mmol) was added. The reaction mixture was stirred at room temperature for 35 min and then concentrated to dryness. The crude material was dissolved in 50 mL of DCM and 30% H$_2$O$_2$ (30 mL) was added. After stirring at room temperature for 30 min, the mixture was diluted with DCM and washed with water, saturated NaHCO$_3$ solution, and then brine. The organic layer was concentrated and purified by flash chromatography (Teledyne ISCO CombiFlash 0% to 100% solvent A/B=hexane/EtOAc, REDISEP® SiO$_2$ 80 g, detecting at 254 nM, and monitoring at 220 nM). Concentration of the appropriate fractions afforded Intermediate 43B (3.94 g, quantitative yield). $^1$H NMR (400 MHz, chloroform-d) δ ppm 7.25-7.14 (m, 4H), 3.69 (s, 3H), 3.59 (s, 2H), 1.51 (s, 18H).

Intermediate 43C: 2-(4-(Di-tert-butoxyphosphoryloxy)phenyl)acetic acid

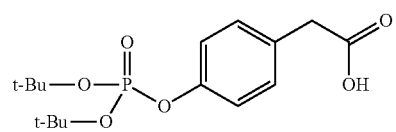

(43C)

To a stirred solution of Intermediate 43B (0.635 g, 1.772 mmol) in THF (12.0 mL) and water (3.00 mL) was added lithium hydroxide (0.122 g, 2.14 mmol). The reaction mixture was stirred at room temperature for 2 hr and then the organics were removed under reduced pressure. The resulting mixture was diluted with 10 mL of pH 4 phosphate solution. The resulting mixture was extracted with EtOAc. The combined EtOAc extracts were washed with brine, dried with anhydrous magnesium sulfate, filtered and concentrated to afford Intermediate 43C (0.462 g, 76%). $^1$H NMR (400 MHz, DMSO-d$_6$) δ ppm 12.30 (br. s., 1H), 7.25 (d, J=8.4 Hz, 2H), 7.13-7.03 (m, 2H), 3.55 (s, 2H), 1.44 (s, 1H).

Intermediate 43D: ((S,Z)-3-((R)-2-((S)-1-Amino-3-trifluoro-1-oxopropan-2-yl)-5,5,5-trifluoropentanamido)-2-oxo-5-(3-fluorophenyl)-9-methyl-2,3-dihydro-1H-benzo[e][1,4]diazepin-1-yl)methyl 2-(4-(di-tert-butoxyphosphoryloxy)phenyl)acetate

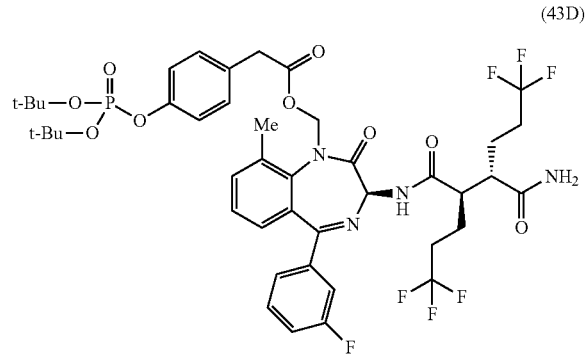 [SMILES: Cc1cccc2c1N(COC(=O)Cc1ccc(OP(=O)(OC(C)(C)C)OC(C)(C)C)cc1)C(=O)[C@@H](NC(=O)[C@H](CCC(F)(F)F)[C@H](CCC(F)(F)F)C(N)=O)N=C2c1cccc(F)c1]

(43D)

To a stirred mixture of Intermediate 43A (195 mg, 0.307 mmol) and triethylamine hydrochloride (85.0 mg, 0.615 mmol) in DCM (3.00 mL) under nitrogen was added sulfuryl chloride (0.037 mL, 0.461 mmol). The mixture was stirred at room temperature for 25 min and then concentrated to dryness to give a yellow solid. Intermediate 43C (221 mg, 0.640 mmol) and Cs$_2$CO$_3$ (417 mg, 1.281 mmol) were combined in DMF (1.50 mL) at room temperature under nitrogen. To this mixture was added a solution of the above yellow solid in DMF (2.00 mL). The resulting mixture was stirred at room temperature for 148 minutes and then diluted with water and EtOAc. The organic layer was separated and washed with 10% LiCl solution and then brine. The organic layer was dried with anhydrous magnesium sulfate, filtered and concentrated to dryness. The crude product was purified by flash chromatography (Teledyne ISCO CombiFlash 0% to 100% solvent A/B=hexane/EtOAc, REDISEP® SiO$_2$ 24 g, detecting at 254 nM, and monitoring at 220 nM). Concentration of the appropriate fractions provided Intermediate 43D (152 mg, 53.5%). HPLC: RT=3.640 min (CHROMOLITH® SpeedROD column 4 6×50 mm, 10-90% aqueous methanol over 4 minutes containing 0.1% TFA, 4 mL/min, monitoring at 220 nm), MS(ES): m/z=931.6 [M+H$^+$]; $^1$H NMR (400 MHz, DMSO-d$_6$) δ 9.47 (d, J=6.8 Hz, 1H), 7.68-7.60 (m, 2H), 7.54-7.46 (m, 1H), 7.44-7.33 (m, 4H), 7.20 (d, J=7.5 Hz, 1H), 7.13 (br. s., 1H), 6.97-6.91 (m, 2H), 6.87-6.80 (m, 2H), 6.05 (d, J=10.3 Hz, 1H), 5.38 (d, J=4.0 Hz, 1H), 5.36 (s, 1H), 3.22 (t, J=1.0 Hz, 2H), 2.81 (dt, J=9.8, 5.0 Hz, 1H), 2.45 (d, J=3.3 Hz, 1H), 2.41 (s, 3H), 2.30-2.20 (m, 1H), 2.18-2.06 (m, 3H), 1.69 (d, J=10.6 Hz, 1H), 1.63-1.51 (m, 3H), 1.43 (s, 18H).

Example 43

To a stirred solution of Intermediate 43D (148 mg, 0.159 mmol) in DCM (1.64 mL) was added TFA (0.16 mL, 2.077 mmol) at 0° C. The mixture was stirred at 0° C. for 10 min and then at room temperature for 40 min, and then concentrated under reduced pressure to afford Example 43 (126.6 mg, 94%). HPLC: RT=9.95 min (H$_2$O/CH$_3$CN with TFA, Sunfire C18 3.5 μm, 4.6×150 mm, gradient=15 min, wavelength=220 and 254 nm); MS(ES): m/z=819.5 [M+H$^+$]; $^1$H NMR (400 MHz, DMSO-d$_6$) δ 9.51 (d, J=5.7 Hz, 1H), 7.66 (d, J=7.7 Hz, 2H), 7.54-7.49 (m, 1H), 7.48-7.40 (m, 3H), 7.37 (d, J=7.7 Hz, 1H), 7.22 (d, J=8.4 Hz, 1H), 7.15 (br. s., 1H), 6.97 (d, J=8.6 Hz, 2H), 6.84 (d, J=8.4 Hz, 2H), 6.07 (d, J=10.6 Hz, 1H), 5.40 (s, 1H), 5.38 (s, 1H), 3.32-3.15 (m, 2H), 2.83 (br. s., 1H), 2.58-2.56 (m, 1H), 2.43 (s, 3H), 2.15 (dd, J=19.7, 8.5 Hz, 4H), 2.01 (s, 1H), 1.71 (s, 2H), 1.67-1.51 (m, 3H).

Example 44

((3S)-3-(((2R,3S)-3-Carbamoyl-6,6,6-trifluoro-2-(3,3,3-trifluoropropyl)hexanoyl)amino)-5-(3-fluorophenyl)-9-methyl-2-oxo-2,3-dihydro-1H-1,4-benzodiazepin-1-yl)methyl L-valyl-L-valinate

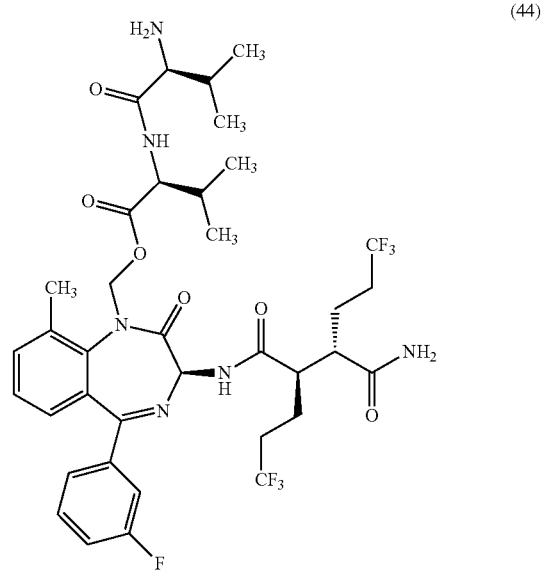 [SMILES: Cc1cccc2c1N(COC(=O)[C@@H](NC(=O)[C@@H](N)C(C)C)C(C)C)C(=O)[C@@H](NC(=O)[C@H](CCC(F)(F)F)[C@H](CCC(F)(F)F)C(N)=O)N=C2c1cccc(F)c1]

(44)

Intermediate 44A: (2R,3S)-3-(Trifluoropropyl)-N1-((S,Z)-1-(methylthiomethyl)-2-oxo-5-(3-fluorophenyl)-9-methyl-2,3-dihydro-1H-benzo[e][1,4]diazepin-3-yl)methyl-2-(3,3,3-trifluoropropyl)succinamide

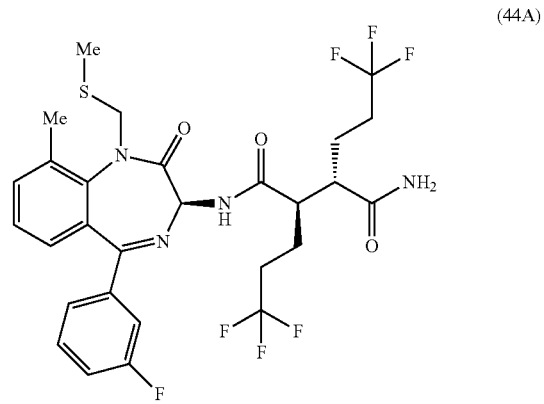 [SMILES: CSCN1C(=O)[C@@H](NC(=O)[C@H](CCC(F)(F)F)[C@H](CCC(F)(F)F)C(N)=O)N=C(c2cccc(F)c2)c2cccc(C)c21]

(44A)

To a mixture of Example 1 (278 mg, 0.484 mmol) in DMF (2.75 mL) was added Cs$_2$CO$_3$ (315 mg, 0.968 mmol) and (chloromethyl)(methyl)sulfane (0.081 mL, 0.919 mmol) under nitrogen. This mixture was stirred at room temperature for 110 min, and then diluted with water. The aqueous layer was extracted with EtOAc. The combined EtOAc extracts were washed with brine. The organic layer was dried over anhydrous magnesium sulfate, filtered and concentrated under reduced pressure to give the crude product. It was purified by flash chromatography (Teledyne ISCO Combi-Flash 0% to 100% solvent A/B=hexane/EtOAc, REDISEP® SiO$_2$ 40 g, detecting at 254 nM, and monitoring at 220 nM). Concentration of the appropriate fractions provided Intermediate 44A (198 mg, 64.5%). HPLC: RT=3.205 min (CHROMOLITH® SpeedROD column 4 6×50 mm, 10-90% aqueous methanol over 4 minutes containing 0.1% TFA, 4 mL/min, monitoring at 220 nm), MS(ES): m/z=635.4 [M+H$^+$]; $^1$H NMR (400 MHz, DMSO-d$_6$) δ 9.49 (d, J=7.3 Hz, 1H), 7.63 (d, J=8.4 Hz, 2H), 7.57-7.51 (m, 1H), 7.49-7.36 (m, 4H), 7.23 (d, J=7.5 Hz, 1H), 7.13 (s, 1H), 5.57 (d, J=14.1 Hz, 1H), 5.33 (d, J=7.0 Hz, 1H), 4.38 (d, J=14.3 Hz, 1H), 2.80 (td, J=9.8, 4.1 Hz, 1H), 2.61-2.54 (m, 1H), 2.46-2.44 (m, 1H), 2.42 (s, 3H), 2.30-2.06 (m, 4H), 1.68 (s, 3H), 1.64-1.48 (m, 3H).

Intermediate 44B: (S)—((S)-3-((2R,3S)-3-Carbamoyl-6,6,6-trifluoro-2-(3,3,3-trifluoropropyl)hexanamido)-5-(3-fluorophenyl)-9-methyl-2-oxo-2,3-dihydro-1H-benzo[e][1,4]diazepin-1-yl)methyl 2-((S)-2-((tert-butoxycarbonyl)amino)-3-methylbutanamido)-3-methylbutanoate

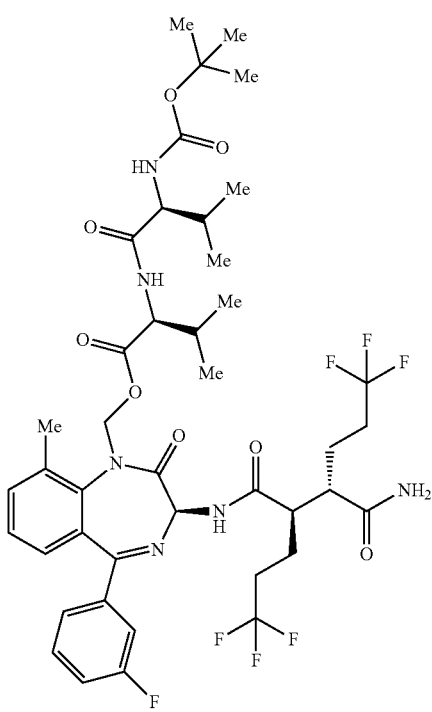

(44B)

To a stirred mixture of Intermediate 44A (157 mg, 0.247 mmol) and triethylamine hydrochloride (68.1 mg, 0.495 mmol) in DCM (3.00 mL) under nitrogen was added sulfuryl chloride (0.030 mL, 0.371 mmol). The mixture was stirred at room temperature for 60 min and then concentrated to dryness to give a yellow solid. The residue was dissolved in DMF (2 mL) and added to a stirred mixture of (S)-2-((S)-2-((tert-butoxycarbonyl)amino)-3-methylbutanamido)-3-methylbutanoic acid (313 mg, 0.989 mmol) and Cs$_2$CO$_3$ (403 mg, 1.236 mmol) in DMF (2.0 mL) at room temperature under nitrogen. The resulting mixture was stirred at room temperature for 2.5 hr, then water and saturated aqueous NaHCO$_3$ were added. A white precipitate formed which was collected by filtration, rinsed with water and dried under vacuum. The crude material was purified by flash chromatography (Teledyne ISCO CombiFlash 20% to 70% solvent A/B=hexane/acetone, REDISEP® SiO$_2$ 80 g, detecting at 254 nM, and monitoring at 220 nM). Concentration of appropriate fractions provided Intermediate 44B (148.4 mg, 66.5%). HPLC: RT=3.486 min (CHROMOLITH® SpeedROD column 4 6×50 mm, 10-90% aqueous methanol over 4 minutes containing 0.1% TFA, 4 mL/min, monitoring at 220 nm), MS(ES): m/z=903.7 [M+H$^+$].

Example 44

To a stirred solution of Intermediate 44B (148 mg, 0.164 mmol) in DCM (4.00 mL) under nitrogen was added 4N HCl in dioxane (0.410 mL, 1.639 mmol). The mixture was stirred at room temperature for 60 min and then concentrated to dryness to give Example 44 (148 mg, 97%). HPLC: RT=8.038 min (CHROMOLITH® SpeedROD column 4 6×50 mm, 10-90% aqueous methanol over 4 minutes containing 0.1% TFA, 4 mL/min, monitoring at 220 nm), MS(ES): m/z=803.6 [M+H$^+$]; $^1$H NMR (500 MHz, DMSO-d$_6$) δ 9.49 (d, J=6.9 Hz, 1H), 8.35 (d, J=7.8 Hz, 1H), 8.02 (d, J=4.4 Hz, 3H), 7.69-7.62 (m, 2H), 7.55-7.48 (m, 1H), 7.45-7.35 (m, 4H), 7.24 (d, J=6.9 Hz, 1H), 7.12 (br. s., 1H), 6.03 (d, J=10.3 Hz, 1H), 5.41-5.34 (m, 2H), 3.93 (dd, J=7.6, 5.4 Hz, 1H), 3.66-3.62 (m, 1H), 2.82 (td, J=10.2, 4.3 Hz, 1H), 2.43 (s, 4H), 2.29-2.07 (m, 3H), 1.99 (dq, J=13.2, 6.8 Hz, 1H), 1.76-1.66 (m, 2H), 1.63-1.49 (m, 3H), 0.88 (dd, J=10.0, 6.9 Hz, 6H), 0.61 (d, J=6.9 Hz, 3H), 0.57 (d, J=6.7 Hz, 3H).

Comparative Compounds 45 to 48

Comparative Compounds 45 to 48 can be prepared according to the procedures described in U.S. Pat. No. 7,053,084 for Examples 8, 12a, 38, and 45a, respectively.

| Comparative Compound | U.S. Pat. No. 7,053,084 | Structure |
|---|---|---|
| 45 | Ex. 8 | 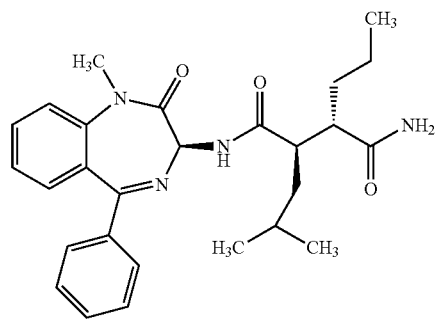 [SMILES: CCC[C@H](C(N)=O)[C@@H](CC(C)C)C(=O)N[C@H]1N=C(c2ccccc2)c2ccccc2N(C)C1=O] |
| 46 | Ex. 12a | 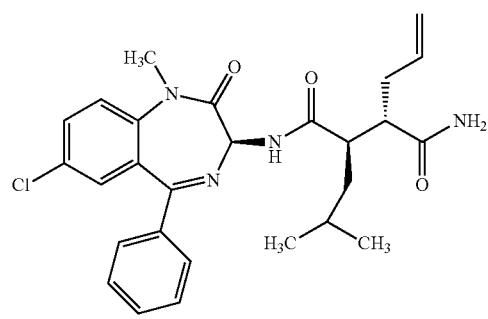 [SMILES: C=CC[C@H](C(N)=O)[C@@H](CC(C)C)C(=O)N[C@H]1N=C(c2ccccc2)c2cc(Cl)ccc2N(C)C1=O] |
| 47 | Ex. 38 | 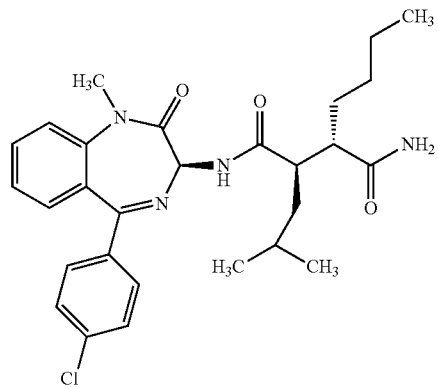 [SMILES: CCCC[C@H](C(N)=O)[C@@H](CC(C)C)C(=O)N[C@H]1N=C(c2ccc(Cl)cc2)c2ccccc2N(C)C1=O] |
| 48 | Ex. 45a | 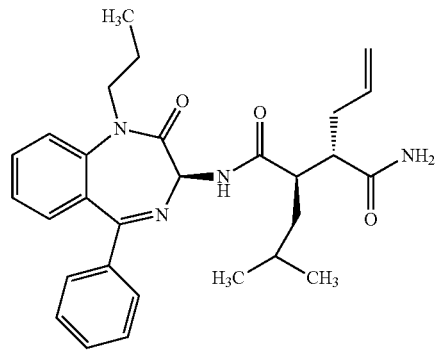 [SMILES: C=CC[C@H](C(N)=O)[C@@H](CC(C)C)C(=O)N[C@H]1N=C(c2ccccc2)c2ccccc2N(CCC)C1=O] |

Example 49

Pharmaceutical Formulation Comprising (2R,3S)—N-((3S)-5-(3-Fluorophenyl)-9-methyl-2-oxo-2,3-dihydro-1H-1,4-benzodiazepin-3-yl)-2,3-bis(3,3,3-trifluoropropyl)succinamide An injection drug product was formulated comprising (2R, 3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide, Example 1, as a single-use, ready-to-use (RTU) sterile solution for intravenous (IV) administration. A vehicle mixture was prepared by admixing 80% v/v Polyethylene glycol 400 and 20% v/v water at room temperature. Example 1 (0.2 mg/ml) was added to the prepared vehicle mixture. The formulation was sonicated for about 20 minutes until Example 1 was dissolved.

Example 50

Pharmaceutical Formulation Comprising (2R,3S)—N-((3S)-5-(3-Fluorophenyl)-9-methyl-2-oxo-2,3-dihydro-1H-1,4-benzodiazepin-3-yl)-2,3-bis(3,3,3-trifluoropropyl)succinamide A drug product was formulated comprising (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide, Example 1, suitable for oral administration as a solution or capsule. The oral formulation comprised 70% v/v polyethylene glycol 300, 10% v/v ethanol, 10% v/v TPGS, 10% v/v CREMOPHOR® RH40, and Example 1 (up to 4 mg/ml drug concentration).

Solid TPGS and CREMOPHOR® were pre-warmed to liquefy the materials. The appropriate amount of each of the excipients was then measured and mixed at room temperature. The required amount of Example 1 was added to the vehicle mixture prepared. The formulation was sonicated for about 20 minutes until Example 1 was dissolved.

Example 51

Pharmaceutical Formulation Comprising (2R,3S)—N-((3S)-5-(3-Fluorophenyl)-9-methyl-2-oxo-2,3-dihydro-1H-1,4-benzodiazepin-3-yl)-2,3-bis(3,3,3-trifluoropropyl)succinamide A drug product was formulated comprising (2R,3S)—N-((3S)-5-(3-fluorophenyl)-9-methyl-2-oxo-2,3-dihydro-1H-1,4-benzodiazepin-3-yl)-2,3-bis(3,3,3-trifluoropropyl)succinamide, Example 1, suitable for oral administration as a solution or capsule. The oral formulation comprised 80% v/v polyethylene glycol 300, 10% v/v ethanol, 10% v/v TPGS, and Example 1 (up to 4 mg/ml drug concentration).

Solid TPGS was pre-warmed to liquefy the material. The appropriate amount of each of the excipients was then measured and mixed at room temperature. The required amount of Example 1 was added to the vehicle mixture prepared. The formulation was sonicated for about 20 minutes until Example 1 was dissolved.

BIOLOGICAL ASSAYS

The pharmacological properties of the compounds of this invention may be confirmed by a number of biological assays. The exemplified biological assays, which follow, have been carried out with compounds of the invention.

Notch-CBF1 Transactivation Assay

The Notch-CBF1 (C-promoter binding factor I) cell based transactivation assay is based on the ability of the released Notch intracellular domain fragments (NICDs) to function as transcription factors in conjunction with CBF1 and other nuclear factors. Luciferase assays were used to measure the antagonism of Notch-CBF1 transcriptional activity. HeLa cervical cancer cells are transiently co-transfected with pCDNA3.1/Hygro plasmids containing truncated Notch 1, Notch 2, Notch 3, or Notch 4 receptors and a PGL3 luciferase reporter vector containing 4 copies of CBF1 binding site. The cells were then tested for Notch-CBF1 activity in the absence or presence of test compounds. HeLa cells, maintained in DMEM (high glucose with HEPES), 1× glutamine/penicillin/streptomycin and 10% Fetal Bovine serum, were transiently transfected in a T175 Flask ($4.5 \times 10^6$ cells/flask) using the Monster Transfection Kit (Minis #MIR2906) according to manufacturers specifications. Table 9 denotes respective DNA quantity for the transfections.

TABLE 9

|  | DNA (µg) | CBF1 (µg) | Vector (µg) | Total DNA (µg) |
| --- | --- | --- | --- | --- |
| human Notch 1 | 6 | 14.4 | 15.6 | 36.0 |
| human Notch 2 | 2 | 14.4 | 19.6 | 36.0 |
| human Notch 3 | 0.3 | 14.4 | 21.3 | 36.0 |
| human Notch 4 | 4 | 14.4 | 17.6 | 36.0 |

Six hours post-transfection, cells were trypsinized and plated into a 384-well black Poly-D-lysine coated tissue culture plate at a density of $5 \times 10^3$ cells/well in 95 µL assay media (DMEM (high glucose with HEPES), 1× glutamine/penicillin/streptomycin, 0.0125% BSA, 1× non-essential amino acids). Assay media (5 µL) containing test compounds in final concentrations ranging from 5 µM to $8.4 \times 10^{-5}$ µM (3 fold serial dilutions) were added to the cells and the cell plates were then incubated for 18 hours at 37° C. and 5% $CO_2$. Control wells contained DMSO vehicle (total counts) or 0.5 µM of an in-house small molecule inhibitor (background counts). Duplicates were used for each sample. Luciferase activity was measured after a 20-minute incubation with 50 µl STEADY-GLO® luciferase reagents according to manufacturer's specifications (Promega, Cat. #E2550) and analyzed by Envision plate reader (PerkinElmer, Boston, Mass.).

The antagonist effect of compounds was expressed as 100×[1-(average sample-average background)/(average total-average background)] where sample is the luciferase activity in the presence of test compound, background is equal to the luciferase activity in the presence of the small molecule inhibitor control and the total is signal induced in DMSO wells. Data was plotted using a four parameter logistic fit equation and the $IC_{50}$ value was defined as the concentration of compound that inhibited 50% of the luciferase activity.

Table 10 below lists the Notch 1 and Notch 3 $IC_{50}$ values for Examples 1-37 of this invention and Comparative Compounds 45-48 measured in the Notch-CBF1 Transactivation Assay hereinabove. In some instances, the value is an average of multiple experiments where N is the number of experiments conducted. The compounds of the present invention, as exemplified by the Examples 1-37 showed Notch 1 values of 12.2 nM or less and Notch 3 $IC_{50}$ values of 15.0 nM or less.

TABLE 10

| Example | Notch 1 (IC$_{50}$, nM) | N | Notch 3 (IC$_{50}$, nM) | N |
|---|---|---|---|---|
| 1 | 7.8 | 8 | 8.5 | 7 |
| 2 | 4.9 | 3 | 4.3 | 2 |
| 3 | 1.8 | 6 | 1.9 | 6 |
| 4 | 8.5 | 3 | 7.3 | 2 |
| 5 | 2.3 | 1 | 4.0 | 1 |
| 6 | 7.2 | 3 | 4.5 | 3 |
| 7 | 4.4 | 2 | 4.4 | 1 |
| 8 | 6.0 | 2 | 11.6 | 1 |
| 9 | 3.0 | 2 | 3.7 | 2 |
| 10 | 2.5 | 3 | 5.4 | 3 |
| 11 | 8.2 | 2 | 15.0 | 1 |
| 12 | 3.0 | 2 | 3.2 | 1 |
| 13 | 3.4 | 2 | 4.9 | 1 |
| 14 | 7.7 | 2 | 12.6 | 1 |
| 15 | 4.4 | 2 | 4.4 | 1 |
| 16 | 5.8 | 2 | 3.7 | 1 |
| 17 | 5.7 | 2 | 2.4 | 1 |
| 18 | 4.6 | 3 | 7.7 | 3 |
| 19 | 4.8 | 5 | 4.0 | 4 |
| 20 | 1.6 | 2 | 1.4 | 1 |
| 21 | 3.3 | 2 | 6.1 | 2 |
| 22 | 3.1 | 2 | 6.3 | 2 |
| 23 | 4.7 | 5 | 8.3 | 4 |
| 24 | 1.4 | 2 | 2.1 | 2 |
| 25 | 1.7 | 3 | 2.9 | 3 |
| 26 | 3.7 | 2 | 3.4 | 3 |
| 27 | 2.8 | 2 | 2.7 | 1 |
| 28 | 4.8 | 3 | 7.2 | 3 |
| 29 | 3.9 | 1 | 5.7 | 1 |
| 30 | 4.3 | 1 | 4.2 | 1 |
| 31 | 2.8 | 2 | 4.6 | 2 |
| 32 | 6.4 | 6 | 6.1 | 6 |
| 33 | 4.3 | 3 | 7.4 | 3 |
| 34 | 4.8 | 3 | 13.4 | 3 |
| 35 | 4.8 | 3 | 7.9 | 2 |
| 36 | 12.2 | 3 | 3.0 | 2 |
| 37 | 6.2 | 1 | 9.3 | 1 |
| Comparative Compound 45 | 64.1 | 1 | 48.3 | 1 |
| Comparative Compound 46 | 42.4 | 2 | 74.5 | 2 |
| Comparative Compound 47 | 5.1 | 3 | 13.5 | 4 |
| Comparative Compound 48 | 12.3 | 1 | 12.5 | 1 |

High Throughput (HT) Metabolic Stability Panel

Compounds administered parenterally enter the blood stream and undergo one or more passes through the liver. Compounds that are not readily metabolized by the liver can be administered at therapeutically effective plasma levels for therapeutically effective periods of time.

Orally administered compounds typically are absorbed through the intestinal walls into the blood stream and undergo a first pass through the liver. Compounds that are not readily metabolized in this first pass through the liver can be distributed to other areas of the body in therapeutically effective amounts.

The metabolic stability assay evaluated CYP-mediated metabolic stability in vitro using human, rat, mouse, dog, and/or monkey microsomes after a ten-minute incubation. Each compound was tested in duplicate.

The results of these assays were expressed as the fraction of parent compound remaining in the reaction mixture after a ten-minute incubation (Percent Remaining). In general, these results were used to evaluate only the extent of CYP-mediated, or NADPH-dependent, metabolism of the test compound. When the compound was significantly metabolized (<40-50% remaining), this indicated high clearance of the compound in vivo due to CYP-mediated metabolism. However, if the compound demonstrated moderate (50-80%) or low (>85%) metabolism in these in vitro assays, high clearance was still possible in vivo via other metabolism and elimination pathways.

The percent remaining results of these assays was predictive of compound clearance in vivo, assuming that CYP-mediated metabolism was a predominant elimination pathway. In different microsomal species, the ranges of results were approximately as shown in Table 11.

TABLE 11

Metabolic Stability-Result Interpretation Guidelines

| CYP-Mediated Clearance | Percent Remaining after 10 minutes | | | | |
|---|---|---|---|---|---|
| | Human | Rat | Mouse | Dog | Monkey |
| Low | >90 | >85 | >85 | >90 | >85 |
| Medium | 60-90 | 40-85 | 50-85 | 55-90 | 40-85 |
| High | <60 | <40 | <50 | <55 | <40 |

Methods and Materials
Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100× stock for incubation with microsomes. Each compound was tested in duplicate separately in each of three species in the Metabolic Stability-Human, Rat, and Mouse assay suite or as individual species in the Metabolic Stability-Dog or Metabolic Stability-Monkey suites. Compound, NADPH, and liver microsome solutions were combined for incubation in three steps:

1. 152 µl of liver microsome suspension, protein concentration of 1.1 mg/ml in 100 mM NaP$_i$, pH 7.4, 5 mM MgCl$_2$ buffer, was pre-warmed at 37° C.

2. 1.7 µl of 50 µM compound (98.6% ACN, 1.4% DMSO) was added to the same tube and pre-incubated at 37° C. for 5 minutes.

3. The reaction was initiated by the addition of 17 µl of pre-warmed 10 mM NADPH solution in 100 mM NaP$_i$, pH 7.4.

The reaction components were mixed well, and 75 µl of the reaction mixture was immediately transferred into 150 µl quench/stop solution (zero-time point, T$_0$). Reactions were incubated at 37° C. for 10 minutes and then an additional 75 µl aliquot was transferred into 150 µl quench solution. Acetonitrile containing 100 µM DMN (a UV standard for injection quality control), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for UV-LC/MS-MS analysis to determine the percent of parent compound that remained in the mixture.

TABLE 12

Metabolic Stability Assay-Reaction Components

| Reaction Components | Final Concentration in the Metabolic Stability Assay |
|---|---|
| Compound (Substrate) | 0.5 µM |
| NaPi Buffer, pH 7.4 | 100 mM |

TABLE 12-continued

Metabolic Stability Assay-Reaction Components

| Reaction Components | Final Concentration in the Metabolic Stability Assay |
|---|---|
| DMSO | 0.014% |
| Acetonitrile | 0.986% |
| Microsomes (human, rat, mouse) (BD/Gentest) | 1 mg/ml protein |
| NADPH | 1.0 mM |
| MgCl$_2$ | 5.0 mM |
| 37° C. Incubation time | 0 minutes and 10 minutes |
| Quench/Stop Solution (ACN + 100 µM DMN) | 150 µl |
| Sample of Reaction | 75 µl |
| Sedimentation of Denatured Microsomes | 15 minutes |
| UV-LC/MS analysis of supernatant | 0.17 µM |

Sample Analysis-Instrumentation

HPLC: Pump-Thermo Surveyor; Autosampler-CTC/LEAP HTS; UV detector-Thermo Surveyor PDA plus; Column-VARIAN® C18, 3 µm, 2×20 mm with a 0.5 µm in-line filter; Mobile Phase for structural integrity pre-analysis: (A) 98% water, 2% acetonitrile with 10 mM ammonium acetate; (B) 10% water, 90% acetonitrile with 10 mM ammonium acetate; Mobile Phase for reaction sample analysis: (A) 98% water, 2% acetonitrile with 0.1% formic acid; (B) 2% water, 98% acetonitrile with 0.1% formic acid; (C) 0.1% ammonium hydroxide in water; (D) 0.1% ammonium hydroxide in acetonitrile.

Mass Spectrometer: Thermo TSQ QUANTUM® Ultra Triple-Quadrapole Mass Spectrometer;

Sample Analysis-Structural Integrity Pre-Analysis

The Metabolic Stability structural integrity pre-analysis was used to assess the purity of compounds being assayed. Compounds were received in 96-well plates as 57 µl of a 3.5 mM DMSO solution. The 3.5 mM compound DMSO stock solutions were diluted 18-fold with a solution containing equal volumes of acetonitrile, isopropanol, and MilliQ-H$_2$O. The resulting solutions (200 µM) were analyzed for structural integrity by LC-UV/MS on a Thermo LCQ Deca XP Plus ion trap mass spectrometer, using a Waters XBridge C18, 5 µm, 2×50 mm column with a Waters Sentry 2.1 mm guard column, and the LC conditions described in the table below, with a 5 µl injection and a flow rate of 1 ml/min. The acquired data reflected purity by UV absorbance at 220 nm. Only results for those compounds with purity greater than 50% were reported.

TABLE 13

Metabolic Stability-Structural Integrity Gradient

| Gradient Time (min) | A % | B % |
|---|---|---|
| 0.00 | 100 | 0 |
| 4.00 | 0 | 100 |
| 5.00 | 0 | 100 |
| 5.10 | 100 | 0 |
| 6.00 | 100 | 0 |

Sample Analysis-Incubated Samples

MS/MS condition optimization was conducted on a Thermo TSQ QUANTUM® triple-quadrapole mass spectrometer equipped with a heated-electrospray (H-ESI) source by automated infusion to obtain the SRM transitions and their corresponding collision energy values. Compound solutions at a concentration of 20 µM in 1:1 methanol:water were infused at a flow rate of 90 µL/min, then combined with the mobile phase at a flow rate of 50 µL/min before being introduced into the source. All compounds were optimized first using mobile phase A and B (50% A and 50% B), and if necessary, using mobile phase C and D (also with a 50:50 composition). The optimized parameters, including polarity, SRM transition and collision energy, were stored in a MICROSOFT ACCESS® database.

The mass spectrometric conditions obtained from automated infusion were used to analyze incubation samples from the Metabolic Stability assay. The injection volume was 5 µl and the flow rate was 0.8 ml/min. The gradient used was shown in the table below. All samples were injected with the gradient using mobile phase A and B first. If necessary (for instance, for chromatographic reasons), samples were re-injected with the same gradient, but using mobile phase C and D. All LC-MS/MS analysis parameters were captured electronically in the raw data files.

TABLE 14

Metabolic Stability-Sample Analysis Gradient

| Gradient Time (min) | A % (or C %) | B % (or D %) |
|---|---|---|
| 0.00 | 95 | 5 |
| 0.20 | 95 | 5 |
| 0.30 | 0 | 100 |
| 1.05 | 0 | 100 |
| 1.10 | 95 | 5 |
| 1.50 | 95 | 5 |

Data Analysis

Peak integration was performed with the XCALIBUR® software. The percent remaining calculation was performed by comparing the LC-MS/MS peak areas from the $T_{10 minute}$ samples to those from the $T_{0 minute}$ samples for each compound.

Quality Control

A set of three compounds was tested along with the test compound in each assay plate. Data was accepted and uploaded only if the results for these control compounds fall into the expected ranges shown below.

TABLE 15

Metabolic Stability Assay - Control Compound Values by Microsome Species

| | Average Percent Remaining ± SD | | | | |
|---|---|---|---|---|---|
| Compound | Human | Rat | Mouse | Dog | Monkey |
| Nefazodone | 0.4 ± 0.4 | 0.7 ± 0.6 | 0.4 ± 0.3 | 0.4 ± 0.4 | 0.6 ± 0.5 |
| Verapamil | 13.3 ± 3.5 | 4.4 ± 2.1 | 13.0 ± 4.2 | 5.6 ± 1.8 | 0.5 ± 0.5 |
| Carbamezepine | 96 ± 6 | 84 ± 9 | 90 ± 10 | 81 ± 7 | 89 ± 13 |

SD = Standard Deviation

Metabolic Stability Half-Life Panel

The rate of metabolism and half-life determined in vitro in human or animal liver microsomes was used to determine intrinsic clearance ($CL_{int}$) and hepatic clearance ($CLh,b$) of a compound. These parameters were useful for predicting in vivo human clearance, which defines the level of drug exposure in vivo (Obach et al., 1997, 1999).

The metabolic stability half-life assay panel evaluates the time-course and the rate of CYP-mediated (NADPH-dependent) metabolism in vitro in human, rat, mouse, dog and monkey microsomes. The time course spans a 45 minute incubation, and includes 0, 5, 10, 15, 30, and 45 minute time-points, at each of which the amount of test compound remaining in the mixture was measured.

Result Interpretation Guideline

The results of the metabolic stability half-life assay are expressed as a half-life ($T_{1/2}$, min). In general, these results should be used to evaluate only the extent of CYP-mediated, or NADPH-dependent, metabolism of the test compound. When the compound was significantly metabolized ($T_{1/2}$<14 minutes), this indicated high clearance in vivo due to CYP-mediated metabolism. However, if the compound demonstrated moderate (14-70 minutes) or low (>70 minutes) metabolism in these in vitro assays, high clearance was still possible in vivo via other metabolism and elimination pathways.

The results of these assays were predictive of compound clearance in vivo, assuming that CYP-mediated metabolism was a predominant elimination pathway. In human microsomes, the ranges of results were approximately as shown in the following table:

TABLE 16

Metabolic Stability Half-Life-Result Interpretation Guidelines

| CYP-Mediated Clearance | $T_{1/2}$, minutes Human |
|---|---|
| Low | >70 |
| Medium | 14-70 |
| High | <14 |

Methods and Materials

Liver microsomes were purchased from BD-Biosciences (Woburn, Mass.) and NADPH from AppliChem Inc; all other reagents were obtained from Sigma.

Incubation with Liver Microsomes

Test compound was received as a 3.5 mM stock solution in 100 percent DMSO. The test compound was diluted to create a 50 µM acetonitrile (ACN) solution containing 1.4% DMSO, which was then used as a 100-fold stock for incubation with microsomes. Each compound was tested in human, rat, mouse, dog and monkey liver microsomes. Compound, NADPH and liver microsome solutions were combined for incubation in three steps:

1. 450 µl of liver microsome suspension, protein concentration of 1.1 mg/ml in 100 mM $NaP_i$, pH 7.4, 5 mM $MgCl_2$ buffer, was pre-warmed at 37° C.

2. 5 µl of 50 µM compound (98.6% ACN, 1.4% DMSO) was added to the same tube and pre-incubated at 37° C. for 5 minutes.

3. The reaction was initiated by the addition of 50 µl of pre-warmed 10 mM NADPH solution in 100 mM $NaP_i$, pH 7.4.

Reaction components were mixed well, and 65 µl were immediately transferred into 130 µl quench/stop solution (zero-time point, $T_0$). Reactions were incubated at 37° C. for 5, 10, 15, 30 and 45 minutes and at each time-point a 65 µl aliquot was transferred into 130 µl of quench solution. Acetonitrile containing Internal Standard (100 ng/ml), was used as the quench solution to terminate metabolic reactions.

Quenched mixtures were centrifuged at 1500 rpm (~500× g) in an ALLEGRA® X-12 centrifuge, SX4750 rotor (Beckman Coulter Inc., Fullerton, Calif.) for fifteen minutes to pellet denatured microsomes. A volume of 90 µl of supernatant extract, containing the mixture of parent compound and its metabolites, was then transferred to a separate 96-well plate for LC/MS-MS analysis to determine the percent of parent compound that was remaining in the mixture.

TABLE 17

Metabolic Stability Half-Life Assays-Reaction Components

| Reaction Components | Final Concentration in the Metabolic Stability Assay |
|---|---|
| Compound (Substrate) | 0.5 µM |
| NaPi Buffer, pH 7.4 | 100 mM |
| DMSO | 0.014% |
| Acetonitrile | 0.986% |
| Microsomes (human, rat, mouse) (BD/Gentest) | 1 mg/ml protein |
| NADPH | 1.0 mM |
| $MgCl_2$ | 5.0 mM |
| 37° C. Incubation time | 0, 5, 10, 15, 30, and 45 minutes |
| Quench/Stop Solution (ACN + 100 µM DMN) | 130 µl |
| Sample of Reaction | 65 µl |
| Sedimentation of Denatured Microsomes | 15 minutes |

Sample Analysis-Instrumentation
HPLC: Pump-Shimadzu LC-20 AD Series Binary Pumps; Autosampler-CTC/LEAP HTS Table 18 below lists the CYP-mediated metabolic half life value for Examples 1-37 of this invention and Comparative Compounds 45-48 measured in the human metabolic stability half-life assay. In some instances, the value is an average of multiple experiments where N is the number of experiments conducted. The compounds of the present invention, as exemplified by Examples 1-37 had metabolic stability half life values of 31 minutes or longer. In contrast, Comparative Compounds 45-48 had metabolic stability half life values of 8 minutes or less.

TABLE 18

| Example | HLM ($t_{1/2}$, min) | N |
|---|---|---|
| 1 | 103 | 8 |
| 2 | 32 | 1 |
| 3 | 73 | 5 |
| 4 | 31 | 1 |
| 5 | 33 | 1 |
| 6 | 33 | 1 |
| 7 | >120 | 1 |
| 8 | 71 | 1 |
| 9 | 113 | 1 |
| 10 | 54 | 2 |
| 11 | 42 | 1 |
| 12 | 53 | 2 |
| 13 | 48 | 2 |
| 14 | 56 | 1 |
| 15 | 101 | 1 |
| 16 | 108 | 1 |
| 17 | 56 | 2 |
| 18 | >120 | 1 |
| 19 | 108 | 1 |
| 20 | >120 | 1 |
| 21 | 107 | 2 |

TABLE 18-continued

| Example | HLM ($t_{1/2}$, min) | N |
|---|---|---|
| 22 | >120 | 1 |
| 23 | 101 | 5 |
| 24 | 62 | 1 |
| 25 | >120 | 1 |
| 26 | 82 | 1 |
| 27 | 115 | 1 |
| 28 | 98 | 3 |
| 29 | 98 | 1 |
| 30 | 92 | 2 |
| 31 | 100 | 1 |
| 32 | 82 | 3 |
| 33 | 82 | 3 |
| 34 | 116 | 2 |
| 35 | 118 | 1 |
| 36 | >120 | 2 |
| 37 | 61 | 1 |
| Comparative Compound 45 | 8 | 1 |
| Comparative Compound 46 | 6 | 1 |
| Comparative Compound 47 | 6 | 1 |
| Comparative Compound 48 | 3 | 1 |

The exemplified compounds of the invention showed the surprising advantage of low clearance due to CYP-mediated metabolism in the human metabolic stability half life assay. The compounds of the present invention, as exemplified by Examples 1-37, had metabolic half lives in the range of 31 minutes to greater than 120 minutes in the human metabolic stability half life assay. In contrast, Comparative Compounds 45-48 had metabolic half lives of 8 minutes or less in the human metabolic stability assay. Comparative Compounds 45-48 showed high clearance in the human metabolic stability assay, indicating that the compounds were removed by liver microsomes.

The compounds of the present invention (Examples 1-37) have been compared to the Comparative Compounds 45-48 disclosed in U.S. Pat. No. 7,456,172, and have been found to be especially advantageous. The compounds of the present invention had the surprising advantage of the combination of activity as inhibitors of Notch 1 and Notch 3 and superior metabolic stability to liver microsomes. As shown in Tables 10 and 18, in the reported tests, Examples 1-37 of this invention had Notch 1 $IC_{50}$ values of 12.2 nM or less and Notch 3 $IC_{50}$ values of 15.0 nM or less; and human metabolic stability half lives of 31 minutes or longer in the human metabolic stability half life assay. In contrast, in similar tests, Comparative Compounds 45-48 had Notch 1 $IC_{50}$ values of in the range of from 5.1 nM to 64.1 nM and Notch 3 $IC_{50}$ values in the range of 12.5 nM to 74.5 nM; and human metabolic stability half lives of 8 minutes or less.

Human Tumor Xenograft Models in Mice

All rodents were obtained from Harlan Sprague Dawley Co. (Indianapolis, Ind.), and maintained in an ammonia-free environment in a defined and pathogen-free colony. All mice were quarantined approximately 1 week prior to their use for tumor propagation and drug efficacy testing. Mice were fed food and water ad libitum. The animal care program of Bristol-Myers Squibb Pharmaceutical Research Institute is fully accredited by the American Association for Accreditation of Laboratory Animal Care (AAALAC). All experiments were performed in accordance with Bristol-Myers Squibb (BMS) animal test methods and guidelines.

Tumor xenografts were grown and maintained subcutaneously (SC) in immunocompromized balb/c nu/nu nude or NOD-SCID mice (Harlan Sprague Dawley). Tumors were propagated as subcutaneous transplants in the appropriate mouse strain (Table 19) using tumor fragments obtained from donor mice.

TABLE 19

Histological Types and Host Mouse Strain/Gender Requirement for the Propagation of Various Human Tumor Xenografts in Mice

| Tumor Type | Histology | Mouse Strain | Sex |
|---|---|---|---|
| TALL-1 | ALL | NOD-SCID | female |
| HPB-ALL | ALL | NOD-SCID | female |
| ALL-SIL | ALL | NOD-SCID | female |
| MDA-MB-157 | breast | NOD-SCID | female |
| MDA-MB-468 | breast | NOD-SCID | female |
| PAT-34 | ovarian | nude | female |
| PAT-50 | ovarian | nude | female |
| PAT-26 | pancreas | nude | female |
| PAT-27 | pancreas | nude | female |

Preclinical Chemotherapy Trials

The required numbers of animals needed to detect a meaningful response were pooled at the start of the experiment and each was given a subcutaneous implant of a tumor fragment (~20 mg) with a 13-gauge trocar. Tumors were allowed to grow to the pre-determined size window (tumors outside the range were excluded) and animals were evenly distributed to various treatment and control groups. There were typically 8 mice per treatment and control groups, with the exception of experiments conducted in the SAL-IGF (this is not included in Table 19) tumor model, in which there were typically 5 mice per treatment and control group. Treatment of each animal was based on individual body weight. Treated animals were checked daily for treatment related toxicity/mortality. Each group of animals was weighed before the initiation of treatment ($Wt_1$) and then again following the last treatment dose ($Wt_2$). The difference in body weight ($Wt_2-Wt_1$) provides a measure of treatment-related toxicity.

Tumor response was determined by measurement of tumors with a caliper twice a week, until the tumors reached a predetermined "target" size of 0.5 gm or 1 gm depending on the tumor type. Tumor weights (mg) were estimated from the formula:

$$\text{Tumor weight} = (\text{length} \times \text{width}^2) \div 2$$

Tumor response criteria are expressed in terms of tumor growth inhibition (% TGI). Tumor growth delay is defined as the difference in time (days) required for the treated tumors (T) to reach a predetermined target size compared to those of the control group (C). For this purpose, the tumor weight of a group is expressed as medium tumor weight (MTW).

Tumor growth inhibition is calculated as follows:

$$\% \text{ Tumor Growth Inhibition} = \frac{\left(1 - \frac{T_t}{T_0} * \frac{C_0}{C_t}\right)}{\left(1 - \frac{C_0}{C_t}\right)}$$

where,
$C_t$=Median control tumor size at end of treatment
$C_0$=Median control tumor size at treatment initiation
$T_t$=Median tumor size of treated group at end of treatment
$T_0$=Median tumor size of treated group at treatment initiation Activity is defined as the achievement of durable tumor growth inhibition of 50% or greater (i.e., TGI≥50%) or log cell kill of 0.5 or greater (LCK≥0.5) for a period equivalent to at least 1 tumor volume doubling time and drug treatment must be for a period equivalent to at least 2 tumor volume doubling time.

Tumor response was also expressed in terms of tumor growth delay (TGD value), defined as the difference in time (days) required for the treated tumors (T) to reach a predetermined target size compared to those of the control group (C).

Whenever possible, antitumor activity was determined at a range of dose levels up to the maximum tolerated dose (MTD) which is defined as the dose level immediately below which excessive toxicity (i.e., more than one death) occurred. When death occurred, the day of death was recorded. Treated mice dying prior to having their tumors reach target size were considered to have died from drug toxicity. No control mice died bearing tumors less than target size. Treatment groups with more than one death caused by drug toxicity were considered to have had excessively toxic treatments and their data were not included in the evaluation of a compound's antitumor efficacy.

Potential drug toxicity interaction affecting treatment tolerability is an important consideration in combination chemotherapy trials. Interpretation of combination therapeutic results must be based on comparison of antitumor activity of the best possible response for the single agents versus the combination at comparably tolerated doses. Therefore, therapeutic synergism was defined as a therapeutic effect achieved with a tolerated regimen of the combined agents that exceeded the optimal effect achieved at any tolerated dose of monotherapy. Statistical evaluations of data were performed using Gehan's generalized Wilcoxon test. Statistical significance was declared at P<0.05.

Drug Administration

In in vitro studies, all agents were dissolved in 100% DMSO and serially diluted in media/10% fetal bovine serum. The following excipients were used for administration of the Notch inhibitors to rodents: ETOH/TPGS/PEG300 (10:10:80). Notch inhibitors were typically administered orally on a schedule of QD×15, 10 day-on-2 day-off-5 day-on, although other schedules had also been evaluated and shown to be efficacious. For example, dosing regimen consisting of QD×12, 4 day-on-3 day-off was shown to be equally efficacious as QD×15, 10 day-on-2 day-off-5 day-on. In the BID studies, the second dose was given 6 to 12 hours after the first dose.

In Vivo Antitumor Activity

Figure 2:
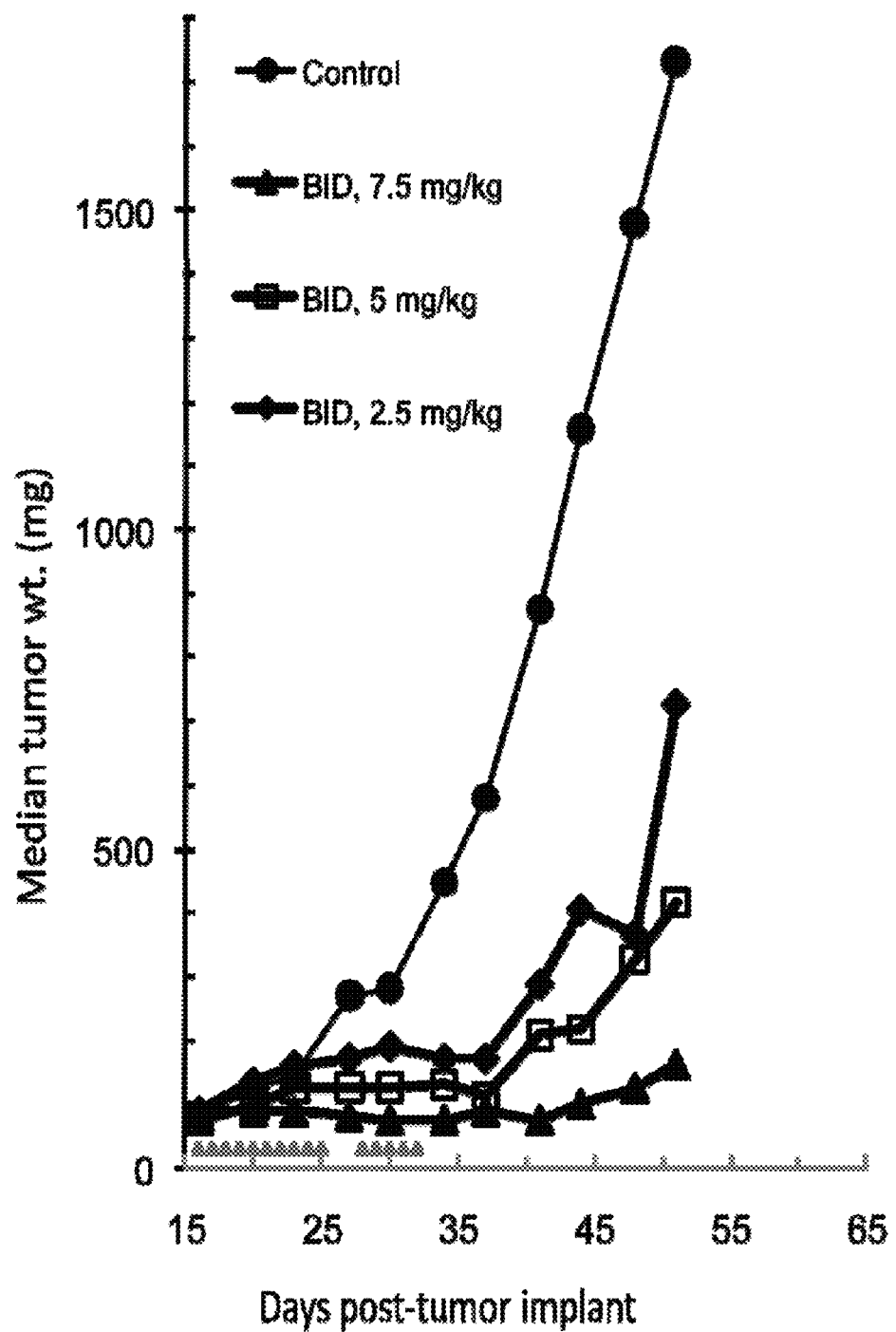
FIG. 2 shows the antitumor efficacy of Example 1 in the MDA-MB-157 Human Breast Carcinoma. Dosed orally on days indicted by (↑); PO, BID×15 (10 days on; 2 days off; 5 days on). Each symbol represents the median tumor burden of a group of 8 mice. (●) control; (◆) Example 1, 2.5 mg/kg/adm, BID; (□) Example 1, 5 mg/kg/adm, BID; (▲) Example 1, 7.5 mg/kg/adm, BID.
Figure 3:
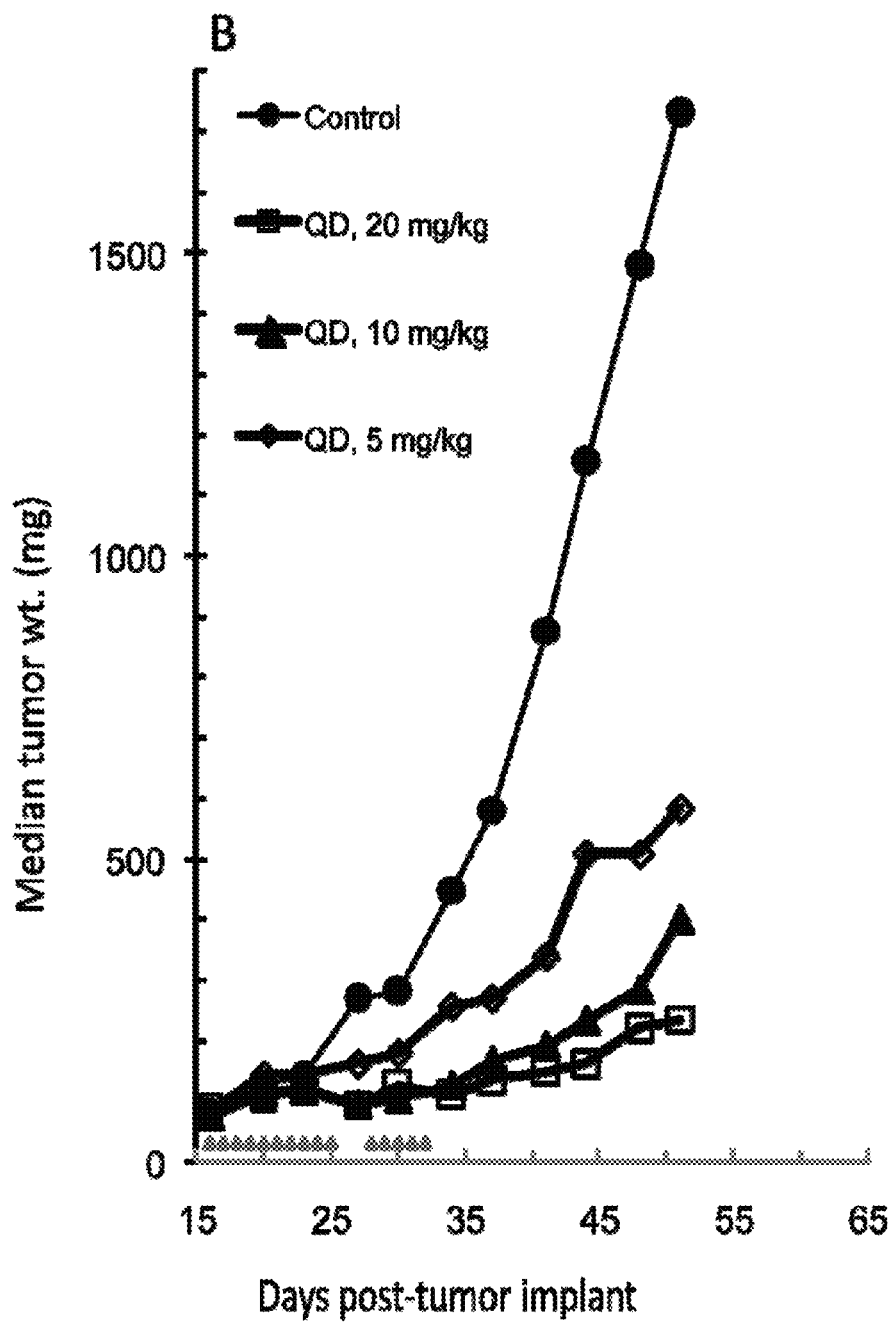
FIG. 3 shows the antitumor efficacy of Example 1 in the MDA-MB-157 Human Breast Carcinoma. Dosed orally on days indicted by (↑); PO, QD×15 (10 days on; 2 days off; 5 days on). Each symbol represents the median tumor burden of a group of 8 mice. (●) control; (◇) Example 1, 5 mg/kg/adm, QD; (▲) Example 1, 10 mg/kg/adm, QD; (□) Example 1, 20 mg/kg/adm, QD.
Figure 4:
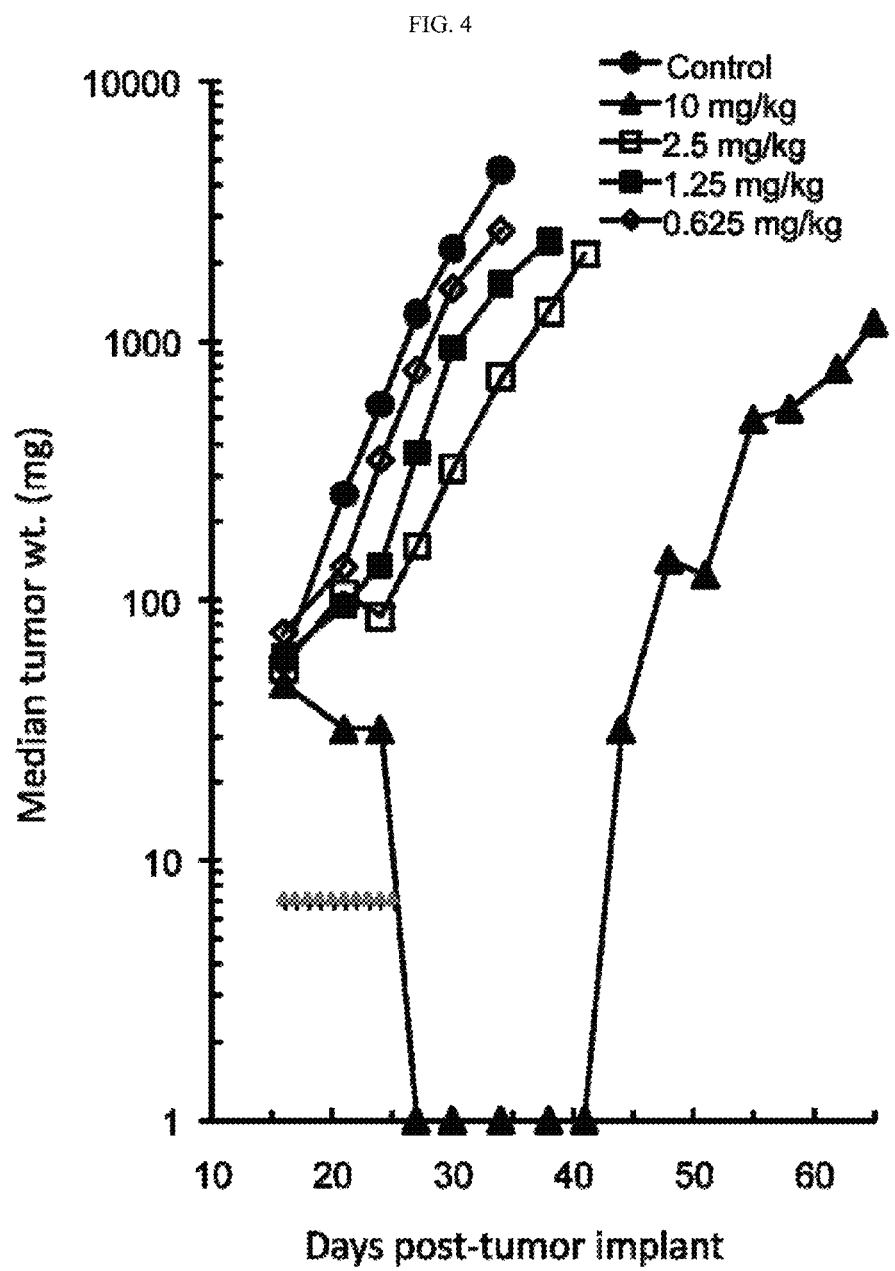
FIG. 4 shows the antitumor efficacy of Example 3 against TALL1 Human T-cell acute lymphoblastic leukemia. Dosed orally on days indicted by (↑); PO, QD×10. Each symbol represents the median tumor burden of a group of 8 mice. (●) Control; (◇) Example 1, 0.625 mg/kg/adm; (■) Example 1, 1.25 mg/kg/adm; (□) Example 1, 2.5 mg/kg/adm; (◊) Example 1, 10 mg/kg.
Figure 5:
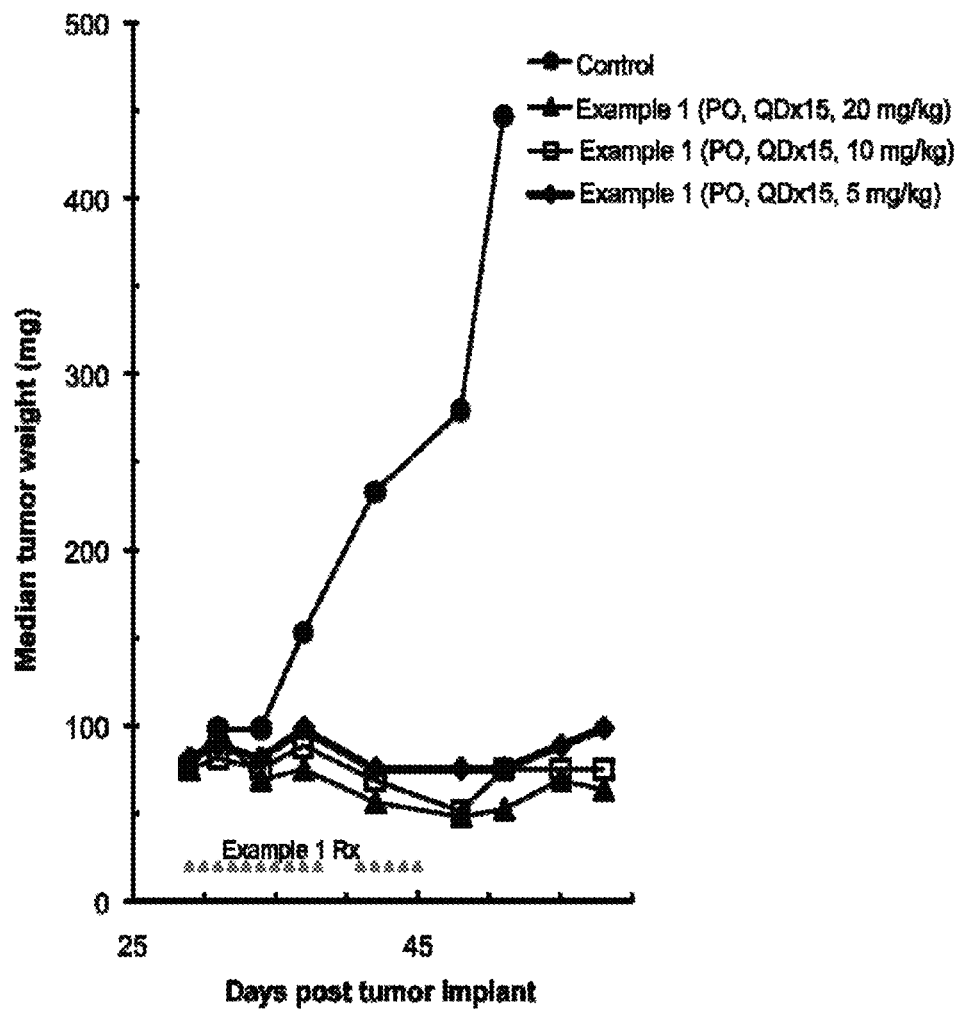
FIG. 5 shows the antitumor efficacy of Example 1 in the HCC-1599 Human Triple Negative Breast Carcinoma with Notch 1 translocation. Dosed orally on days indicted by (↑); PO, QD×15 (10 days on; 2 days off; 5 days on). Each symbol represents the median tumor burden of a group of 8 mice. (●) control; (◆) Example 1, 5 mg/kg/adm, QD; (□) Example 1, 10 mg/kg/adm, QD; (▲) Example 1, 20 mg/kg/adm, QD.
Figure 6:
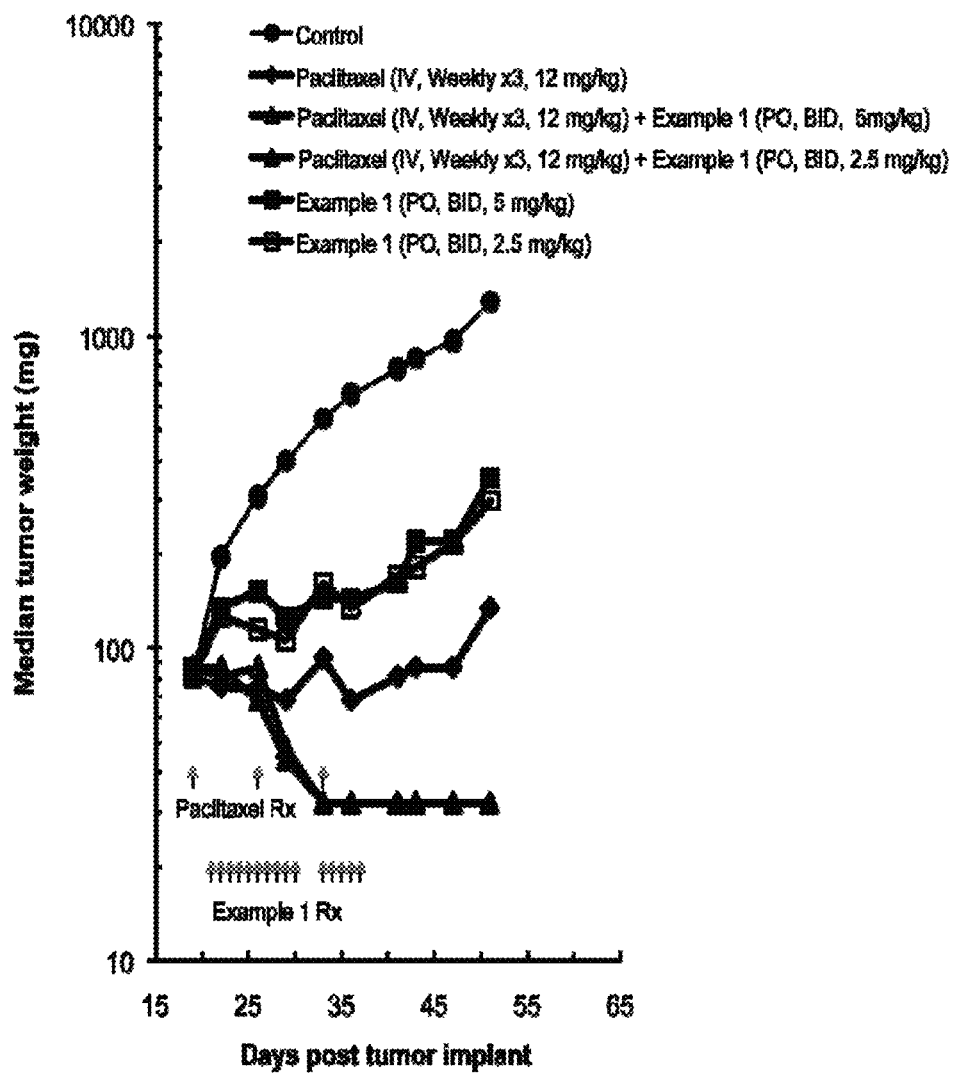
FIG. 6 shows the synergistic antitumor efficacy by combined chemotherapy with Example 1 and paclitaxel in the MDA-MB-468 Human Breast Carcinoma. Each symbol represents the median tumor burden of a group of 8 mice. (●) control; (◆) Paclitaxel, 12 mg/kg/adm, Q7D×3, IV; (□) Example 1, 2.5 mg/kg/adm, PO, BID×15 (10 days on; 2 days off; 5 days on); (■) Example 1, 5 mg/kg/adm, PO, BID×15 (10 days on; 2 days off; 5 days on); (▲) Combination of Paclitaxel and Example 1, 2.5 mg/kg/adm; (Δ) Combination of Paclitaxel and Example 1, 5 mg/kg/adm.

The antitumor activity of Example 1 orally administered (PO) was evaluated in human tumor xenografts implanted in mice. As shown in FIGS. 1-4, Example 1 exhibited antitumor activity.

Table 20 below lists the antitumor activity of examples of this invention measured in the Human Tumor Xenograft Models in mice. The compounds of the present invention, as exemplified by Examples 1 and 3, showed antitumor activity with oral administration (PO).

TABLE 20

| | | Oral Administration | | |
|---|---|---|---|---|
| | | | Antitumor Activity | |
| Example | Dose (mg/kg) | TALL1 (LCK) | MDA-MB-157 (% TGI) | MDA-MB-468 (% TGI) |
| 1 | 10-20 | >4.3 | 91 | 98 |
| 3 | 10 | 4.0 | NA | NA |

TALL1: QD×10.
MDA-MD-157 and MDA-MB-468: QD×15, 10 day-on-2 day-off-5 day on.
QD—once daily.
LCK—Log Cell Kill.

Prodrug Evaluation: Single-Dose Pharmacokinetics in Rats

Male SPRAGUE DAWLEY® rats (250-300 g) were used for the pharmacokinetic studies. Rats were fasted overnight prior to dosing and fed 4 hrs post dose. In each study, groups of animals (N=2-3) received the test compound by oral gavage. Blood samples (~0.3 mL) were collected from the jugular vein into $K_2$EDTA-containing tubes at 0.5, 1, 3, 5, 7, and 24 h post dose. Plasma samples, obtained by centrifugation at 4° C. (1500-2000× g), were stored at −20° C. until analysis by LC/MS/MS.

Data Analysis for Pharmacokinetic Assays

The pharmacokinetic parameters were obtained by non-compartmental analysis of plasma concentration (determined by LC/MS/MS) vs. time data (ThermoKinetica Software version 5.0). The peak concentration ($C_{max}$) and time for $C_{max}$, $T_{max}$, were recorded directly from experimental observations. The area under the curve from time zero to the last sampling time ($AUC_{0-t}$) was calculated using a combination of linear and log trapezoidal summations. The total plasma clearance (CLTp), steady-state volume of distribution (Vss), apparent elimination half-life ($t_{1/2}$) and mean residence time (MRT) were estimated after IV administration. Estimation of $t_{1/2}$ was made using a minimum of 3 time points with quantifiable concentrations. The absolute oral bioavailability F was estimated as the ratio of dose-normalized AUC values following oral and IV doses. The plasma exposures of Example 1 ($AUC_{0-24\,h}$ or $AUC_{0-7}$ h) after administration of the prodrugs were compared with the exposure after administration of Example 1. The relative bioavailabilities of the prodrugs to Example 1 were estimated (Table 21).

TABLE 21

Administration of Prodrug Example to Rat: Blood Levels of Example 1

| Example | Dose (mg/kg) | $AUC_{0-24\,h}$ of Example 1 after Administration of Prodrug (nM · hr) | % Relative Bioavailability to Example 1 |
|---|---|---|---|
| 38 | 6.44 | 865 | 66 |
| 40 | 6.35 | 276* | 39 |
| 42 | 6.16 | 1540 | 117 |
| 43 | 3.00 | 193 | 35 |
| 44 | 7.62 | 557 | 42 |

*$AUC_{0-7\,h}$

What is claimed is:
1. A compound of Formula (I):

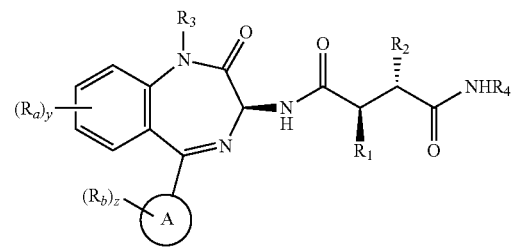

and/or at least one salt thereof, wherein:
$R_1$ is —$CH_2CH_2CF_3$;
$R_2$ is —$CH_2CH_2CF_3$ or —$CH_2CH_2CH_2CF_3$;
$R_3$ is H, —$CH_3$, or $R_x$;
$R_4$ is H or $R_y$;

$R_x$ is: —CH$_2$OC(O)CH(CH$_3$)NH$_2$, —CH$_2$OC(O)CH(NH$_2$)CH(CH$_3$)$_2$, —CH$_2$OC(O)CH((CH(CH$_3$)$_2$)NHC(O)CH(NH$_2$)CH(CH$_3$)$_2$,

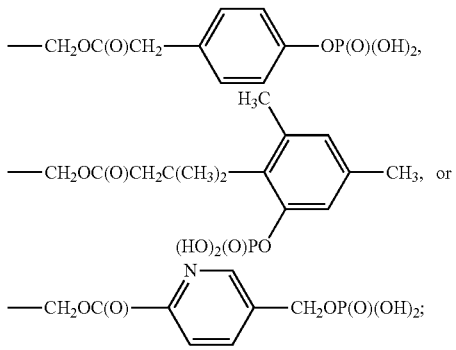

$R_y$ is: —SCH$_2$CH(NH$_2$)C(O)OH, —SCH$_2$CH(NH$_2$)C(O)OCH$_3$, or —SCH$_2$CH(NH$_2$)C(O)OC(CH$_3$)$_3$;
Ring A is phenyl or pyridinyl;
each $R_a$ is independently Cl, C$_{1-3}$ alkyl, —CH$_2$OH, —CF$_3$, cyclopropyl, —OCH$_3$, and/or —O(cyclopropyl);
y is zero, 1, or 2; and
z is zero;
provided that if Ring A is phenyl, then y is 1 or 2 and at least one $R_a$ is C$_{1-3}$ alkyl, —CH$_2$OH, —CF$_3$, cyclopropyl, or —O(cyclopropyl);
provided that if $R_3$ is $R_x$ then $R_4$ is H; and
provided that if $R_4$ is $R_y$ then $R_3$ is H or —CH$_3$.

2. The compound according to claim 1 and/or at least one salt thereof, wherein:
Ring A is phenyl;
$R_3$ is H.

3. The compound according to claim 1 and/or at least one salt thereof, wherein:
$R_2$ is —CH$_2$CH$_2$CF$_3$;
Ring A is phenyl.

4. The compound according to claim 1 and/or at least one salt thereof, wherein:
$R_2$ is —CH$_2$CH$_2$CF$_3$;
Ring A is phenyl;
$R_a$ is C$_{1-3}$ alkyl or —CH$_2$OH; and
y is 1.

5. The compound according to claim 1 having the structure:

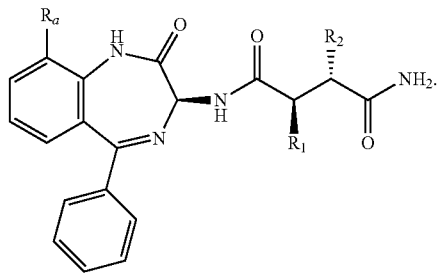

6. A pharmaceutical composition comprising a compound according to claim 1 and/or at least one salt thereof; and a pharmaceutically acceptable carrier.

7. The compound according to claim 1, wherein:
$R_3$ is H; and
$R_4$ is H.

8. The compound according to claim 1 selected from:
(2R,3S)—N-((3S)-9-isopropyl-2-oxo-5-phenyl-2,3-dihydro-1H-1,4-benzodiazepin-3-yl)-2,3-bis(3,3,3-trifluoropropyl)succinamide (13);
(2R,3S)—N-((3S)-9-(cyclopropyloxy)-2-oxo-5-phenyl-2,3-dihydro-1H-1,4-benzodiazepin-3-yl)-3-(4,4,4-trifluorobutyl)-2-(3,3,3-trifluoropropyl)succinamide (16);
(2R,3S)—N-((3S)-9-(cyclopropyloxy)-2-oxo-5-phenyl-2,3-dihydro-1H-1,4-benzodiazepin-3-yl)-2,3-bis(3,3,3-trifluoropropyl)succinamide (19);
(2R,3S)—N-((3S)-9-methyl-2-oxo-5-phenyl-2,3-dihydro-1H-1,4-benzodiazepin-3-yl)-2,3-bis(3,3,3-trifluoropropyl) succinamide (23);
(2R,3S)—N-((3S)-9-cyclopropyl-2-oxo-5-phenyl-2,3-dihydro-1H-1,4-benzodiazepin-3-yl)-2,3-bis(3,3,3-trifluoropropyl)succinamide (24);
and salts thereof.

9. The compound according to claim 1 wherein $R_4$ is H.

10. The compound according to claim 1 wherein $R_3$ is H or —CH$_3$.

11. The compound according to claim 1 wherein:
$R_3$ is H or —CH$_3$; and
$R_4$ is H.

* * * * *